(12) United States Patent
Alvaro et al.

(10) Patent No.: US 7,919,491 B2
(45) Date of Patent: Apr. 5, 2011

(54) PYRIDINE DERIVATIVES AND THEIR USE IN THE TREATMENT OF PSYCHOTIC DISORDERS

(75) Inventors: Giuseppe Alvaro, Verona (IT); Sandro Belvedere, Verona (IT)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 12/636,849

(22) Filed: Dec. 14, 2009

(65) Prior Publication Data

US 2010/0152175 A1 Jun. 17, 2010

Related U.S. Application Data

(63) Continuation of application No. 12/065,923, filed as application No. PCT/EP2006/008845 on Sep. 7, 2006, now Pat. No. 7,683,056.

(30) Foreign Application Priority Data

Sep. 9, 2005 (GB) .................................. 0518472.6
Jun. 6, 2006 (GB) .................................. 0611153.8

(51) Int. Cl.
| | |
|---|---|
| *C07D 513/04* | (2006.01) |
| *C07D 487/04* | (2006.01) |
| *C07D 498/04* | (2006.01) |
| *A61K 31/4981* | (2006.01) |
| *A61K 31/5383* | (2006.01) |

(52) U.S. Cl. ..................................... 514/230.5; 544/105
(58) Field of Classification Search ................ 514/230.5
See application file for complete search history.

(56) References Cited

U.S. PATENT DOCUMENTS

2005/0090533 A1   4/2005   Hoffmann

FOREIGN PATENT DOCUMENTS

| EP | 1035115 B1 | 9/2000 |
|---|---|---|
| WO | 03/066621 | 8/2003 |
| WO | 03/066635 | 8/2003 |
| WO | 2005/002577 | 1/2005 |

OTHER PUBLICATIONS

Natsugari, H. et al.; Novel, Potent and orally active substance P Antagonists: Synthesis and Antagonist Activity of N-Benzylcarboxamide Derivatives of Pyrido [3,4-b] pyridine; Journal of Medicinal Chemistry; 1995; 38; 3106-3120; American Chemical Society.

Ikeura, Y., et al.; Potent NK1 Receptor Antagonists: Synthesis and Antagonistic Activity of various Heterocycles with anN-[3,5-Bis(trifluoremethyl)benzyl]-N-methylcarbamoyl Substituent; Chem. Pharm. Bull.; 1997; 45/10; 1642-1652; Pharmaceutical Society of Japan.

*Primary Examiner* — Kahsay T Habte
(74) *Attorney, Agent, or Firm* — J. Scott Young

(57) ABSTRACT

A pyridine derivative novel compounds of formula (I) or a pharmaceutically

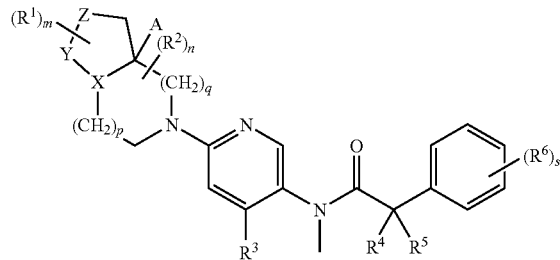

acceptable salt thereof where all variables are defined herein. The compounds are useful in the treatment of psychotic disorders.

6 Claims, No Drawings

PYRIDINE DERIVATIVES AND THEIR USE IN THE TREATMENT OF PSYCHOTIC DISORDERS

CROSS-REFERENCE TO RELATED APPLICATIONS

This application is filed as a continuation application of U.S. Ser. No. 12/065,923, filed May 8, 2008, which is a National Phase Application of International Application No. PCT/EP2006/008845 filed Sep. 7, 2006, which claims priority from GB 0518472.6 filed Sep. 9, 2005 and GB 0611153.8 filed Jun. 6, 2006.

FIELD OF THE INVENTION

The present invention relates to novel nitrogen containing bicyclic derivatives having pharmacological activity, processes for their preparation, to compositions containing them and to their use in the treatment of psychotic disorders, in particular schizophrenia.

BACKGROUND OF THE INVENTION

WO 2005/002577 (F. Hoffmann-La Roche AG) describes a series of pyridine derivatives which are clamed to be dual NK1/NK3 antagonists for treating schizophrenia.

DESCRIPTION OF THE INVENTION

The present invention provides, in a first aspect, a compound of formula (I) or a pharmaceutically acceptable salt thereof:

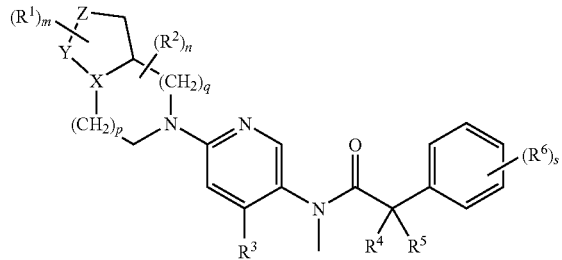

(I)

wherein:
X represents a nitrogen or sulphur atom;
Y represents —C(H$_2$)—, (—C(H$_2$)—)$_2$, —S(O$_2$)— or —C(=O)—;
Z represents —C(H$_2$)—, —S(O$_2$)—, —N(R$^z$)—, or an oxygen or sulphur atom;
R$^z$ represents hydrogen, C$_{1-6}$ alkyl, C$_{1-6}$ alkoxy, —COR$^7$ or SO$_2$R$^7$;
R$^1$ represents halogen, C$_{1-6}$ alkyl, C$_{1-6}$ alkoxy, =O, haloC$_{1-6}$ alkyl or haloC$_{1-6}$ alkoxy;
m represents an integer from 0 to 3;
R$^2$ represents halogen, =O, C$_{1-6}$ alkyl (optionally substituted by one or more hydroxyl groups), —COOR$^7$, —CONR$^7$R$^8$, C$_{1-6}$ alkoxy, haloC$_{1-6}$ alkyl or haloC$_{1-6}$ alkoxy;
n represents an integer from 0 to 3;
p and q independently represent an integer from 0 to 2;
R$^3$ represents an -aryl, -heteroaryl, -heterocyclyl, -aryl-aryl, -aryl-heteroaryl, -aryl-heterocyclyl, -heteroaryl-aryl, -heteroaryl-heteroaryl, -heteroaryl-heterocyclyl, -heterocyclyl-aryl, -heterocyclyl-heteroaryl or -heterocyclyl-heterocyclyl group, all of which may be optionally substituted by one or more (e.g. 1, 2 or 3) halogen, C$_{1-6}$ alkyl, C$_{3-8}$ cycloalkyl, C$_{1-6}$ alkoxy, hydroxyl, haloC$_{1-6}$ alkyl, haloC$_{1-6}$ alkoxy, cyano, —S—C$_{1-6}$ alkyl, —SO—C$_{1-6}$ alkyl, —SO$_2$—C$_{1-6}$ alkyl, —COR$^7$, —CONR$^7$R$^8$, —NR$^7$R$^8$, NR$^7$COC$_{1-6}$ alkyl, NR$^7$SO$_2$—C$_{1-6}$ alkyl, C$_{1-6}$ alkyl-NR$^7$R$^8$, —OCONR$^7$R$^8$, —NR$^7$CO$_2$R$^8$ or —SO$_2$NR$^7$R$^8$ groups;
R$^4$ and R$^5$ independently represent C$_{1-6}$ alkyl, or R$^4$ and R$^5$ together with the carbon atom to which they are attached may together form a C$_{3-8}$ cycloalkyl group;
R$^6$ represents halogen, C$_{1-6}$ alkyl, C$_{3-8}$ cycloalkyl, C$_{1-6}$ alkoxy, haloC$_{1-6}$ alkyl or haloC$_{1-6}$ alkoxy;
s represents an integer from 0 to 4;
R$^7$ and R$^8$ independently represent hydrogen, C$_{1-6}$ alkyl or C$_{3-8}$ cycloalkyl;
or solvates thereof.

In a further aspect the invention provides a compound of formula (I) or a pharmaceutically acceptable salt thereof:

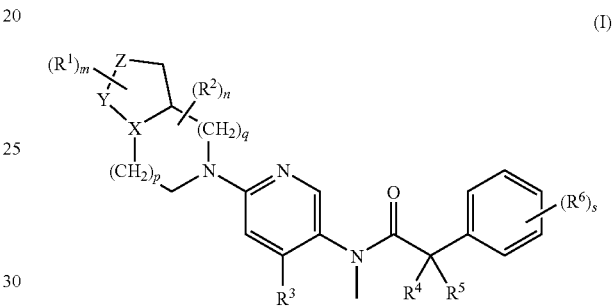

(I)

wherein:
X represents a nitrogen atom;
Y represents —C(H$_2$)—, (—C(H$_2$)—)$_2$, —S(O$_2$)— or —C(=O)—;
Z represents —C(H$_2$)—, —S(O$_2$)—, —N(R$^z$)—, or an oxygen or sulphur atom;
R$^z$ represents hydrogen, C$_{1-6}$ alkyl, C$_{1-6}$ alkoxy, —COR$^7$ or SO$_2$R$^7$;
R$^1$ represents halogen, C$_{1-6}$ alkyl, C$_{1-6}$ alkoxy, =O, haloC$_{1-6}$ alkyl or haloC$_{1-6}$ alkoxy;
m represents an integer from 0 to 3;
R$^2$ represents halogen, =O, C$_{1-6}$ alkyl (optionally substituted by one or more hydroxyl groups), —COOR$^7$, —CONR$^7$R$^8$, C$_{1-6}$ alkoxy, haloC$_{1-6}$ alkyl or haloC$_{1-6}$ alkoxy;
n represents an integer from 0 to 3;
p and q independently represent an integer from 0 to 2;
R$^3$ represents an -aryl, -heteroaryl, -heterocyclyl, -aryl-aryl, -aryl-heteroaryl, -aryl-heterocyclyl, -heteroaryl-aryl, -heteroaryl-heteroaryl, -heteroaryl-heterocyclyl, -heterocyclyl-aryl, -heterocyclyl-heteroaryl or -heterocyclyl-heterocyclyl group, all of which may be optionally substituted by one or more (e.g. 1, 2 or 3) halogen, C$_{1-6}$ alkyl, C$_{3-8}$ cycloalkyl, C$_{1-6}$ alkoxy, hydroxyl, haloC$_{1-6}$ alkyl, haloC$_{1-6}$ alkoxy, cyano, —S—C$_{1-6}$ alkyl, —SO—C$_{1-6}$ alkyl, —SO$_2$—C$_{1-6}$ alkyl, —COR$^7$, —CONR$^7$R$^8$, —NR$^7$R$^8$, NR$^7$COC$_{1-6}$ alkyl, NR$^7$SO$_2$—C$_{1-6}$ alkyl, C$_{1-6}$ alkyl-NR$^7$R$^8$, —OCONR$^7$R$^8$, —NR$^7$CO$_2$R$^8$ or —SO$_2$NR$^7$R$^8$ groups;
R$^4$ and R$^5$ independently represent C$_{1-6}$ alkyl, or R$^4$ and R$^5$ together with the carbon atom to which they are attached may together form a C$_{3-8}$ cycloalkyl group;
R$^6$ represents halogen, C$_{1-6}$ alkyl, C$_{3-8}$ cycloalkyl, C$_{1-6}$ alkoxy, haloC$_{1-6}$ alkyl or haloC$_{1-6}$ alkoxy;
s represents an integer from 0 to 4;
R$^7$ and R$^8$ independently represent hydrogen, C$_{1-6}$ alkyl or C$_{3-8}$ cycloalkyl; or solvates thereof.

In another aspect the invention provides a compound of formula (I) or a pharmaceutically acceptable salt thereof:

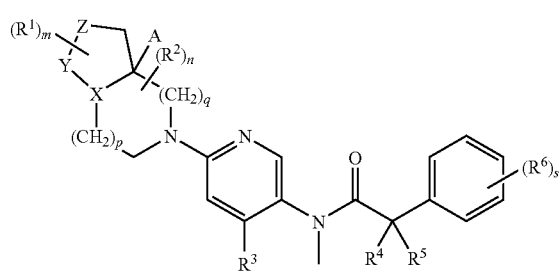

wherein:
X represents a nitrogen atom;
Y represents —C(H$_2$)—, (—C(H$_2$)—)$_2$, —S(O$_2$)— or —C(═O)—;
Z represents —C(H$_2$)—, —S(O$_2$)—, —N(R$^z$)—, or an oxygen or sulphur atom;
A represents hydrogen or —CH$_2$OH;
R$^z$ represents hydrogen, C$_{1-6}$ alkyl, C$_{1-6}$ alkoxy, —COR$^7$ or SO$_2$R$^7$;
R$^1$ represents halogen, C$_{1-6}$ alkyl, C$_{1-6}$ alkoxy, ═O, haloC$_{1-6}$ alkyl, haloC$_{1-6}$ alkoxy, hydroxyl or CH$_2$OH;
m represents an integer from 0 to 3;
R$^2$ represents halogen, ═O, C$_{1-6}$ alkyl (optionally substituted by one or more hydroxyl groups), —COOR$^7$, —CONR$^7$R$^8$, C$_{1-6}$ alkoxy, haloC$_{1-6}$ alkyl, haloC$_{1-6}$ alkoxy or C$_{1-6}$alkylOC$_{1-6}$alkyl;
n represents an integer from 0 to 3;
p and q independently represent an integer from 0 to 2;
R$^3$ represents an -aryl, -heteroaryl, -heterocyclyl, -aryl-aryl, -aryl-heteroaryl, -aryl-heterocyclyl, -heteroaryl-aryl, -heteroaryl-heteroaryl, -heteroaryl-heterocyclyl, -heterocyclylaryl, -heterocyclyl-heteroaryl or -heterocyclyl-heterocyclyl group, all of which may be optionally substituted by one or more (e.g. 1, 2 or 3) halogen, C$_{1-6}$ alkyl (optionally substituted by one or more hydroxyl groups), C$_{3-8}$ cycloalkyl, C$_{1-6}$ alkoxy, hydroxyl, haloC$_{1-6}$ alkyl, haloC$_{1-6}$ alkoxy, cyano, —S—C$_{1-6}$ alkyl, —SO—C$_{1-6}$ alkyl, —SO$_2$—C$_{1-6}$ alkyl, —COR$^7$, —CONR$^7$R$^8$, —NR$^7$R$^8$, —NR$^7$COC$_{1-6}$ alkyl, —NR$^7$SO$_2$—C$_{1-6}$ alkyl, C$_{1-6}$ alkyl-NR$^7$R$^8$, —OCONR$^7$R$^8$, —NR$^7$CO$_2$R$^8$ or —SO$_2$NR$^7$R$^8$ groups;
R$^4$ and R$^5$ independently represent C$_{1-6}$ alkyl, or R$^4$ and R$^5$ together with the carbon atom to which they are attached may together form a C$_{3-8}$ cycloalkyl group;
R$^6$ represents halogen, C$_{1-6}$ alkyl, C$_{3-8}$ cycloalkyl, C$_{1-6}$ alkoxy, haloC$_{1-6}$ alkyl or haloC$_{1-6}$ alkoxy;
s represents an integer from 0 to 4;
R$^7$ and R$^8$ independently represent hydrogen, C$_{1-6}$ alkyl or C$_{3-8}$ cycloalkyl;
or solvates thereof.

The term 'C$_{1-6}$ alkyl' as used herein as a group or a part of the group refers to a linear or branched saturated hydrocarbon group containing from 1 to 6 carbon atoms. Examples of such groups include methyl, ethyl, n-propyl, isopropyl, n-butyl, isobutyl, sec-butyl, tert butyl, n-pentyl, isopentyl, neopentyl or hexyl and the like.

The term 'C$_{1-6}$ alkoxy' as used herein refers to an —O—C$_{1-6}$ alkyl group wherein C$_{1-6}$ alkyl is as defined herein. Examples of such groups include methoxy, ethoxy, propoxy, butoxy, pentoxy or hexoxy and the like.

The term 'C$_{3-8}$ cycloalkyl' as used herein refers to a saturated monocyclic hydrocarbon ring of 3 to 8 carbon atoms. Examples of such groups include cyclopropyl, cyclobutyl, cyclopentyl, cyclohexyl, cycloheptyl or cyclooctyl and the like.

The term 'halogen' as used herein refers to a fluorine, chlorine, bromine or iodine atom.

The term 'haloC$_{1-6}$ alkyl' as used herein refers to a C$_{1-6}$ alkyl group as defined herein wherein at least one hydrogen atom is replaced with halogen. Examples of such groups include fluoroethyl, trifluoromethyl or trifluoroethyl and the like.

The term 'haloC$_{1-6}$ alkoxy' as used herein refers to a C$_{1-6}$ alkoxy group as herein defined wherein at least one hydrogen atom is replaced with halogen. Examples of such groups include difluoromethoxy or trifluoromethoxy and the like.

The term 'aryl' as used herein refers to a C$_{6-12}$ monocyclic or bicyclic hydrocarbon ring wherein at least one ring is aromatic. Examples of such groups include phenyl, naphthyl or tetrahydronaphthalenyl and the like.

The term 'heteroaryl' as used herein refers to a 5-6 membered monocyclic aromatic or a fused 8-10 membered bicyclic aromatic ring containing 1 to 4 heteroatoms selected from oxygen, nitrogen and sulphur. Examples of such monocyclic aromatic rings include thienyl, furyl, furazanyl, pyrrolyl, triazolyl, tetrazolyl, imidazolyl, oxazolyl, thiazolyl, oxadiazolyl, isothiazolyl, isoxazolyl, thiadiazolyl, pyranyl, pyrazolyl, pyrimidyl, pyridazinyl, pyrazinyl, pyridyl, triazinyl, tetrazinyl and the like. Examples of such fused aromatic rings include quinolinyl, isoquinolinyl, quinazolinyl, quinoxalinyl, pteridinyl, cinnolinyl, phthalazinyl, naphthyridinyl, indolyl, isoindolyl, azaindolyl, indolizinyl, indazolyl, purinyl, pyrrolopyridinyl, furopyridinyl, benzofuranyl, isobenzofuranyl, benzothienyl, benzoimidazolyl, benzoxazolyl, benzoisoxazolyl, benzothiazolyl, benzoisothiazolyl, benzoxadiazolyl, benzothiadiazolyl and the like.

The term 'heterocyclyl' refers to a 4-7 membered monocyclic ring or a fused 8-12 membered bicyclic ring which may be saturated or partially unsaturated containing 1 to 4 heteroatoms selected from oxygen, nitrogen or sulphur. Examples of such monocyclic rings include pyrrolidinyl, azetidinyl, pyrazolidinyl, oxazolidinyl, piperidinyl, piperazinyl, morpholinyl, thiomorpholinyl, thiazolidinyl, hydantoinyl, valerolactamyl, oxiranyl, oxetanyl, dioxolanyl, dioxanyl, oxathiolanyl, oxathianyl, dithianyl, dihydrofuranyl, tetrahydrofuranyl, dihydropyranyl, tetrahydropyranyl, tetrahydropyridinyl, tetrahydropyrimidinyl, tetrahydrothiophenyl, tetrahydrothiopyranyl, diazepanyl, azepanyl and the like. Examples of such bicyclic rings include indolinyl, isoindolinyl, benzopyranyl, quinuclidinyl, 2,3,4,5-tetrahydro-1H-3-benzazepine, tetrahydroisoquinolinyl and the like.

In one embodiment, p and q both represent 1, X represents a nitrogen atom, Y represents —C(H$_2$)— and Z represents —C(H$_2$)—, for example, the bicyclic moiety attached to the pyridinyl ring in formula (I) is hexahydropyrrolopyrazinyl (e.g. hexahydropyrrolo[1,2-a]pyrazin-2(1H)-yl).

In an alternative embodiment, p and q both represent 1, X represents a nitrogen atom, Y represents (—C(H$_2$)—)$_2$ and Z represents an oxygen atom, for example, the bicyclic moiety attached to the pyridinyl ring in formula (I) is hexahydropyrazino-oxazinyl (e.g. hexahydropyrazino[2,1-c][1,4]oxazin-8(1H)-yl).

In a further alternative embodiment, p and q both represent 1, X represents a nitrogen atom, Y represents —S(O$_2$)— and Z represents —C(H$_2$)—, for example, the bicyclic moiety attached to the pyridinyl ring in formula (I) is dioxidohexahydroisothiazolopyrazinyl (e.g. 1,1-dioxidohexahydro-5H-isothiazolo[2,3-a]pyrazin-5-yl).

In a yet further alternative embodiment, p and q both represent 1, X represents a nitrogen atom, Y represents —C(=O)— and Z represents —C(H$_2$)—, for example, the bicyclic moiety attached to the pyridinyl ring in formula (I) is oxohexahydropyrrolopyrazinyl (e.g. 6-oxohexahydropyrrolo[1,2-a]pyrazin-2(1H)-yl).

In a yet further alternative embodiment, p represents 1, q represents 2, X represents a nitrogen atom, Y represents —C(H$_2$)— and Z represents —C(H$_2$)—, for example, the bicyclic moiety attached to the pyridinyl ring in formula (I) is octahydropyrrolodiazepinyl (e.g. octahydro-3H-pyrrolo[1,2-d][1,4]diazepin-3-yl).

In a yet further alternative embodiment, p represents 2, q represents 1, X represents a nitrogen atom, Y represents —C(H$_2$)— and Z represents —C(H$_2$)—, for example, the bicyclic moiety attached to the pyridinyl ring in formula (I) is oxahexahydropyrrolodiazepinyl (e.g. oxohexahydro-1H-pyrrolo[1,2-a][1,4]diazepin-2(3H)-yl).

In a yet further alternative embodiment, p and q both represent 1, X represents a nitrogen atom, Y represents (—C(H$_2$)—)$_2$ and Z represents —S(O$_2$)—, for example, the bicyclic moiety attached to the pyridinyl ring in formula (I) is dioxidohexahydropyrazinothiazinyl (e.g. 2,2-dioxidohexahydropyrazino[2,1-c][1,4]thiazin-8(1H)-yl).

In a yet further embodiment, p and q both represent 1, X represents nitrogen, Y represents (—C(H$_2$)—)$_2$ and Z represents N(R$^z$)—, for example, the bicyclic moiety attached to the pyridinyl ring in formula (I) is octahydropyrazinopyrazinyl (e.g. octahydro-2H-pyrazino[1,2-a]pyrazin-2-yl).

In a yet further embodiment, when p represents zero and q represent 1, X represents nitrogen, Y represents —C(H$_2$)— and Z represents —C(H$_2$)—, for example, the bicyclic moiety attached to the pyridinyl ring in formula (I) is oxotetrahydropyrroloimidazolyl (e.g. oxotetrahydro-1H-pyrrolo[1,2-c]imidazol-2(3H)-yl).

In one embodiment, m represents 0.

In another embodiment, m represents 1.

In one embodiment, when m represents 1, R$^1$ represents =O, hydroxyl, —CH$_2$OH.

In one embodiment, n represents 0 or 1.

In a further embodiment, when n represents 1, R$^2$ represents =O or C$_{1-6}$ alkyl (optionally substituted by one or more hydroxyl groups; e.g. —CH$_2$—OH or CH$_3$).

In another embodiment, when n represents 1, R$^2$ represents C$_{1-6}$alkylOC$_{1-6}$alkyl (e.g. —CH$_2$OCH$_3$) or haloC$_{1-6}$ alkyl (e.g. —CH$_2$F).

In a yet further embodiment, when n represents 1, R$^2$ represents C$_{1-6}$ alkyl substituted by a hydroxyl group (e.g. —CH$_2$—OH).

In one embodiment A represents hydrogen.

In another embodiment A represents —CH$_2$OH.

In one embodiment, p and q either both represent 1 or one of p or q represents 1 and the other of p or q represents 2. In a further embodiment, p and q both represent 1.

In a yet further embodiment when q represents 1, p represents 0.

In one embodiment, R$^7$ represents C$_{1-6}$alkyl (e.g. methyl).

In one embodiment, when Z represents —N(R$^z$)—, R$^z$ represents hydrogen, C$_{1-6}$ alkyl, —COR$^7$ or SO$_2$R$^7$.

In another embodiment, R$^z$ represents —COR$^7$.

In another embodiment, R$^z$ represents C$_{1-6}$alkyl or —SO$_2$R$^7$.

In a yet further embodiment when R$^z$ represents —COR$^7$, R$^7$ represents C$_{1-6}$alkyl (e.g. methyl).

In a yet further embodiment when R$^z$ represents —SO$_2$R$^7$, R$^7$ represents C$_{1-6}$alkyl (e.g. methyl).

In one embodiment, R$^3$ represents -aryl (e.g. phenyl) mono substituted by a halogen (e.g. 2-chlorine) or C$_{1-6}$ alkyl (e.g. 2-methyl) group or -aryl (e.g. phenyl) di substituted by a halogen (e.g. 4-fluorine) and C$_{1-6}$ alkyl (e.g. 2-methyl) group.

In a further embodiment, R$^3$ represents -aryl (e.g. phenyl) di substituted by a halogen (e.g. 4-fluorine) and C$_{1-6}$ alkyl (e.g. 2-methyl) group (e.g. 4-fluoro-2-methylphenyl).

In a further embodiment R$^3$ represents -aryl (e.g. phenyl) monosubstitued by C$_{1-6}$alkyl substituted by one or more hydroxyl groups (e.g. —CH$_2$OH) or -aryl (e.g. phenyl) di substituted by a halogen (e.g. 2-chloro-4-fluorophenyl) or a halogen (e.g. 5-fluorine) and a C$_{1-6}$ alkyl (e.g. 2-methyl) group (e.g. 5-fluoro-2-methylphenyl).

In a further embodiment R$^3$ represents -heteroaryl (e.g. pyridinyl) monosubstitued by C$_{1-6}$alkyl (e.g. 6-methylpyridin-3-yl)) or -heteroaryl (e.g. pyridinyl) di substituted by a halogen (e.g. 4-fluorine) and a C$_{1-6}$ alkyl (e.g. 2-methyl) group (e.g. 4-fluoro-2-methylpyridin-3-yl).

In one embodiment, R$^4$ and R$^5$ both represent C$_{1-6}$ alkyl (e.g. methyl), or R$^4$ and R$^5$ together with the carbon atom to which they are attached together form a C$_{3-8}$ cycloalkyl (e.g. cyclopropyl) group. In a further embodiment, R$^4$ and R$^5$ both represent C$_{1-6}$ alkyl (e.g. methyl).

In a yet further embodiment R$^4$ and R$^5$ together with the carbon atom to which they are attached together form a C$_{3-8}$ cycloalkyl (e.g. cyclopropyl) group.

In one embodiment, s represents 2 and both R$^6$ groups are haloC$_{1-6}$ alkyl (such as trifluoromethyl groups, e.g. 3,5-bis(trifluoromethyl)).

In one embodiment, when p and q both represent 1, X represents a nitrogen atom, Y represents (—C(H$_2$)—)$_2$ and Z represents an oxygen atom, n represents 1, R$^2$ represents C$_{1-6}$ alkyl substituted by a hydroxyl group, R$^3$ represents -aryl di substituted by a halogen and C$_{1-6}$ alkyl group, R$^4$ and R$^5$ both represent C$_{1-6}$ alkyl and s represents 2 wherein both R$^6$ groups are haloC$_{1-6}$ alkyl.

In one embodiment, when p and q both represent 1, X represents a nitrogen atom, Y represents (—C(H$_2$)—)$_2$ and Z represents —S(O$_2$)—, n represents 1, R$^2$ represents C$_{1-6}$ alkyl substituted by a hydroxyl group, R$^3$ represents -aryl di substituted by a halogen and C$_{1-6}$ alkyl group, R$^4$ and R$^5$ both represent C$_{1-6}$ alkyl and s represents 2 wherein both R$^6$ groups are haloC$_{1-6}$ alkyl.

In one embodiment, when p and q both represent 1, X represents nitrogen, Y represents (—C(H$_2$)—)$_2$ and Z represents —N(R$^z$)—, n represents 1, R$^2$ represents C$_{1-6}$ alkyl substituted by a hydroxyl group, R$^3$ represents -aryl di substituted by a halogen and C$_{1-6}$ alkyl group, R$^4$ and R$^5$ both represent C$_{1-6}$ alkyl and s represents 2 wherein both R$^6$ groups are haloC$_{1-6}$ alkyl.

In a yet further embodiment, p and q both represent 1, n and m both represent 0, A represents hydrogen, X represents nitrogen, Y represents (—C(H$_2$)—)$_2$, Z represents —N(R$^z$)—, R$^3$ represents -aryl substituted by a halogen and C$_{1-6}$ alkyl group, R$^4$ and R$^5$ both represent C$_{1-6}$ alkyl, s represents 2 wherein both R$^6$ groups are haloC$_{1-6}$ alkyl and R$^z$ represents —COR$_7$, wherein R$_7$ is C$_{1-6}$alkyl.

Compounds according to the invention include examples E1-E33 as shown below, or a pharmaceutically acceptable salt thereof.

Compounds according to the invention further include examples E34-E40 as shown below, or a pharmaceutically acceptable salt thereof.

Compounds according to the invention further include examples E41-E104 as shown below, or a pharmaceutically acceptable salt thereof.

In one embodiment, the invention provides a compound selected from the group consisting of:

2-[3,5-bis(trifluoromethyl)phenyl]-N-{4-(4-fluoro-2-methyl phenyl)-6-[(7S,9aS)-7-(hydroxymethyl)hexahydropyrazino[2,1-c][1,4]oxazin-8(1H)-yl]-3-pyridinyl}-N,2-dimethylpropanamide, 2-[3,5-bis(trifluoromethyl)phenyl]-N-{4-(4-fluoro-2-methyl phenyl)-6-[(7S,9aR)-7-(hydroxymethyl)hexahydropyrazino[2,1-c][1,4]oxazin-8(1H)-yl]-3-pyridinyl}-N,2-dimethylpropanamide, 2-[3,5-bis(trifluoromethyl)phenyl]-N-{4-(4-fluoro-2-methyl phenyl)-6-[(7S)-7-(hydroxymethyl)-2,2-dioxidohexahydropyrazino[2,1-c][1,4]thiazin-8(1H)-yl]-3-pyridinyl}-N,2-dimethylpropanamide, N-[6-[(3S)-8-acetyl-3-(hydroxymethyl)octahydro-2H-pyrazino[1,2-a]pyrazin-2-yl]-4-(4-fluoro-2-methylphenyl)-3-pyridinyl]-2-[3,5-bis(trifluoromethyl)phenyl]-N,2-dimethylpropanamide, or a pharmaceutically acceptable salt thereof.

In a further embodiment, the invention provides 2-[3,5-bis(trifluoromethyl)phenyl]-N-{4-(4-fluoro-2-methylphenyl)-6-[(7S,9aR)-7-(hydroxymethyl)hexahydropyrazino[2,1-c][1,4]oxazin-8(1H)-yl]-3-pyridinyl}-N,2-dimethylpropanamide or a pharmaceutically acceptable salt thereof.

In a further embodiment, the invention provides N-[6-[(9aS or 9aR)-8-acetyloctahydro-2H-pyrazino[1,2-a]pyrazin-2-yl]-4-(4-fluoro-2-methylphenyl)-3-pyridinyl]-2-[3,5-bis(trifluoromethyl)phenyl]-N,2-dimethylpropanamide (Enantiomer 2) or a pharmaceutically acceptable salt thereof, wherein "Enantiomer 2" means a single enantiomer of unknown absolute stereochemistry prepared according to Example 72 described hereinbelow.

Compounds of formula (I) may form acid addition salts with acids, such as conventional pharmaceutically acceptable acids, for example maleic, hydrochloric, hydrobromic, phosphoric, acetic, fumaric, salicylic, sulphate, citric, lactic, mandelic, tartaric and methanesulphonic. Salts, solvates and hydrates of compounds of formula (I) therefore form an aspect of the invention.

As used herein, the term "salt" refers to any salt of a compound according to the present invention prepared from an inorganic or organic acid or base, quaternary ammonium salts and internally formed salts. Physiologically acceptable salts are particularly suitable for medical applications because of their greater aqueous solubility relative to the parent compounds. Such salts must clearly have a physiologically acceptable anion or cation. Suitably physiologically acceptable salts of the compounds of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfanilic, alginic, galacturonic and arylsulfonic, for example benzenesulfonic and p-toluenesulfonic, acids; base addition salts formed with alkali metals and alkaline earth metals and organic bases such as N,N-dibenzylethylenediamine, chloroprocaine, choline, diethanolamine, ethylenediamine, meglumaine (N-methylglucamine), lysine and procaine; and internally formed salts. Salts having a non-physiologically acceptable anion or cation are within the scope of the invention as useful intermediates for the preparation of physiologically acceptable salts and/or for use in non-therapeutic, for example, in vitro, situations.

The subject invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as 2H, 3H, 11C, 13C, 14C, 15N, 17O, 18O, 31P, 32P, 35S, 18F, 36Cl, 123I and 125I.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as 3H, 14C are incorporated, are useful in drug and/or substrate tissue distribution assays. Tritiated, i.e., 3H, and carbon-14, i.e., 14C, isotopes are particularly preferred for their ease of preparation and detectability. 11C and 18F isotopes are particularly useful in PET (positron emission tomography), and 125I isotopes are particularly useful in SPECT (single photon emission computerized tomography), all useful in brain imaging. Further, substitution with heavier isotopes such as deuterium, i.e., 2H, can afford certain therapeutic advantages resulting from greater metabolic stability, for example increased in vivo half-life or reduced dosage requirements and, hence, may be preferred in some circumstances. Isotopically labelled compounds of formula I and following of this invention can generally be prepared by carrying out the procedures disclosed in the Schemes and/or in the Examples below, by substituting a readily available isotopically labelled reagent for a non-isotopically labelled reagent.

Certain compounds of formula (I) are capable of existing in stereoisomeric forms. It will be understood that the invention encompasses all geometric and optical isomers of these compounds and the mixtures thereof including racemates. * indicates a stereocentre of fixed but unknown stereochemistry i.e. either R or S stereochemistry. Diastereoisomer 1 or Diastereoisomer 2 means a compound of the invention or an intermediate thereof as a single diastereoisomer whose absolute configuration at one stereocentre was not determined. Enantiomer 1 or Enantiomer 2 means a compound of the invention or an intermediate thereof as a single enantiomer whose absolute configuration was not determined. Tautomers also form an aspect of the invention.

The present invention also provides a process for the preparation of a compound of formula (I) or a pharmaceutically acceptable salt thereof, which process comprises:

(a) reacting a compound of formula (II)

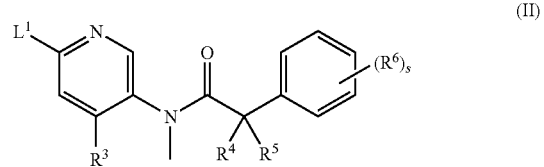

wherein $R^3$, $R^4$, $R^5$, $R^6$ and s are as defined above and $L^1$ represents a suitable leaving group such as a halogen atom (e.g. chlorine), with a compound of formula (III)

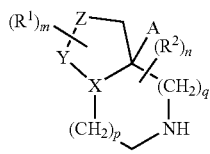

(III)

or an optionally protected derivative thereof, wherein $R^1$, $R^2$, m, n, p, q, X, Y, Z and A are as defined above; optionally thereafter followed by
(b) deprotecting a compound of formula (I) which is protected; and
(c) interconversion to other compounds of formula (I).

When p and q both represent 1, X represents a nitrogen atom, Y represents —C(=O)— and Z represents —C(H$_2$)—, process (a) may be performed in the presence of a suitable base such as potassium carbonate and a suitable solvent such as DMSO at a suitable temperature, such as 150-180° C.

When p and q both represent 1, X represents a nitrogen atom, Y represents —C(H$_2$)— and Z represents —C(H$_2$)—, process (a) may be performed in the presence of a suitable base such as potassium carbonate and a suitable solvent such as DMSO at a suitable temperature, such as 180° C. by microwave irradiation.

When p and q both represent 1, X represents a nitrogen atom, Y represents —C(H$_2$)— and Z represents —C(H$_2$)—, n represents 1, $R^2$ represents $C_{1-6}$ alkyl substituted by a hydroxyl group (e.g. —CH$_2$—OH), process (a) may be performed in the presence of a suitable base such as potassium tertbutoxide or caesium carbonate, a suitable solvent such as DMSO, a suitable catalyst such as bis(dibenzylideneacetone) palladium (0.05 eq) a suitable ligand such as dicyclohexylphosphino-2'-(N,N-dimethylamino)biphenyl (0.125 eq) at a suitable temperature, such as 120° C. by microwave irradiation; or in the alternative, process a) may be performed in the presence of a suitable base such as potassium carbonate and a suitable solvent such as DMSO at a suitable temperature, such as between 110 and 160° C.

Alternatively, when p and q both represent 1, X represents a nitrogen atom, Y represents —C(H$_2$)— and Z represents —C(H$_2$)—, n represents 1, $R^2$ represents $C_{1-6}$ alkyl substituted by a hydroxyl group (e.g. —CH$_2$—OH), process (a) may be performed on the derivative wherein the hydroxyl group of $R^2$ is protected as an O-TBDMS derivative, in a suitable solvent such as toluene, in the presence of a suitable catalyst such as bis-tri tert-butylphosphine palladium, a suitable base such as aqueous sodium hydroxide and a suitable phase transfer catalyst such as aqueous cetyltrimethylammonium chloride at a temperature such as 80-95° C. This process can be followed by removal of the TBDMS protecting group using tetrabutylammonium fluoride in a suitable solvent such as THF, or hydrochloric acid in a suitable solvent such as methanol.

Alternatively, when p and q both represent 1, X represents nitrogen, Y represents —(C(H$_2$)—)$_2$, Z represents an oxygen atom, —S(O$_2$)— or —N(R$^z$), n represents 1 and $R^2$ represents $C_{1-6}$ alkyl substituted by a hydroxyl group (e.g. —CH$_2$—OH) process (a) may be performed on the derivative wherein the hydroxyl group of $R^2$ is protected as an O-TBDMS derivative in a suitable solvent such as toluene, in the presence of a suitable catalyst such as bis-tri tert-butylphosphine palladium, a suitable base such as aqueous sodium hydroxide and a suitable phase transfer catalyst such as aqueous hexadecyltrimethylammonium chloride at a temperature such as 80-95° C. This process can be followed by removal of the TBDMS protecting group using tetrabutylammonium fluoride in a suitable solvent such as THF, or hydrochloric acid in a suitable solvent such as methanol.

Alternatively, when p and q both represent 1, X represents nitrogen, Y represents —(C(H$_2$)—)$_2$, Z represents an oxygen atom or —N(R$^z$), n represents 1 and $R^2$ represents $C_{1-6}$ alkyl or haloC$_{1-6}$ alkyl, process (a) may be performed in a suitable solvent such as toluene, in the presence of a suitable catalyst such as bis-tri tert-butylphosphine palladium, a suitable base such as aqueous sodium hydroxide and a suitable phase transfer catalyst such as aqueous hexadecyltrimethylammonium chloride at a temperature such as 80-95° C.

Alternatively, when p and q both represent 1, X represents nitrogen, Y represents —(C(H$_2$)—)$_2$, Z represents —N(R$^z$), n represents 0, m represents 1, and $R^1$ represents —CH$_2$—OH process (a) may be performed in the presence of a suitable base such as potassium carbonate and a suitable solvent such as DMSO at a suitable temperature, such as 150° C.

When p and q both represent 1, X represents a nitrogen atom, Y represents (—C(H$_2$)—)$_2$ and Z represents an oxygen atom or when p and q both represent 1, X represents a nitrogen atom, Y represents —S(O$_2$)— and Z represents —C(H$_2$)—, or when p represents 1, q represents 2, X represents a nitrogen atom, Y represents —C(H$_2$)— and Z represents —C(H$_2$)—, or when p represents 2, q represents 1, X represents a nitrogen atom, Y represents —C(H$_2$)—, Z represents —C(H$_2$)—, n represents 1 and $R^2$ represents =O, process (a) may typically be performed in the presence of a suitable base such as potassium carbonate, a suitable reaction promoter such as copper iodide in a suitable solvent such as DMSO at a suitable temperature such as 150° C. by microwave irradiation.

When p represents 1, q represents 1, X represents a nitrogen atom, Y represents —C(H$_2$)—, Z represents —C(H$_2$)—, n represents 1 and $R^2$ represents =O, process (a) may typically be performed in the presence of N,N'-dimethylethylenediamine, a suitable base such as caesium carbonate, a suitable reaction promoter such as copper iodide in a suitable solvent such as dioxane, at a suitable temperature such as 80-120° C.

When p and q both represent 1, m and n both represent 0, X represents a nitrogen atom, Y represents (—C(H$_2$)—)$_2$ and Z represents NH, process (a) may be performed in the presence of a suitable base such as potassium carbonate and a suitable solvent such as DMSO at a suitable temperature, such as 130° C.

In process (b), examples of protecting groups and the means for their removal can be found in T. W. Greene 'Protective Groups in Organic Synthesis' (J. Wiley and Sons, 1991). Suitable amine protecting groups include sulfonyl (e.g. tosyl), acyl (e.g. acetyl, 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid in dioxan or trifluoroacetic acid in dichloromethane) or reductively (e.g. hydrogenolysis of a benzyl group or reductive removal of a 2',2',2'-trichloroethoxycarbonyl group using zinc in acetic acid) as appropriate. Other suitable amine protecting groups include trifluoroacetyl (—COCF$_3$) which may be removed by base catalysed hydrolysis or a solid phase resin bound benzyl group, such as a Merrifield resin bound 2,6-dimethoxybenzyl group (Ellman linker), which may be removed by acid catalysed hydrolysis, for example with trifluoroacetic acid.

Process (c) may be performed using conventional interconversion procedures such as epimerisation, oxidation, reduction, alkylation, nucleophilic or electrophilic aromatic substitution, ester hydrolysis, amide bond formation or transition metal mediated coupling reactions. Examples of transition metal mediated coupling reactions useful as interconversion procedures include the following: Palladium catalysed coupling reactions between organic electrophiles, such as aryl halides, and organometallic reagents, for example boronic acids (Suzuki cross-coupling reactions); Palladium catalysed amination and amidation reactions between organic electrophiles, such as aryl halides, and nucleophiles, such as amines and amides; Copper catalysed amidation reactions between organic electrophiles (such as aryl halides) and nucleophiles such as amides; and Copper mediated coupling reactions between phenols and boronic acids.

For example, compounds of formula (I) wherein p and q both represent 1, m and n both represent 0, X represents a nitrogen atom, Y represents ($-C(H_2)-$)$_2$, Z represents $N(R^z)$, and $R^z$ represents $COR^7$ may be prepared from compounds of formula (I) wherein p and q both represent 1, m and n both represent 0, X represents a nitrogen atom, Y represents ($-C(H_2)-$)$_2$ and Z represents NH, via acylation using the appropriate acid chloride, in the presence of a suitable base, such as triethylamine, in a suitable solvent, such as dichloromethane. Similarly, compounds of formula (I) wherein p and q both represent 1, m and n both represent 0, X represents a nitrogen atom, Y represents ($-C(H_2)-$)$_2$, Z represents $N(R^z)$, and $R^z$ represents $SO_2R^7$ may be prepared from compounds of formula (I) wherein p and q both represent 1, m and n both represent 0, X represents a nitrogen atom, Y represents ($-C(H_2)-$)$_2$ and Z represents NH, via sulfonylation using the appropriate sulfonyl chloride in the presence of a suitable base, such as triethylamine, in a suitable solvent, such as dichloromethane. Compounds of formula (I) wherein p and q both represent 1, m and n both represent 0, X represents a nitrogen atom, Y represents ($-C(H_2)-$)$_2$, Z represents $N(R^z)$, and $R^z$ represents $C_{1-6}$alkyl, may be prepared from compounds of formula (I) wherein p and q both represent 1, m and n both represent 0, X represents a nitrogen atom, Y represents ($-C(H_2)-$)$_2$ and Z represents NH, via reductive alkylation employing the appropriate aldehyde in a suitable solvent, such as acetonitrile, followed by treatment with sodium triacetoxyborohydride. Compounds of formula (I) wherein p and q both represent 1, m represents 0, n represents 1, $R^2$ represents $C_{1-6}$alkyl$OC_{1-6}$alkyl, X represents a nitrogen atom, Y represents ($-C(H_2)-$)$_2$, Z represents $-S(O)_2-$, may be prepared from compounds of formula (I) wherein p and q both represent 1, m represents 0, n represents 1, $R^2$ represents $C_{1-6}$alkyl substituted by one hydroxyl group, X represents a nitrogen atom, Y represents ($-C(H_2)-$)$_2$, and Z represents $-S(O)_2$, via alkylation employing a suitable alkyl halide in the presence of a base, such as sodium hydride, in a suitable solvent such as THF.

Compounds of formula (II) may be prepared in accordance with the methodology provided in WO 2005/002577.

Compounds of formula (III) wherein p and q both represent 1, m and n both represent 0, X represents a nitrogen atom, Y represents $-S(O_2)-$ and Z represents $-C(H_2)-$ may be prepared in accordance with the following scheme:

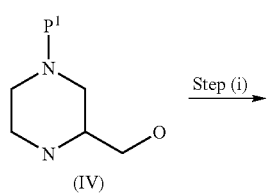

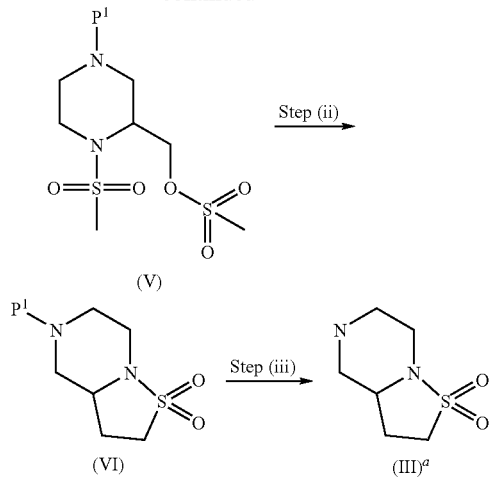

wherein $P^1$ represents a suitable protecting group such as Boc.

Step (i) typically comprises reacting a compound of formula (IV) with methanesulfonyl chloride in the presence of a suitable solvent such as dichloromethane and a suitable base such as triethylamine.

Step (ii) typically comprises reacting a compound of formula (V) with sec-butyllithium in the presence of a suitable solvent such as tetrahydrofuran.

Step (iii) typically comprises a deprotection reaction, for example, when $P^1$ represents Boc said deprotection reaction may typically comprise reacting a compound of formula (VI) with a mixture of dichloromethane and trifluoroacetic acid.

Compounds of formula (III) wherein p and q both represent 1, m represents 0, n represents 1, $R^2$ represents $=O$, X represents a nitrogen atom, Y represents $-C(H_2)-$ and Z represents $-C(H_2)-$ may be prepared in accordance with the following scheme:

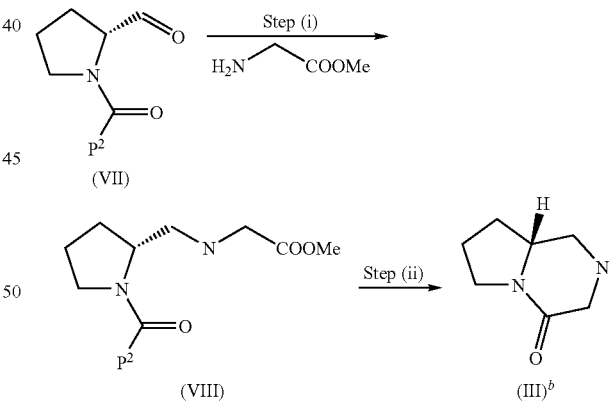

wherein $P^2$ represents a suitable protecting group such as t-butoxy.

Step (i) typically comprises reaction in the presence of sodium triacetoxyborohydride and a suitable acid, such as hydrochloric acid.

Step (ii) typically comprises a deprotection reaction, for example, when $P^2$ represents t-butoxy said deprotection reaction may typically comprise reacting a compound of formula (VIII) with a mixture of dichloromethane and trifluoroacetic acid, followed by purification on a SCX (Strong Cationic Exchange) silica cartridge and heating the basic methanolic fractions at a suitable temperature, such as 40° C.

Compounds of formula (III) wherein p and q both represent 1, m represents 0, n represents 1, $R^2$ represents =O, X represents a nitrogen atom, Y represents —C($H_2$)— and Z represents —C($H_2$)— may also be prepared in accordance with the following scheme:

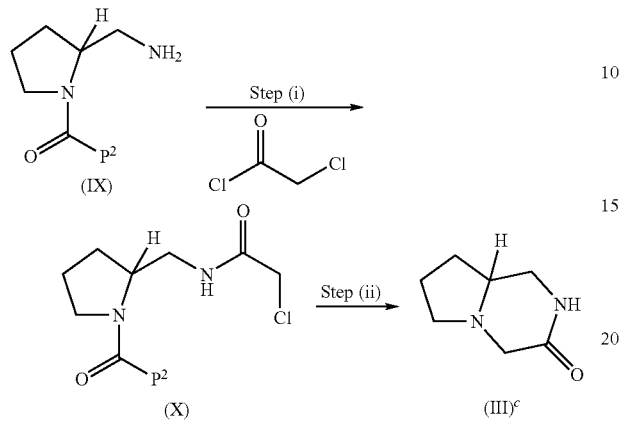

wherein $P^2$ represents a suitable protecting group such as t-butoxy.

Step (i) typically comprises reaction with chloroacetyl chloride in the presence of a suitable base such as N,N-diisopropylethylamine in dichloromethane.

Step (ii) typically comprises a deprotection reaction, for example, when $P^2$ represents t-butoxy said deprotection reaction may typically comprise reacting a compound of formula (X) with a mixture of dichloromethane and trifluoroacetic acid, followed by purification on a SCX (Strong Cationic Exchange) silica cartridge and heating of the resulting intermediate with a base such as sodium carbonate in acetonitrile at a suitable temperature, such as 60° C.

Compounds of formula (III) wherein p represents 1, q represents 2, m represents 0, n represents 1, $R^2$ represents =O, X represents a nitrogen atom, Y represents —C($H_2$)— and Z represents —C($H_2$)—, or wherein p represents 1, q represents 2, m and n both represent 0, X represents a nitrogen atom, Y represents —C($H_2$)— and Z represents —C($H_2$)— may be prepared in accordance with the following scheme:

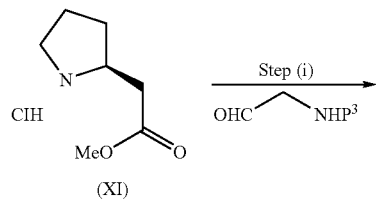

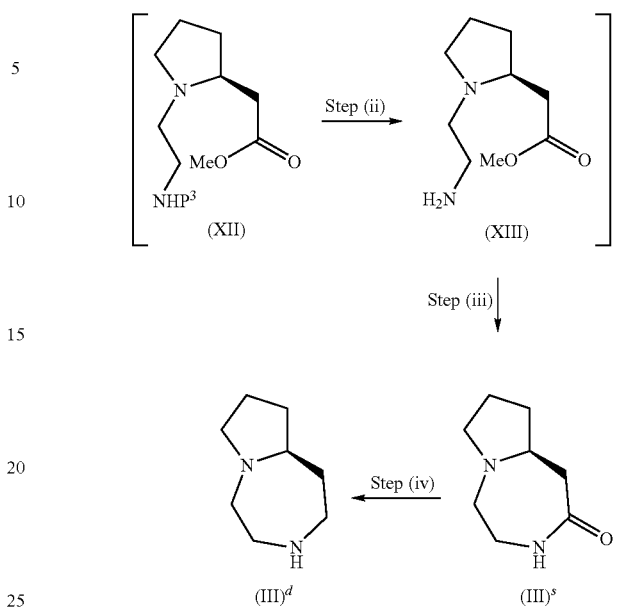

wherein $P^3$ represents a suitable protecting group such as Boc.

Step (i) typically comprises reaction with 1,1-dimethylethyl (2-oxoethyl)carbamate in the presence of sodium triacetoxyborohydride in a suitable solvent such as 1,2-dichloroethane.

Step (ii) typically comprises a deprotection reaction, for example, when $P^3$ represents Boc, said deprotection reaction may typically comprise reacting a compound of formula (XII) with trifluoroacetic acid in dichloromethane, and then purifying the product on a SCX (Strong Cationic Exchange) silica cartridge.

Step (iii) typically comprises heating the previous deprotected intermediate in a suitable solvent such as acetonitrile at a suitable temperature, such as 60° C.

Step (iv) typically comprises the use of borane tetrahydrofuran complex solution at a suitable temperature, such as 0° C., followed by treatment with an aqueous acid, such as hydrochloric acid, and purification on a SCX (Strong Cationic Exchange) silica cartridge.

Compounds of formula (III) wherein p and q both represent 1, m represents 0, n represents 1, $R^2$ represents =O, X represents a nitrogen atom, Y represents (—C($H_2$)—)$_2$ and Z represents an oxygen atom may be prepared in accordance with the following scheme:

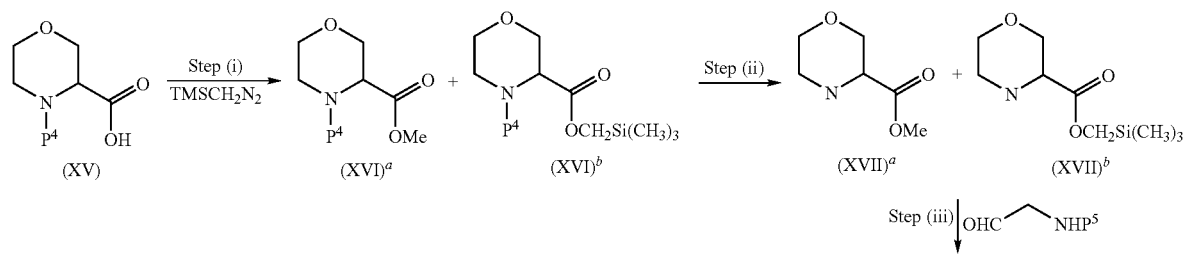

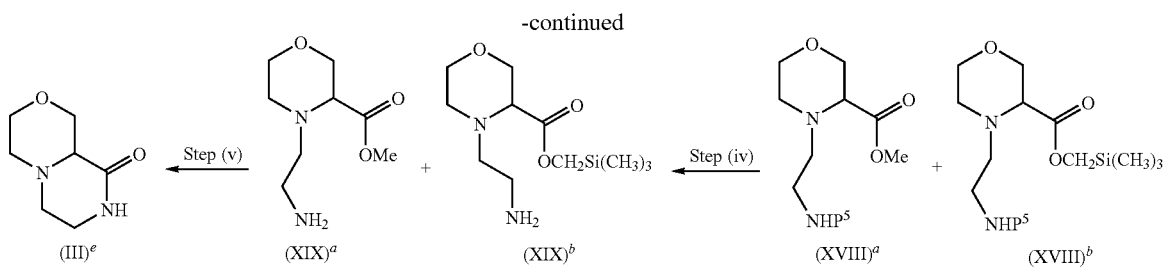

wherein P⁴ and P⁵ represent a suitable protecting group such as Boc.

Step (i) typically comprises reacting a compound of formula (XV) with a trimethylsilyl diazomethane solution at room temperature.

Step (ii) typically comprises a deprotection reaction, for example, when P⁴ represents Boc, said deprotection reaction may typically comprise reacting the compounds of formulae (XVI)$^a$ and (XVI)$^b$ with trifluoroacetic acid in dichloromethane.

Step (iii) typically comprises reacting the compounds of formulae (XVII)$^a$ and (XVII)$^b$ with N-boc-2-aminoacetaldehyde in the presence of sodium triacetoxyborohydride in a suitable solvent such as 1,2-dichloroethane.

Step (iv) typically comprises a deprotection reaction, for example, when P⁵ represents Boc, said deprotection reaction may typically comprise reacting the compounds of formulae (XVIII)$^a$ and (XVIII)$^b$ with trifluoroacetic acid in dichloromethane, followed by purification on a SCX (Strong Cationic Exchange) silica cartridge.

Step (v) typically comprises heating at a suitable temperature such as 40° C. the compounds of formulae (XIX)$^a$ and (XIX)$^b$ in a suitable solvent such as methanol.

Compounds of formula (III) wherein p and q both represent 1, m and n both represent 0, X represents a nitrogen atom, Y represents (—C(H₂)—)₂ and Z represents —S(O₂)— may be prepared in accordance with the following scheme:

wherein P⁶ and P⁷ represent a suitable protecting group such as Boc.

Step (i) typically comprises reacting a compound of formula (XX) with MCPBA (3-chloroperbenzoic acid) in dichloromethane.

Step (ii) typically comprises a deprotection reaction, for example, when P⁶ represents Boc, said deprotection reaction may typically comprise reacting the compound of formula (XXI) with trifluoroacetic acid in dichloromethane.

Step (iii) typically comprises reacting a compound of formula (XXII) with N-boc-2-aminoacetaldehyde in the presence of sodium triacetoxyborohydride in a suitable solvent such as 1,2-dichloroethane.

Step (iv) typically comprises a deprotection reaction, for example, when P⁷ represents Boc, said deprotection reaction may typically comprise reacting the compound of formula (XXIII) with trifluoroacetic acid in dichloromethane followed by purification on a SCX (Strong Cationic Exchange) silica cartridge.

Step (v) typically comprises reacting a compound of formula (XXIV) with borane tetrahydrofuran complex solution at a suitable temperature, such as 50° C., followed by treatment with an aqueous acid, such as hydrochloric acid, and purification on a SCX (Strong Cationic Exchange) silica cartridge.

Compounds of formula (III) wherein p and q both represent 1, n represents 0, X represents a nitrogen atom, Y represents

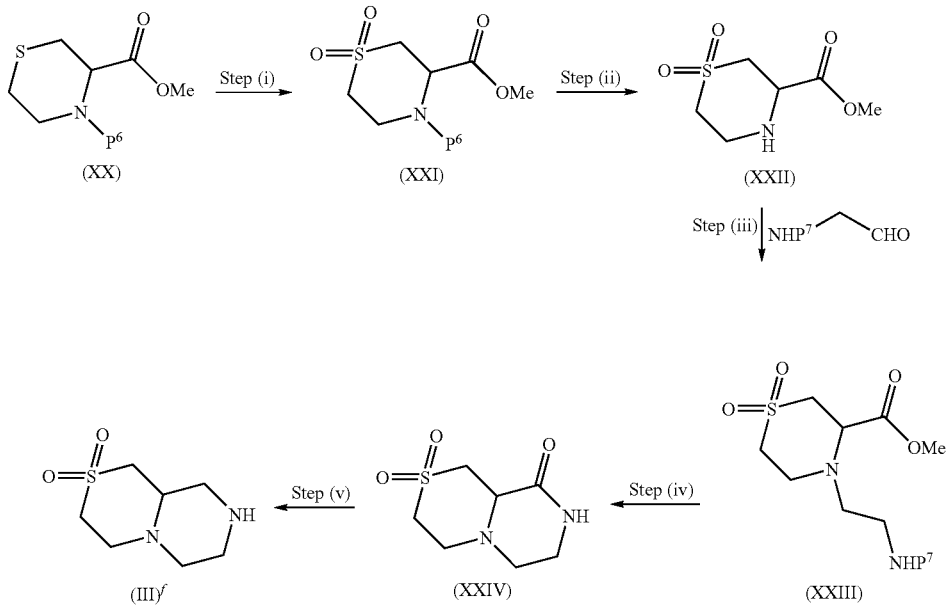

—C(H$_2$)—, Z represents —C(H$_2$)—, m represents 2 and both R$^1$ groups represent fluorine may be prepared in accordance with the following scheme:

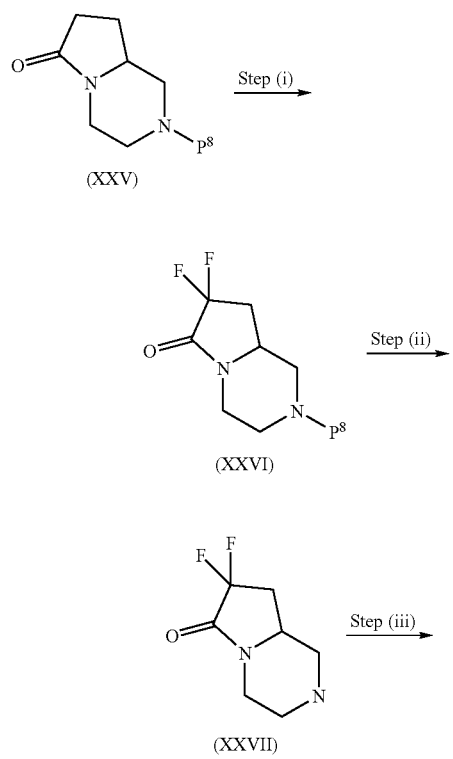

wherein P$^8$ represents a suitable protecting group such as t-butoxycarbonyl.

Step (i) typically comprises reaction with a suitable base such as lithium bis(dimethylethylsilyl)amide in a suitable solvent such as THF at a suitable temperature such as −78° C., followed by a suitable fluorinating agent such as N-fluorobenzenesulfonimide.

Step (ii) typically comprises a deprotection reaction, for example, when P$^8$ represents t-butoxy carbonyl said deprotection reaction may typically comprise reacting a compound of formula (XXVI) with a mixture of dichloromethane and trifluoroacetic acid, followed by purification on a SCX (Strong Cationic Exchange) silica cartridge.

Step (iii) typically comprises reacting a compound of formula (XXVII) with borane tetrahydrofuran complex solution at a suitable temperature, such as 50° C., followed by treatment with an aqueous acid, such as hydrochloric acid, and purification on a SCX (Strong Cationic Exchange) silica cartridge.

Compounds of formula (III) wherein p and q both represent 1, m represents 0, X represents a nitrogen atom, Y and Z both represent —C(H$_2$)—, n represents 1 and R$^2$ represents haloC$_{1-6}$ alkyl (e.g. fluoroethyl) may be prepared in accordance with the following scheme:

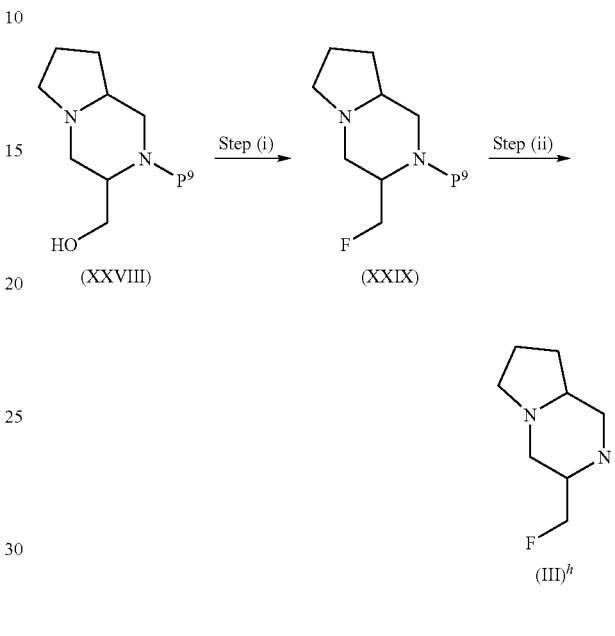

wherein P$^9$ represents a suitable protecting group such as benzyl.

Step (i) typically comprises reaction with a fluorinating agent such as DAST ((diethylamino)sulfur trifluoride) in a suitable solvent such as dichloromethane at a suitable temperature such as room temperature.

Step (ii) typically comprises a deprotection reaction, for example, when P$^9$ represents benzyl said deprotection reaction may typically comprise reacting a compound of formula (XXIX) with hydrogen in the presence of a suitable catalyst such as palladium on carbon, followed by purification on a SCX (Strong Cationic Exchange) silica cartridge.

Compounds of formula (I) wherein p represents 0, q represents 1, m represents 0, n represent 1, R$^2$ represents =O, X represents a nitrogen atom and Y and Z both represent —C(H$_2$)—, may be prepared in accordance with the following scheme:

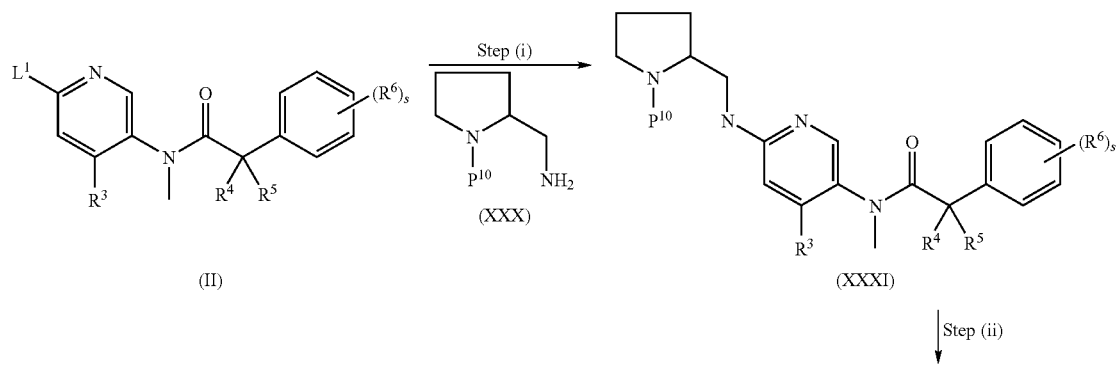

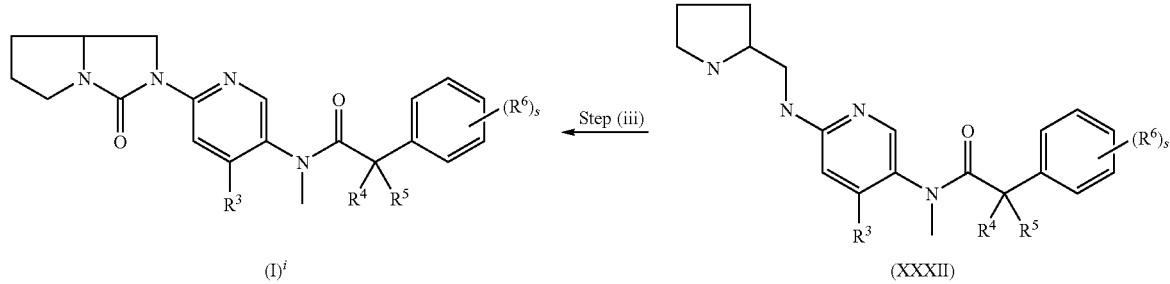

wherein $L^1$, $R^3$, $R^4$, $R^5$, $R^6$ and s are as defined above and $P^{10}$ represents a suitable leaving group such as Boc.

Step (i) typically comprises reaction with 1,1-dimethylethyl 2-(aminomethyl)-1-pyrrolidinecarboxylate in a suitable solvent such as DMSO in the presence of a suitable base such as potassium carbonate at a suitable temperature such as 180° C. under microwave irradiation.

Step (ii) typically comprises a deprotection reaction, for example, when $P^{10}$ represents Boc said deprotection reaction may typically comprise reacting a compound of formula (–) with a mixture of dichloromethane and trifluoroacetic acid, followed by purification on a SCX (Strong Cationic Exchange) silica cartridge Step (iii) typically comprises reacting a compound of formula (XXXI) with triphosgene in the presence of a suitable base such as triethylamine at a suitable temperature such as room temperature.

Compounds of formula (I) wherein p and q both represent 1, m represents 0, n represents 1, $R^2$ represents —$CONH_2$, $CO_2H$ or $CO_2Et$, X represents a nitrogen atom and Y and Z both represent —$C(H_2)$— may be prepared in accordance with the following scheme:

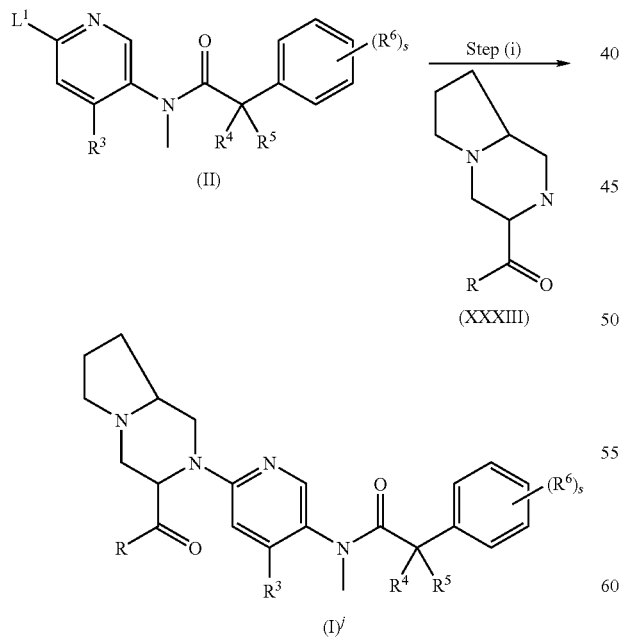

wherein $L^1$, $R^3$, $R^4$, $R^5$, $R^6$ and s are as defined above and R represents $NH_2$, OH or OEt.

Step (i) typically comprises reaction with octahydropyrrolo[1,2-a]pyrazine-3-carboxylic acid, amide or ester in a suitable in the presence of a suitable base such as triethylamine at a suitable temperature such as 150° C.

Compounds of formula (III) wherein p and q both represent 1, X represents nitrogen, Y represents $(C(H_2)-)_2$, Z represents an oxygen atom, m represents 0, n represents 1 and $R^2$ represents $C_{1-6}$ alkyl substituted by a hydroxyl group, protected as the TBDMS derivative, may be prepared according to the following scheme:

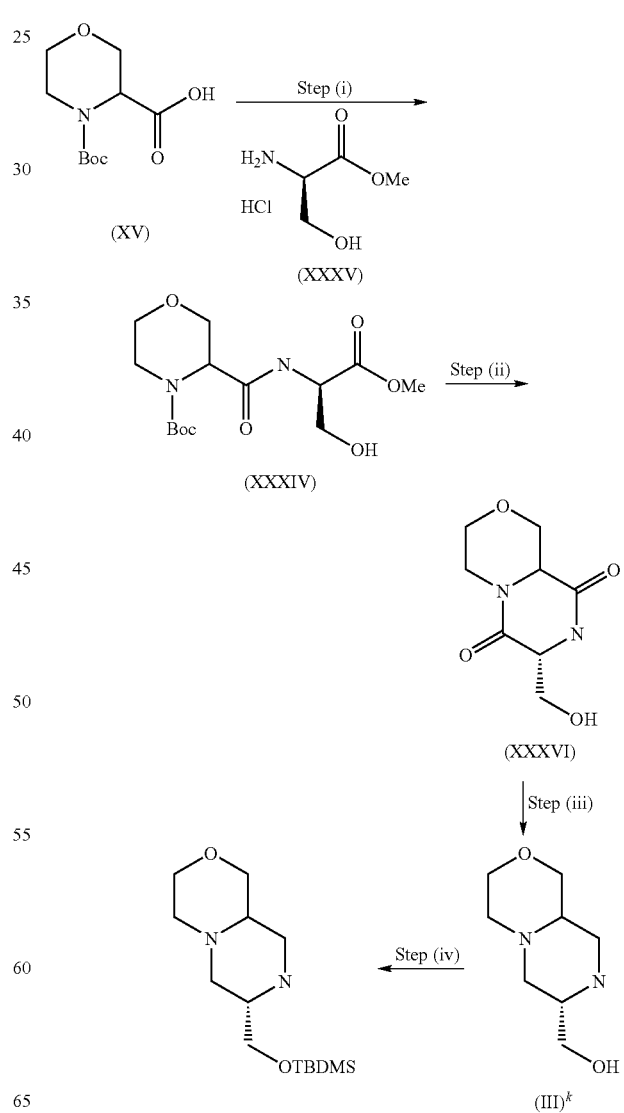

Step (i) typically comprises reaction of the carboxylic acid (XV) with the amine of formula (XXXV) in a suitable solvent, such as dichloromethane, in the presence of a suitable coupling reagent such as O-benzotriazol-1-yl-N,N,N',N'-tetramethyluronium tetrafluoroborate (TBTU) and a suitable base, such as diisopropylethylamine at a suitable temperature, such as room temperature.

Step (ii) typically comprises deprotection of (XXXIV) using a suitable reagent such as trifluoroacetic acid, followed by purification on a SCX (Strong Cationic Exchange) silica cartridge and subsequent cyclisation at a suitable temperature, such as 50° C.

Step (iii) typically comprises reduction of (XXXVI) using a suitable reducing agent such as $BH_3$-THF at a suitable temperature such as reflux.

Step (iv) typically comprises reaction of $(III)^k$ with tert-butyldimethylsilyl chloride (TBDMSCl) in a suitable solvent, such as dichloromethane, in the presence of a suitable base, such as triethylamine at a suitable temperature, such as room temperature.

Compounds of formula (III) wherein p and q both represent 1, X represents nitrogen, Y represents —$(C(H_2)—)_2$, Z represents an oxygen atom, m represents 0, n represents 1 and $R^2$ represents $C_{1-6}$ alkyl may be prepared in an analogous manner to that described above, starting from the appropriate amine in place of that of formula (XXXV) above.

Compounds of formula (III) wherein p and q both represent 1, X represents nitrogen, Y represents —$(C(H_2)—)_2$, Z represents —$N(R^z)$—, m represents 0, n represents 1 and $R^2$ represents $C_{1-6}$ alkyl substituted by a hydroxyl group, protected as the TBDMS derivative, may be prepared in an analogous manner to that described above when Z represents an oxygen atom, starting from the corresponding carboxylic acid wherein Z represents N—$P^{11}$ and $P^{11}$ represents a suitable protecting group such as Boc. Compounds of formula example after step (iv), via deprotonation employing a suitable base such as triethylamine followed by reaction of the resultant anion with $R^z$-$L^2$, wherein $L^2$ is a suitable leaving group such as halogen, under standard conditions, described in many standard organic chemistry texts, such as 'March's Advanced Organic Chemistry: Reactions, Mechanisms and Structure' by Michael B. Smith and Jerry March, fifth edition (Wiley, 2001), incorporated herein by reference.

Compounds of formula (III) wherein p and q both represent 1, X represents nitrogen, Y represents —$(C(H_2)—)_2$, Z represents —$N(R^z)$—, m represents 0, n represents 1 and $R^2$ represents $C_{1-6}$ alkyl, may be prepared in an analogous manner to that described above when Z represents an oxygen atom, starting from the corresponding carboxylic acid, wherein Z represents N—$P^{11}$ and $P^{11}$ represents a suitable protecting group such as Boc, and the appropriate amine in place of that of formula (XXXV) above. Compounds of formula (III) wherein $R^z$ is $C_{1-6}$ alkyl, $C_{1-6}$ alkoxy, —$COR^7$ or —$SO_2R^7$ may be derived from compounds of formula (III) when $R^z$ is hydrogen at any suitable point in the synthetic sequence via deprotonation employing a suitable base such as triethylamine followed by reaction of the resultant anion with $R^z$-$L^2$, wherein $L^2$ is a suitable leaving group such as halogen, under standard conditions, described in many standard organic chemistry texts, such as 'March's Advanced Organic Chemistry: Reactions, Mechanisms and Structure' by Michael B. Smith and Jerry March, fifth edition (Wiley, 2001), incorporated herein by reference.

Compounds of formula (III) wherein p and q both represent 1, X represents nitrogen, Y represents —$(C(H_2)—)_2$, Z represents —$S(O_2)$—, n represents 1 and $R^2$ represents $C_{1-6}$ alkyl substituted by a hydroxyl group, protected as the TBDMS derivative, may be prepared according to the following scheme:

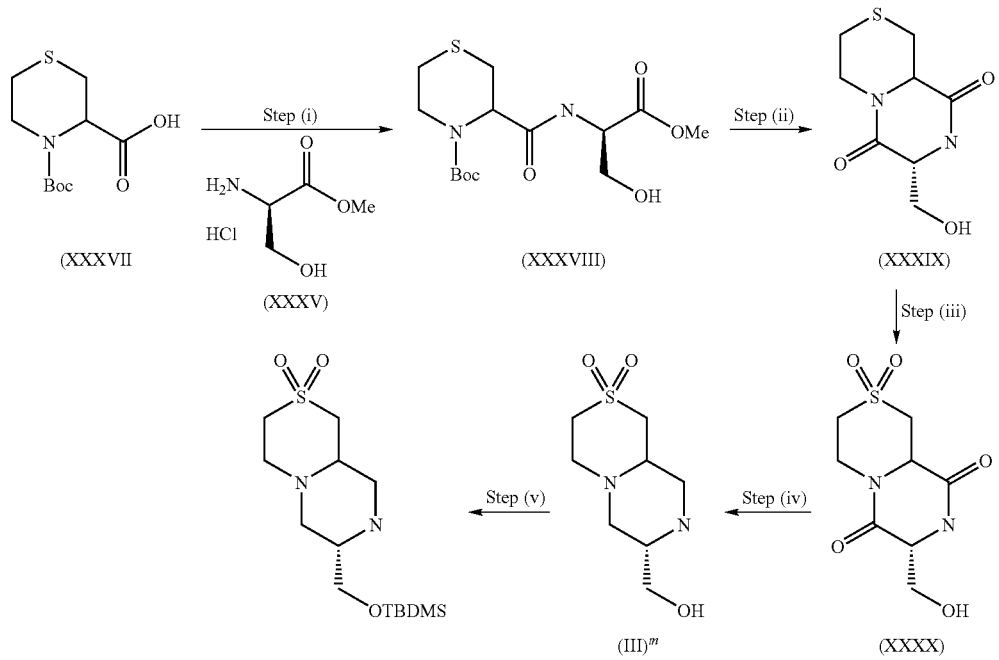

(III) wherein $R^z$ is $C_{1-6}$ alkyl, $C_{1-6}$ alkoxy, —$COR^7$ or $SO_2R^7$ may be derived from compounds of formula (III) when $R^z$ is hydrogen at any suitable point in the synthetic sequence, for Step (i) typically comprises reaction of the carboxylic acid (XXXVII) with the amine of formula (XXXV) in a suitable solvent, such as dichloromethane, in the presence of a suitable coupling reagent such as O-benzotriazol-1-yl-N,N,N'N'-tetramethyluronium tetrafluoroborate (TBTU) and a suitable base, such as diisopropylethylamine at a suitable temperature, such as room temperature.

Step (ii) typically comprises deprotection of (XXXVIII) using a suitable reagent such as trifluoroacetic acid, followed by purification on a SCX (Strong Cationic Exchange) silica cartridge and subsequent cyclisation under suitable conditions, such as microwave irradiation.

Step (iii) typically comprises oxidation of (XXXIX) employing a suitable oxidising agent such as 3-chloroperoxybenzoic acid (m-CPBA), in a suitable solvent such as dichloromethane, at a suitable temperature, such as room temperature.

Step (iv) typically comprises reduction of (XXXX) using a suitable reducing agent such as $BH_3$-THF at a suitable temperature such as reflux.

Step (v) typically comprises reaction of (III)'" with tert-butyldimethylsilyl chloride
(TBDMSCl) in a suitable solvent, such as dichloromethane, in the presence of a suitable base, such as triethylamine at a suitable temperature, such as room temperature.

Compounds of formula (III) wherein p and q both represent 1, m represents 0, n represents 1, $R^2$ represents =O, X represents a nitrogen atom, Y represents $(-C(H_2)-)_2$ and Z represents NH may be prepared in accordance with the following scheme:

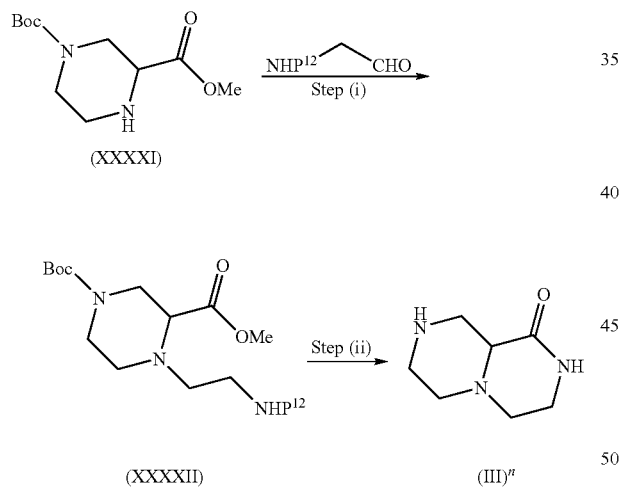

(XXXXI)

(XXXXII)              (III)"

wherein $P^{12}$ represents a suitable protecting group such as Boc.

Step (i) typically comprises reacting a compound of formula (XXXXI) with N-boc-2-aminoacetaldehyde in the presence of sodium triacetoxyborohydride in a suitable solvent such as 1,2-dichloroethane.

Step (ii) typically comprises a deprotection reaction, for example, when $P^{12}$ represents Boc, said deprotection reaction may typically comprise reacting the compound of formula (XXXXII) with trifluoroacetic acid in dichloromethane followed by purification on a SCX (Strong Cationic Exchange) silica cartridge, followed by cyclization.

Compounds of formula (III) wherein p and q both represent 1, m and n both represent 0, X represents a nitrogen atom, Y represents $(-C(H_2)-)_2$ and Z represents NH may be prepared from compounds of formula (III)" via reduction with a suitable reducing agent such as borane-THF, at elevated temperature, such as 75° C., in a suitable solvent, such as THF.

Compounds of formula (III) wherein p and q both represent 1, m represents 1, n represents 0, $R^1$ represents hydroxyl, X represents a nitrogen atom, Y represents $-C(H_2)$ and Z represents $-C(H_2)$ may be prepared in accordance with the following scheme:

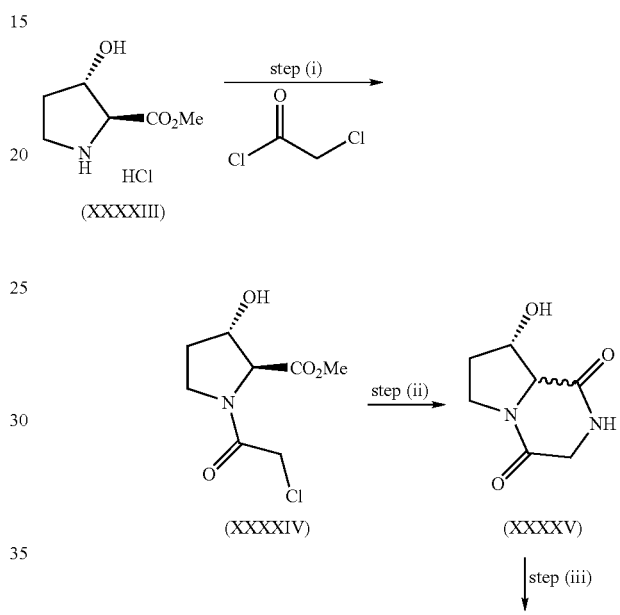

Step (i) typically comprises reacting a compound of formula (XXXXIII) with chloroacetyl chloride in the presence of a suitable base, such as triethylamine.

Step (ii) typically comprises treating (XXXXIV) with methanolic ammonia at room temperature.

Step (iii) typically comprises reduction of the diketopiperazine of formula (XXXXV) with a suitable reducing agent, such as $LiAlH_4$, in a suitable solvent, such as THF, at room temperature.

Compounds of formula (III) wherein p and q both represent 1, m and n both represent 0, X represents a nitrogen atom, Y represents $-C(H_2)$, Z represents $-C(H_2)$ and A represents $CH_2OH$ may be prepared in accordance with the following scheme:

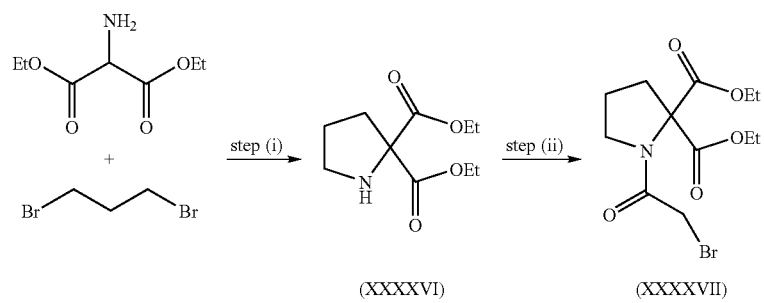

(XXXXVI) (XXXXVII)

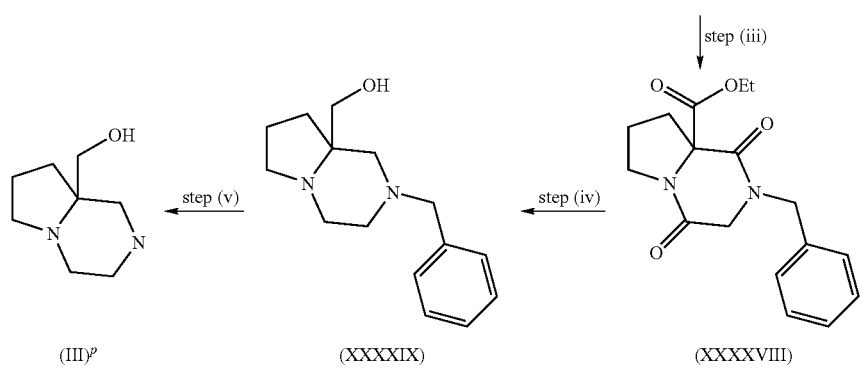

(III)^p  (XXXXIX)  (XXXXVIII)

Typically compounds of formula (XXXXVI) may be prepared by reacting diethyl aminomalonate with 1,3-dibromopropane in the presence of sodium ethoxide, in a suitable solvent such as ethanol, at a suitable elevated temperature, such as reflux (step (i)).

Typically step (ii) may be performed via reaction of (XXXXVI) with bromoacetyl bromide in the presence of a suitable base, such as potassium carbonate at 0° C.

Typically step (iii) involves treatment of (XXXXVII) with benzylamine in a suitable solvent, such as acetonitrile, at room temperature.

Typically step (iv) involves reduction of (XXXXVIII) using a suitable reducing agent such as LiAlH$_4$, in a suitable solvent such as THF at elevated temperature, such as reflux.

Typically step (v) involves deprotection under standard conditions, such as treating with ammonium formate and palladium on carbon, in a suitable solvent such as methanol, at an elevated temperature, such as reflux.

Compounds of formula (III) wherein p and q both represent 1, m represents 0, n represents 1, $R^2$ represents CH$_2$OH, X represents a nitrogen atom, Y represents —C(H$_2$), Z represents —C(H$_2$) may be prepared in accordance with the following scheme:

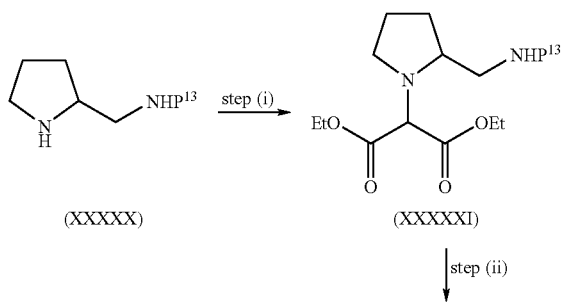

(XXXXX)  (XXXXXI)

-continued

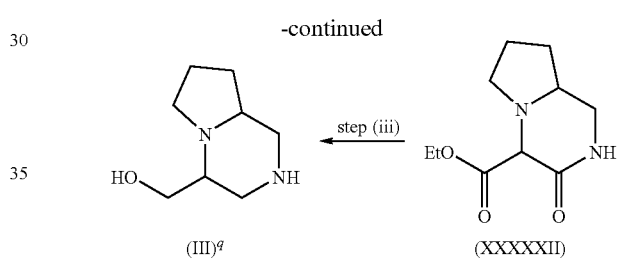

(III)^q  (XXXXXII)

wherein $P^{13}$ represents a suitable protecting group such as benzyloxycarbonyl.

Typically step (i) may be performed by reaction of a compound of formula (XXXXX) with diethylbromomalonate in the presence of a base, such as potassium carbonate, in a suitable solvent, such as acetonitrile at room temperature.

Typically step (ii) may be performed via deprotection of compound (XXXXXI) under standard conditions, such as under an atmosphere of hydrogen in the presence of palladium on carbon, followed by cyclization at an elevated temperature, such as 50° C.

Typically step (iii) may be performed via reduction of the ester moiety of (XXXXXII) employing a suitable reducing agent, such as LiBH$_4$ in a solvent such as THF, followed by reduction of the amide carbonyl moiety employing a suitable reagent, such as BH$_3$-THF, at elevated temperature, such as reflux.

Compounds of formula (III) wherein p and q both represent 1, X represents nitrogen, Y represents —(C(H$_2$)—)$_2$, Z represents an oxygen atom, m represents 0, n represents 1 and $R^2$ represents haloC$_{1-6}$ alkyl may be prepared from compounds of formula (III)$^k$ via protection of the secondary NH, for example using a benzyl group, followed by conversion of the hydroxyalkyl moiety to a haloC$_{1-6}$ alkyl moiety via treatment with a halogenating agent such as DAST [(diethylamino)sulphur trifluoride], followed by deprotection under standard conditions.

Compounds of formula (III) wherein p represents 1, q represents 1, m represents 0, n represents 1, R² represents =O, X represents a nitrogen atom, Y represents —C(H₂)— and Z represents —C(H₂)— may be prepared in accordance with the following scheme:

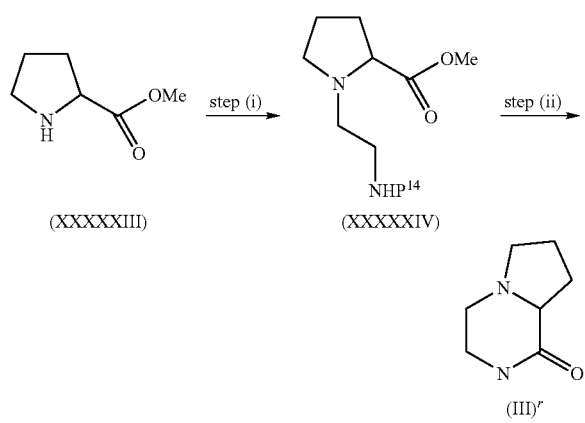

wherein P¹⁴ represents a suitable protecting group such as Boc.

Typically step (i) may be performed via reaction of (XXXXXIII) with 1,1-dimethylethyl (2-oxoethyl)carbamate in the presence of sodium triacetoxyborohydride in a suitable solvent such as 1,2-dichloroethane.

Step (ii) typically comprises a deprotection reaction, for example, when P represents Boc, said deprotection reaction may typically comprise reacting a compound of formula (XXXXXIV) with trifluoroacetic acid in dichloromethane, and then purifying the product on a SCX (Strong Cationic Exchange) silica cartridge. The deprotected intermediate may then be cyclized via heating at a suitable temperature, such as 40° C.

Compounds of formula (IV), (VII), (IX), (XI), (XV), (XX), (XXV), (XXVIII), (XXX), (XXXIII), (XXXV), (XXXVII), (XXXXI), (XXXXIII), (XXXXX) and (XXXXXIII) are either known or may be prepared in accordance with known procedures.

Compounds of formula (I) and their pharmaceutically acceptable salts have affinity for and are antagonists of the NK1 and NK3 receptor and thus may be of use in the treatment of psychotic disorders.

Within the context of the present invention, the terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

Within the context of the present invention, the term "psychotic disorder" includes:—

Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

Compounds of formula (I) and pharmaceutically acceptable salts and solvates thereof may also be of use in the treatment of the following disorders:—

Depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90):

Anxiety disorders including Panic Attack; Panic Disorder including Panic Disorder without Agoraphobia (300.01) and Panic Disorder with Agoraphobia (300.21); Agoraphobia; Agoraphobia Without History of Panic Disorder (300.22), Specific Phobia (300.29, formerly Simple Phobia) including the subtypes Animal Type, Natural Environment Type, Blood-Injection-Injury Type, Situational Type and Other Type), Social Phobia (Social Anxiety Disorder, 300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder, Separation Anxiety Disorder (309.21), Adjustment Disorders with Anxiety (309.24) and Anxiety Disorder Not Otherwise Specified (300.00):

Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); *Cannabis*-Related Disorders such as *Cannabis* Dependence (304.30), *Cannabis* Abuse (305.20), *Cannabis* Intoxication (292.89), *Cannabis* Intoxication Delirium, *Cannabis*-Induced Psychotic Disorder, *Cannabis*-Induced Anxiety Disorder and *Cannabis*-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide:

Sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition, in particular sleep disturbances associated with such diseases as neurological disorders, neuropathic pain, restless leg syndrome, heart and lung diseases; and Substance-Induced Sleep Disorder including the subtypes Insomnia Type, Hypersomnia Type, Parasomnia Type and Mixed Type; sleep apnea and jet-lag syndrome:

Eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; Binge Eating Disorder; and Eating Disorder Not Otherwise Specified (307.50):

Autism Spectrum Disorders including Autistic Disorder (299.00), Asperger's Disorder (299.80), Rett's Disorder (299.80), Childhood Disintegrative Disorder (299.10) and Pervasive Disorder Not Otherwise Specified (299.80, including Atypical Autism).

Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23):

Personality Disorders including the subtypes Paranoid Personality Disorder (301.0), Schizoid Personality Disorder (301.20), Schizotypal Personality Disorder (301.22), Antisocial Personality Disorder (301.7), Borderline Personality Disorder (301.83), Histrionic Personality Disorder (301.50), Narcissistic Personality Disorder (301.81), Avoidant Personality Disorder (301.82), Dependent Personality Disorder (301.6), Obsessive-Compulsive Personality Disorder (301.4) and Personality Disorder Not Otherwise Specified (301.9):

Enhancement of cognition including the treatment of cognition impairment in other diseases such as schizophrenia, bipolar disorder, depression, other psychiatric disorders and psychotic conditions associated with cognitive impairment, e.g. Alzheimer's disease: and Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).

All of the various forms and sub-forms of the disorders mentioned herein are contemplated as part of the present invention.

Thus the invention also provides a compound of formula (I) or a pharmaceutically acceptable salt thereof, for use as a therapeutic substance in the treatment or prophylaxis of the above psychotic disorders, in particular schizophrenia.

The invention further provides a method of treating schizophrenia which comprises administering to a host in need thereof an effective amount of a compound of formula (I) or a pharmaceutically acceptable salt thereof.

In another aspect, the invention provides the use of a compound of formula (I) or a pharmaceutically acceptable salt thereof in the manufacture of a medicament for use in the treatment of schizophrenia.

The invention further provides a method of treatment or prophylaxis of the above disorders, in mammals including humans, which comprises administering to the sufferer a therapeutically effective amount of a compound of formula (I) or a pharmaceutically acceptable salt thereof.

In another aspect, the invention provides the use of a compound of formula (I) or a pharmaceutically acceptable salt thereof in the manufacture of a medicament for use in the treatment of the above disorders.

When used in therapy, the compounds of formula (I) are usually formulated in a standard pharmaceutical composition. Such compositions can be prepared using standard procedures.

Thus, the present invention further provides a pharmaceutical composition for use in the treatment of the above disorders which comprises the compound of formula (I) or a pharmaceutically acceptable salt thereof and a pharmaceutically acceptable carrier.

The present invention further provides a pharmaceutical composition which comprises the compound of formula (I) or a pharmaceutically acceptable salt thereof and a pharmaceutically acceptable carrier.

The compounds of the invention may be used in combination with the following agents to treat or prevent psychotic disorders: i) antipsychotics; ii) drugs for extrapyramidal side effects, for example anticholinergics (such as benztropine, biperiden, procyclidine and trihexyphenidyl), antihistamines (such as diphenhydramine) and dopaminergics (such as amantadine); iii) antidepressants; iv) anxiolytics; and v) cognitive enhancers for example cholinesterase inhibitors (such as tacrine, donepezil, rivastigmine and galantamine).

The compounds of the invention may be used in combination with antidepressants to treat or prevent depression and mood disorders.

The compounds of the invention may be used in combination with the following agents to treat or prevent bipolar disease: i) mood stabilisers; ii) antipsychotics; and iii) antidepressants.

The compounds of the invention may be used in combination with the following agents to treat or prevent anxiety disorders: i) anxiolytics; and ii) antidepressants.

The compounds of the invention may be used in combination with the following agents to improve nicotine withdrawal and reduce nicotine craving: i) nicotine replacement therapy for example a sublingual formulation of nicotine beta-cyclodextrin and nicotine patches; and ii) bupropion.

The compounds of the invention may be used in combination with the following agents to improve alcohol withdrawal and reduce alcohol craving: i) NMDA receptor antagonists for example acamprosate; ii) GABA receptor agonists for example tetrabamate; and iii) Opioid receptor antagonists for example naltrexone.

The compounds of the invention may be used in combination with the following agents to improve opiate withdrawal and reduce opiate craving: i) opioid mu receptor agonist/opioid kappa receptor antagonist for example buprenorphine; ii) opioid receptor antagonists for example naltrexone; and iii) vasodilatory antihypertensives for example lofexidine.

The compounds of the invention may be used in combination with the following agents to treat or prevent sleeping disorders: i) benzodiazepines for example temazepam, lormetazepam, estazolam and triazolam; ii) non-benzodiazepine hypnotics for example zolpidem, zopiclone, zaleplon and indiplon; iii) barbiturates for example aprobarbital, butabarbital, pentobarbital, secobarbita and phenobarbital; iv) antidepressants; v) other sedative-hypnotics for example chloral hydrate and chlormethiazole.

The compounds of the invention may be used in combination with the following agents to treat anorexia: i) appetite stimulants for example cyproheptidine; ii) antidepressants; iii) antipsychotics; iv) zinc; and v) premenstral agents for example pyridoxine and progesterones.

The compounds of the invention may be used in combination with the following agents to treat or prevent bulimia: i) antidepressants; ii) opioid receptor antagonists; iii) antiemetics for example ondansetron; iv) testosterone receptor antagonists for example flutamide; v) mood stabilisers; vi) zinc; and vii) premenstral agents.

The compounds of the invention may be used in combination with the following agents to treat or prevent autism: i) antipsychotics; ii) antidepressants; iii) anxiolytics; and iv) stimulants for example methylphenidate, amphetamine formulations and pemoline.

The compounds of the invention may be used in combination with the following agents to treat or prevent ADHD: i) stimulants for example methylphenidate, amphetamine formulations and pemoline; and ii) non-stimulants for example norepinephrine reuptake inhibitors (such as atomoxetine), alpha 2 adrenoceptor agonists (such as clonidine), antidepressants, modafinil, and cholinesterase inhibitors (such as galantamine and donezepil).

The compounds of the invention may be used in combination with the following agents to treat personality disorders: i) antipsychotics; ii) antidepressants; iii) mood stabilisers; and iv) anxiolytics.

The compounds of the invention may be used in combination with the following agents to treat or prevent male sexual dysfunction: i) phosphodiesterase V inhibitors, for example vardenafil and sildenafil; ii) dopamine agonists/dopamine transport inhibitors for example apomorphine and buproprion; iii) alpha adrenoceptor antagonists for example phentolamine; iv) prostaglandin agonists for example alprostadil; v) testosterone agonists such as testosterone; vi) serotonin transport inhibitors for example serotonin reuptake inhibitors; v) noradrenaline transport inhibitors for example reboxetine and vii) 5-HT1A agonists, for example flibanserine.

The compounds of the invention may be used in combination with the same agents specified for male sexual dysfunction to treat or prevent female sexual dysfunction, and in addition an estrogen agonist such as estradiol.

Antipsychotic drugs include Typical Antipsychotics (for example chlorpromazine, thioridazine, mesoridazine, fluphenazine, perphenazine, prochlorperazine, trifluoperazine, thiothixine, haloperidol, molindone and loxapine); and Atypical Antipsychotics (for example clozapine, olanzapine, risperidone, quetiapine, aripirazole, ziprasidone and amisulpride).

Antidepressant drugs include serotonin reuptake inhibitors (such as citalopram, escitalopram, fluoxetine, paroxetine and sertraline); dual serotonin/noradrenaline reuptake inhibitors (such as venlafaxine, duloxetine and milnacipran); Noradrenaline reuptake inhibitors (such as reboxetine); tricyclic antidepressants (such as amitriptyline, clomipramine, imipramine, maprotiline, nortriptyline and trimipramine); monoamine oxidase inhibitors (such as isocarboxazide, moclobemide, phenelzine and tranylcypromine); and others (such as bupropion, mianserin, mirtazapine, nefazodone and trazodone).

Mood stabiliser drugs include lithium, sodium valproate/valproic acid/divalproex, carbamazepine, lamotrigine, gabapentin, topiramate and tiagabine.

Anxiolytics include benzodiazepines such as alprazolam and lorazepam.

The invention thus provides, in a further aspect, a combination comprising a compound of formula (I) or a pharmaceutically acceptable derivative thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Compositions suitable for transdermal administration include ointments, gels and patches.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months.

EXPERIMENTAL

The following Descriptions and Examples illustrate the preparation of compounds of the invention.

Proton Magnetic Resonance (NMR) spectra were recorded on Varian instruments at 300, 400 or 500 MHz, on Bruker instrument at 300 MHz, chemical shifts are reported in ppm (δ) using the residual solvent line as internal standard. Splitting patterns are designed as s, singlet; d, doublet; t, triplet; q, quartet; m, multiplet; b, broad. The NMR spectra were recorded at temperature ranging from 25 to 90° C.; when more than one conformer was detected the chemical shifts for the most abundant one is reported. Mass spectra (MS) were taken on a 4 II triple quadrupole Mass Spectrometer (Micromass UK) or on a Agilent MSD 1100 Mass Spectrometer, operating in ES (+) and ES (−) ionization mode or on a Agilent LC/MSD 1100 Mass Spectrometer, operating in ES (+) and ES (−) ionization mode coupled with HPLC instrument Agilent 1100 Series [LC/MS-ES (+): analysis performed on a Supelcosil ABZ +Plus (33×4.6 mm, 3 µm) (mobile phase: 100% [water+0.1% $HCO_2H$] for 1 min, then from 100% [water+0.1% $HCO_2H$] to 5% [water+0.1% $HCO_2H$] and 95% [$CH_3CN$] in 5 min, finally under these conditions for 2 min; T=40° C.; flux=1 ml/min; LC/MS-ES (−): analysis performed on a Supelcosil ABZ +Plus (33×4.6 mm, 3 µm) (mobile phase: 100% [water+0.05% $NH_3$] for 1 min, then from 100% [water+0.05% $NH_3$ to 5% [water+0.05% $NH_3$] and 95% [$CH_3CN$] in 5 min, finally under these conditions for 2 min; T=40° C.; flux=1 ml/min]. In the mass spectra only one peak in the molecular ion cluster is reported. Optical rotations were determined at 20° C. with a Jasco DIP360 instrument (I=10 cm, cell volume=1 ml, λ=589 nm) unless otherwise stated. Flash silica gel chromatography was carried out over silica gel 230-400 mesh supplied by Merck AG Darmstadt, Germany or over Varian Mega Be—Si pre-packed cartridges or over pre-packed Biotage silica cartridges.

HPLC (walk -up) refers to HPLC analysis performed on a Luna C18 (mobile phase: from 100% [water+0.05% TFA] to 5% [water+0.05% TFA] and 95% [$CH_3CN$+TFA 0.05%] in 8 min; T=40° C.; flux=1 ml/min).

UPLC refers to UPLC analysis performed on a UPLC Waters Acquity System. UPLC/MS refers to UPLC analysis performed on a UPLC Waters Acquity System coupled with an MS-Detector Waters ZQ (single quad.), ms range 100-1000. UPLC mobile phase data:

Gradient Before Sample Organiser

A=H$_2$O+0.1% formic acid
B=MeCN+0.075% formic acid

| Time (min) | Flow rate (mL/min) | % A | % B | curve |
|---|---|---|---|---|
| 1. Initial | 1.000 | 97.0 | 3.0 | init |
| 2. 0.10 | 1.000 | 94.0 | 6.0 | 6 |
| 3. 0.60 | 1.000 | 30.0 | 70.0 | 6 |
| 4. 1.10 | 1.000 | 1.0 | 99.0 | 6 |
| 5. 1.45 | 1.000 | 97.0 | 3.0 | 11 |

Gradient after Sample Organiser (Adjusted to Give Same Retention Times as Those Achieved Prior to Installation of the Sample Organiser)

| Time (min) | Flow Rate | % A | % B | Curve |
|---|---|---|---|---|
| 1. Initial | 1.000 | 97.0 | 3.0 | Initial |
| 2. 0.05 | 1.000 | 94.0 | 6.0 | 6 |
| 3. 0.57 | 1.000 | 30.0 | 70.0 | 6 |
| 4. 1.06 | 1.000 | 1.0 | 99.0 | 6 |
| 5. 1.45 | 1.000 | 97.0 | 3.0 | 11 | curve 6 = linear gradient
curve 11 = change at the end

Waters Acquity 2996 PDA

| | |
|---|---|
| Start Wavelength (nm) | 210.00 |
| End Wavelength (nm) | 350.00 |
| Resolution (nm) | 2.4 |
| Sampling Rate (spectra/s) | 20.000 |
| Filter Response | 0 |
| Exposure Time (ms) | Automatic |
| Interpolate 656 | Yes |
| Acquisition stop time (mins) | 1.50 |

T.l.c. refers to thin layer chromatography on 0.25 mm silica gel plates (60E-254 Merck) and visualized with UV light. For phase separations performed by using microfiltration devices: phase separation cartridge with polypropylene frit by Whatman or Alltech.

SCX means: SCX-cartridges (loading 0.75 mmol\g) by Varian.

Solutions were dried over anhydrous sodium sulphate.

The following abbreviations are used in the text: AcOEt=ethyl acetate, CH=cyclohexane, DCM=methylene chloride, DIPEA=N,N-diisopropylethylamine, DMF=N,N'-dimethylformamide, Et$_2$O=diethyl ether, EtOH=ethanol, MeOH=methanol, TEA=triethylamine, THF=tetrahydrofuran, TFA=trifluoroacetic acid, CH$_3$CN=acetonitrile, std=saturated.

\* indicates a stereocentre of fixed but unknown stereochemistry i.e. either R or S stereochemistry.

Diastereoisomer 1 or Diastereoisomer 2 means a compound of the invention or an intermediate thereof as a single diastereoisomer whose absolute configuration at one stereocentre was not determined.

Enantiomer 1 or Enantiomer 2 means a compound of the invention or an intermediate thereof as a single enantiomer whose absolute configuration was not determined.

Description 1

1-[3,5-Bis(trifluoromethyl)phenyl]-N-[6-chloro-4-(4-fluoro-2-methylphenyl)-3-pyridinyl]cyclopropan-ecarboxamide (D1)

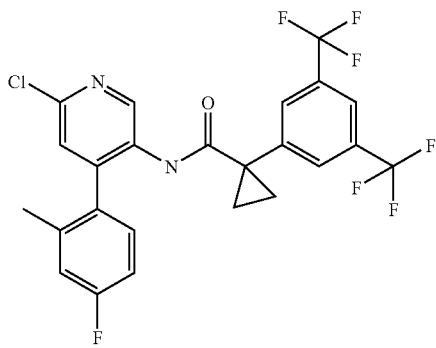

1-[3,5-Bis(trifluoromethyl)phenyl]cyclopropanecarboxylic acid (400 mg, 1.34 mmol) was dissolved in dichloromethane (6 ml), oxalyl chloride (0.24 ml, 2.68 mmol) was added, followed by dimethylformamide (5 µl, cat.). The solution was stirred for 3 hrs. The solution was concentrated under vacuum. The crude was dissolved in toluene, 6-chloro-4-(4-fluoro-2-methylphenyl)-3-pyridinamine (380 mg, 1.61 mmol) was added, followed by diisopropylethylamine (0.7 ml, 4 mmol) and dimethylaminopyridine (164 mg, 1.34 mmol), and the solution was warmed at 100° C. overnight. The solution was added to ethyl acetate, washed with saturated aqueous NH$_4$Cl and brine and concentrated under vacuum. The product was isolated by chromatography (silica, cyclohexane/EtOAc 90/10-80/20) as a white solid: 635 mg, 1.23 mmol, 92% yield.

MS (ES/+): m/z=517 [M+H]$^+$.
NMR (CDCl$_3$): δ (ppm): 9.61 (s, 1H); 7.79 (s, 1H); 7.68 (s, 2H); 7.01 (s, 1H); 6.81-6.68 (m, 3H); 6.43 (s, 1H); 1.88 (s, 3H); 1.60 (s, 4H)
Rf: 0.35 (cyclohexane/EtOAc 80/20)

Description 2

1-[3,5-Bis(trifluoromethyl)phenyl]-N-[6-chloro-4-(4-fluoro-2-methylphenyl)-3-pyridinyl]cyclopropan-ecarboxamide (D2)

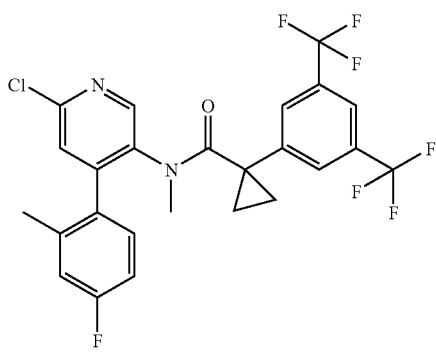

1-[3,5-Bis(trifluoromethyl)phenyl]-N-[6-chloro-4-(4-fluoro-2-methylphenyl)-3-pyridinyl]cyclopropanecarboxamide (D1; 310 mg, 0.6 mmol) was dissolved in dimethylformamide (6 ml). Methyl iodide (51.6 µl, 1.2 mmol) was added, followed by cesium carbonate (393 mg, 1.2 mmol), and the suspension was stirred overnight). The suspension was partitioned between ethyl acetate and saturated aqueous NH₄Cl, and the organic phase was washed with brine and concentrated under vacuum. The product was isolated by chromatography (silica, cyclohexane/EtOAc 90/10-80/20) as a white solid: 300 mg, 0.56 mmol, 93% yield.

MS (ES/+): m/z=531 [M+H]⁺.

NMR (DMSO-d₆): δ (ppm) 8.34 (s, 1H); 7.88 (s, 1H); 7.70 (s, 2H); 7.40 (s, 1H); 7.06 (dd, 1H), 6.90 (m, 2H); 2.97 (s, 3H), 2.11 (s, 3H), 1.21-1.37 (m, 4H)

Rf: 0.3 (cyclohexane/EtOAc 80/20)

Description 3

1,1-Dimethylethyl (2R)-2-({[2-(methyloxy)-2-oxoethyl]amino}methyl)-1-pyrrolidinecarboxylate (D3)

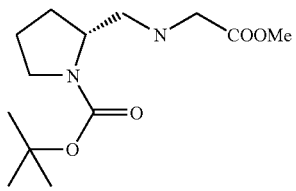

1,1-Dimethylethyl (2R)-2-formyl-1-pyrrolidinecarboxylate (1 g, 5.02 mmol) was dissolved in 20 ml of anhydrous dichloroethane. Methyl glycinate hydrochloride (0.95 g, 7.57 mmol) was added, followed after 30 min by sodium triacetoxyborohydride (2.2 g, 10.38 mmol). The reaction was stirred for 8 hrs at room temperature. The reaction mixture was diluted with methanol to obtain a clear solution, which was passed through a SCX cartridge. The product was eluted with 1 M methanolic ammonia. The product was isolated by chromatography (silica, dichloromethane/methanol 95/5) as colourless oil: 800 mg, 2.94 mmol.

MS (ES/+): m/z=273 [M+H]⁺.

NMR (CDCl₃): δ (ppm): 4.01 (bs, 1H); 3.75 (s, 3H); 3.53-3.30 (m, 4H); 2.94-2.53 (m, 3H); 1.92-1.76 (m, 3H); 1.48 (s, 9H).

Rf: 0.40 (cyclohexane/EtOAc 1/1)

Description 4

(8aR)-Hexahydropyrrolo[1,2-a]pyrazin-4(1H)-one (D4)

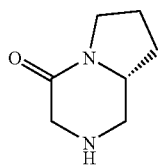

1,1-Dimethylethyl (2R)-2-({[2-(methyloxy)-2-oxoethyl]amino}methyl)-1-pyrrolidinecarboxylate (D3; 800 mg, 2.94 mmol) was dissolved in methylene chloride (10 ml) and treated with trifluoroacetic acid (2.5 ml) for 2 h. The reaction mixture was loaded as such on a SCX column and the non-basic compounds were washed away with methanol. The ninhydrine-positive fractions eluted with 1M methanolic ammonia were concentrated under vacuum at 40° C. for 30 min, isolating the title compound as a pale yellow oil: 410 mg, 2.92 mmol, 99% yield.

MS (ES/+): m/z=141 [M+H]⁺.

NMR (DMSO-d₆): δ (ppm) 3.69 (q, 1H), 3.62-3.45 (m, 3H), 3.45-3.35 (m, 2H), 2.52 (t, 1H), 2.13-1.96 (m, 2H), 1.85-1.72 (m, 1H), 1.50-1.37 (m, 1H).

Description 5

(9aS)-Hexahydro-1H-pyrrolo[1,2-d][1,4]diazepin-2(3H)-one (D5)

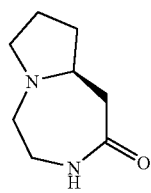

Methyl (2S)-2-pyrrolidinylacetate hydrochloride (1.08 g, 6.04 mmol) was dissolved in 20 ml of anhydrous dichloroethane. 1,1-Dimethylethyl (2-oxoethyl)carbamate (1.2 g, 7.25 mmol) was added, followed after 30 min by sodium triacetoxyborohydride (2.68 g, 12.08 mmol). The reaction was stirred for 3 hrs at room temperature. The reaction mixture was diluted with methanol to obtain a clear solution, which was passed through a SCX cartridge. The product was eluted with 1 M methanolic ammonia. The solvent was removed under reduced pressure leaving the product as a pale-yellow oil. The crude was dissolved in methylene chloride (20 ml) and treated with trifluoroacetic acid (5 ml) for 1 h. The reaction mixture was loaded as such on a SCX column and the non-basic compounds were washed away with methanol. The ninhydrine-positive fractions eluted with 1M methanolic ammonia were concentrated. The residue was redissolved in acetonitrile (20 ml) and stirred at 60° C. for 2 h. The solvent was removed under reduced pressure and the product purified by chromatography (silica, CH₂Cl₂/MeOH 95/5, Rf=0.4) and isolated as a white solid: 315 mg, 2.04 mmol, 34% yield.

MS (ES/+): 155 [M+H]⁺.

NMR (DMSO-d₆): δ (ppm) 7.50 (bs, 1H), 3.35-3.21 (m, 1H), 3.05-2.95 (m, 2H), 2.56-2.43 (m, 2H), 2.26-2.11 (m, 2H), 2.08-1.96 (m, 2H), 1.94-1.83 (m, 1H), 1.72-1.52 (m, 2H), 1.41-1.29 (m, 1H).

Rf: 0.2 (dichloromethane/methanol 95/5)

Description 6

(9aS)-Octahydro-1H-pyrrolo[1,2-d][1,4]diazepine (D6)

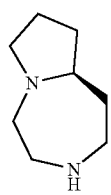

Borane tetrahydrofuran complex solution (1M, 17.8 ml) was added to a solution of (9aS)-hexahydro-1H-pyrrolo[1,2-d][1,4]diazepin-2(3H)-one (D5; 160 mg, 1.04 mmol) in tetrahydrofuran (5 ml) at 0° C. and the mixture is stirred at room temperature for 30 min. HCl water solution 6N, 20 ml) was added slowly at 0° C. and the solution was warmed at 60° C. for 4 hrs. The solvent was removed under reduced pressure and the product isolated by elution with 1M methanolic ammonia from a SCX cartridge (brownish oil, 120 mg, 83% yield).

MS (ES/+): m/z=141 [M+H]$^+$.

NMR (DMSO-d$_6$): δ (ppm): 7.55 (bs, 1H), 3.65-3.09 (m, 3H), 3.08-2.82 (m, 2H), 2.55-2.39 (m, 2H), 2.38-2.27 (m, 1H), 2.27-2.09 (m, 1H), 2.08-1.79 (m, 2H), 1.78-1.48 (m, 2H), 1.47-1.27 (m, 2H).

Description 7

Hexahydropyrazino[2,1-c][1,4]oxazin-9(6H)-one (D7)

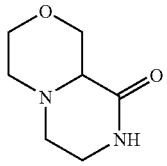

To a stirred suspension of N-Boc morpholine-2-carboxylic acid (991 mg, 4.29 mmol) in 10 ml of diethyl ether was added a solution of trimethylsilyldiazomethane (4 ml, 2M in hexanes, 8 mmol). After addition of methanol, the starting material went into solution and vigorous evolution of nitrogen was observed. After 1 h 30 min., a TLC analysis showed complete disappearance of the starting material. The solvent was removed under reduced pressure, leaving the crude product as an oil (1.3 g), which contained both the expected methyl ester and the trimethylsilylmethyl ester (MS (ES/+): m/z=268 [M+Na]$^+$, 146 [M-Boc]$^+$, 340 [M+TMS+Na]$^+$, 218 [M+TMS-Boc]$^+$. The crude was dissolved in methylene chloride (10 ml) and treated with trifluoroacetic acid (2.5 ml) for 1 h 30 min. The free amine compounds were obtained collecting the ninhydrine-positive fractions eluted with 1M methanolic ammonia from a SCX column. After solvent removal, the crude (pale yellow oil, 670 mg, MS (ES/+): m/z=146 [M+H]$^+$, 218 [M+TMS+H]$^+$) was reacted with N-boc-2-aminoacetaldehyde (756 mg, 4.75 mmol) in anhydrous 1,2-dichloroethane (13 ml) in the presence of sodium triacetoxyborohydride (1.8 g, 8.44 mmol) for 16 h under nitrogen atmosphere. The reaction was diluted with methanol and loaded on a SCX column. The fractions eluted with 1 M methanolic ammonia were concentrated. The residual crude oil (880 mg, MS (ES/+): m/z=289 [M+H]$^+$, 361 [M+TMS+H]$^+$) was dissolved in anhydrous methylene chloride (12 ml) and treated with 4 ml of TFA for 30 min at 0° C. and at room temperature for 3 h. The reaction mixture was loaded as such on a SCX column and the non-basic compounds were washed away with methanol. The ninhydrine-positive fractions eluted with 1M methanolic ammonia were concentrated. The residue was re-dissolved in methanol (20 ml) and stirred at 40° C. for 30 min. The solvent was removed under reduced pressure and the product purified by chromatography (silica, CH$_2$Cl$_2$/MeOH 95/5, Rf=0.25) and isolated as a white solid: obtained 395 mg (2.53 mmol).

MS (ES/+): 157 [M+H]$^+$, 179 [M+Na]$^+$.

NMR (CDCl$_3$): δ (ppm) 5.77 (br.s, 1H); 4.32 (dd, 1H); 3.87 (br.d, 1H); 3.70 (t, 1H); 3.63 (td, 1H); 3.53 (t, 1H); 3.30-3.22 (m, 2H); 2.98-2.86 (m, 1H); 2.80 (d, 1H); 2.63 (td, 1H); 2.49 (td, 1H).

Description 8

1,1-Dimethylethyl 4-(methylsulfonyl)-3-{[(methylsulfonyl) oxy]methyl}-1-piperazinecarboxylate (D8)

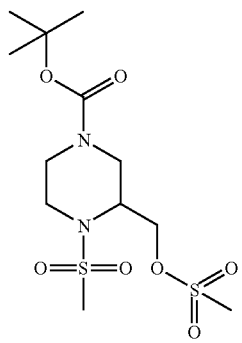

To a solution of 4.65 g of 1,1-dimethylethyl 3-(hydroxymethyl)-1-piperazinecarboxylate in 30 ml of dry dichloromethane, under N$_2$ at 0° C., 4.75 ml of TEA were added, followed by the slow addition of 3.7 ml of methanesulfonylchloride. After 12 h of vigorous stirring at room temperature, reaction mixture was taken up with dichloromethane/H$_2$O, phases separated and the aqueous one back extracted with dichloromethane. Collected organics were dried over Na$_2$SO$_4$ and concentrated under vacuum to give crude material that was purified by chromatography on silica eluting with dichloromethane/MeOH from 100/0 to 90/10 to give 4 g of pure title material as colourless foam.

Rf (DCM/MeOH 9/1)=0.8

$^1$H NMR (CDCl$_3$) δ: 1.48 (s, 9H), 2.96 (bs, 1H), 2.98 (s, 3H), 3.08 (s, 3H), 3.11 (bs, 1H), 3.2 (td, 1H), 3.71 (d, 1H), 4.02 (bs, 1H), 4.12 (bd, 1H), 4.23 (bm, 1H), 4.3 (bm, 1H), 4.4 (bm, 1H).

Description 9

1,1-Dimethylethyl hexahydro-5H-isothiazolo[2,3-a]pyrazine-5-carboxylate 1,1-dioxide (D9)

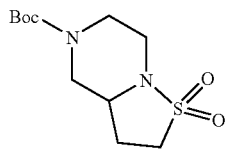

To a solution of 4 g of 1,1-dimethylethyl 4-(methylsulfonyl)-3-{[(methylsulfonyl) oxy]methyl}-1-piperazinecarboxylate (D8) in 50 ml of dry THF, under N$_2$ at −78° C., 11.8 ml of 1M secBu—Li in THF were added drop wise. After 30 min the mixture was allowed to slowly reach room temperature. After 2.5 h the reaction was quenched with 20 ml of water, taken up with 100 ml of ethyl acetate and the phases separated. The aqueous one was back extracted with ethyl acetate (2×50 ml). Collected organics were dried over Na₂SO₄ and concentrated under vacuum to give crude material that was purified by chromatography on silica eluting with cyclohexaney/EtOAc from 7/3/to 6/4 to get, after evaporation of the solvent, 2.438 g of pure title material as a white solid.

Rf (Cy/EA 1/1)=0.45

MS (ES/+): 177 (M-Boc), 221 (M-iBu), 299 (M+Na⁺).

¹H NMR (CDCl₃) δ: 1.49 (s, 9H), 2.02 (m, 1H), 2.42 (m, 1H), 2.67 (bs, 1H), 2.81 (td, 1H), 2.95 (bs, 1H), 3.15 (m, 1H), 3.18 (m, 1H), 3.27 (td, 1H), 3.41 (d, 1H), 4.17 (b, 1H), 4.32 (b, 1H).

Description 10

Hexahydro-2H-isothiazolo[2,3-a]pyrazine 1,1-dioxide (D10)

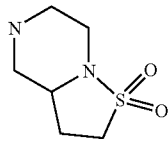

To a solution of 1.5 g of 1,1-dimethylethyl hexahydro-5H-isothiazolo[2,3-a]pyrazine-5-carboxylate 1,1-dioxide (D9) in 20 ml of dry dichloromethane, under N₂ at 0° C., 5 ml of TFA were added drop wise and left to react at 0° C. for 1 h. Then reaction mixture was evaporated under vacuum and crude solid material purified by 50 g SCX cartridge, loading with DCM/MeOH, washing with DCM/MeOH then only with MeOH; product was recovered eluting with 1M NH₃ in MeOH. Solvent evaporation gave 0.95 g of pure title compound as white solid.

MS (ES/+): 177 [M+H]⁺

¹H NMR (CDCl₃) δ: 1.97 (m, 1H), 2.36 (m, 1H), 2.59 (dd, 1H), 2.80 (dd, 2H), 3.1 (m. 3H), 3.19 (m, 2H), 3.41 (m, 1H).

Description 11

1,1-Dimethylethyl (2S)-2-{[(chloroacetyl)amino]methyl}-1-pyrrolidinecarboxylate (D11)

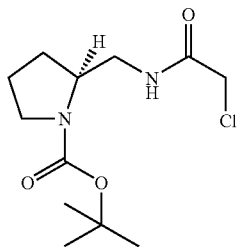

DIPEA (1.34 ml, 7.5 mmol) was added to a solution of 1,1-dimethylethyl (2S)-2-(aminomethyl)-1-pyrrolidinecarboxylate (1 g, 5 mmol) in 50 ml of DCM; then chloroacetyl chloride (0.418 ml, 5.25 mmol) was slowly added and the reaction mixture stirred 1 h before being worked up. DCM was added and the organic phase was washed with a saturated solution of ammonium chloride. The crude was purified by flash chromatography eluting with cyclohexane/ethyl acetate 8/2 affording 1.24 g of the target material.

MS (ES/+): 299-301 [M+Na]⁺

NMR (CDCl₃): δ (ppm) 8.43-8.28 (br.s., 1H), 4.03 (s, 2H), 3.76-3.65 (m, 1H), 3.31-3.14 (m, 3H), 3.15-3.04 (m, 1H), 1.89-1.60 (m, 4H), 1.40 (s, (H).

Description 12

(8aS)-Hexahydropyrrolo[1,2-a]pyrazin-3(4H)-one (D12)

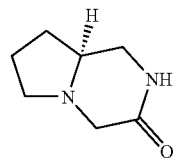

1,1-Dimethylethyl (2S)-2-{[(chloroacetyl)amino]methyl}-1-pyrrolidinecarboxylate (D11; 1.24, 4.5 mmol), was dissolved in 20 ml of DCM and treated with TFA (5 ml) at room temperature. After 1 h complete conversion into the desired material was observed and the reaction mixture was loaded onto a SCX cartridge. The product obtained after elution with 2M NH₃ in MeOH was then dissolved in acetonitrile (30 ml) and treated with sodium carbonate (1.43 g, 10.34 mmol). The reaction mixture was heated at 60° C. for 6 hours; the crude obtained after removal is purified by flash-chromatography eluting with dichloromethane/MeOH 95/5 affording 310 mg.

MS (ES/+): 141 [M+H]⁺

NMR (CDCl₃): δ (ppm) 7.80-7.59 (br. s, 1H), 3.38 (d, 1H), 3.28-3.17 (m, 1H), 2.99 (dt, 1H), 2.89 (t, 1H), 2.69 (d, 1H), 2.30-2.17 (m, 1H), 2.06-1.96 (m, 1H), 1.92-1.80 (m, 1H), 1.81-1.71 (m, 2H), 1.41-1.29 (m, 1H).

Description 13

1,1-Dimethylethyl (2R)-2-{[(chloroacetyl)amino]methyl}-1-pyrrolidinecarboxylate (D13)

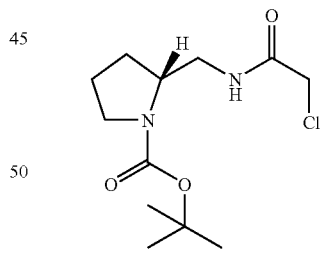

DIPEA (1.34 ml, 7.5 mmol) was added to a solution of 1,1-dimethylethyl (2R)-2-(aminomethyl)-1-pyrrolidinecarboxylate (1 g, 5 mmol) in 50 ml of DCM; then chloroacetyl chloride (0.418 ml, 5.25 mmol) was slowly added and the reaction mixture stirred 1 h before being worked up. DCM was added and the organic phase was washed with a saturated solution of ammonium chloride. The crude was purified by flash chromatography eluting with cyclohexane/ethyl acetate 8/2 affording 1.28 g of the target material.

MS (ES/+): 299-301 [M+Na]⁺

NMR (CDCl₃): δ (ppm) 8.43-8.28 (br.s., 1H), 4.03 (s, 2H), 3.76-3.65 (m, 1H), 3.31-3.14 (m, 3H), 3.15-3.04 (m, 1H), 1.89-1.60 (m, 4H), 1.40 (s, (H).

Description 14

(8aR)-Hexahydropyrrolo[1,2-a]pyrazin-3(4H)-one (D14)

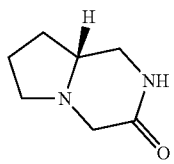

1,1-Dimethylethyl (2R)-2-{[(chloroacetyl)amino]methyl}-1-pyrrolidinecarboxylate (D13; 1.24 g, 4.5 mmol), was dissolved in 20 ml of DCM and treated with TFA (5 ml) at room temperature. After 1 h complete conversion into the desired material was observed and the reaction mixture was loaded onto a SCX cartridge. The product obtained after elution with 2M $NH_3$ in MeOH was then dissolved in acetonitrile (30 ml) and treated with sodium carbonate (1.43 g, 10.34 mmol). The reaction mixture was heated at 60° C. for 6 hours; the crude obtained after removal is purified by flash-chromatography eluting with dichloromethane/MeOH 95/5 affording 250 mg of the desired compound.

MS (ES/+): 141 [M+H]$^+$

NMR (CDCl$_3$): δ (ppm) 7.80-7.59 (br. s, 1H), 3.38 (d, 1H), 3.28-3.17 (m, 1H), 2.99 (dt, 1H), 2.89 (t, 1H), 2.69 (d, 1H), 2.30-2.17 (m, 1H), 2.06-1.96 (m, 1H), 1.92-1.80 (m, 1H), 1.81-1.71 (m, 2H), 1.41-1.29 (m, 1H).

Description 15

4-(1,1-Dimethylethyl) 3-methyl 3,4-thiomorpholinedicarboxylate 1,1-dioxide (D15)

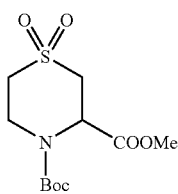

The preparation was done in two batches. In the first, to a stirred solution of 4-(1,1-dimethylethyl) 3-methyl 3,4-thiomorpholinedicarboxylate (WO 2001/040185) (936 mg, 3.59 mmol) in 3 ml of dichloromethane was added 55% 3-chloroperbenzoic acid (2.353 g, 7.50 mmol) at 0° C. while stirring under nitrogen atmosphere. The reaction was allowed to reach room temperature in 1 h. An additional aliquot of 55% 3-chloroperbenzoic acid (500 mg, 1.59 mmol) was added and the reaction stirred for 15 min. The reaction solution was washed with aqueous saturated sodium bicarbonate and sodium thiosulfate. The organic phase was dried over Na$_2$SO$_4$ and the solvent removed leaving the crude product, 1.01 g. In the second batch, the same procedure was applied to convert 714 mg (3.59 mmol) of 4-(1,1-dimethylethyl) 3-methyl 3,4-thiomorpholinedicarboxylate using 2.134 g of 55% 3-chloroperbenzoic acid (6.80 mmol) in 5 ml of dichloromethane, obtaining 1.23 g of crude product. The combined crude reactions were purified by chromatography (silica, cyclohexane/ethyl acetate 70/30) to give 1.73 g of the target compound.

MS (ES/+): 316 [M+Na]$^+$, 194 [M-Boc+1]$^+$.

NMR (DMSO-d$_6$): δ (ppm) 5.55-5.17 (ms, 1H); 4.41-4.21 (dt, 1H); 3.73-3.63 (m, 3H); 3.62-3.35 (m, 3H); 3.28-3.10 (td, 1H); 3.10-2.96 (dd, 1H); 1.56-1.24 (m, 9H).

Description 16

Methyl 3-thiomorpholinecarboxylate 1,1-dioxide (D16)

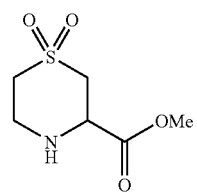

To a solution of 4-(1,1-dimethylethyl) 3-methyl 3,4-thiomorpholinedicarboxylate 1,1-dioxide (D15; 1.73 g, 5.9 mmol) in 17 ml of anhydrous methylene chloride, trifluoroacetic acid (4.2 ml) was added dropwise while stirring at 0° C. under nitrogen atmosphere. The solution was stirred for 3 h, while allowing it to reach room temperature. The solvent was removed under reduced pressure and the residue was loaded on a SCX cartridge, washed with methanol and eluted with 0.5M methanolic ammonia. The basic fractions were collected and the solvent removed leaving 1.08 g of the target product.

MS (ES/+): 194 [M+Na]$^+$.

NMR (DMSO-d$_6$): δ (ppm) 4.14-3.92 (br s, 1H); 3.84-3.70 (dd, 1H); 3.65-3.59 (s, 3H); 3.34-3.15 (m, 2H); 3.11-2.99 (m, 1H); 3.11-2.78 (m, 2H); 3.05-2.80 (m, 1H).

Description 17

Methyl 4-[2-({[(1,1-dimethylethyl)oxy]carbonyl}amino)ethyl]-3-thiomorpholinecarboxylate 1,1-dioxide (D17)

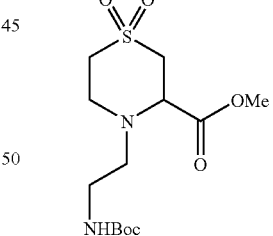

To a stirred solution of methyl 3-thiomorpholinecarboxylate 1,1-dioxide (D16; 1.08 g, 5.6 mmol) in 14 ml of anhydrous 1,2-dichloroethane was added N-boc-2-aminoacetaldehyde (1.1 g, 6.7 mmol) and acetic acid (0.316 ml, 5.6 mmol). After 30 min. sodium triacetoxyborohydride (1.78 g, 8.4 mmol) was added and the solution stirred at room temperature. Additional aliquots of N-boc-2-aminoacetaldehyde and sodium triacetoxyborohydride (1.0 g, 4.7 mmol) were added and the reaction continued overnight. The solvent was removed under reduced pressure and the residue was purified by SCX column, followed by chromatography (silica, cyclohexane:ethyl acetate 70:30 to 1:1) and again SCX, to give 295 mg of the target compound.

MS (ES/+): 337 [M+1]+.

NMR (DMSO-d$_6$): δ (ppm) 6.77-6.55 (m, 1H), 4.17-4.08 (m, 1H), 3.69-3.57 (s, 3H), 3.48-3.31 (m, 3H); 3.17-2.89 (m, 5H); 2.80-2.71 (m, 1H); 2.70-2.61 (m, 1H); 1.44-1.29 (s, 9H).

Description 18

Hexahydropyrazino[2,1-c][1,4]thiazin-9(6H)-one 2,2-dioxide (D18)

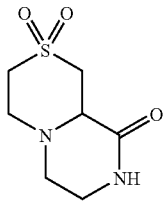

To a solution of methyl 4-[2-({[(1,1-dimethylethyl)oxy]carbonyl}amino)ethyl]-3-thiomorpholinecarboxylate 1,1-dioxide (D17; 295 mg, 0.88 mmol) in 3 ml of anhydrous dichloromethane was added 1 ml of trifluoroacetic acid and the resulting solution was stirred at room temperature under nitrogen for 1 h 30 min. The solvent was removed under reduced pressure and the residue loaded on a SCX column, washed with methanol and eluted with methanolic ammonia. The product was purified further by chromatography (silica cartridge, cyclohexane to ethyl acetate, then dichloromethane to dichloromethane:methanol 70:30) to give 165 mg of the target compound.

MS (ES/+): 205 [M+1]+.

NMR (DMSO-d$_6$): δ (ppm) 8.14-8.08 (br.s, 1H), 3.36-3.27 (m, 2H), 3.26-3.19 (m, 2H), 3.19-3.15 (m, 1H); 3.13-3.04 (m, 3H); 2.99-2.92 (dd, 1H); 2.68-2.61 (m, 1H); 2.59-2.52 (dt, 1H).

Description 19

Octahydropyrazino[2,1-c][1,4]thiazine 2,2-dioxide (D19)

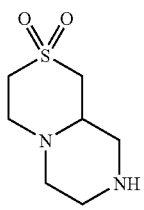

To a suspension of hexahydropyrazino[2,1-c][1,4]thiazin-9(6H)-one 2,2-dioxide (D18; 165 mg, 0.81 mmol) in 1 ml of anhydrous THF were added successive aliquots of a 1M solution of borane THF complex in THF (total 20.4 ml, 20.4 mmol) and the reaction stirred at room temperature and 50° C., until disappearance of the starting material. Hydrochloric acid (5M, 2 ml) was added to the solution and stirring was continued at 50° C. for 12 h. The solvent was removed under reduced pressure and the residue loaded on a SCX cartridge, washed with methanol and eluted with 0.5M methanolic ammonia. The basic fractions were collected and the solvent removed leaving 172 mg of the target product, partially contaminated by the starting material.

MS (ES/+): 191 [M+1]+.

NMR (CD3OD): δ (ppm) 3.50-2.70 (m, 13H); 2.42-2.33 (dt, 1H).

Description 20

(7R,9aR)-7-(hydroxymethyl)hexahydropyrazino[2,1-c][1,4]oxazine-6,9-dione and (7R,9aS)-7-(hydroxymethyl)hexahydropyrazino[2,1-c][1,4]oxazine-6,9-dione (D20)

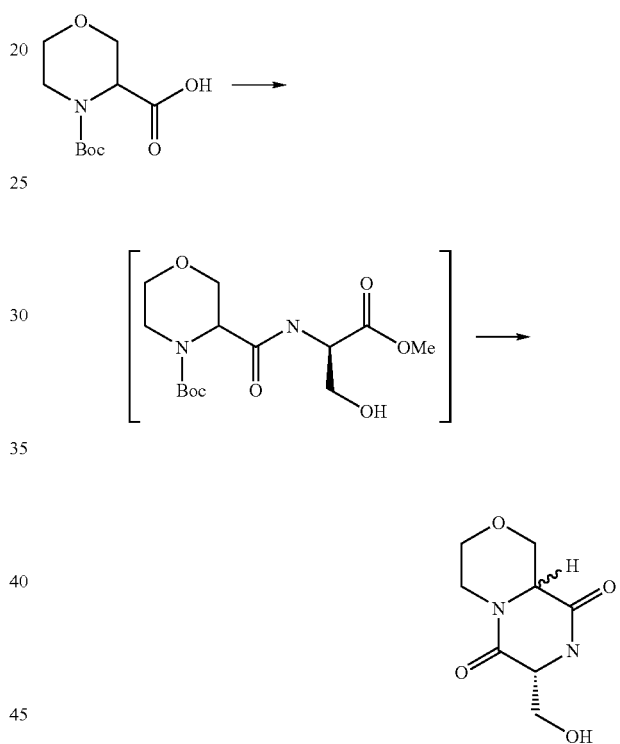

N-Boc morpholine 2-carboxylic acid (Astatech, 1.34 g, 5.80 mmol) was suspended in 15 mL of anhydrous dichloromethane, and treated with O-benzotriazol-1-yl-N,N,N'N'-tetramethyluronium tetrafluoroborate (TBTU) (2.4 g, 7.47 mmol) and diisopropylethylamine (2 mL, 11.47 mmol). The reaction was stirred for 40 min. A solution of D-serine methyl ester hydrochloride (1.8 g, 11.57 mmol) and diisopropylethylamine (2 mL, 11.47 mmol) in dichloromethane (15 mL) was prepared and added to the reaction mixture. The reaction was left stirring at room temperature overnight. UPLC-MS analysis showed conversion to the product. The reaction was diluted with dichloromethane (40 mL) and extracted with sat. NaHCO$_3$ (2×40 mL), dried (Na$_2$SO$_4$), and the solvent was removed. The crude was taken to the next step without further purification.

It was dissolved in 20 mL of dichloromethane and treated with 10 mL of TFA. The reaction was stirred at room temperature and checked by UPLC-MS after 4 h which showed disappearance of the peak for the starting material, replaced by a new one for the deprotected species (m/z=233, M+1). The reaction mixture was loaded as such on a SCX cartridge, washed with MeOH (4 column volumes) and eluted with 0.5 M methanolic ammonia. The basic, ninhydrin-positive fractions were collected and the solvent removed. The residue was dissolved in 10 mL of MeOH and stirred at 50° C. under $N_2$ overnight (16 h). The reaction was cooled down and a precipitate formed, which was collected by filtration to give 370 mg of the title compound. Direct MS: m/z=223 (M+Na).

$^1$H-NMR: consistent with structure. Approx. 60:40 ratio of diastereoisomers:

1H NMR (400 MHz, DMSO-$d_6$) δ ppm 8.17-8.26 (s, 0.4H) 8.09-8.17 (s, 0.6H) 5.17-5.25 (m, 0.4H) 5.09-5.17 (m, 0.6H) 3.95-4.29 (m, 3H) 3.60-3.91 (m, 3H) 3.33-3.55 (m, 2H) 2.61-2.90 (m, 0.6H) 1.03-1.15 (t, 0.4H).

Description 21

(7S,9aR)-octahydropyrazino[2,1-c][1,4]oxazin-7-ylmethanol and (7S,9aS)-octahydropyrazino[2,1-c][1,4]oxazin-7-ylmethanol (D21)

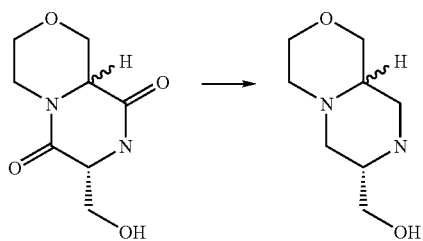

(7R,9aR)-7-(hydroxymethyl)hexahydropyrazino[2,1-c][1,4]oxazine-6,9-dione and (7R,9aS)-7-(hydroxymethyl)hexahydropyrazino[2,1-c][1,4]oxazine-6,9-dione (D20) (365 mg, 1.82 mmol) was treated with 20 mL of 1M $BH_3$-THF solution at room temperature. The suspension was refluxed for 17 h and checked by direct MS, showing complete conversion to the product. It was cooled to 0° C., and 2 mL of MeOH were added slowly, followed by 1 mL of conc. HCl (to pH <1). The solution was warmed to 70° C., stirred for 2 h and checked by direct MS. The solution was brought room temperature, the solvent removed and the residue taken up in MeOH (a few drops of water added), loaded on a SCX cartridge, washed with MeOH (5 column volumes) and eluted with 2M methanolic ammonia. The ninhydrin-positive fractions were collected and the solvent removed, leaving the title product as a clear oil. 320 mg. Direct MS: m/z=173 (M+1).

$^1$H-NMR consistent with structure, appears to be a mixture of diastereomers in approx. 60:40 ratio:

1H NMR (400 MHz, DMSO-$d_6$) δ ppm 4.50-4.59 (m, 0.4H) 4.38-4.48 (m, 0.6H) 2.96-3.74 (m, 6H) 2.57-2.78 (m, 2H) 2.34-2.41 (m, 2H) 1.86-2.28 (m, 4H) 1.69 (t, 1H)

Description 22 and Description 23

(7S,9aS)-7-({[(1,1-dimethylethyl)(dimethyl)silyl]oxy}methyl)octahydropyrazino[2,1-c][1,4]oxazine (D22) and (7S,9aR)-7-({[(1,1-dimethylethyl)(dimethyl)silyl]oxy}methyl)octahydropyrazino[2,1-c][1,4]oxazine (D23)

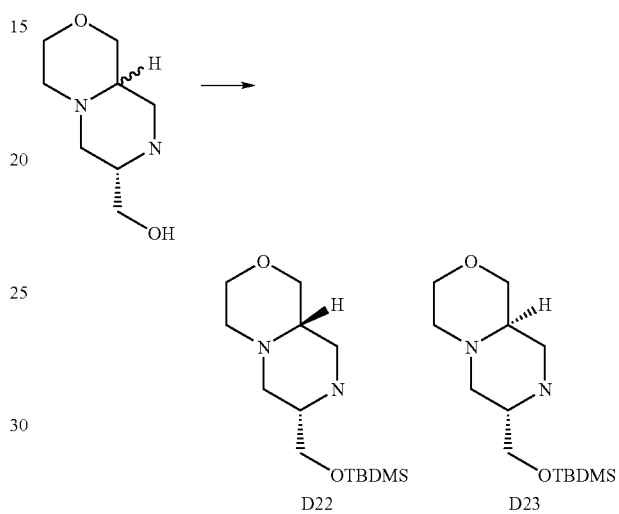

(7S,9aR)-octahydropyrazino[2,1-c][1,4]oxazin-7-ylmethanol and (7S,9aS)-octahydropyrazino[2,1-c][1,4]oxazin-7-ylmethanol (D21) (315 mg, 1.83 mmol) was dissolved in 10 mL of anhydrous dichloromethane and treated with $Et_3N$ (600 µL, 4.30 mmol) and TDBMSCl (590 mg, 3.91 mmol). The reaction was stirred overnight at room temperature (17 h). It was diluted with dichloromethane (30 mL) and extracted with sat. $NaHCO_3$ (2×20 mL). TLC analysis (EtOAc:MeOH 95:5) showed 2 main products. The organics were dried and the solvent removed leaving an oil, which was purified by flash chromatography (silica, EtOAc→EtOAc:MeOH 90:10). Isolated Two Products:

(7S,9aS)-7-({[(1,1-dimethylethyl)(dimethyl)silyl]oxy}methyl)octahydropyrazino[2,1-c][1,4]oxazine (D22), 253 mg. Direct MS: m/z=287 (M+1).

1H NMR (500 MHz, DMSO-$d_6$) δ ppm 3.72-3.79 (m, 1H) 3.62-3.71 (m, 2H) 3.37-3.56 (m, 2H) 2.99 (t, 1H) 2.65-2.78 (m, 1H) 2.55-2.64 (m, 1H) 2.25-2.44 (m, 3H) 2.02-2.16 (m, 2H) 1.90-2.02 (m, 1H) 0.75-0.90 (s, 9H)-0.05-0.05 (s, 6H).

Identified as the cis isomer based on ROESY cross peaks.

(7S,9aR)-7-({[(1,1-dimethylethyl)(dimethyl)silyl]oxy}methyl)octahydropyrazino[2,1-c][1,4]oxazine (D23), 202 mg. Direct MS: m/z=287 (M+1).

1H NMR (500 MHz, DMSO-$d_6$) δ ppm 3.68 (d, 1H) 3.56 (d, 1H) 3.47 (t, 1H) 3.36-3.43 (m, 2H) 3.02 (t, 1H) 2.68-2.76 (m, 1H) 2.62-2.68 (m, 2H) 2.50-2.56 (m, 1H) 2.22 (t, 1H) 2.11-2.18 (m, 1H) 1.90-1.97 (m, 1H) 1.70 (t, 1H) 0.84 (s, 9H) 0.02 (s, 6H)

Identified as the Trans Isomer Based on ROESY Cross Peaks.

Description 24

2-[3,5-bis(trifluoromethyl)phenyl]-N-[6-[(7S,9aS)-7-({[(1,1-dimethylethyl)(dimethyl)silyl]oxy}methyl)hexahydropyrazino[2,1-c][1,4]oxazin-8(1H)-yl]-4-(4-fluoro-2-methylphenyl)-3-pyridinyl]-N,2-dimethylpropanamide (D24)

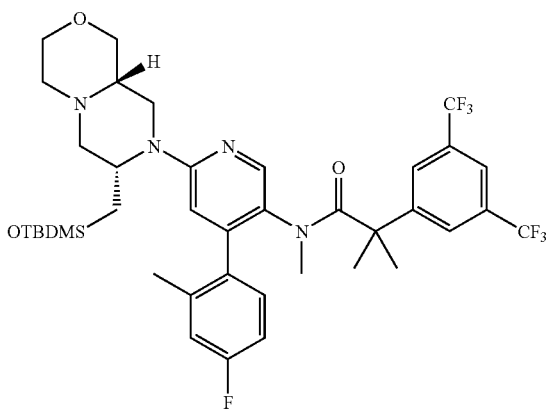

Method a):

(7S,9aS)-7-({[(1,1-dimethylethyl)(dimethyl)silyl]oxy}methyl)octahydropyrazino[2,1-c][1,4]oxazine (D22) (250 mg, 0.872 mmol) was dissolved in 3.8 mL of toluene. To this solution was added 2-[3,5-bis(trifluoromethyl)phenyl]-N-[6-chloro-4-(4-fluoro-2-methylphenyl)-3-pyridinyl]-N,2-dimethylpropanamide [WO 2005/002577] (460 mg, 0.863 mmol), followed by bis-tri-tert-butylphosphine palladium (110 mg, 0.215 mmol), hexadecyltrimethylammonium chloride (45 μL of a 25% aqueous solution) and sodium hydroxide solution (85 μL of a 50% aqueous solution, 0.85 mmol). The solution was degassed by 3 freeze-pump-thaw cycles, then stirred at 90° C. After 4 h, UPLC/MS analysis indicated conversion to the target compound and no trace of starting chloropyridine. The reaction was brought to room temperature, diluted with EtOAc (20 mL) and washed with sat. NaHCO₃ (10 mL). The organics were dried and the solvent evaporated. The product was isolated by flash chromatography (cyclohexane→cyclohexane:EtOAc 85:15) as a white solid: 390 mg (0.498 mmol, 57%) taken to the next step without further characterization.

Method b):

To a stirred solution of (7S,9aS)-7-({[(1,1-dimethylethyl)(dimethyl)silyl]oxy}methyl)octahydropyrazino[2,1-c][1,4]oxazine (D107, 5 g, 17.45 mmoles) in 150 ml of dry toluene at room temperature under nitrogen, a solution of 2-[3,5-bis(trifluoromethyl)phenyl]-N-[6-chloro-4-(4-fluoro-2-methylphenyl)-3-pyridinyl]-N,2-dimethylpropanamide (7.75 g, 14.54 mmoles) in 50 ml of dry toluene was added, followed by sodium tert-butoxide (2.1 g, 21.81 mmoles) and bis(tri-tert-butyl phosphine) palladium (1.49 g, 2.908 mmoles). The resulting mixture was heated at reflux temperature for 4 hours. The mixture was allowed to cool down to room temperature and filtered over Sterimat. The filtrate was then diluted with ethyl acetate (200 ml) and with sodium hydrogen carbonates (sat. solution, 200 ml). Phases were separated and the aqueous layer was extracted with ethyl acetate (2×150 ml). The combined organic extracts were dried (Na₂SO₄) and concentrated under vacuum to a residue, purified by silica gel chromatography eluting with 10 to 20% EtOAc/Cyclohexane to afford the title compound as pale yellow foam (10.1 g).

UPLC/MS: peak at Rt=1.26 min with m/z=783.35 [M+H]⁺
HPLC (walk-up): Rt=6.98 min (area %=98.22)

Description 25

2-[3,5-bis(trifluoromethyl)phenyl]-N-[6-[(7S,9aR)-7-({[(1,1-dimethylethyl)(dimethyl)silyl]oxy}methyl)hexahydropyrazino[2,1-c][1,4]oxazin-8(1H)-yl]-4-(4-fluoro-2-methylphenyl)-3-pyridinyl]-N,2-dimethylpropanamide (D25)

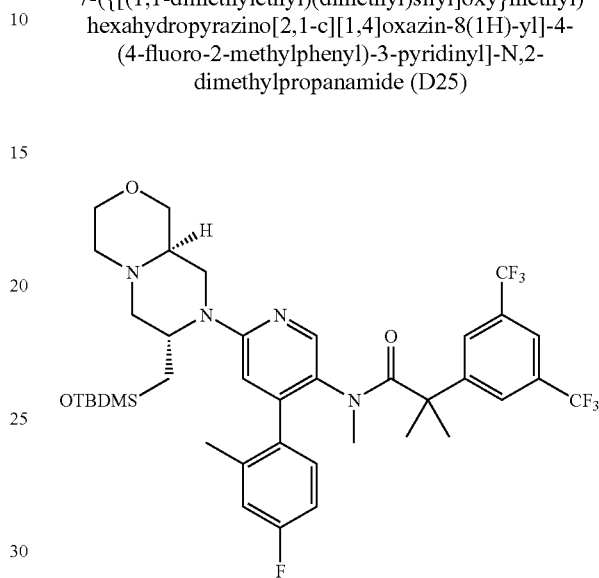

(7S,9aR)-7-({[(1,1-dimethylethyl)(dimethyl)silyl]oxy}methyl)octahydropyrazino[2,1-c][1,4]oxazine (D23) (140 mg, 0.489 mmol) was dissolved in 2 mL of toluene. To this solution was added the 2-chloropyridine (236 mg, 0.444 mmol), followed by bis-tri-tert-butylphosphine palladium (60 mg, 0.117 mmol), hexadecyltrimethylammonium chloride (25 μL of a 25% aqueous solution) and sodium hydroxide solution (45 μL of a 50% aqueous solution). The solution was degassed by 3 freeze-pump-thaw cycles, then stirred at 90° C. UPLC/MS analysis after 4 h indicated only partial conversion to the target compound. More catalyst (20 mg, 0.039 mmol) was added and the reaction left at the same temperature for additional 2 h, but no change was observed in the conversion to product. The solution was diluted with EtOAc (20 mL) and washed with sat. NaHCO₃ (10 mL). The product was isolated by flash chromatography (cyclohexane:EtOAc 94:6→50:50) as a pale yellow oil: 87 mg (0.111 mmol, 23%) taken to the next step without further characterization.

Description 26

1,1-dimethylethyl (3R or S)-({[(1R)-1-(hydroxymethyl)-2-(methyloxy)-2-oxoethyl]amino}carbonyl)-4-thiomorpholinecarboxylate (non-preferred name) (D26)—Diastereoisomer 1

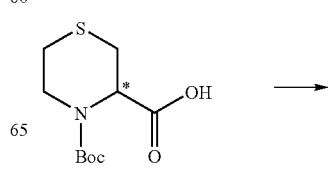

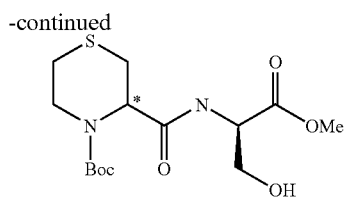

To a solution of N-Boc thiomorpholine carboxylic acid (0.488 g, 1.97 mmol) and O-benzotriazol-1-yl-N,N,N',N'-tetramethyluronium tetrafluoroborate (TBTU) (0.697 g, 2.17 mmol) in 5 mL of anhydrous dichloromethane was added DIPEA (0.7 mL, 3.95 mmol) and the solution was stirred for 30 mins. To a suspension of D-serine methyl ester hydrochloride (0.47 g, 3.95 mmol) in 5 mL of anhydrous dichloromethane was added DIPEA (0.7 mL, 3.95 mmol) and the resulting solution was stirred for 30 mins. Then the solution containing the serine free base was added to the reaction mixture and it was left stirring at room temperature overnight.

Water was added to the reaction mixture and the two phases were separated. The aqueous layer was extracted with dichloromethane (3×) and the combined organic phases were dried ($Na_2SO_4$) and evaporated to dryness. This crude material (1.66 g) was used in the next step without further purification.

UPLC-MS: m/z=349 (M+1) @ t=0.59 min

Description 27

(7R,9aR or 9aS)-7-(hydroxymethyl)hexahydropyrazino[2,1-c][1,4]thiazine-6,9-dione (D27)—Diastereoisomer 1 of (D32)

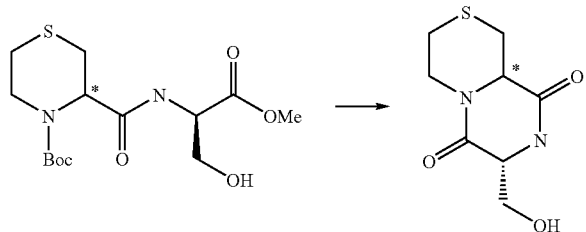

To a solution of the crude 1,1-dimethylethyl (3R or S)-({[(1R)-1-(hydroxymethyl)-2-(methyloxy)-2-oxoethyl]amino}carbonyl)-4-thiomorpholinecarboxylate (D26) in 20 mL of dichloromethane were added 10 mL of TFA. The reaction mixture was stirred at room temperature for 4 hrs. The solvent was removed under reduced pressure and the residue was taken up in MeOH and loaded on a SCX cartridge. The fractions eluted with methanolic ammonia were collected, the volume was reduced and the solution was stirred at 50° C. for 45 min. Then it was irradiated three times by microwave [set parameters: T=80° C., t=10 min (1×); T=120° C., t=5 min (2×)]. The solvent was removed and after 2 days the crude revealed the formation of a white solid. So it was precipitated with DME and it was collected by filtration, washing with $Et_2O$, to give the 1$^{st}$ batch of the title compound (120 mg, y=28% over 2 steps). The filtered solution was evaporated to dryness and the resulting crude, dissolved in DME, was irradiated two times by microwave (set parameters: T=130° C., t=30 min). After filtration, the 2$^{nd}$ batch of the title compound was isolated as a brownish solid (94 mg, y=22% over 2 steps). The filtered solution was treated in the same way as before and after four microwave irradiation [set parameters: T=130° C., t=30 min (3×) and t=90 min (1×)] the 3$^{rd}$ batch of the title compound was isolated as a brownish solid (50 mg, y=12% over 2 steps).

Since the purity of these three batches was very similar by NMR analysis, all of them were used in the next step.

UPLC/MS: m/z=217 (M+1) @ t=0.36 min

1H NMR (500 MHz, DMSO-$d_6$) δ ppm 8.03-8.27 (m, 1H) 5.04 (t, 1H) 4.73 (td, 1H) 3.98 (dd, 1H) 3.86-3.90 (m, 1H) 3.72-3.79 (m, 1H) 3.47-3.57 (m, 1H) 2.90 (d, 1H) 2.80 (d, 1H) 2.73-2.81 (m, 1H) 2.45-2.64 (m, 2H)

Description 28

(7R,9aR or 9aS)-7-(hydroxymethyl)hexahydropyrazino[2,1-c][1,4]thiazine-6,9-dione 2,2-dioxide (D28)—Diastereoisomer 1 of (D33)

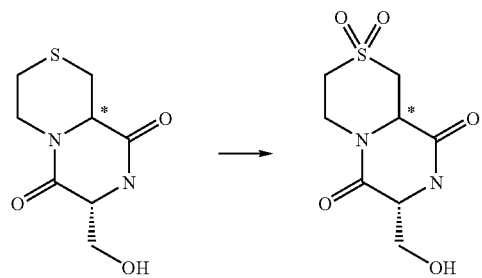

To a suspension of the starting (7R,9aR or 9aS)-7-(hydroxymethyl)hexahydropyrazino[2,1-c][1,4]thiazine-6,9-dione (D27) (264 mg, 1.22 mmol) in dichloromethane (5 mL) was added 77% m-CPBA (684 mg, 3.05 mmol) and the reaction mixture was stirred at room temperature for 3 hrs. The solvent was removed and the crude was purified by chromatography (silica, $CH_2Cl_2$:2M $NH_3$ in MeOH 95:5 to 8:2) to give the title compound as a white solid (200 mg, y=66%).

HPLC/MS: m/z=249 (M+1) @ t=0.21 min

1H NMR (500 MHz, DMSO-$d_6$) δ ppm 8.34-8.47 (m, 1H) 5.11 (t, 1H) 4.80 (dt, 1H) 4.25 (dd, 1H) 3.89-3.99 (m, 1H) 3.72-3.84 (m, 1H) 3.62 (t, 1H) 3.49-3.59 (m, 1H) 3.23-3.37 (m, 2H) 3.13 (t, 1H) 3.01 (t, 1H)

Description 29

[(7S,9aR or 9aS)-2,2-dioxidooctahydropyrazino[2,1-c][1,4]thiazin-7-yl]methanol (D29)—Diastereoisomer 1 of (D34)

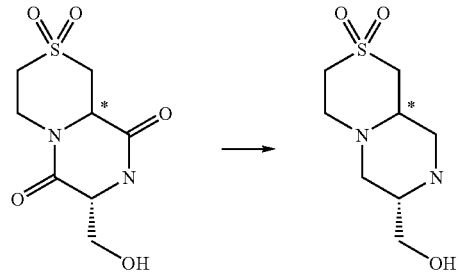

To a solution of the starting (7R,9aR or 9aS)-7-(hydroxymethyl)hexahydropyrazino[2,1-c][1,4]thiazine-6,9-dione 2,2-dioxide (D28) (200 mg, 0.806 mmol) was added 8.06 mL of 1M BH$_3$-THF solution at room temperature. The suspension was refluxed overnight and checked by UPLC/MS. HCl 6 N (ca. 8 mL) was added to the reaction mixture, cooled to 0° C., and the resulting solution was refluxed for 1 hr. The crude was purified by SCX cartridge to give the title compound as a white solid (182 mg, quantitative yield)

HPLC/MS: m/z=221 (M+1) @ t=0.17 min

1H NMR (400 MHz, DMSO-d$_6$) δ ppm 4.56 (t, 1H) 3.18-3.26 (m, 2H) 2.94-3.15 (m, 4H) 2.72-2.80 (m, 3H) 2.56-2.64 (m, 1H) 2.44-2.53 (m, 1H) 2.22-2.36 (m, 2H) 1.74 (t, 1H)

Description 30

(7S,9aR or 9aS)-7-({[(1,1-dimethylethyl)(dimethyl)silyl]oxy}methyl)octahydropyrazino[2,1-c][1,4]thiazine 2,2-dioxide (D30)—Diastereoisomer 1

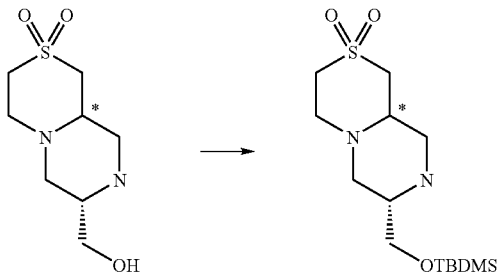

To a suspension of [(7S,9aR or 9aS)-2,2-dioxidooctahydropyrazino[2,1-c][1,4]thiazin-7-yl]methanol (D29) (182 mg, 0.818 mmol) in 8 mL of anhydrous dichloromethane was added Et$_3$N (340 μL, 2.45 mmol) and TDBMSCl (246 mg, 1.64 mmol). The reaction mixture was stirred for 15 hrs at room temperature and then the homogeneous solution was left still for 2 days.

Sat. NaHCO$_3$ was added and the two phases were separated. The aq. layer was extracted with dichloromethane (3×) and the combined organic phases were dried with Na$_2$SO$_4$ and evaporated to dryness. The crude was purified by chromatography (silica, CH$_2$Cl$_2$: MeOH1:0 to 99:1) to give the title compound as a white solid (150 mg, y=55%).

UPLC/MS: m/z=335 (M+1) @ t=0.54 min

1H NMR (400 MHz, DMSO-d$_6$) δ ppm 3.39-3.48 (m, 1H) 3.31-3.40 (m, 1H) 3.13 (t, 1H) 2.91-3.09 (m, 3H) 2.70-2.85 (m, 3H) 2.56-2.65 (m, 1H) 2.42-2.51 (m, 1H) 2.27-2.36 (m, 1H) 2.19-2.30 (m, 1H) 1.91-2.06 (m, 1H) 1.74 (t, 1H) 0.80 (s, 9H)-0.02 (s, 6H)

Description 31

2-[3,5-bis(trifluoromethyl)phenyl]-N-[6-[(7S,9aR or 9aS)-7-({[(1,1-dimethylethyl)(dimethyl)silyl]oxy}methyl)-2,2-dioxidohexahydropyrazino[2,1-c][1,4]thiazin-8(1H)-yl]-4-(4-fluoro-2-methylphenyl)-3-pyridinyl]-N,2-dimethylpropanamide (D31)—Diastereoisomer 1

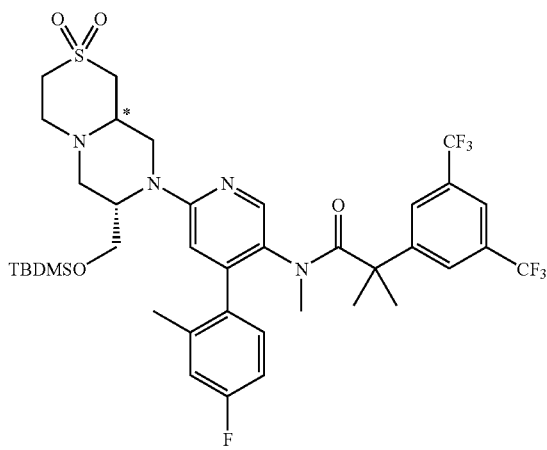

To a solution of (7S,9aR or 9aS)-7-({[(1,1-dimethylethyl)(dimethyl)silyl]oxy}methyl)octahydropyrazino[2,1-c][1,4]thiazine 2,2-dioxide (D30) (147 mg, 0.44 mmol) and 2-[3,5-bis(trifluoromethyl)phenyl]-N-[6-chloro-4-(4-fluoro-2-methylphenyl)-3-pyridinyl]-N,2-dimethylpropanamide [WO 2005/002577] (180 mg, 0.338 mmol) in 3 mL of anhydrous toluene were added bis-tri-tert-butylphosphine palladium (34.5 mg, 0.068 mmol), hexadecyltrimethylammonium chloride (21.6 μL of a 25% aqueous solution) and sodium hydroxide solution (40 μL of a 50% aqueous solution). The reaction mixture was degassed by freeze-pump-thaw cycles and then it was stirred at 90° C. for 12 hrs. During this reaction time further amounts of the palladium catalyst (17+17 mg) were added. EtOAc and NaHCO$_3$ were added to the reaction mixture and the two phases were separated. The aqueous phase was extracted with EtOAc (3×) and the combined organic phases were dried (Na$_2$SO$_4$) and evaporated to dryness. The crude was purified by chromatography (silica, cyclohexane: EtOAc 9:1 to 75:25) to give the title compound as a white solid (172 mg, yield=47%).

MS: m/z=831 (M+1) and 416 (M/2+1)

HPLC/MS: m/z=831 (M+1) and 416 (M/2+1) @ t=1.22 min

1H NMR (500 MHz, DMSO-d$_6$) δ ppm 8.01 (s, 1H) 7.86 (s, 1H) 7.60-7.82 (m, 2H) 7.16 (d, 1H) 6.98-7.14 (m, 2H) 6.67 (s, 1H) 4.36-4.54 (m, 1H) 3.91-4.12 (m, 1H) 3.80-3.94 (m, 1H) 3.58-3.73 (m, 1H) 3.08-3.47 (m, 5H) 2.87-3.00 (m, 1H) 2.72-2.82 (m, 1H) 2.51 (s, 3H) 2.42-2.67 (m, 3H) 2.19 (s, 3H) 1.49 (s, 3H) 1.34 (s, 3H) 0.78 (s, 9H) 0.00 (s, 6H)

Description 32

(7R,9aR)-7-(hydroxymethyl)hexahydropyrazino[2,1-c][1,4]thiazine-6,9-dione and (7R,9aS)-7-(hydroxymethyl)hexahydropyrazino[2,1-c][1,4]thiazine-6,9-dione (D32)

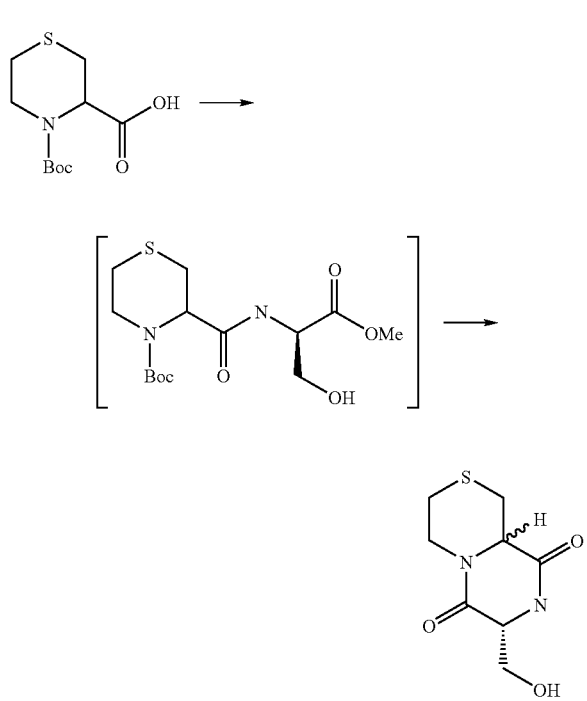

To a solution of N-Boc thiomorpholine carboxylic acid (0.803 g, 2.96 mmol) in 16 mL of anhydrous dichloromethane was added O-benzotriazol-1-yl-N,N,N'/N'-tetramethyluronium tetrafluoroborate (TBTU) (1.03 g, 3.22 mmol) and the solution was stirred for 45 min. A solution of D-serine methyl ester hydrochloride (0.911 g, 5.85 mmol) and Huenig's base (1.02 mL, 5.85 mmol) in dichloromethane was prepared and added to the reaction mixture. The reaction was left stirring at room temperature overnight. UPLC-MS analysis showed conversion to the product. The reaction was diluted with dichloromethane and extracted with water, dried (Na$_2$SO$_4$), and the solvent was removed. The crude (1.73 g) was taken to the next step without further purification.

It was dissolved in 60 mL of dichloromethane and added 15 mL of TFA at 0° C. The reaction stirred at room temperature for 2 h. The solvent was removed under reduced pressure and the residue was taken up in MeOH and loaded on a SCX cartridge. The fractions coming from SCX were collected, the solvent removed and the residue dissolved in methanol and stirred at 50° C. overnight, then at 90° C. for 21 h. The reaction was cooled down kept in a freezer. The precipitate that formed was collected by filtration and the mother liquour concentrated by removing the colvent. The two fractions were analysed by $^1$H-NMR, which was consistent with the product, as a mixture of diastereoisomers. They were combined and used in the next step without further purification.

Description D33

(7R,9aR)-7-(hydroxymethyl)hexahydropyrazino[2,1-c][1,4]thiazine-6,9-dione 2,2-dioxide and (7R,9aS)-7-(hydroxymethyl)hexahydropyrazino[2,1-c][1,4]thiazine-6,9-dione 2,2-dioxide (D33)

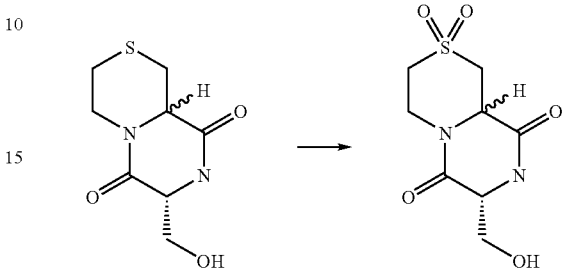

To a suspension of (7R,9aR)-7-(hydroxymethyl)hexahydropyrazino[2,1-c][1,4]thiazine-6,9-dione and (7R,9aS)-7-(hydroxymethyl)hexahydropyrazino[2,1-c][1,4]thiazine-6,9-dione (D32) (851 mg, 3.94 mmol) in dichloromethane (17 mL), was added 77% m-CPBA (2.21 g, 9.84 mmol) and the reaction was left at room temperature for 2 h. A precipitate formed and was separated and washed with MeOH. The liquid phase was concentrated. The product was isolated by flash chromatography (CH$_2$Cl$_2$→CH$_2$Cl$_2$: 0.5M NH$_3$ in MeOH 85:15), obtaining 594 mg, 2.39 mmol.

1H NMR (500 MHz, DMSO-d$_6$) δ ppm 8.44 (s, 1H) 8.41 (s, 1H) 5.48 (t, 1H) 5.12 (t, 1H) 4.80 (dt, 1H) 4.70-4.76 (m, 2H) 4.37 (dd, 1H) 4.25 (dd, 1H) 4.07-4.12 (m, 1H) 3.89-3.99 (m, 1H) 3.72-3.85 (m, 2H) 3.62 (t, 1H) 3.52-3.57 (m, 1H) 3.23-3.47 (m, 4H) 2.95-3.18 (m, 6H). Mixture of diastereoisomers (ratio about 55/45).

Description 34

[(7S,9aR)-2,2-dioxidooctahydropyrazino[2,1-c][1,4]thiazin-7-yl]methanol and [(7S,9aS)-2,2-dioxidooctahydropyrazino[2,1-c][1,4]thiazin-7-yl]methanol (D34)

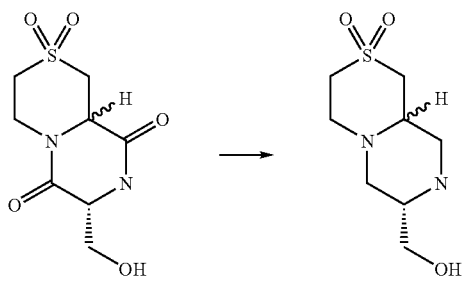

To (7R,9aR)-7-(hydroxymethyl)hexahydropyrazino[2,1-c][1,4]thiazine-6,9-dione 2,2-dioxide and (7R,9aS)-7-(hydroxymethyl)hexahydropyrazino[2,1-c][1,4]thiazine-6,9-dione 2,2-dioxide (D33) (592 mg, 2.39 mmol) was added 24 mL of 1M BH$_3$-THF solution at room temperature. The suspension was refluxed overnight, and checked by UPLC/MS: product peaks seen at 0.17 and 0.37 min, both with m/z=221 (M+1). The excess BH$_3$ was quenched by addition of MeOH (10 mL) at 0° C., followed by conc. HCl (2 mL) and the solution was heated to 80° C. and stirred for 4 h. The crude was purified by SCX cartridge, leaving the expected product: 398 mg, 1.81 mmol.

1H NMR (400 MHz, DMSO-$d_6$) δ ppm 4.50 (t, 1H) 4.60 (t, 1H) 3.33-3.43 (m, 2H) 2.99-3.29 (m, 12H) 2.75-2.93 (m, 2H) 2.56-2.72 (m, 2H) 2.25-2.38 (m, 3H) 1.76 (t, 1H). The sample consists of a mixture of diastereoisomers (ratio about 60/40).

Description 35 and Description 30

(7S,9aS or R)-7-({[(1,1-dimethylethyl)(dimethyl)silyl]oxy}methyl)octahydropyrazino[2,1-c][1,4]thiazine 2,2-dioxide (D35)—Diastereoisomer 2 and (7S,9aR or S)-7-({[(1,1-dimethylethyl)(dimethyl)silyl]oxy}methyl)octahydropyrazino[2,1-c][1,4]thiazine 2,2-dioxide (D30)—Diastereoisomer 1

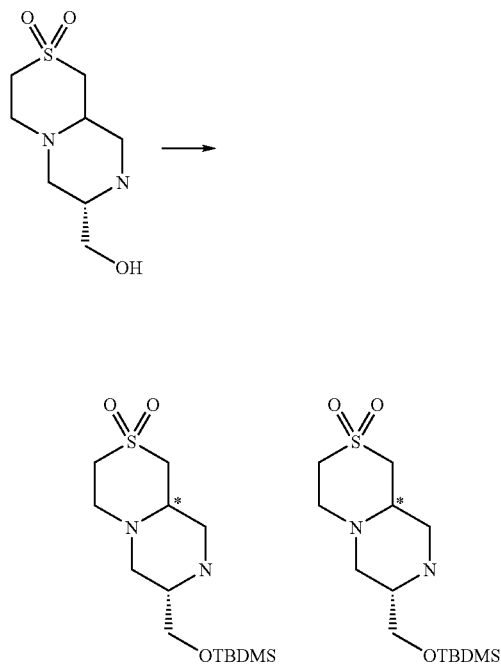

To a solution of starting aminoalcohol (397 mg, 1.80 mmol) in 9 mL of anhydrous dichloromethane was added Et$_3$N (880 μL, 6.31 mmol) and TDBMSCl (815 mg, 5.41 mmol). The reaction was stirred overnight at room temperature. It was checked by UPLC/MS: peak for the products at 0.56 min, m/z=335 (M+1). It was diluted with dichloromethane and extracted with sat. NaHCO$_3$. The organics were dried (Na$_2$SO$_4$) and the solvent removed. The crude was purified by flash chromatography (silica, CH$_2$Cl$_2$→CH$_2$Cl$_2$:MeOH 90:10). Isolated two products: (7S,9aS or R)-7-({[(1,1-dimethylethyl)(dimethyl)silyl]oxy}methyl)octahydropyrazino[2,1-c][1,4]thiazine 2,2-dioxide (D35)—Diastereoisomer 2 1H NMR (500 MHz, DMSO-$d_6$) δ ppm 3.49-3.59 (m, 2H) 2.99-3.20 (m, 3H) 2.79-2.92 (m, 3H) 2.63-2.77 (m, 3H) 2.54-2.63 (m, 2H) 2.20-2.28 (m, 1H) 0.78-0.87 (m, 9H) −0.05-0.04 (m, 6H) (7S,9aR or S)-7-({[(1,1-dimethylethyl)(dimethyl)silyl]oxy}methyl)octahydropyrazino[2,1-c][1,4]thiazine 2,2-dioxide (D30)—Diastereoisomer 1 1H NMR (500 MHz, DMSO-$d_6$) δ ppm 3.43-3.50 (m, 1H) 3.36-3.43 (m, 1H) 3.11-3.23 (m, 1H) 2.96-3.11 (m, 3H) 2.74-2.86 (m, 3H) 2.59-2.69 (m, 1H) 2.23-2.39 (m, 2H) 1.95-2.10 (m, 1H) 1.77 (t, 1H) 0.80-0.89 (m, 9H) −0.03-0.06 (m, 6H) consistent with the previously obtained diastereomer (D30)

Description 36

2-[3,5-Bis(trifluoromethyl)phenyl]-N-[6-[(7S,9aS or R)-7-({[(1,1-dimethylethyl)(dimethyl)silyl]oxy}methyl)-2,2-dioxidohexahydropyrazino[2,1-c][1,4]thiazin-8(1H)-yl]-4-(4-fluoro-2-methylphenyl)-3-pyridinyl]-N,2-dimethylpropanamide (D36)—Diastereomer 2

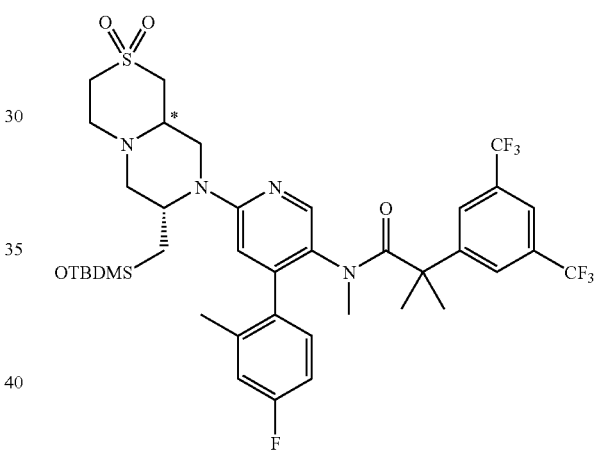

To a solution of (7S,9aS or R)-7-({[(1,1-dimethylethyl)(dimethyl)silyl]oxy}methyl)octahydropyrazino[2,1-c][1,4]thiazine 2,2-dioxide (D35) (111 mg, 0.331 mmol) in 2.2 mL of toluene was added 2-[3,5-bis(trifluoromethyl)phenyl]-N-[6-chloro-4-(4-fluoro-2-methylphenyl)-3-pyridinyl]-N,2-dimethylpropanamide [WO 2005/002577] (136 mg, 0.254 mmol), bis-tri tert-butylphosphine palladium (26 mg, 0.051 mmol), hexadecyltrimethylammonium chloride (16 μL of a 25% aqueous solution) and, at last, sodium hydroxide solution (31 μL of a 50% aqueous solution). The solution was degassed by freeze-pump-thaw cycles, then stirred at 90° C. for 3.5 h. A check by UPLC/MS showed the product peak at 1.22 min., m/z=831 (M+1), 416 (M/2+1). The solution was diluted with EtOAc, washed with sat. NaHCO$_3$, and the organics dried (Na$_2$SO$_4$). The product was isolated by flash chromatography (cyclohexane:EtOAc 100:0→40:60): 160 mg (0.192 mmol) taken to the next step without further characterization.

Description 37

(3R,9aR)-3-(hydroxymethyl)tetrahydro-2H-pyrazino[1,2-a]pyrazine-1,4(3H,6H)-dione and (3R,9aS)-3-(hydroxymethyl)tetrahydro-2H-pyrazino[1,2-a]pyrazine-1,4(3H,6H)-dione (D37)

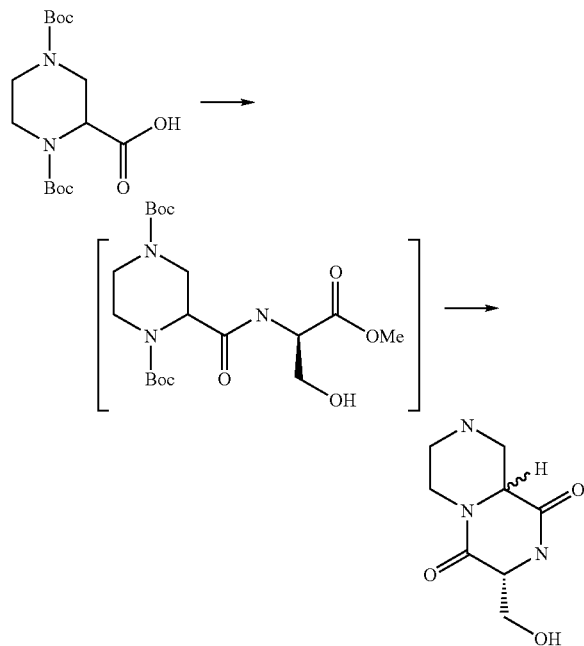

To a solution of 1,4-bis{[(1,1-dimethylethyl)oxy]carbonyl}-2-piperazinecarboxylic acid (10.88 g, 32.93 mmol) in 100 mL of dichloromethane was added O-benzotriazol-1-yl-N,N,N',N'-tetramethyluronium tetrafluoroborate (TBTU) (11.62 g, 36.19 mmol) and diisopropylethylamine (8.6 mL, 54.28 mmol). The reaction was stirred for 1 h. In the meantime, a solution of D-serine methyl ester hydrochloride (10.24 g, 65.81 mmol) and diisopropylethylamine (11.50 mL, 65.9 mmol) in dichloromethane was prepared and finally added to the reaction mixture. The reaction was left stirring at room temperature for 2.5 h. UPLC-MS analysis showed no more starting material and conversion to the product (peak at 0.67 min, m/z=432, M+1). The reaction was diluted with dichloromethane and extracted with sat. NaHCO$_3$, dried (Na$_2$SO$_4$), and the solvent removed. The crude (23.5 g) was taken to the next step without further purification.

It was dissolved in 80 mL of dichloromethane and treated with 20 mL of TFA, added at 0° C. The reaction was stirred at room temperature for 2 h, stored in a freezer overnight, and then added again with 10 mL of TFA and stirred at room temperature for 8 h. It was stored again in freezer, then added more TFA (20 mL) and stirred at room temperature for 5 h. After addition at 0° C. of 30 mL of TFA and heating at 30° C. for 3 h, the reaction appeared by UPLC/MS not to contain starting material anymore. Product seen at 0.20 min, m/z=232 (M+1). The reaction volume was reduced by evaporation and the crude was purified by SCX. The basic fractions were stirred at 50° C. overnight. The solution was concentrated and the solid residue triturated with MeOH (5 mL) and diethyl ether, leaving 4.44 g of product. Mixture (2:1) of two diastereomers.

1H NMR (400 MHz, DMSO-d$_6$) δ ppm 8.02-8.07 (s, 0.66H) 7.98-8.02 (s, 0.33H) 5.00-5.21 (m, 1H) 4.14-4.33 (m, 1H) 3.67-3.89 (m, 3H) 3.41-3.55 (m, 1H) 3.10-3.29 (m, 2H) 2.76-2.94 (m, 1H) 2.26-2.68 (m, 3H).

Description 38

(3S,9aR)-octahydro-2H-pyrazino[1,2-a]pyrazin-3-ylmethanol and (3S,9aS)-octahydro-2H-pyrazino[1,2-a]pyrazin-3-ylmethanol (D38)

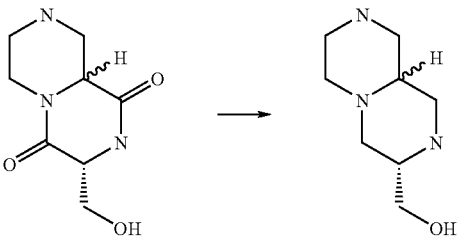

(3R,9aR)-3-(hydroxymethyl)tetrahydro-2H-pyrazino[1,2-a]pyrazine-1,4(3H,6H)-dione and (3R,9aS)-3-(hydroxymethyl)tetrahydro-2H-pyrazino[1,2-a]pyrazine-1,4(3H,6H)-dione (D37)(4.44 g, 22.28 mmol) was divided into two equal portions. Each portion was treated at 0° C. with 110 mL of 1M BH$_3$-THF solution and brought to reflux (80° C.) for 24 h. The reaction was checked by direct UPLC/MS and was not complete. A further aliquot of 50 mL of 1M BH$_3$-THF solution was added to each reaction, and they were kept at 80° C. for additional 16 h. They were checked again by MS and found to be complete (for both m/z=172, M+1). The reaction flasks were cooled to −10° C. and treated with 30 mL of 6M HCl. The resulting solutions were warmed to 80° C. and stirred for 3.5 h. Both reactions were checked by direct MS (m/z=172, M+1 for both samples). The reaction mixture was purified by SCX, obtaining 4.07 g of product. $^1$H NMR consistent with the structure, mixture of diastereoisomers.

Description 39

(3S,9aR)-3-({[(1,1-dimethylethyl)(dimethyl)silyl]oxy}methyl)octahydro-2H-pyrazino[1,2-a]pyrazine and (3S,9aS)-3-({[(1,1-dimethylethyl)(dimethyl)silyl]oxy}methyl)octahydro-2H-pyrazino[1,2-a]pyrazine (D39)

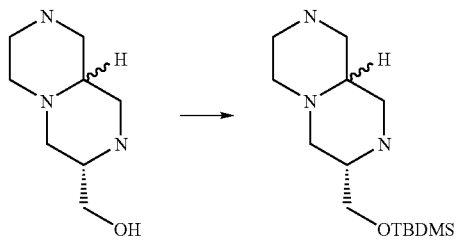

(3S,9aR)-octahydro-2H-pyrazino[1,2-a]pyrazin-3-ylmethanol and (3S,9aS)-octahydro-2H-pyrazino[1,2-a]pyrazin-3-ylmethanol (D38) (4.065 g, 23.75 mmol) was dissolved in 100 mL of dichloromethane and treated with Et$_3$N (9.32 mL, 71.25 mmol) and TDBMSCl (8.4 g, 59.38 mmol).

The reaction was stirred at room temperature for 70 h. It was checked by UPLC/MS, which showed conversion to product: peaks at 0.45 and 0.46 min, m/z=286 (M+1). It was diluted with dichloromethane, extracted with sat. NaHCO$_3$ and brine, and the dried over Na$_2$SO$_4$. The crude was purified by flash chromatography (silica, CH$_2$Cl$_2$→CH$_2$Cl$_2$:MeOH 80:20), to give 4.410 g of the expected product.

Spectrum consistent with the product. Mixture of diastereomers, roughly 2:1 ratio.

1H NMR (400 MHz, DMSO-d$_6$) δ ppm 3.67-3.81 (m, 1H) 3.35-3.48 (m, 1H) 2.58-2.84 (m, 5H) 2.18-2.58 (m, 3H) 1.93-2.17 (m, 2H) 1.74-1.93 (m, 1H) 1.63-1.74 (m, 1H) 0.87 (s, 3H) 0.86 (s, 6H) 0.04 (2, 2H) 0.02 (s, 4H).

Description 40

(7S,9aR)-2-acetyl-7-({[(1,1-dimethylethyl)(dimethyl)silyl]oxy}methyl)octahydro-2H-pyrazino[1,2-a]pyrazine and (7S,9aS)-2-acetyl-7-({[(1,1-dimethylethyl)(dimethyl)silyl]oxy}methyl)octahydro-2H-pyrazino[1,2-a]pyrazine (D40)

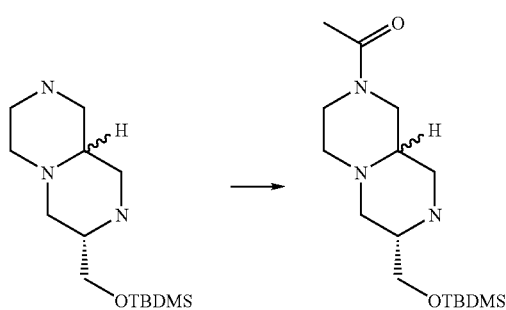

To a solution of (3S,9aR)-3-({[(1,1-dimethylethyl)(dimethyl)silyl]oxy}methyl)octahydro-2H-pyrazino[1,2-a]pyrazine and (3S,9aS)-3-({[(1,1-dimethylethyl)(dimethyl)silyl]oxy}methyl)octahydro-2H-pyrazino[1,2-a]pyrazine (D39) (4.407 g, 15.44 mmol) in 100 mL of dichloromethane was added triethylamine (3.23 mL, 23.16 mmol) and it was brought to −50° C. A solution of acetic anhydride (1.459 mL, 15.44 mmol) in 16 mL of dichloromethane was added dropwise in 45 min. The reaction was stirred at −50° C. for additional 30 min. and then let back to room temperature. The reaction was checked by UPLC/MS, which showed the two diastereomeric products at 0.54 and 0.57 min, m/z=328 (M+1). The reaction mixture was diluted with dichloromethane, extracted with sat. NaHCO$_3$ and brine, and the dried over Na$_2$SO$_4$. The crude was purified by flash chromatography (silica, CH$_2$Cl$_2$→CH$_2$Cl$_2$: 0.5 M NH$_3$ in MeOH 90:10), obtaining 4.334 g.

1H NMR (400 MHz, DMSO-d$_6$) indicated a mixture of diastereoisomers with diagnostic peaks at 0.05 ppm, and 0.03 ppm.

Description 41 and Description 42

N-[6-[(3S,9aR or S)-8-acetyl-3-({[(1,1-dimethylethyl)(dimethyl)silyl]oxy}methyl)octahydro-2H-pyrazino[1,2-a]pyrazin-2-yl]-4-(4-fluoro-2-methylphenyl)-3-pyridinyl]-2-[3,5-bis(trifluoromethyl)phenyl]-N,2-dimethylpropanamide (D41)—Diastereoisomer 1 and N-[6-[(3S,9aS or R)-8-acetyl-3-({[(1,1-dimethylethyl)(dimethyl)silyl]oxy}methyl)octahydro-2H-pyrazino[1,2-a]pyrazin-2-yl]-4-(4-fluoro-2-methylphenyl)-3-pyridinyl]-2-[3,5-bis(trifluoromethyl)phenyl]-N,2-dimethylpropanamide (D42)—Diastereoisomer 2

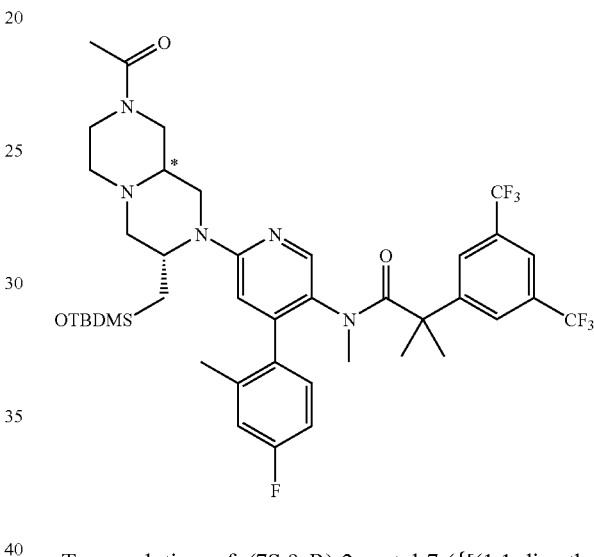

To a solution of (7S,9aR)-2-acetyl-7-({[(1,1-dimethylethyl)(dimethyl)silyl]oxy}methyl)octahydro-2H-pyrazino[1,2-a]pyrazine and (7S,9aS)-2-acetyl-7-({[(1,1-dimethylethyl)(dimethyl)silyl]oxy}methyl)octahydro-2H-pyrazino[1,2-a]pyrazine (D40) (1.5 g, 5.72 mmol) in 20 mL of toluene was added 2-[3,5-bis(trifluoromethyl)phenyl]-N-[6-chloro-4-(4-fluoro-2-methylphenyl)-3-pyridinyl]-N,2-dimethylpropanamide [WO 2005/002577] (2.034 g, 3.816 mmol), bis-tri tert-butylphosphine palladium (440 mg, 0.86 mmol), hexadecyltrimethylammonium chloride (73 μL of a 25% aqueous solution) and, at last, sodium hydroxide solution (456 μL of a 50% aqueous solution). The solution was degassed by two freeze-pump-thaw cycles, then stirred at 90° C. for 4 h. More bis-tri-tert-butylphosphine palladium (187 mg, 0.37 mmol) was added and the reaction stirred at 90° C. for additional 4 h. The reaction was checked by UPLC/MS, which showed peaks for the expected products at 0.93 and 1.17 min., m/z=824 (M+1) for both. The solution was diluted with EtOAc, washed with sat. NaHCO$_3$, brine, and the organics dried (Na$_2$SO$_4$). The products were isolated by flash chromatography (cyclohexane:EtOAc 70:30→0:100). (D41) Diastereoisomer 1, 1.1686 g, UPLC/MS: peak at 1.17 min, m/z=824. M+1. (D42) Diastereoisomer 2, 1.0916 g, UPLC/MS: peak at 0.93 min, m/z=824. M+1.

Description 43

N-(phenylmethyl)-D-serine (D43)

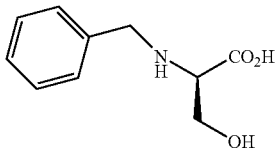

The title compound was made according to the procedure described G. R. Brown, J. Chem. Soc. Perkin Trans 1, 1985, 2577. Benzaldehyde (10.16 mL, 0.1 mol) was added to a vigorously stirred solution of D-Serine (10.47 g, 0.1 mol) in 2N NaOH solution (50 mL), stirred for 30 minutes at R.T. before cooling in an ice-salt bath to ~6° C. before adding Sodium Borohydride (1.06 g, 27.90 mmol) portionwise over 40 minutes. The reaction was stirred at R.T. for 1 hour before adding more benzaldehyde (10.16 mL, 0.1 mol) and cooling down in an ice-salt bath to between 6-10° C. and then adding more sodium Borohydride (1.06 g, 27.90 mmol) portionwise over 45 minutes. The reaction mixture was stirred at R.T. for 2 hours, washed with $Et_2O$. Made sure all solid material in solution, hence diluted with water before washing with $Et_2O\times$ 2. Aqueous layer acidified to ~pH 6.5, using c.HCl solution. Solid precipitated out. Filtered, dried in the vacuum oven overnight at 40° C. to afford a white solid in 46% yield.

NMR (DMSO-$d_6$) δ 7.44-7.30 (5H, m), 3.98 (2H, q), 3.73-3.61 (1H, m), 3.14 (1H, m).

Description 44

(3R)-5-oxo-4-(phenylmethyl)-3-morpholinecarboxylic acid (D44)

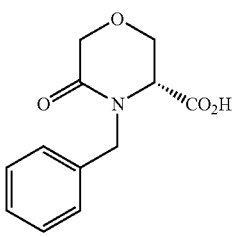

The title compound was prepared according to the method described by H. H. Otto, Helvetica Chimica Acta, 2004, 87, 90. To an ice cooled solution of N-(phenylmethyl)-D-serine (8.90 g, 45.59 mmol) in 2N NaOH solution (50 mL) was added chloroacetyl chloride (4.36 mL, 54.71 mmol), dropwise over 15 minutes. The reaction was stirred for 30 minutes before adding 30% NaOH solution (4.5 g in 15 mL) and stirring at R.T. for 2 and ½ hours. It was cooled in an ice bath before adding c.HCl solution to pH<1. solid precipitated out. Filtered. Suspended in isopropanol and heated at reflux for 10 minutes. Filtered hot. Solvent evaporated to afford a pale yellow solid. Triturated with $Et_2O$ to afford the title compound as a cream solid in 29% yield.

MS (API+): m/z 236.1 (MH+: 100%) @ retention time 1.61 min

Description 45

Ethyl (3R)-5-oxo-4-(phenylmethyl)-3-morpholinecarboxylate (D45)

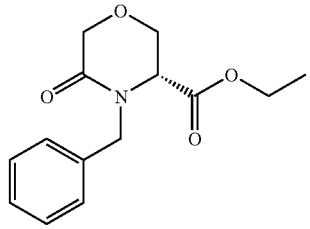

The title compound was prepared according to the procedure described by H. H. Otto, Helvetica Chimica Acta, 2004, 87, 90 using (3R)-5-oxo-4-(phenylmethyl)-3-morpholinecarboxylic acid (D44, 3.13 g, 13.33 mmol) in EtOH (30 mL), cooling in an ice bath before adding Thionyl Chloride (1.46 mL) dropwise, and then stirring at R.T. for 6 hours. Added more thionyl chloride (1 mL) and stirring at R.T. overnight. Added more thionyl chloride (1 mL) and stirred for 4 hours, added further thionyl chloride (0.5 mL) and stirred overnight again. Added thionyl chloride (0.2 mL) and left stirring for 5 hours. Solvent evaporated to afford the title compound as an orange oil in quantitative yield.

MS (API+): m/z 264.1 (MH+; 100%) @ retention time 2.28 min $[\alpha]_D$=−11.4°, where I=1 cm, c=0.5 in DCM

Description 46

Ethyl (3R)-4-(phenylmethyl)-3-morpholinecarboxylate (D46)

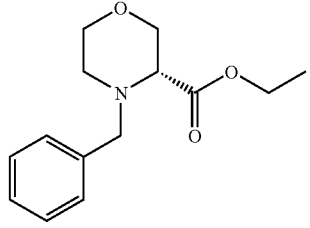

The title Compound was prepared according to the procedure used by G. R. Brown, J. Chem. Soc. Perkin Trans 1, 1985, 2577, using ethyl (3R)-5-oxo-4-(phenylmethyl)-3-morpholinecarboxylate (D45, 3.64 g, 13.84 mmol) in dry THF (70 mL), cooled in an ice bath before adding borane-dimethylsulphide complex (1.84 mL, 10 M), slowly. The reaction mixture was allowed to warm up to room temperature overnight. Stirred for further six hours, added more borane-dimethylsulphide complex and stirred at R.T. over the weekend. Reaction quenched carefully with water, dropwise till the effervescence had finished. Solvent evaporated. Residue dissolved in water, basified to pH ~10 using 2N NaOH solution before extracting with $Et_2O$. Organic layer was then extracted with 2N HCl solution. Acid layer was then basified using 2N NaOH solution before extracting with Et₂O×3. Combined extracts were dried (MgSO₄). Filtered. Evaporated under reduced pressure to afford the title compound as a colourless oil in a 68% yield.

MS (API+): m/z 250.1 (MH+: 100%) @ retention time 1.88 min

[α]$_D$=+103°, where I=1 cm, c=0.5 in DCM

Description 47

(3R)-4-(phenylmethyl)-3-morpholinecarboxylic acid (D47)

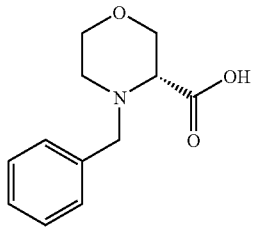

Ethyl (3R)-4-(phenylmethyl)-3-morpholinecarboxylate (D46, 2.33 g, 9.36 mmol) was dissolved in a mixture of THF/EtOH/H₂O (1:1:1 45 mL) before treating with Lithium Hydroxide monohydrate (0.432 g, 10.29 mmol) and heating at 50° C. overnight. Reaction not finished. Added more Lithium Hydroxide monohydrate (0.200 g, 4.76 mmol) and left heating for a further 24 hours. Added more Lithium Hydroxide (0.100 g, 2.38 mmol) and heated for a further 6 hours. Added more Lithium Hydroxide (0.100 g, 2.38 mmol) and heated for a further 16 hours.

Cooled to R.T. Reaction neutralised using 2N HCl solution. Solvent evaporated. Residue partitioned between DCM and Water. Aqueous layer extracted with 10% MeOH/DCM ×5. Combined extracts dried (MgSO₄). Filtered. Solvent evaporated under reduced pressure to afford the title compound as a white foam in a 94% yield.

MS (API+): m/z 222.1 (MH+; 100%) @ retention time 0.96 min

[α]$_D$=+73°, where I=1 cm, c=0.5 in MeOH

Description 48

Methyl N-{[(3R)-4-(phenylmethyl)-3-morpholinyl]carbonyl}-D-serinate (D48)

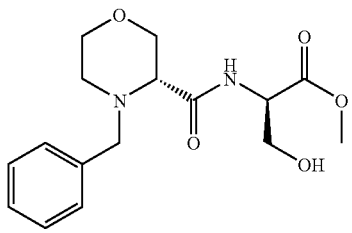

(3R)-4-(phenylmethyl)-3-morpholinecarboxylic acid (D47, 1.93 g, 8.73 mmol) was dissolved in dry DCM (20 mL) with a little DMF (2 mL). To it was added TBTU (3.62 g, 11.27 mmol) followed by DIPEA (3.02 mL, 17.29 mmol) and stirred for 40 minutes at R.T., under argon before adding a solution of D-Ser-Methylester hydrochloride (2.70 g, 17.37 mmol), and DIPEA (3.02 mL, 17.29 mmol) in dry DCM (15 mL). The resulting mixture was stirred for 45 minutes before being allowed to stand overnight. Diluted with DCM (60 mL), washed with sat NaHCO₃ solution (2×60 mL). Dried (Na₂SO₄). Filtered. Solvent evaporated under reduced pressure to afford an orange oil. Used crude in the next step.

MS (API+): m/z 323.1 (MH+; 100%) @ retention time 1.17 min

[α]$_D$=+11.8°, where I=1 cm, c=0.5 in DCM

Description 49

(7S,9aS)-octahydropyrazino[2,1-c][1,4]oxazin-7-ylmethanol (D49)

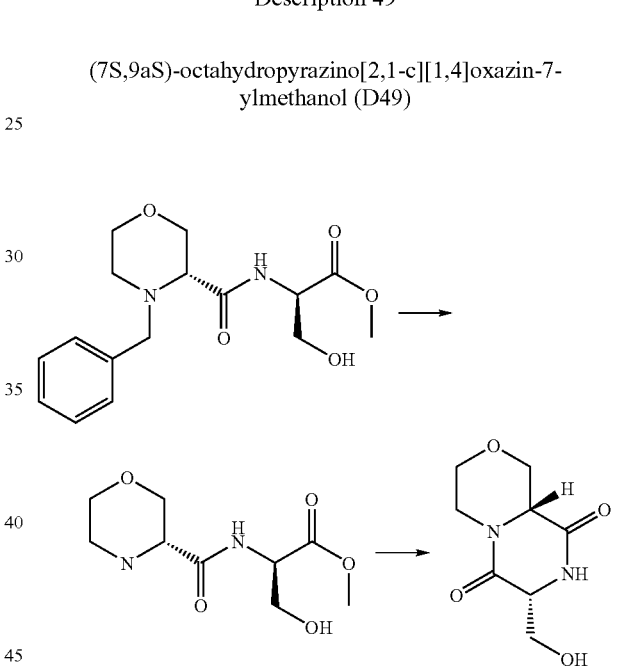

Methyl N-{[(3R)-4-(phenylmethyl)-3-morpholinyl]carbonyl}-D-serinate (D48, 3.72 g, 11.55 mmol) was dissolved in EtOH (50 mL), treated with 10% Pd on C (450 mg) then placed under an atmosphere of hydrogen over the weekend. Left stirring for further 6 hours. Added 10% Pd on C (200 mg) and left under an atmosphere of hydrogen overnight. Catalyst removed by filtration through kieselguhr washed with acid, washing well with EtOH. Solvent removed under reduced pressure to afford a colourless oil. Oil dissolved in dry MeOH (15 mL) and heated at 50° C. overnight. Left heating for a further 3 hours before cooling to R.T. Solvent removed under reduced pressure. Residue triturated with DCM to afford the title compound as an off white solid in 35% yield over the 2 steps.

MS (ELSD+): 201.1 (MH+; 100%) @ retention time 0.49 min

[α]$_D$=+37.6°, where I=1 cm, c=0.5 in MeOH

Description 50

(7S,9aS)-octahydropyrazino[2,1-c][1,4]oxazin-7-ylmethanol (D50)

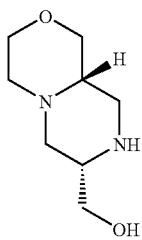

(7S,9aS)-octahydropyrazino[2,1-c][1,4]oxazin-7-ylmethanol (D49, 800 mg, 4 mmol) was suspended in dry THF (20 mL), before being treated with 1M borane THF complex solution (40 mL) and heating at reflux for 17 hours. Cooled to R.T., MeOH (8 mL) added dropwise followed by c.HCl solution (3.2 mL). The resulting mixture was heated at 70° C. for 2 hours. Cooled to R.T., solvent evaporated under reduced pressure. Residue placed on a 10 g SCX column in MeOH with some water. Column washed with MeOH (3×25 mL) before eluting the compound with NH$_3$ in MeOH (4×25 mL). Solvent evaporated under reduced pressure to afford the title compound as a colourless oil in a quantitative yield.

MS (ELSD+): m/z 173.1 (MH+; 100%) @ retention time 0.31 min $[\alpha]_D$=+3.6°, where l=1 cm, c=0.5 in MeOH

Description 51

(7S,9aS)-7-({[(1,1-dimethylethyl)(dimethyl)silyl]oxy}methyl)octahydropyrazino[2,1-c][1,4]oxazine (D51)

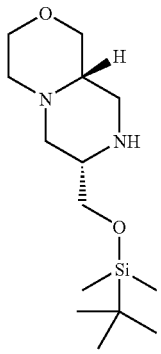

(7S,9aS)-octahydropyrazino[2,1-c][1,4]oxazin-7-ylmethanol (D50, 680 mg, 3.95 mmol) was almost dissolved in dry DCM (12 mL) before adding Et$_3$N (1.10 mL, 7.90 mmol), followed by TBDMS-Chloride (894 mg, 5.93 mmol). The resulting reaction mixture was stirred over the weekend at R.T., under argon. Left stirring for 2 more hours.

Diluted with DCM, washed with sat NaHCO$_3$ solution (2×20 mL). Dried (MgSO$_4$). Filtered. Solvent evaporated. Residue purified on a 25+M horizon column eluting with 10% EtOAc/Pet Ether to EtOAc to 10% MeOH/EtOAc. Solvent evaporated under reduced pressure to afford the title compound as a pale yellow oil in a 62% yield.

1H NMR (400 MHz; DMSO-d6) δ 3.77-3.63 (3H, m), 3.50-3.40 (2H, m), 2.98 (1H, t), 2.71 (1H, br m), 2.61 (1H, dd), 2.42-2.28 (4H, m), 2.14-2.05 (2H, m), 1.96 (1H, m), 0.83 (9H, s), 0.01 (6H, s)

$[\alpha]_D$=+4.4°, where l=1 cm, c=0.5 in DCM

Description 52

2-[3,5-bis(trifluoromethyl)phenyl]-N-(6'-chloro-4-methyl-3,4'-bipyridin-3'-yl)-N,2-dimethylpropanamide (D52)

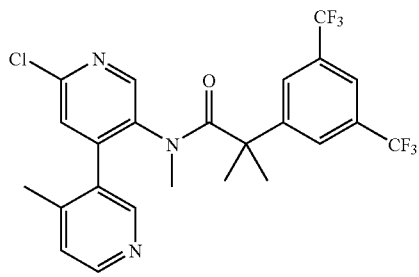

2-[3,5-bis(trifluoromethyl)phenyl]-N-(6-chloro-4-iodo-3-pyridinyl)-N,2-dimethylpropanamide (400 mg, 0.726 mmol), 4-methylpyridine-3 boronic acid (130 mg, 0.944 mmol), sodium carbonate (0.8 mL, 2M), tetrakistriphenylphosphine palladium (7.8 mg, 0.00726 mmol) was added in dioxane (4 mL) and stirred under argon before heating in the microwave at 110° C. for 30 minutes, added more 4-methylpyridine-3 boronic acid (67.5 mg, 0.49 mmol) and tetrakistriphenylphosphinepalladium (7.8 mg, 0.00726 mmol) and heated at 110° C. for 30 minutes. therefore added more 4-methylpyridine-3 boronic acid (51 mg, 037 mmol), tetrakistriphenylphosphinepalladium (7.8 mg, 0.00726 mmol) and heated under microwave conditions at 110° C. for 30 minutes, therefore added 4-methylpyridine-3 boronic acid (47 mg, 0.34 mmol), tetrakistriphenylphosphinepalladium (7.8 mg, 0.00726 mmol) and heated at 110° C. for 30 minutes. Residue partitioned between EtOAc and Brine. Aqueous layer was extracted with EtOAc ×3. Combined extracts were dried and solvent evaporated. Residue purified on a 12+M horizon column eluting with Pet Ether to 1:1 EtOAc: Pet Ether. Unable to isolate clean fractions. Sample sent to be purified by Mass Directed Auto-Prep (MDAP) chromatography, white solid didn't dissolve was found to be desired material. This was combined with product isolated from the MDAP to afford the title compound as a white solid in an 83% yield.

MS (API+): m/z 516.1 (MH+; 100%)

Description 53

2-[3,5-bis(trifluoromethyl)phenyl]-N-{6'-[(7S,9aS)-7-({[(1,1-dimethylethyl)(dimethyl)silyl]oxy}methyl)hexahydropyrazino[2,1-c][1,4]oxazin-8(1H)-yl]-4-methyl-3,4'-bipyridin-3'-yl}-N,2-dimethylpropanamide (D53)

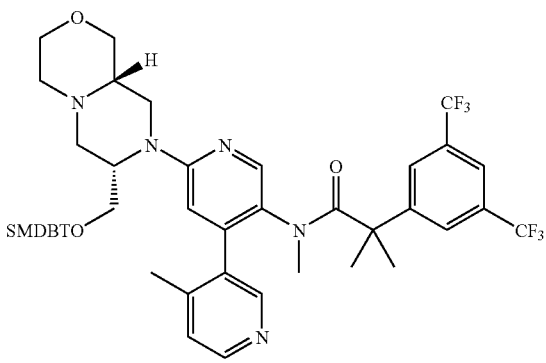

The 2-[3,5-bis(trifluoromethyl)phenyl]-N-(6'-chloro-4-methyl-3,4'-bipyridin-3'-yl)-N,2-dimethylpropanamide (D52, 77 mg, 0.15 mmol), (7S,9aS)-7-({[(1,1-dimethylethyl)(dimethyl)silyl]oxy}methyl)octahydropyrazino[2,1-c][1,4]oxazine (D51, 51.5 mg, 0.18 mmol), sodium t-Butoxide (18 mg, 0.19 mmol) were degassed together in dry toluene (1.5 mL) for 5 mins before adding Bis(dibenzyleneacetone) Palladium (9 mg, 0.015 mmol) and 2-Dicyclohexylphosphino-2'-(N'N'-dimethylamino)biphenyl (15 mg, 0.038 mmol) and heating under microwave conditions at 130° C. for 30 mins. Diluted with EtOAC, washed with sat. NaHCO$_3$×1, brine ×1, dried (MgSO4). Filtered. Solvent evaporated. Residue purified eluting with Pent to EtOAc. No Fractions isolated clean. Mixed fractions combined, solvent evaporated and residue re-purified on a 2 g SCX column, washing with MeOH (2×10 mL) before eluting the compound off with NH3 in MeOH (3×10 mL). Solvent evaporated under reduced pressure to afford a gummy solid (86 mg).

MS (API+: 766.4 (MH+; 100%)+652.2 (MH+; –TBDMS; 20%)

Crude product was used directly without further purification.

Description 54

2-[3,5-bis(trifluoromethyl)phenyl]-N-(6'-chloro-6-fluoro-2-methyl-3,4'-bipyridin-3'-yl)-N,2-dimethylpropanamide (D54)

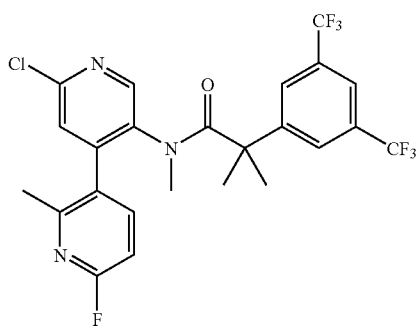

2-[3,5-bis(trifluoromethyl)phenyl]-N-(6-chloro-4-iodo-3-pyridinyl)-N,2-dimethylpropanamide (200 mg, 0.363 mmol), 2-fluoro-6-methylpiperidine-5 boronic acid (73 mg, 0.472 mmol), sodium carbonate solution (0.4 mL, 2M), tetrakistriphenylphosphinepalladium (4 mg, 0.00363 mmol) in dioxan (2 mL) were heated together in the microwave at 110° C. for 30 minutes. The mixture was partitioned between EtOAc and sat NaHCO$_3$ solution. Aqueous layer extracted with EtOAc ×3. Combined extracts dried and evaporated. Residue purified on a 12+M horizon column eluting with Pet Et$_2$O to 60% EtOAc/Pet Et$_2$O, Solvent evaporated under reduced pressure to afford the title compound in quantitative yield.

MS (API+): m/z 534.2 (MH+; 100%)

Description 55

2-[3,5-bis(trifluoromethyl)phenyl]-N-[6-chloro-4-(5-fluoro-2-methylphenyl)-3-pyridinyl]-N,2-dimethylpropanamide (D55)

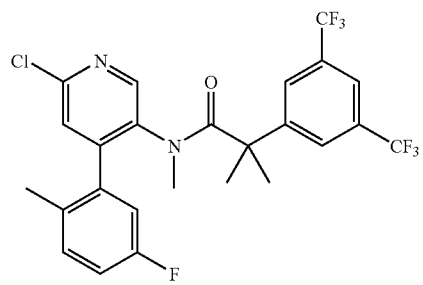

2-[3,5-bis(trifluoromethyl)phenyl]-N-(6-chloro-4-iodo-3-pyridinyl)-N,2-dimethylpropanamide (200 mg, 0.363 mmol), 2-methyl-5-fluorobenzene boronic acid (73 mg, 0.472 mmol), sodium carbonate (0.4 mL, 2M solution), tetrakistriphenylphosphinepalladium (4 mg, 0.00363 mmol) in dioxan were heated together in the microwave at 110° C. for 30 minutes. The mixture was partitioned between EtOAc and Brine. The Aqueous layer was extracted with EtOAc×3. The combined extracts were dried and evaporated. The residue was purified on a 12+M column eluting with Pet Et$_2$O to 60% EtOAc/Pet Et$_2$O to afford the title compound in a 27% yield.

MS (API+): m/z 533.1 (MH+; 100%)

Description 56

2-[3,5-bis(trifluoromethyl)phenyl]-N-[6-[(7S,9aS)-7-({[(1,1-dimethylethyl)(dimethyl)silyl]oxy}methyl)hexahydropyrazino[2,1-c][1,4]oxazin-8(1H)-yl]-4-(5-fluoro-2-methylphenyl)-3-pyridinyl]-N,2-dimethylpropanamide (D56)

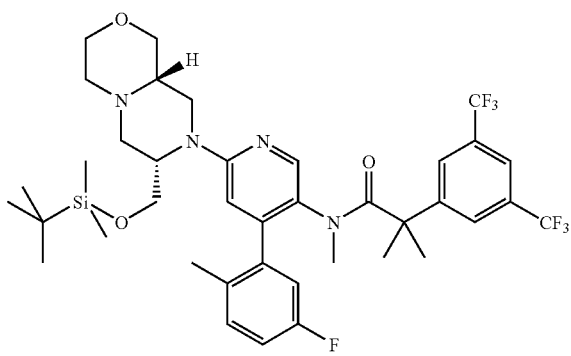

2-[3,5-bis(trifluoromethyl)phenyl]-N-[6-chloro-4-(5-fluoro-2-methylphenyl)-3-pyridinyl]-N,2-dimethylpropanamide (D55, 50 mg, 0.094 mmol), (7S,9aS)-7-({[(1,1-dimethylethyl)(dimethyl)silyl]oxy}methyl)octahydropyrazino[2,1-c][1,4]oxazine (D51, 34 mg, 0.116 mmol) were dissolved in toluene (1.5 mL). Bis tritertbutylphosphine palladium (12.5 mg, 0.0244 mmol), followed by hexadecyltrimethylammoium chloride (204, 25% aq sol), and finally sodium hydroxide solution (0.11 mL, 50% aq sol) were added. The mixture was degassed for 5 minutes before heating at 90° C. for 2 hours. Reaction cooled to R.T., diluted with EtOAc, washed with sat NaHCO$_3$ solution, dried (MgSO$_4$). Filtered. Solvent evaporated to afford a yellow sticky solid. Used crude in the next step.

MS (API+): 783.4 (MH+; 60%)

Description 57

2-[3,5-bis(trifluoromethyl)phenyl]-N-[6-chloro-4-(2-chloro-4-fluorophenyl)-3-pyridinyl]-N,2-dimethylpropanamide (D57)

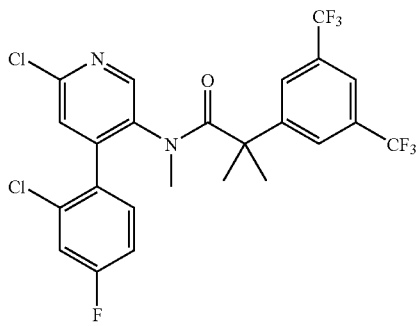

2-[3,5-bis(trifluoromethyl)phenyl]-N-(6-chloro-4-iodo-3-pyridinyl)-N,2-dimethylpropanamide (200 mg, 0.363 mmol), 2-chloro-4-fluorobenzene boronic acid (82 mg, 0.472 mmol), sodium carbonate (0.4 mL, 2M solution), tetrakistriphenylphosphinepalladium (4 mg, 0.00363 mmol) in dioxan (2 mL) were heated together in the microwave at 110° C. for 30 minutes. The mixture was partitioned between EtOAc and Brine. The Aqueous layer was extracted with EtOAc ×3. The combined extracts were dried and evaporated. The residue was purified on a 25+M column eluting with 0-50% EtOAc/Pet Et$_2$O. Impurities still seen. Sent to MDAP for purification to afford the title compound in a 96% yield.

MS (API+): m/z 553.1 (MH+; 100%)

Description 58

2-[3,5-bis(trifluoromethyl)phenyl]-N-{4-(2-chloro-4-fluorophenyl)-6-[(7S,9aS)-7-({[(1,1-dimethylethyl)(dimethyl)silyl]oxy}methyl)hexahydropyrazino[2,1-c][1,4]oxazin-8(1H)-yl]-3-pyridinyl}-N,2-dimethylpropanamide (D58)

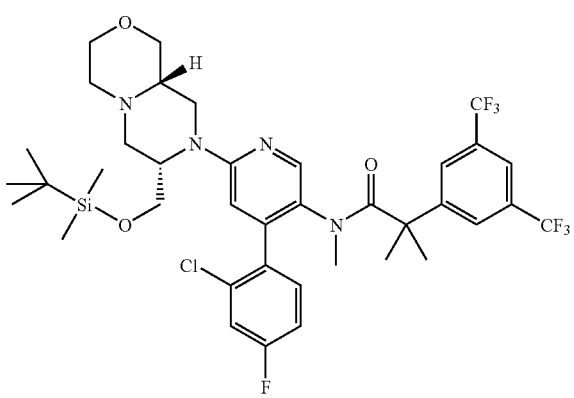

2-[3,5-bis(trifluoromethyl)phenyl]-N-[6-chloro-4-(2-chloro-4-fluorophenyl)-3-pyridinyl]-N,2-dimethylpropanamide (D57, 60 mg, 0.11 mmol), (7S,9aS)-7-({[(1,1-dimethylethyl)(dimethyl)silyl]oxy}methyl)octahydropyrazino[2,1-c][1,4]oxazine (D51, 37 mg, 0.13 mmol), sodium t-Butoxide (13 mg, 00.1375 mmol) were degassed together in toluene (1.2 mL) for 10 minutes before adding bis(dibenzyleneacetone) palladium (6 mg, 0.011 mmol) and 2-dicyclohexylphosphino-2'-(N,N-dimethylamino)biphenyl (11 mg, 0.0275 mmol) and heating at 100° C. for 30 minutes under microwave conditions. Added more bis(dibenzyleneacetone) palladium (6 mg, 0.011 mmol) and 2-dicyclohexylphosphino-2'-(N,N-dimethylamino)biphenyl (11 mg, 0.0275 mmol) and heated for a further 30 minutes at 100° C. under microwave conditions. Diluted with EtOAc, washed with sat NaHCO$_3$ solution ×1, brine ×1, dried (MgSO$_4$). Filtered. Solvent evaporated under reduced pressure. Residue purified eluting with 0-100% EtOAc/Pent. Solvent evaporated to afford a brown gum of the title compound in 25% yield.

MS (API+): m/z 803.4 (MH+; 40%)

Description 59

2-[3,5-bis(trifluoromethyl)phenyl]-N-[6-chloro-4-(2-formylphenyl)-3-pyridinyl]-N,2-dimethylpropanamide (D59)

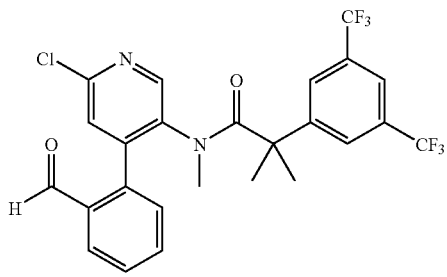

2-[3,5-bis(trifluoromethyl)phenyl]-N-(6-chloro-4-iodo-3-pyridinyl)-N,2-dimethylpropanamide (200 mg, 0.363 mmol), benzaldehyde-2-boronic acid (71 mg, 0.472 mmol), sodium carbonate (0.4 mL, 2M solution), tetrakistriphenylphosphinepalladium (4 mg, 0.00363 mmol) in dioxan (2 mL) were heated together in the microwave at 110° C. for 30 minutes. The mixture was partitioned between EtOAc and Brine. The Aqueous layer was extracted with EtOAc ×3. The combined extracts were dried and evaporated. The residue was purified on a 25+M column eluting with 0-50% EtOAc/Pet Et$_2$O to afford the title compound as a yellow solid in 55% yield.

MS (API+): m/z 529.1 (MH+; 100%)

Description 60

2-[3,5-bis(trifluoromethyl)phenyl]-N-[6-[(7S,9aS)-7-({[(1,1-dimethylethyl)(dimethyl)silyl]oxy}methyl)hexahydropyrazino[2,1-c][1,4]oxazin-8(1H)-yl]-4-(2-formylphenyl)-3-pyridinyl]-N,2-dimethylpropanamide (D60)

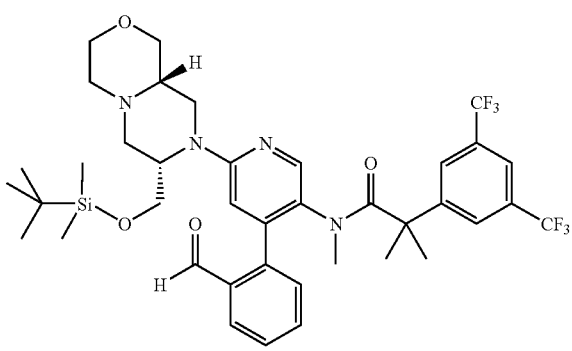

2-[3,5-bis(trifluoromethyl)phenyl]-N-[6-chloro-4-(2-formyl phenyl)-3-pyridinyl]-N,2-dimethylpropanamide (D59, 106 mg, 0.201 mmol), (7S,9aS)-7-({[(1,1-dimethylethyl)(dimethyl)silyl]oxy}methyl)octahydropyrazino[2,1-c][1,4]oxazine (D51, 72 mg, 0.251 mmol) were dissolved in toluene (2 mL). Bis tritertbutylphosphine palladium (27 mg, 0.052 mmol), followed by hexadecyltrimethylammoium chloride (30 μL, 25% aq sol), and finally sodium hydroxide solution (0.25 mL, 50% aq sol) were added. The mixture was degassed for 5 minutes before heating at 90° C. for 2 hours. Reaction cooled to R.T., diluted with EtOAc, washed with sat NaHCO$_3$ solution, dried (MgSO$_4$). Filtered. Solvent evaporated. Residue purified eluting with 0-50% EtOAc/Pent. Solvent evaporated under reduced pressure to afford a pale yellow solid in 18% yield.

MS (API+): m/z 779.4 (MH+; 100%).

Description 61

2-[3,5-bis(trifluoromethyl)phenyl]-N-{6-[(7S,9aS)-7-({[(1,1-dimethylethyl)(dimethyl)silyl]oxy}methyl)hexahydropyrazino[2,1-c][1,4]oxazin-8(1H)-yl]-4-[2-(hydroxymethyl)phenyl]-3-pyridinyl}-N,2-dimethylpropanamide (D61)

2-[3,5-bis(trifluoromethyl)phenyl]-N-[6-[(7S,9aS)-7-({[(1,1-dimethylethyl)(dimethyl)silyl]oxy}methyl)hexahydropyrazino[2,1-c][1,4]oxazin-8(1H)-yl]-4-(2-formylphenyl)-3-pyridinyl]-N,2-dimethylpropanamide (D60, 27.7 mg, 0.0356 mmol) was suspended in dry THF (1.5 mL) before adding sodium borohydride (3 mg, 0.078 mmol) and stirring for 1 hour. Added more sodium borohydride (3 mg, 0.078 mmol) and left stirring for a further 1 and ½ hours. Reaction quenched with water, diluted with EtOAc. Organic layer washed with water, dried (MgSO$_4$). Filtered. Solvent evaporated to afford the title compound as an off white solid in 89% yield. Used crude in the next step.

MS (API+): m/z 781.4 (MH+; 100%).

Description 62

2-[3,5-bis(trifluoromethyl)phenyl]-N-(4-(4-fluoro-2-methylphenyl)-6-{[(2S)-2-pyrrolidinylmethyl]amino}-3-pyridinyl)-N,2-dimethylpropanamide (D62)

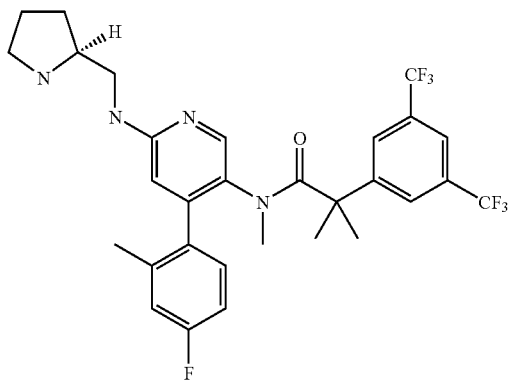

A suspension of 2-[3,5-bis(trifluoromethyl)phenyl]-N-[6-chloro-4-(4-fluoro-2-methylphenyl)-3-pyridinyl]-N,2-dimethylpropanamide [WO 2005/002577] (1.5 g, 2.81 mmol) 1,1-dimethylethyl (2R)-2-(aminomethyl)-1-pyrrolidinecarboxylate (N-Boc prolinamine) (1.41 g, 7.025 mmol) and potassium carbonate (777 mg, 5.62 mmol) in 6 mL of DMSO was heated for 18 h at 150° C. (temperature detected 138° C.). A HPLC/MS check showed a 50% conversion with partial loss of the Boc protecting group. The reaction was heated under microwave irradiation to 160° C. for 1 h and to 180° C. for two cycles of 1 h and 1.5 h, respectively. The suspension was diluted with dichloromethane and extracted with sat. NaHCO₃ and the organics were dried (Na₂SO₄) and the solution was loaded on a SCX cartridge, washed with dichloromethane (100 mL) and methanol (200 mL, this wash allowed the recovery of the unreacted chloropyridine) and eluted with 2M NH₃ in MeOH. The crude thus obtained, which contained both the Boc-protected and unprotected compounds, was purified by flash chromatography (silica, cyclohexane:EtOAc 80:20 to EtOAc). Isolated 350 mg of Boc-protected amine and 410 mg of the title compound. This last compound was purified further by a boc-protection, flash chromatography, TFA deprotection and SCX isolation procedure. Final yield: 165 mg. O.A.HPLC, peak @ 5.20 min, >99% purity (UV).

Description 63 diethyl 2,2-pyrrolidinedicarboxylate (D63)

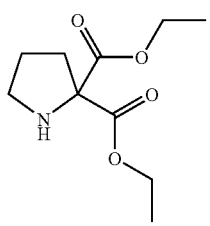

To a solution of sodium ethoxide (5.14 g) in absolute ethanol (75 mL) at 0° C. under a nitrogen atmosphere, a solution of diethyl aminomalonate (hydrochloride salt, 8 g) in absolute ethanol (75 mL) was slowly added. A yellow suspension was obtained at the end of the addition. 1,3-dibromo propane (7.7 mL) was then added and the resulting mixture was stirred at reflux temperature for 5 hours. The mixture was allowed to cool down to rt, then ethanol was removed in vacuo to give a yellow solid. This was dissolved in HCl (1M solution, 20 mL) and then washed with ethyl ether (2×50 mL). Phases were separated and the aqueous phase was brought to pH=9 by adding NaOH (1M solution). It was then extracted with ethyl ether (3×50 mL) and washed with brine (20 mL). The organic phase was dried and concentrated in vacuo to give the desired compound (2.35 g) as yellow oil.

MS (ES/+) m/z=216 [M+H]⁺.

Description 64 diethyl 1-(bromoacetyl)-2,2-pyrrolidinedicarboxylate (D64)

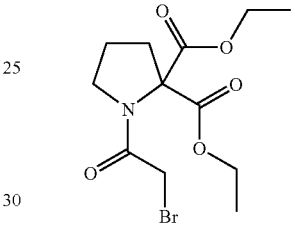

To a solution of diethyl 2,2-pyrrolidinedicarboxylate (D63, 900 mg) in dichloromethane (9 mL) at 0° C., potassium carbonate (0.5M solution, 12.5 mL) and bromoacetyl bromide (0.55 mL) were added. The resulting mixture was stirred at 0° C. for 2 hours. The mixture was then diluted with water and then allowed to reach r.t. Ethyl acetate (15 mL) was added and phases were separated. The aqueous phase was then extracted with ethyl acetate (2×10 mL) and washed with brine (20 mL). The organic phase was dried and concentrated in vacuo to give the desired compound (1.06 g) as orange oil.

T.l.c.: CH/AcOEt 1:1, Rf=0.47.

UPLC/MS: peak at Rt=0.63 min with m/z=336, 338 [M+H]⁺.

Description 65 ethyl 1,4-dioxo-2-(phenylmethyl)hexahydropyrrolo[1,2-a]pyrazine-8a(6H)-carboxylate (D65)

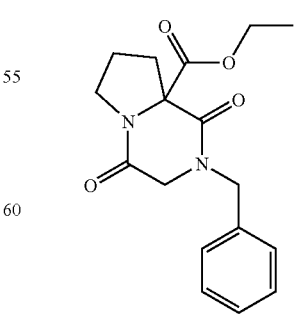

To a solution of diethyl 1-(bromoacetyl)-2,2-pyrrolidinedicarboxylate (D64, 950 mg) in acetonitrile (10 mL) at r.t, benzylamine (340 microL) was added. The resulting mixture was stirred at r.t. for 3.5 hours: the formation of a white solid was observed. The suspension was then filtered over a Gooch funnel. The organic filtrate was diluted with ethyl acetate (15 mL) and washed with water (2×10 mL). The organic phase was dried and concentrated in vacuo to a residue which was purified by flash chromatography (Cycl/EtOAc from 50/50 to 35:65) to give the desired compound (200 mg) as colourless oil.

T.l.c.: CH/AcOEt 7:3, Rf=0.53.

UPLC/MS: peak at Rt=0.62 min with m/z=317 [M+H]$^+$.

1H NMR (500 MHz, CHLOROFORM-d) d ppm 7.34 (t, 1H) 7.32 (t, 2H) 7.23 (dd, 2 H) 4.97 (d, 1H) 4.25 (d, 1H) 4.19-4.25 (m, 2H) 4.01 (d, 1H) 3.74 (d, 1H) 3.67-3.76 (m, 1H) 3.55-3.63 (m, 1H) 2.71-2.80 (m, 1H) 2.36-2.46 (m, 1H) 1.93-2.11 (m, 2H) 1.21 (t, 3H).

Description 66

[2-(phenylmethyl)hexahydropyrrolo[1,2-a]pyrazin-8a(6H)-yl]methanol (D66)

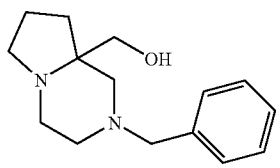

To a solution of ethyl 1,4-dioxo-2-(phenylmethyl)hexahydropyrrolo[1,2-a]pyrazine-8a(6H)-carboxylate (D65, 450 mg) in anhydrous THF (5 mL) under a Nitrogen atmosphere at 0° C., lithium aluminium hydride (1M in THF, 14 mL) was added dropwise. The resulting mixture was stirred at 0° C. for 10 minutes, then allowed to reach rt and stirred at this temperature for 45 minutes. It was then heated at reflux temperature for 3.5 hours and then allowed to cool to r.t. Water (540 microL), NaOH (1M solution, 540 microL) and water (1.6 mL) were then added to the solution and the formation of a white precipitate was observed. The suspension was stirred at rt for 30-40 minutes then filtered over a Gooch funnel. The organic filtrate was dried and concentrated in vacuo to a residue which was purified by flash chromatography (DCM/MeOH from 100/0 to 90:10) to give the desired compound (162 mg) as orange oil.

T.l.c.: DCM/MeOH 9:1, Rf=0.43.

UPLC/MS: peak at Rt=0.43 min with m/z=247 [M+H]$^+$.

Description 67 hexahydropyrrolo[1,2-a]pyrazin-8a(6H)-ylmethanol (D67)

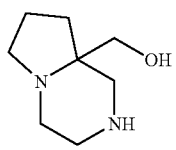

To a solution of [2-(phenylmethyl)hexahydropyrrolo[1,2-a]pyrazin-8a(6H)-yl]methanol (D66, 180 mg) in anhydrous methanol (5 mL) under a Nitrogen atmosphere at rt, ammonium formate (475 mg) and palladium (10% on carbon, 13 mg) were added. The resulting suspension was heated at reflux temperature for 3.5 hours, then allowed to cool to r.t. and filtered over Celite. The organic extract was dried and concentrated in vacuo to give the desired compound (120 mg) as orange waxy solid.

UPLC/MS: peak at Rt=0.15 min with m/z=157 [M+H]$^+$.

1H NMR (400 MHz, DMSO-d$_6$) d ppm 5.09 (br. s., 1H) 3.61 (d, 1H) 3.34 (br. s., 1H) 2.89-3.09 (m, 5H) 2.76-2.89 (m, 2H) 2.72 (d, 1H) 1.62-1.84 (m, 3H) 1.49-1.61 (m, 1H)

Description 68 methyl (3S)-3-hydroxy-L-prolinate hydrochloride (D68)

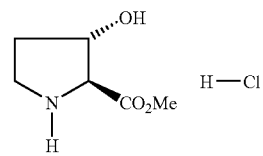

Hydrogen chloride gas was bubbled through a suspension of trans-3-hydroxy-L-proline (1.5 g, 11.4 mmol) in 20 ml of freshly distilled MeOH at 0° C. for 30 min. The resulting clear solution was stirred overnight, then concentrated under reduced pressure to afford the title compound as a white solid (1.96 g). Yield 94%.

Reference: U.S. Pat. Appl. 2004 19,063.

Description 69 methyl (3S)-1-(chloroacetyl)-3-hydroxy-L-prolinate (D69)

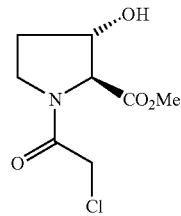

To a solution of the methyl (3S)-3-hydroxy-L-prolinate hydrochloride (D68, 1.8 g, 9.9 mmol) and Et$_3$N (3 ml, 21.8 mmol) in 10 ml of dry benzene at the temperature of 7-8° C. was added dropwise a solution of chloroacetyl chloride (0.87 ml, 10.9 mmol) in 5 ml of dry benzene. After 24 h at rt, the precipitated was filtered off and washed with AcOEt. The filtrate was evaporated, and the crude oil was purified by flash chromatography column (Cy/AcOEt 1/4 as eluent). The title compound was isolated as a colourless oil (1.48 g). Yield 67%.

Reference: *Khimiko-Farmatsevticheskii Zhurnal* 1984, 18, 1445-8; *Eur. J. Org. Chem.* 2000, 657.

Description 70

(8S)-8-hydroxyhexahydropyrrolo[1,2-a]pyrazine-1,4-dione (D70)

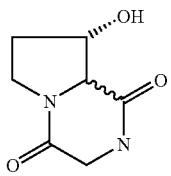

A mixture of methyl (3S)-1-(chloroacetyl)-3-hydroxy-L-prolinate (D69, 1.48 g, 6.7 mmol) in 10 ml of MeOH and 60 ml of a saturated solution of $NH_3$ in MeOH was stirred for 48 h at rt. The solvent was evaporated under reduced pressure, to afford a solid. Analysis indicated this to be the title compound as a pair of diastereoisomers. After a short chromatography column ($CHCl_3$/MeOH 8/2 as eluent) the title compound was isolated as a foamy solid (1 g). Yield 88%.

Reference: *Khimiko-Farmatsevticheskii Zhurnal* 1984, 18, 1445-8

Description 71

(8S)-octahydropyrrolo[1,2-a]pyrazin-8-ol (D71)

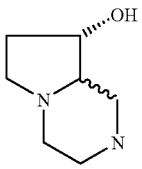

Into a stirred, cooled (0° C.) suspension of $LiAlH_4$ (3.3 g, 88 mmol) in 60 ml of dry THF, was introduced (8S)-8-hydroxyhexahydropyrrolo[1,2-a]pyrazine-1,4-dione (D70, 750 mg, 4.4 mmol) in small portions. The mixture was then allowed to reach rt and stirred for 48 h, after which it was cooled to 0° C. THF was introduced (70 ml), then successively a saturated solution of Na—K-tartrate (5 ml) and a 20% aqueous NaOH solution (5 ml) were dropped into the flask, under vigorous stirring. The suspension was stirred for 30 min at rt, and filtered. The pale filter cake was washed with 100 ml of $CHCl_3$ and the combined filtrates and washings were evaporated in vacuo to give 500 mg of the title compound. From GC-MS analysis 2 diastereomeric products were still observed. Yield 80%.

1H NMR (500 MHz, DMSO-d6) δ ppm 4.01 (s, 1H) 2.93 (t, 1H) 2.87 (d, 1H) 2.80 (d, 1H) 2.71 (d, 1H) 2.49-2.61 (m, 2H) 1.89-2.06 (m, 2H) 1.74-1.91 (m, 2H) 1.48-1.56 (m, 1H) 1.34-1.42 (m, 1H)

Reference: *J. Org. Chem.* 1995, 60, 3916.

Description 72 cis-Octahydropyrrolo[1,2-a]pyrazin-1-ylmethanol (D72)

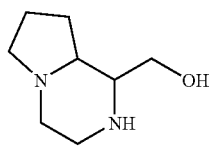

To a solution of cis-methyl-3-oxooctahydropyrrolo[1,2-a]pyrazine-1-carboxylate (Prepared according literature procedure: Heterocycles, 52(3), 2000)(270 mg) in anhydrous THF (10 mL) under a Nitrogen atmosphere at 0° C., lithium aluminium hydride (1M in THF, 6.8 mL) was added dropwise. The resulting mixture was stirred at 0° C. for 1 hour, then allowed to reach rt and stirred at this temperature for 30 minutes. Water (260 microL), NaOH (1M solution, 260 microL) and water (780 microL) were then added to the solution and the formation of a white precipitate was observed. The suspension was filtered over a Gooch funnel. The organic filtrate was dried and concentrated in vacuo to give the desired compound (198 mg) as yellow oil.

UPLC/MS: peak at Rt=0.15 min with m/z=157 [M+H]+.

1H NMR (500 MHz, CHLOROFORM-d) d ppm 3.94-4.04 (m, 1H) 3.75 (dd, 1H) 3.19 (td, 1H) 3.07-3.15 (m, 1H) 3.05 (t, 1H) 2.96-3.04 (m, 1H) 2.78-2.90 (m, 2H) 2.29-2.40 (m, 1H) 2.17 (td, 1H) 2.02-2.15 (m, 1H) 1.58-1.86 (m, 4H).

Description 73 cis-1-({[(1,1-dimethylethyl)(dimethyl)silyl]oxy}methyl)octahydropyrrolo[1,2-a]pyrazine (D73)

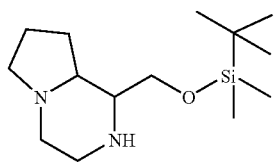

To a solution of cis-Octahydropyrrolo[1,2-a]pyrazin-1-ylmethanol (D72, 198 mg) in anhydrous DCM (10 mL) under a Nitrogen atmosphere at room temperature, triethylamine (350 microL) and t-butyldimethylsilylchloride (286 mg) were added. The resulting solution was stirred at room temperature overnight then diluted with water (5 mL). The aqueous phase was extracted with DCM (2×10 mL). The combined organic extracts were dried and concentrated in vacuo to a residue which was purified by flash chromatography (DCM/0.5M $NH_3$ in MeOH from 100/0 to 90/10) to give the desired compound (195 mg) as yellow oil.

UPLC/MS: peak at Rt=0.80 min with m/z=271 [M+H]+.

1H NMR (500 MHz, CHLOROFORM-d) d ppm 3.84 (t, 1H) 3.61 (dd, 1H) 3.11-3.21 (m, 1H) 2.99 (dd, 2H) 2.82-2.88 (m, 1H) 2.71-2.79 (m, 1H) 2.41-2.50 (m, 1H) 2.19-2.35 (m, 2H) 1.71-1.85 (m, 1H) 1.94 (br. s., 1H) 1.53-1.73 (m, 3H) 0.90 (s, 9H) 0.07 (s, 6H)

Description 74 cis-2-[3,5-bis(trifluoromethyl)phenyl]-N-[6-[1-({[(1,1-dimethylethyl)(dimethyl)silyl]oxy}methyl)hexahydropyrrolo[1,2-a]pyrazin-2(1H)-yl]-4-(4-fluoro-2-methylphenyl)-3-pyridinyl]-N,2-dimethylpropanamide (D74)

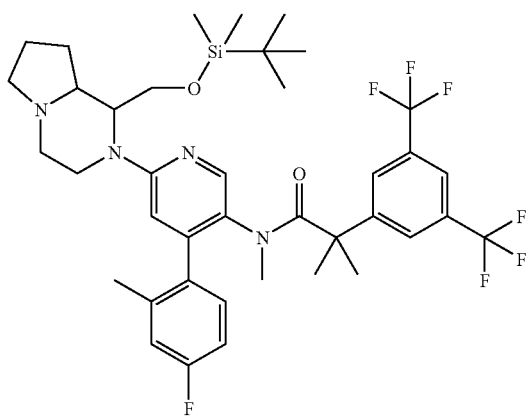

To a solution of cis-1-({[(1,1-dimethylethyl)(dimethyl)silyl]oxy}methyl)octahydropyrrolo[1,2-a]pyrazine (D73, 50 mg) in dry toluene (0.5 mL), a solution of 2-[3,5-bis(trifluoromethyl)phenyl]-N-[6-chloro-4-(4-fluoro-2-methylphenyl)-3-pyridinyl]-N,2-dimethylpropanamide [WO 2005/002577] (75 mg) in dry toluene (0.5 mL) was added at rt. Hexadecyltrimethylammonium chloride (25% aqueous solution, 132 microL), bis(tri-tert-butyl phosphine) palladium (19 mg) and NaOH (50% aqueous solution, 245 microL) were added. The resulting mixture was degassed by two freeze-thaw cycles and allowed to reach rt under a nitrogen atmosphere. The mixture was then heated at 90° C. for 5 hours. The mixture was allowed to cool down to rt, diluted with ethyl acetate (1 mL) and washed with a saturated solution of NaHCO$_3$ (1 mL). The aqueous phase was extracted with ethyl acetate (3×2.5 mL). The combined organic extracts were dried and concentrated in vacuo to a residue which was purified by flash chromatography (Cycl/EtOAc 1:1) to give the desired compound (10.5 mg) as yellow oil.

T.l.c.: Cycl/EtOAc 1:1, Rf=0.49.

UPLC/MS: peak at Rt=0.87 min with m/z=767 [M+H]$^+$.

Description 75 methyl 1-[2-({[(1,1-dimethylethyl)oxy]carbonyl}amino)ethyl]-L-prolinate (D75)

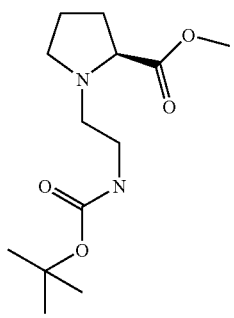

To a solution of methyl L-prolinate (892 mg, 6.93 mmol) in dichloroethane (20 ml) was added at r.t. 1,1-dimethylethyl (2-oxoethyl)carbamate (1 g, 6.3 mmol) and the reaction mixture was stirred for 30 min. Sodium triacetoxyborohydride (2.34 g, 12.6 mmol) was added and the reaction mixture was stirred for 3 hrs.

The title compound (1 g) was isolated after purification via SCX.

1H NMR (400 MHz, CHLOROFORM-d) δ ppm 5.11-5.49 (m, 1H) 3.59-3.88 (m, 4H) 3.05-3.41 (m, 4H) 2.71-2.90 (m, 1H) 2.54-2.73 (m, 1H) 2.34-2.51 (m, 1H) 2.03-2.30 (m, 1H) 1.27-2.04 (m, 11H)

Description 76

(8aS)-hexahydropyrrolo[1,2-a]pyrazin-1(2H)-one (D76)

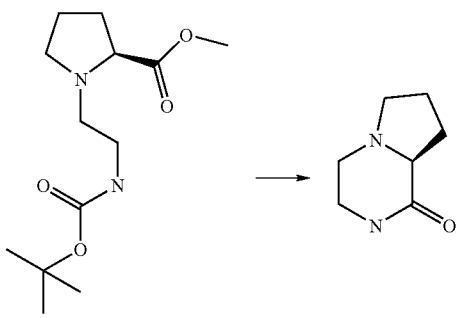

To a solution of methyl 1-[2-({[(1,1-dimethylethyl)oxy]carbonyl}amino)ethyl]-L-prolinate (D75, 1 g) in dichloromethane (20 ml) was added at r.t. TFA (5 ml) and the reaction mixture was stirred for 1 hr. The mixture was diluted with MeOH and it was filtered trough SCX cartridge. The fractions eluted with methanolic ammonia were evaporated in vacuo keeping the bath temperature at 40° C.

The crude was purified by chromatography (silica cartridge, CH$_2$Cl$_2$:MeOH 95:5) to give the title compound (420 mg).

1H NMR (400 MHz, CHLOROFORM-d) δ ppm 5.86-6.38 (m, 1H) 3.47-3.70 (m, 1H) 3.24-3.47 (m, 2H) 2.87-3.13 (m, 3H) 2.65-2.87 (m, 1H) 2.14-2.37 (m, 1H) 1.69-2.10 (m, 3H)

Description 77

1-(1,1-dimethylethyl) 3-ethyl 4-[2-({[(1,1-dimethylethyl)oxy]carbonyl}amino)ethyl]-1,3-piperazinedicarboxylate (D77)

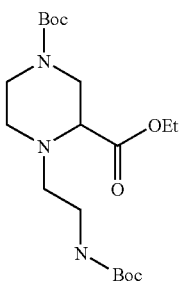

To a solution of 1-(1,1-dimethylethyl) 3-ethyl 1,3-piperazinedicarboxylate [EP1486498, 2004] (2.023 g, 8.28 mmol) in 10 mL of dichloroethane was added a solution of N-boc- 2-aminoacetaldehyde (1.87 g, 12.42 mmol) in 20 mL of dichloroethane. The solution was stirred at room temperature and under nitrogen atmosphere for 30 min. Sodium triacetoxyborohydride (3.32 g, 16.56 mmol) was then added and the reaction kept at room temperature overnight. The product was isolated on a SCX cartridge. 2.492 g.

LC/MS: peak at 2.16 min, m/z=402 (M+1).

Description 78 hexahydro-2H-pyrazino[1,2-a]pyrazin-1(6H)-one (D78)

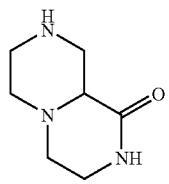

To a solution of 1-(1,1-dimethylethyl) 3-ethyl 4-[2-({[(1,1-dimethylethyl)oxy]carbonyl}amino)ethyl]-1,3-piperazinedicarboxylate (D77, 2.492 g, 6.21 mmol) in dichloromethane (30 mL) kept at 0° C. was added TFA (10 mL) dropwise. The solution was kept at 0° C. for 2 h, and then at room temperature for 6 h. The deprotected product was isolated by SCX and the resulting solution was evaporated at 50° C. to induce cyclization. The target product was purified by reverse phase chromatography (Oasis HLB 6 g×4 columns, eluted with water), obtaining 372 mg of the title compound.

1H NMR (500 MHz, DMSO-$d_6$) δ ppm 7.65 (br. s., 1H) 3.20-3.30 (m, 2H) 2.98-3.07 (m, 1H) 2.84 (d, 1H) 2.72-2.80 (m, 2H) 2.68 (dt, 1H) 2.49-2.52 (m, 1H) 2.40-2.46 (m, 1H) 2.35 (dt, 1H) 2.12 (dt, 1H)

Description 79 octahydro-2H-pyrazino[1,2-a]pyrazine (D79)

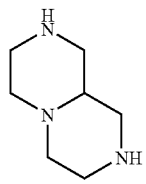

To a suspension of hexahydro-2H-pyrazino[1,2-a]pyrazin-1(6H)-one (D78, 339 mg, 2.184 mmol) in 3.5 mL of THF kept at 0° C. were added dropwise 21.84 mL of a 1M borane-THF solution. The reaction was kept at 75° C. under nitrogen atmosphere for 3 h, then quenched by slow addition MeOH at 0° C. After 30 min at room temperature, 5 mL of a 37% HCl aqueous solution diluted in 10 mL of MeOH were added and the resulting solution was heated to 50° C. for 2.5 h. The solvent was removed and the residue purified by SCX, leaving 251 mg of the title compound.

MS (direct): m/z=142 (M+1)

1H NMR (500 MHz, DMSO-$d_6$) δ ppm 2.44-2.77 (m, 8H) 2.17 (t, 2H) 1.97 (dt, 2H) 1.73-1.84 (m, 1H)

Description 80

2-[3,5-bis(trifluoromethyl)phenyl]-N-[4-(4-fluoro-2-methylphenyl)-6-(octahydro-2H-pyrazino[1,2-a]pyrazin-2-yl)-3-pyridinyl]-N,2-dimethylpropanamide (D80)

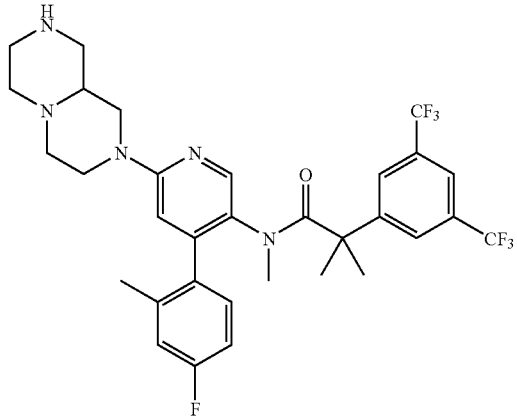

To a solution of octahydro-2H-pyrazino[1,2-a]pyrazine (D79, 197 mg, 1.395 mmol) in 6 mL of DMSO was added 2-[3,5-bis(trifluoromethyl)phenyl]-N-[6-chloro-4-(4-fluoro-2-methylphenyl)-3-pyridinyl]-N,2-dimethylpropanamide [WO 2005/002577] (372 mg, 0.698 mmol) and potassium carbonate (289 mg, 2.09 mmol) and the reaction was heated at 130° C. for 22 h. The product was isolated by SCX, and the obtained crude (451 mg) was used in the following reactions without further purification.

MS (direct): m/z=638 (M+1).

Description 81

(3R,8aS)-3-({[(1,1-dimethylethyl)(dimethyl)silyl]oxy}methyl)octahydropyrrolo[1,2-a]pyrazine (D81)

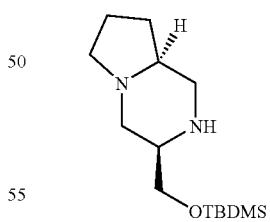

To a solution of (3R,8aS)-octahydropyrrolo[1,2-a]pyrazin-3-ylmethanol (Tetrahedron Asymmetry, 1996, 7(7), 1999-2005), 220 mg, 1.41 mmol) in 8 mL of dichloromethane was added triethylamine (262 μL, 2.82 mmol) and a solution of tert-butyldimethylsilyl chloride (170 mg, 1.7 mmol) in dichloromethane (1 mL) and the solution was stirred at room temperature for 3 h. Additional tert-butyldimethylsilyl chloride (113 mg, 1.1 mmol) was added, and the solution left at room temperature overnight. More triethylamine (261 μL, 2.82 mmol) and tert-butyldimethylsilyl chloride (71 mg, 0.69 mmol) was added again, and the reaction left at room temperature for 5 h. The reaction was diluted with dichloromethane and extracted with sat. NaHCO$_3$ and brine. The product was isolated by flash chromatography (dichloromethane to dichloromethane: 0.5 M NH$_3$ in MeOH 9:1), obtaining 259 mg of the title compound.

1H NMR (500 MHz, CHLOROFORM-d) δ ppm 3.89 (t, 1H) 3.60 (dd, 1H) 3.01-3.10 (m, 3H) 2.95 (dt, 1H) 2.79 (dd, 1H) 2.75 (dd, 1H) 2.49 (dd, 1H) 2.23-2.40 (m, 2H) 1.66-1.89 (m, 3H) 1.43-1.57 (m, 1H) 0.90 (s, 9H) 0.08 (s, 6H) LC/MS (check at 5 h reaction): peak @0.49 min, m/z=271 (M+1).

Description 82

(3S,8aS)-3-({[(1,1-dimethylethyl)(dimethyl)silyl]oxy}methyl)octahydropyrrolo[1,2-a]pyrazine (D82)

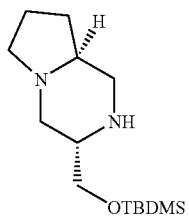

To a solution of (3R,8aS)-octahydropyrrolo[1,2-a]pyrazin-3-ylmethanol (Tetrahedron Asymmetry, 1996, 7(7), 1999-2005) (531.5 mg, 3.39 mmol) in 20 mL of dichloromethane was added triethylamine (1.423 mL, 10.17 mmol) and tert-butyldimethylsilyl chloride (1.026 g, 6.78 mmol). The solution was stirred at room temperature for 2 days. The reaction was diluted with dichloromethane and extracted with sat. NaHCO$_3$ and brine. The product was isolated by flash chromatography (dichloromethane to dichloromethane: MeOH 99:1 to 90:10), obtaining 157 mg of the title compound.

1H NMR (400 MHz, CHLOROFORM-d) δ ppm 3.60-3.70 (m, 1H) 3.47-3.59 (m, 1 H) 2.90-3.28 (m, 3H) 2.50-2.73 (m, 1H) 2.09-2.30 (m, 1H) 1.79-2.09 (m, 2H) 1.37-1.80 (m, 5H) 0.87-0.97 (s, 9H) 0.03-0.13 (s, 6H).

Description 83 and 84

(3S,9aS or 9aR)-3-(hydroxymethyl)tetrahydro-2H-pyrazino[1,2-a]pyrazine-1,4(3H,6H)-dione (D83—Diatereoisomer 1) and (3S,9aR or 9aS)-3-(hydroxymethyl)tetrahydro-2H-pyrazino[1,2-a]pyrazine-1,4(3H,6H)-dione (D84—Diastereoisomer 2)

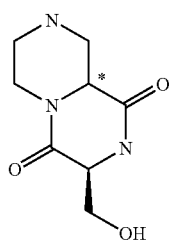

To a solution of the N,N'-di-boc-piperazine-2-carboxylic acid (2 g) in 60 mL of dichloromethane was added HOBt (817 mg) and EDC (1.74 g). The reaction was stirred for 30 min. In the meantime, a solution of L-serine methyl ester hydrochloride (1.413 g, n mmol) and diisopropylethylamine (1.62 mL) in 20 mL of dichloromethane was prepared and finally added to the reaction mixture. The reaction was left stirring at room temperature overnight. UPLC-MS analysis showed the expected product (peak at 0.67 min, m/z=432 (M+1), 376 (M-t-Bu), 320 (M-Boc+1)). The reaction was diluted with dichloromethane and extracted with sat. NaHCO$_3$, dried (Na$_2$SO$_4$), and the solvent removed. The crude (2.75 g) was taken to the next step without further purification.

It was dissolved in 30 mL of dichloromethane and treated with 10 mL of TFA, added at 0° C. The reaction was stirred at room temperature for 1.5 h. It was checked by UPLC/MS, which showed the expected deprotection product at 0.20 min, m/z=232 (M+1). The crude was purified by SCX. The basic fractions were stirred at 50° C. and evaporated. The solid thus obtained was suspended in 5 mL of MeOH and filtered to give the title compound (D83—Diastereoisomer 1) as a white solid 333 mg.

D 83:

1H NMR (400 MHz, DMSO-d$_6$) δ ppm 7.99 (s, 1H) 5.07 (t, 1H) 4.15 (dd, 1H) 3.67-3.77 (m, 3H) 3.40-3.49 (m, 1H) 3.20 (dd, 1H) 2.82 (dd, 1H) 2.45-2.52 (m, 1H) 2.31-2.42 (m, 2H)

UPLC/MS: Peak @ 0.16 min, m/z=200 (M+1).

The solution was concentrated to give a second solid (976 mg) as a mixture of title compounds: (Mixture of D83—Diastereoisomer 1 and D84—Diastereoisomer 2).

D83+D84:

1H NMR (400 MHz, DMSO-d$_6$) δ ppm 7.93-8.08 (m, 1H) 5.06-5.19 (m, 1H) 4.14-4.33 (m, 1H) 3.67-3.77 (m, 3H) 3.40-3.49 (m, 1H) 3.11-3.23 (m, 1H) 2.75-2.90 (m, 1H) 2.45-2.52 (m, 1H) 2.31-2.42 (m, 2H).

UPLC/MS: Peak @ 0.16 min, m/z=200 (M+1).

Description 85

(3R,9aS or 9aR)-octahydro-2H-pyrazino[1,2-a]pyrazin-3-ylmethanol (D85—Diastereoisomer 1)

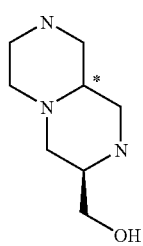

To a flask containing (3S,9aS or 9aR)-3-(hydroxymethyl)tetrahydro-2H-pyrazino[1,2-a]pyrazine-1,4(3H,6H)-dione (D83, 217 mg) was added 1M BH$_3$-THF solution (10.9 mL) and the reaction was brought to reflux (80° C.) overnight. The reaction flask was cooled to 0° C. and treated with 20 mL of MeOH and conc. HCl (2.5 mL). The resulting solution was heated to 60° C. for 4 h. The reaction was checked by direct MS (m/z=172 (M+1), 184 (M+BH$_3$)). The reaction mixture was purified by SCX, obtaining 174 mg of the title compound.

1H NMR (400 MHz, DMSO-d$_6$) δ ppm 4.39-4.63 (m, 1H) 3.17-3.26 (m, 2H) 2.56-2.79 (m, 6H) 2.14-2.31 (m, 2H) 1.92-2.04 (m, 1H) 1.72-1.85 (m, 1H) 1.66 (t, 1H).

Description 86

(3R,9aS or 9aR)-3-{[(1,1-dimethylethyl)(dimethyl)silyl]methyl}octahydro-2H-pyrazino[1,2-a]pyrazine (D86—Diasteroisomer 1)

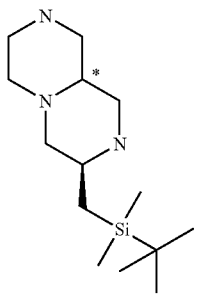

The starting (3R,9aS or 9aR)-octahydro-2H-pyrazino[1,2-a]pyrazin-3-ylmethanol (D85, 173 mg) was dissolved in 6 mL of dichloromethane and treated with Et$_3$N (420 μL) and TDBMSCl (305 mg). The reaction was stirred at room temperature for 3 days. More TDBMSCl (144 mg, n mmol) was added and the reaction stirred again overnight. It was checked by UPLC/MS, which showed conversion to product: peak at 0.47 min, m/z=286 (M+1). The crude was purified by flash chromatography (silica, CH$_2$Cl$_2$ to CH$_2$Cl$_2$: (0.5 M NH$_3$ in MeOH) 90:10), to give 218 mg of the expected product.

1H NMR (400 MHz, DMSO-d$_6$) δ ppm 3.34-3.53 (m, 2H) 2.92-3.12 (m, 2H) 2.60-2.92 (m, 6H) 2.26-2.39 (m, 1H) 2.11-2.27 (m, 1H) 1.98-2.11 (m, 1H) 1.70-1.83 (m, 1H) 1.23 (t, 1H) 0.80-0.92 (m, 9H) −0.02-0.09 (m, 6H).

Description 87

(7R,9aR or 9aS)-2-acetyl-7-{[(1,1-dimethylethyl)(dimethyl)silyl]methyl}octahydro-2H-pyrazino[1,2-a]pyrazine (D87—Diastereoisomer 1)

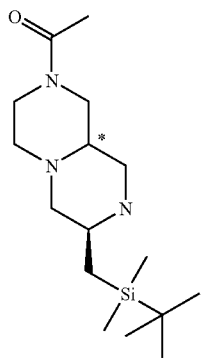

To a solution of the (3R,9aS or 9aR)-3-{[(1,1-dimethylethyl)(dimethyl)silyl]methyl}octahydro-2H-pyrazino[1,2-a]pyrazine (D86, 217 mg) in 9 mL of dichloromethane was added triethylamine (212 μL) and it was brought to −10° C. A solution of acetyl chloride (54 μL) in 2 mL of dichloromethane was added dropwise. After 15 min the reaction was quenched by addition of MeOH. The crude was purified by flash chromatography (silica, CH$_2$Cl$_2$ to CH$_2$Cl$_2$: (0.5 M NH$_3$ in MeOH) 95:5). The sample thus obtained was dissolved in CH$_2$Cl$_2$ and extracted with sat. NaHCO3. The organics were dried and the solvent removed, leading to the title compound (128 mg).

LC/MS: m/z=328 (M+1)

1H NMR (500 MHz, DMSO-d$_6$) δ ppm 4.25 (dd, 1H) 3.62 (dd, 1H) 3.36-3.46 (m, 2H) 2.83 (dd, 1H) 2.62-2.76 (m, 4H) 2.55-2.62 (m, 1H) 2.26-2.33 (m, 1H) 1.96 (s, 3H) 1.85-1.92 (m, 1H) 1.80 (t, 1H) 1.67 (t, 1H) 0.84 (s, 9H) 0.01 (s, 6H).

Description 88

N-[6-((3R,9aR or 9aS)-8-acetyl-3-{[(1,1-dimethylethyl)(dimethyl)silyl]methyl}octahydro-2H-pyrazino[1,2-a]pyrazin-2-yl)-4-(4-fluoro-2-methylphenyl)-3-pyridinyl]-2-[3,5-bis(trifluoromethyl)phenyl]-N,2-dimethylpropanamide (D88—Diastereisomer 1)

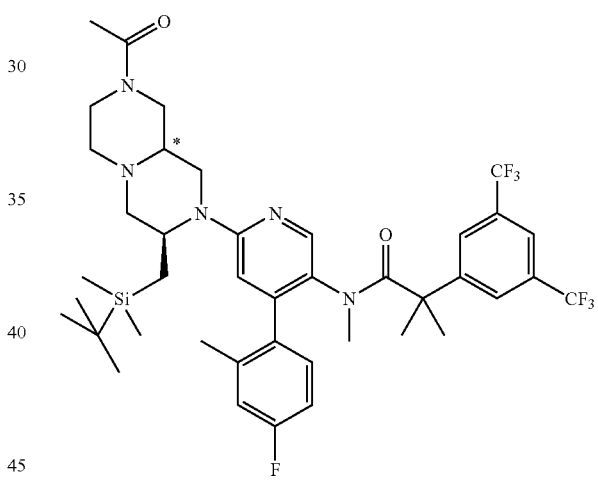

To a solution of (7R,9aR or 9aS)-2-acetyl-7-{[(1,1-dimethylethyl)(dimethyl)silyl]methyl}octahydro-2H-pyrazino[1,2-a]pyrazine (D87, 125 mg, 5.72 mmol) in 1.5 mL of toluene was added 2-[3,5-bis(trifluoromethyl)phenyl]-N-[6-chloro-4-(4-fluoro-2-methylphenyl)-3-pyridinyl]-N,2-dimethylpropanamide [WO 2005/002577] (156 mg, n mmol), bis-tri tert-butylphosphine palladium (30 mg, n mmol), hexadecyltrimethylammonium chloride (19 μL of a 25% aqueous solution) and, at last, sodium hydroxide solution (35 μL of a 50% aqueous solution). The solution was degassed by freeze-pump-thaw cycles, then stirred at 90° C. for 3.75 h. It was checked by UPLC/MS, which showed peaks for the expected product at 0.94 min. (m/z=824 (M+1), 412 (M+2)/2). The solution was diluted with EtOAc, washed with sat. NaHCO$_3$ and brine. The product were isolated by flash chromatography (cyclohexane:EtOAc 50:50→0:100), obtaining 149 mg of the title compound that were brought directly to the next step.

Description 89

(3R)-octahydro-2H-pyrazino[1,2-a]pyrazin-3-yl-methanol (D89)

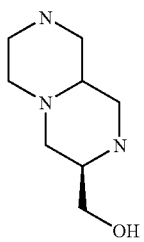

To a flask containing (3S,9aS or 9aR)-3-(hydroxymethyl)tetrahydro-2H-pyrazino[1,2-a]pyrazine-1,4(3H,6H)-dione and (3S,9aR or 9aS)-3-(hydroxymethyl)tetrahydro-2H-pyrazino[1,2-a]pyrazine-1,4(3H,6H)-dione (D83, Diastereoisomer 1 plus D84, Diastereoisomer 2, 976 mg, 4.9 mmol) was added 1M $BH_3$-THF solution (49 mL) under nitrogen and the reaction was brought to reflux (80° C.) overnight. The reaction flask was cooled to 0° C. and treated with 25 mL of MeOH. Conc. HCl was added and the resulting solution was heated to 60° C. for 5 h. The reaction was checked by direct MS (m/z=184 (M+$BH_3$)). The reaction mixture was purified by SCX, obtaining 528 mg of product.

Description 90

(3R)-3-({[(1,1-dimethylethyl)(dimethyl)silyl]oxy}methyl)octahydro-2H-pyrazino[1,2-a]pyrazine (D90)

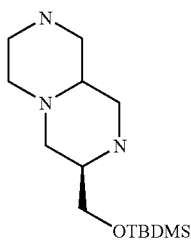

The starting (3R)-octahydro-2H-pyrazino[1,2-a]pyrazin-3-ylmethanol (D89, 528 mg, 3.08 mmol) was dissolved in 20 mL of dichloromethane and treated with $Et_3N$ (1.29 mL, 9.25 mmol) and TDBMSCl (929.5 mg, 6.17 mmol). The reaction was stirred at room temperature overnight and then for additional 24 h. It was checked by UPLC/MS, which showed conversion to product: peak at 0.47 min, m/z=286 (M+1), 172 (M-TBDMS+1). The crude was purified by flash chromatography (silica, $CH_2Cl_2$: (0.5 M $NH_3$ in MeOH) 98:2 to 85:15). The residue obtained evaporating the fractions containing the product was dissolved in dichloromethane:MeOH 90:10 and the insoluble material was filtered away. The solution was evaporated to give 638 mg of the target product.

1H NMR (400 MHz, CHLOROFORM-d) δ ppm 4.02-4.15 (m, 1H) 3.82-3.95 (m, 1H) 3.52-3.67 (m, 2H) 3.30-3.49 (m, 3H) 3.03-3.19 (m, 1H) 2.91-3.03 (m, 1H) 2.66-2.89 (m, 6H) 1.50 (t, 1H) 0.85-0.96 (m, 9H) 0.05-0.16 (m, 6H).

Description 91

(7R,9aS or 9aR)-2-acetyl-7-{[(1,1-dimethylethyl)(dimethyl)silyl]methyl}octahydro-2H-pyrazino[1,2-a]pyrazine (D91—Diastereisomer 2)

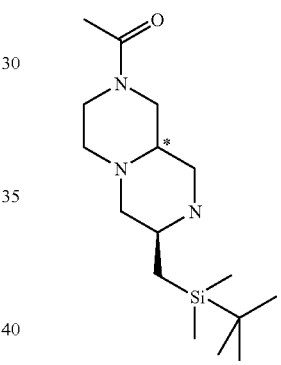

To a solution of (3R)-3-({[(1,1-dimethylethyl)(dimethyl)silyl]oxy}methyl)octahydro-2H-pyrazino[1,2-a]pyrazine (D90, 635 mg, 2.224 mmol) in 15 mL of dichloromethane was added triethylamine (620 μL, 4.45 mmol) and it was brought to −10° C. A solution of acetyl chloride (79 μL, 1.11 mmol, 0.5 eq.) in 0.5 mL of dichloromethane was added dropwise. The reaction was brought to −45° C. and additional 0.25 eq. (39.5 μL) of acetyl chloride diluted in 0.5 mL of dichloromethane were added. The temperature was lowered to −50° C. and 0.25 eq. (39.5 μL) of acetyl chloride diluted in 0.5 mL of dichloromethane were added again. The crude was purified by flash chromatography (silica, $CH_2Cl_2$ to $CH_2Cl_2$: (0.5 M $NH_3$ in MeOH) 95:5). A sample of clean title compound was thus obtained: 121 mg.

MS (direct): m/z=328 (M+1)

1H NMR (500 MHz, DMSO-$d_6$) δ ppm 4.25 (d, 1H) 3.77 (t, 1H) 3.67-3.74 (m, 2H) 3.11 (t, 1H) 2.63-2.78 (m, 2H) 2.53-2.61 (m, 2H) 2.34-2.46 (m, 2H) 2.11 (dd, 1H) 1.95-2.03 (m, 1H) 1.96 (s, 3H) 1.82-1.90 (m, 1H) 0.83-0.90 (m, 9H) 0.04 (s, 6H).

Description 92

N-[6-((3R,9aS or 9aR)-8-acetyl-3-{[(1,1-dimethylethyl)(dimethyl)silyl]methyl}octahydro-2H-pyrazino[1,2-a]pyrazin-2-yl)-4-(4-fluoro-2-methylphenyl)-3-pyridinyl]-2-[3,5-bis(trifluoromethyl)phenyl]-N,2-dimethylpropanamide (D92—Diastereoisomer 2)

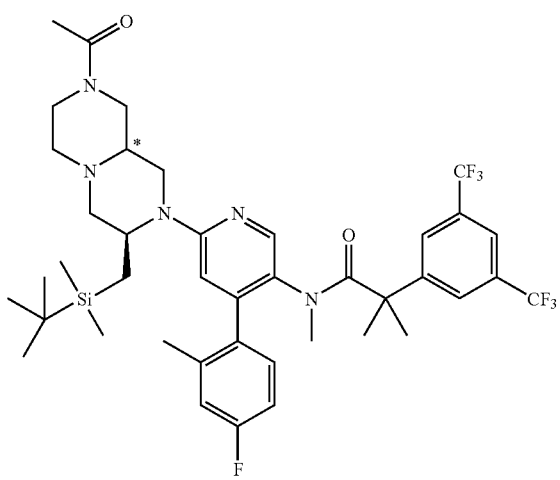

To a solution of (7R,9aS or 9aR)-2-acetyl-7-{[(1,1-dimethylethyl)(dimethyl)silyl]methyl}octahydro-2H-pyrazino[1,2-a]pyrazine (D91, 117 mg, 0.357 mmol) in 1.5 mL of toluene was added 2-[3,5-bis(trifluoromethyl)phenyl]-N-[6-chloro-4-(4-fluoro-2-methylphenyl)-3-pyridinyl]-N,2-dimethylpropanamide [WO 2005/002577] (146.5 mg, 0.275 mmol), bis-tri tert-butylphosphine palladium (28 mg, 0.055 mmol), hexadecyltrimethylammonium chloride (18 μL of a 25% aqueous solution) and, at last, sodium hydroxide solution (33 μL of a 50% aqueous solution). The solution was degassed by freeze-pump-thaw cycles, then stirred at 90° C. for 3 h. It was checked by UPLC/MS, which showed peaks for the expected product at 1.21 min. (m/z=824 (M+1), 412 (M+2)/2). The solution was diluted with EtOAc, washed with sat. NaHCO₃ and brine. The title compound was isolated by flash chromatography (silica, cyclohexane:EtOAc 50:50→0:100), obtaining 199 mg that were brought directly to the next step.

Description 93

(3R)-3-methyltetrahydro-2H-pyrazino[1,2-a]pyrazine-1,4(3H,6H)-dione (D93)

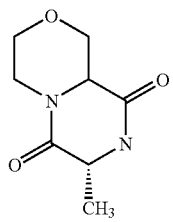

To a solution of N-boc-morpholine-3-carboxylic acid (2 g, 9.379 mmol) in 60 mL of dichloromethane and was added TBTU (3.313 g, 10.32 mmol) and diisopropylethyl amine (1.96 mL, 11.25 mmol). The reaction was stirred for 30 min. In the meantime, a solution of D-alanine methyl ester hydrochloride (1.93 g, 18.76 mmol) and diisopropylethylamine (3.27 mL, 18.76 mmol) in 20 mL of dichloromethane was prepared and finally added to the reaction mixture. The reaction was left stirring at room temperature for 2 h. UPLC-MS analysis showed the expected product (peak at 0.60 min, m/z=317 (M+1), 261 (M−t-Bu+1), 217 (M−Boc+1)). The reaction was diluted with dichloromethane and extracted with sat. NaHCO₃, dried (Na₂SO₄), and the solvent removed. The crude (5.56 g) was taken to the next step without further purification.

It was dissolved in 50 mL of dichloromethane and treated with 50 mL of TFA, added at 0° C. The reaction was stirred at room temperature for 30 min. It was checked by UPLC/MS, which showed the expected deprotection product. The crude was purified by SCX. The fractions containing the product were concentrated and the resulting solution was stirred at 50° C. for 9 h and at 80° C. for additional 19 h. UPLC/MS analysis showed formation of the cyclized product: peak at 0.34 min, m/z=185 (M+1). The solution was run through a SCX cartridge and thus was obtained the title compound, 1.095 g.

1H NMR (400 MHz, DMSO-d₆) δ ppm 8.36 (br. s., 1H) 3.80-4.22 (m, 5H) 3.33-3.41 (m, 2H) 2.68-2.84 (m, 1H) 1.25-1.37 (m, 3H).

Description 94 and 95

(7R,9aR or 9aS)-7-methyloctahydropyrazino[2,1-c][1,4]oxazine (D94—Diastereoisomer 1) and (7R,9aS or 9aR)-7-methyloctahydropyrazino[2,1-c][1,4]oxazine (D95—Diastereoisomer 2)

To a flask containing (3R)-3-methyltetrahydro-2H-pyrazino[1,2-a]pyrazine-1,4(3H,6H)-dione, mix of diastereomers, (D93, 923 mg, 5.01 mmol) was added 1M BH₃-THF solution (50 mL) and it was heated to 90° C. for 14 h. To the suspension were added 30 mL of 6M HCl and it was heated to 90° C. for 2 h. MS analysis: m/z=157 (M+1 of the target product). The reaction mixture was purified by SCX, followed by flash chromatography (silica, dichloromethane:(NH₃ in MeOH)=95:5 to 80:20. The two title compounds were isolated:

Diastereoisomer 1 (D94) (102 mg):
1H NMR (400 MHz, DMSO-d₆) δ ppm 3.65-3.73 (m, 1H) 3.53-3.60 (m, 1H) 3.43-3.52 (m, 1H) 3.02 (t, 1H) 2.68-2.81 (m, 1H) 2.52-2.68 (m, 3H) 2.25 (t, 1H) 2.07-2.19 (m, 1H) 1.88-2.00 (m, 1H) 1.68 (t, 1H) 0.91 (d, 3H)

Diastereoisomer 2 (D95) (29 mg):
1H NMR (400 MHz, DMSO-d₆) δ ppm 3.63-3.72 (m, 1H) 3.46-3.56 (m, 2H) 3.09 (t, 1H) 2.95-3.03 (m, 1H) 2.31-2.47 (m, 3H) 2.17-2.24 (m, 1H) 2.06-2.17 (m, 1H) 1.87-2.04 (m, 1H) 1.21-1.28 (m, 1H) 1.17 (d, 3H)

Description 96

2-[3,5-bis(trifluoromethyl)phenyl]-N-{4-(4-fluoro-2-methylphenyl)-6-[(7R)-7-(hydroxymethyl)octahydro-2H-pyrazino[1,2-a]pyrazin-2-yl]-3-pyridinyl}-N,2-dimethylpropanamide (D96)

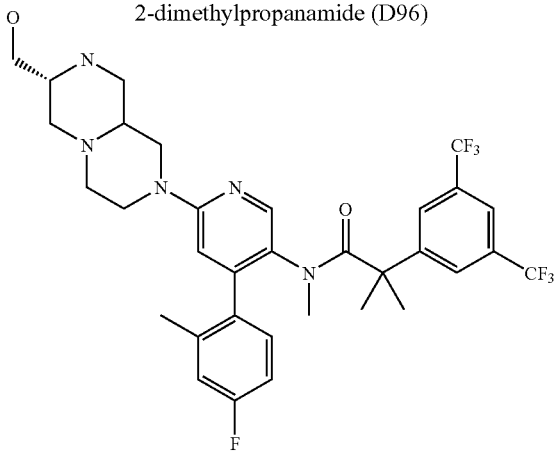

To a solution of (3R)-octahydro-2H-pyrazino[1,2-a]pyrazin-3-ylmethanol (D89, Mixture of diastereoisomers of unknown ratio, 83.5 mg, 0.496 mmol) in 1.6 mL of DMSO were added $K_2CO_3$ (78 mg) and 2-[3,5-bis(trifluoromethyl)phenyl]-N-[6-chloro-4-(4-fluoro-2-methylphenyl)-3-pyridinyl]-N,2-dimethylpropanamide [WO 2005/002577] (100 mg). The reaction was left at 150° C. for 23 h. It was checked by UPLC/MS, which showed a peak for the expected product at 0.71 min. (m/z=668 (M+1), 334 (M+2)/2). The solution was diluted with dichloromethane, extracted with water and dried ($Na_2SO_4$). The title compound obtained (113.5 mg) was taken to the next step without further purification.

1H NMR (400 MHz, DMSO-$d_6$) δ ppm 8.02 (br. s., 1H) 7.88 (br. s., 1H) 7.71 (br. s., 2H) 7.01-7.25 (m, 3H) 6.62-6.75 (m, 1H) 4.38-4.58 (m, 1H) 4.14-4.30 (m, 1H) 4.00-4.15 (m, 1H) 3.58-3.70 (m, 1H) 3.49-3.59 (m, 1H) 3.20-3.36 (m, 2H) 2.79-2.93 (m, 2H) 2.63-2.79 (m, 4H) 2.02-2.35 (m, 6H) 1.83-2.02 (m, 1H) 1.13-1.58 (m, 6H)

Ratio of Diastereoisomers not determined.

Description 97

{(3R)-2-acetyl-8-[5-[{2-[3,5-bis(trifluoromethyl)phenyl]-2-methylpropanoyl}(methyl)amino]-4-(4-fluoro-2-methylphenyl)-2-pyridinyl]octahydro-2H-pyrazino[1,2-a]pyrazin-3-yl}methyl acetate (D97)

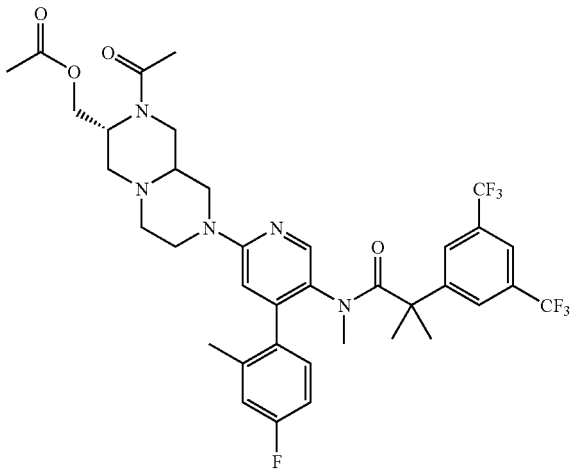

To a solution of 2-[3,5-bis(trifluoromethyl)phenyl]-N-{4-(4-fluoro-2-methylphenyl)-6-[(7R)-7-(hydroxymethyl)octahydro-2H-pyrazino[1,2-a]pyrazin-2-yl]-3-pyridinyl}-N,2-dimethylpropanamide (D96, 56 mg, 0.0838 mmol) in 10 mL of dichloromethane were added $Et_3N$ (35 μL) and a solution of acetyl chloride (15 μL) in dichloromethane (0.3 mL). The reaction was stirred at room temperature for 3 h. It was checked by UPLC/MS, which showed a peak for the expected product at 0.89 min. (m/z=752 (M+1), 376 (M+2)/2). The solution was diluted with dichloromethane, extracted with water and dried ($Na_2SO_4$). The crude was purified by flash chromatography (cyclohexane to EtOAc), obtaining 28.5 mg of the title compound.

1H NMR (400 MHz, CHLOROFORM-d) δ ppm 8.00 (br. s., 1H) 7.78 (br. s., 1H) 7.65 (br. s., 2H) 6.80-7.08 (m, 3H) 6.41-6.52 (m, 1H) 4.42-4.70 (m, 2H) 4.17-4.40 (m, 2H) 3.95-4.17 (m, 2H) 3.53-3.65 (m, 1H) 2.98-3.26 (m, 2H) 2.74-2.93 (m, 3H) 2.49-2.74 (m, 3H) 2.21-2.47 (m, 5H) 2.02-2.21 (m, 9H) 1.46-1.55 (m, 3H)

UPLC/MS: peak @ 0.89 min. m/z=752 (M+1), 376 (M+2)/2.

Ratio of Diastereoisomers not determined.

Description 98

(3R)-3-methyltetrahydro-2H-pyrazino[1,2-a]pyrazine-1,4(3H,6H)-dione (D98)

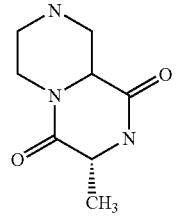

To a solution of N,N'-diboc-piperazine-2-carboxylic acid (2 g, 6.06 mmol) in 50 mL of dichloromethane and was added TBTU (2.138 g, 6.66 mmol) and diisopropylethyl amine (1.3 mL, 7.26 mmol). The reaction was stirred for 45 min. In the meantime, a suspension of D-alanine methyl ester hydrochloride (1.249 g, 12.11 mmol) and diisopropylethylamine (3.27 mL, 18.76 mmol) in 20 mL of dichloromethane and 5 mL of DMF was stirred and finally added to the reaction mixture. The reaction was left stirring at room temperature overnight. UPLC-MS analysis showed the expected product (peak at 0.72 min, m/z=416 (M+1), 360 (M-t-Bu+1). The reaction was diluted with dichloromethane and extracted with sat. $NaHCO_3$, dried ($Na_2SO_4$), and the solvent removed. The crude (4.242 g) was taken to the next step without further purification.

It was dissolved in 50 mL of dichloromethane and to the solution was added dropwise TFA (50 mL) at 0° C. The reaction was stirred at room temperature for 2 h. It was checked by UPLC/MS. The reaction mixture was evaporated and the crude was purified by SCX. The fractions containing the product were collected and their volume reduced and the resulting solution was stirred at 60° C. overnight. UPLC/MS analysis showed formation of the cyclized product: peak at 0.17 min, m/z=184 (M+1). The solvent was removed and the residue taken treated in methanol. The white precipitate was collected by filtration, giving 353 mg of the title compound (additional 156 mg of precipitate formed from the solution).

1H NMR (400 MHz, DMSO-$d_6$) δ ppm 8.24 (br. s., 0.5H) 7.96 (br. s., 0.5H) 3.79-4.29 (m, 2H) 3.10-3.31 (m, 1H) 2.73-3.11 (m, 2H) 2.52-2.73 (m, 2H) 1.30 (d, 1.5H) 1.21 (d, 1.5H)

Description 99

(3R)-3-methyloctahydro-2H-pyrazino[1,2-a]pyrazine (D99)

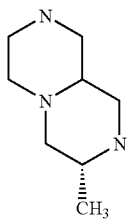

To a flask containing (3R)-3-methyltetrahydro-2H-pyrazino[1,2-a]pyrazine-1,4(3H,6H)-dione (D98, 353 mg, 1.927 mmol) was added 1M BH$_3$-THF solution (20 mL) and it was heated to reflux for 20 h. MS analysis: m/z=156 (M+1 of the target product). To the reaction were added at 0° C. 10 mL of 6M HCl and it was heated to 90° C. for 20 h. The reaction mixture was purified by SCX, obtaining 243 mg of the target compound.

1H NMR (400 MHz, DMSO-d$_6$) consistent with a mixture of diastereomers of the target compound.

Description 100 and 101

(7R,9aR or 9aS)-2-acetyl-7-methyloctahydro-2H-pyrazino[1,2-a]pyrazine (D100, Diastereoisomer 1) and (7R,9aS or 9aR)-2-acetyl-7-methyloctahydro-2H-pyrazino[1,2-a]pyrazine (D101, Diastereoisomer 2)

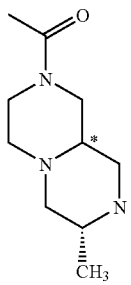

To a solution (3R)-3-methyloctahydro-2H-pyrazino[1,2-a]pyrazine (D99, 243 mg, 1.232 mmol) in DMF (35 mL) was added triethylamine (260 µL, 1.848 mmol). The solution was cooled to −60° C. and a solution of acetic anhydride (95 µL, 0.986 mmol) in DMF (3 mL) was added dropwise. The reaction was allowed to reach −60° C. slowly. UPLC/MS analysis: peaks @ 0.18 and 0.24 min, both m/z=198 (M+1 of the target product). The reaction mixture was purified by SCX, followed by flash chromatography (silica, dichloromethane to dichloromethane:MeOH 85:15) Two different samples were thus obtained:
Diastereoisomer 1 (D100) (101.5 mg):
1H NMR (500 MHz, DMSO-d$_6$) δ ppm 4.26 (dd, 1H) 4.16 (dd, 1H) 2.52-2.82 (m, 5H) 2.26-2.33 (m, 1H) 2.16 (t, 1H) 1.96 (s, 3H) 1.83-1.90 (m, 1H) 1.56-1.70 (m, 2H) 0.90 (d, 3H)
Diastereoisomer 1 and 2 (D100 plus D101) (75 mg):

The NMR sample consisted of a mixture of two components, ratio ca. 3:1. The major component is equal to Diastereoisomer 1. The minor one appears consistent with its Diastereoisomer 2.

Description 102

Methyl N-(phenylmethyl)-D-serinate (D102)

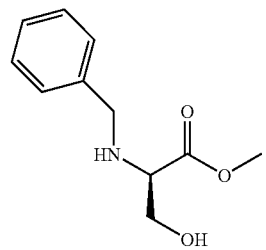

The title compound was prepared according to literature (ref. *JOC*, 1990, 55(1), 111-122) starting from (D)-serine methyl ester hydrochloride (98%, from Aldrich) (D)-serine methyl ester hydrochloride (10 g, 0.065 moles) was suspended in 50 ml of anhydrous methanol and cooled to 0° C. under nitrogen. Triethylamine (9 ml, 0.065 moles) was added dropwise, followed by benzaldehyde (6.6 ml, 0.065 moles). The reaction mixture was then warmed up and stirred at room temperature for 2 hours. Sodium borohydride (4.85 g, 0.13 moles) were added in small portions over 2 hours. The resulting mixture was stirred at room temperature overnight. The mixture was then slowly added to 50 ml of HCl (20% solution) at 0° C. and the resulting solution was washed with diethyl ether (50 ml). The aqueous layer was then brought to basic pH by adding solid potassium carbonate and extracted with diethyl ether (3×50 ml). The combined organic extracts were dried (Na$_2$SO$_4$) and concentrated under vacuum to afford the title compound as colourless oil (10.95 g). m/z=210 [M+H]$^+$

Description 103

1,1-dimethylethyl (3R)-3-{[[(1R)-1-(hydroxymethyl)-2-(methyloxy)-2-oxoethyl]phenylmethyl)amino]carbonyl}-4-morpholinecarboxylate (non-preferred name) (D103)

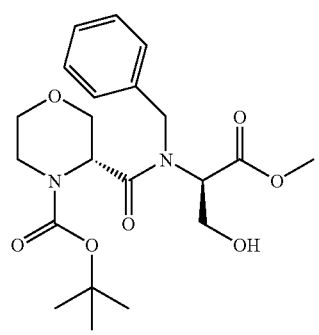

To a stirred suspension of (R)-4-Boc-morpholine-3-carboxylic acid (30 g, 0.13 moles, from J&W PharmLab) in 500 ml of anhydrous DCM at room temperature under nitrogen, N-(3-dimethylaminopropyl)-N'-ethylcarbodiimide hydrochloride (37.4 g, 0.195 moles) and 1-hydroxybenzotriazole hydrate (19.3 g, 0.143 moles) were added in portions. At the end of addition the suspension became almost a clear solution. The mixture was stirred at room temperature for 45 minutes and then Methyl N-(phenylmethyl)-D-serinate (D102, 28.6 g, 0.137 moles) and N,N-diisopropylethylamine (45.3 ml, 0.26 moles) were added in small portions. The mixture was stirred at room temperature for 26 hours and then was additioned with ammonium chloride (sat. solution, 250 ml) and DCM (150 ml). Phases were separated and the aqueous layer was extracted with DCM (3×150 ml) and EtAc (1×200 ml). The combined organic extracts were washed with brine (2×500 ml), dried (Na₂SO₄), concentrated under vacuum and the residue purified by silica gel chromatography eluting with 0 to 30% EtOAc/Cyclohexane to afford the title compound as yellow oil (38.7 g).

UPLC/MS: peak at Rt=0.62 min with m/z=423.1 [M+H]⁺

Description 104

(7R,9aR)-7-(hydroxymethyl)-8-(phenylmethyl)
hexahydropyrazino[2,1-c][1,4]oxazine-6,9-dione)
(D104)

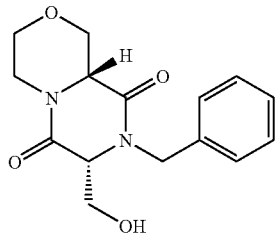

To a stirred solution of 1,1-dimethylethyl (3R)-3-{[[(1R)-1-(hydroxymethyl)-2-(methyloxy)-2-oxoethyl]phenylmethyl)amino]carbonyl}-4-morpholinecarboxylate (D103, 38.7 g, 0.092 moles) in 400 ml of DCM at room temperature, trifluoroacetic acid (68.3 ml, 0.92 moles) was slowly added. The resulting orange solution was stirred at room temperature overnight. It was then cooled by an ice-water bath and brought to pH=7-8 by adding sodium hydrogen carbonate (sat. solution, 250 ml and as solid). Phases were separated and the aqueous layer was extracted with DCM (3×300 ml). The combined organic extracts were dried (Na₂SO₄), concentrated under vacuum to afford a residue, which was dissolved in 270 ml of methanol and heated to 56-58° C. for 2 hours. The mixture was then allowed to cool down to room temperature and the solvent was removed under vacuum to afford a solid residue, which was treated with 100 ml of a mixture cyclohexane/EtOAc 8/2. The resulting suspension was stirred at room temperature for 30-40 minutes and then the solid was filtered off and collected to afford the title compound (18.7 g) as white solid.

UPLC/MS: peak at Rt=0.49 min with m/z=291.09 [M+H]⁺

1H NMR (400 MHz, DMSO-d₆) δ ppm 7.26-7.37 (m, 5H) 5.41 (t, 1H) 5.09 (d, 1H) 4.31 (dd, 1H) 4.23 (dd, 1H) 4.01-4.07 (m, 2H) 3.69-3.84 (m, 4H) 3.59 (t, 1H) 3.33 (td, 1H) 2.85 (td, 1H).

Description 105

[(7S,9aS)-8-(phenylmethyl)octahydropyrazino[2,1-c]
[1,4]oxazin-7-yl]methanol (D105)

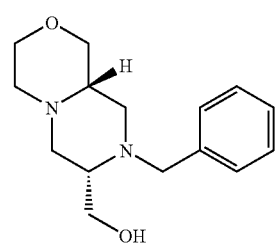

To a stirred suspension of (7R,9aR)-7-(hydroxymethyl)-8-(phenylmethyl)hexahydropyrazino[2,1-c][1,4]oxazine-6,9-dione) (D104, 18.7 g, 0.064 moles) in 190 ml of anhydrous THF at 0° C. under nitrogen, borane (THF complex solution, 1M in THF, 385 ml, 0.386 moles) was added over 45 minutes keeping the internal temperature below 10° C. At the end of the addition the mixture became a colourless solution. The mixture was then allowed to warm to room temperature and then heated to 70° C. for 28 hours.

The mixture was then allowed to cool down to room temperature and then to 0° C. by an ice-water bath. Methanol (47 ml, 1.15 moles) and HCl 6M (32 ml, 0.128 moles) were then slowly added, carefully monitoring the gas evolution. The resulting mixture was then allowed to warm to room temperature and stirred overnight. The mixture was then heated to 55° C. for 8 hours and then cooled down to room temperature. The white precipitate was filtered off and the filtrate was concentrated under vacuum to afford a residue, which was dissolved in 50 ml of water and 100 ml of DCM. The white precipitate which was previously filtered off was collected and dissolved in 70 ml of water and added to the previous mixture. Phases were separated and the aqueous layer was extracted with DCM (3×150 ml). The aqueous layer was then brought to pH=7 by adding 250 ml of NaOH 3N and extracted again with DCM (3×100 ml) and ethyl acetate (3×200 ml). The combined organic extracts were dried (Na₂SO₄) and concentrated under vacuum to afford the title compound as pale yellow foam (16.9 g).

UPLC/MS: peak at Rt=0.40 min with m/z=263.13 [M+H]⁺

Description 106

(7S,9aS)-7-({[(1,1-dimethylethyl)(dimethyl)silyl]oxy}methyl)-8-(phenylmethyl)octahydropyrazino[2,1-c][1,4]oxazine (D106)

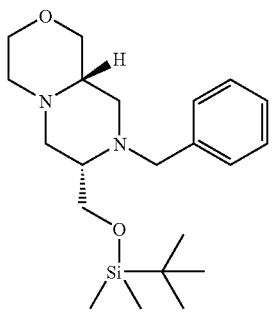

Method a):

To a stirred solution of [(7S,9aS)-8-(phenylmethyl)octahydropyrazino[2,1-c][1,4]oxazin-7-yl]methanol (D105, 15.3 g, 0.058 moles) in 153 ml of DCM at room temperature, imidazole (4.76 g, 0.070 moles) and tert-butyldimethylsilyl chloride (8.35 g, 0.055 moles) were added. The resulting mixture was stirred at room temperature for 1 hour. Imidazole (0.476 g, 5.8 mmoles) and tert-butyldimethylsilyl chloride (8.35 g, 0.055 moles) were then added a second time and the mixture stirred overnight. Imidazole (0.476 g, 0.006 moles) and tert-butyldimethylsilyl chloride (5.27 g, 0.035 moles) were then added a third time and the mixture stirred for further 4 hours. DCM (153 ml) was added and the imidazole (2.4, 0.035 moles) and tert-butyldimethylsilyl chloride (5.27 g, 0.035 moles) were then added a fourth time. The mixture was stirred overnight. Water (150 ml) and sodium hydrogen carbonate (sat. solution, 150 ml) were then added and phases were separated. The aqueous layer was extracted with DCM (150 ml) and the combined organic extracts were dried ($Na_2SO_4$) and concentrated under vacuum to a residue, purified by silica gel chromatography eluting with 5 to 10% EtOAc/Cyclohexane to afford the title compound as an oil (22.2 g).

1H NMR (500 MHz, DMSO-$d_6$) δ ppm 7.32-7.36 (m, 4H) 7.24-7.29 (m, 1H) 4.00 (t, 1H) 3.90 (dd, 1H) 3.88 (d, 1H) 3.77 (dd, 1H) 3.70 (d, 1H) 3.52-3.58 (m, 1H) 3.48-3.56 (m, 1H) 3.07 (t, 1H) 2.75-2.83 (m, 2H) 2.25-2.37 (m, 4H) 2.12-2.23 (m, 2H) 0.90 (s, 9H) 0.08 (s, 3H) 0.06 (s, 3H)

HPLC (walk-up): Rt=4.826 min (area %=98.69)

Method b)

To a stirred solution of [(7S,9aS)-8-(phenylmethyl)octahydropyrazino[2,1-c][1,4]oxazin-7-yl]methanol (D105, 29.8 g, 0.114 moles) in 447 ml of DCM at room temperature, imidazole (9.27 g, 0.136 moles) and tert-butyldimethylsilyl chloride (42.7 g, 0.284 moles) were added. The resulting mixture was stirred at room temperature overnight. Water (300 ml), sodium hydrogen carbonate (sat. solution, 300 ml) and DCM (150 ml) were then added and phases were separated. The aqueous layer was extracted with DCM (300 ml) and the combined organic extracts were dried ($Na_2SO_4$) and concentrated under vacuum to a residue, purified by silica gel chromatography eluting with 5 to 10% EtOAc/Cyclohexane to afford the title compound as light yellow oil (50.95 g).

HPLC (walk-up): Rt=4.865 min (area %=99.55).

Description 107

(7S,9aS)-7-({[(1,1-dimethylethyl)(dimethyl)silyl]oxy}methyl)octahydropyrazino[2,1c][1,4]oxazine (D107)

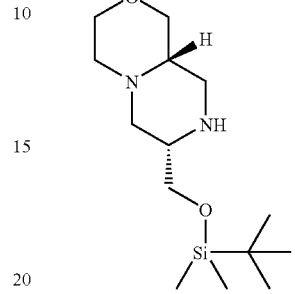

To a stirred solution of (7S,9aS)-7-({[(1,1-dimethylethyl)(dimethyl)silyl]oxy}methyl)-8-(phenylmethyl)octahydropyrazino[2,1-c][1,4]oxazine (D106, 22.2 g, 0.059 moles) in 660 ml of methanol at room temperature under nitrogen, palladium on carbon (10 wt %, wet, 6.28 g, 0.006 moles) and ammonium formate (37.2 g, 0.59 moles) were added. The resulting mixture was stirred at 80° C. for 1-1.5 hours. The resulting mixture was then allowed to cool down to room temperature and filtered over Celite. The filtrate was concentrated under vacuum to afford the title compound (16 g) as pale yellow oil.

UPLC/MS: no UV visible peak. Mass m/z=287.18 $[M+H]^+$

CASS ID 8341, NMR and LC/MS

1H NMR (500 MHz, DMSO-$d_6$) δ ppm 3.74 (t, 1H) 3.62-3.70 (m, 2H) 3.48 (dd, 1H) 3.39-3.46 (m, 1H) 2.98 (t, 1H) 2.67-2.73 (m, 1H) 2.60 (dd, 1H) 2.40 (dd, 1 H) 2.26-2.37 (m, 2H) 2.23 (br. s., 1H) 2.12 (dd, 1H) 2.04-2.10 (m, 1H) 1.90-2.00 (m, 1H) 0.81 (s, 9H)-0.00 (s, 6H)

ROESY cross peak pattern in accordance with the syn relative stereochemistry.

Description 108

1,1-dimethylethyl (2R)-2-[({[(phenylmethyl)oxy]carbonyl}amino)methyl]-1-pyrrolidinecarboxylate) (D108)

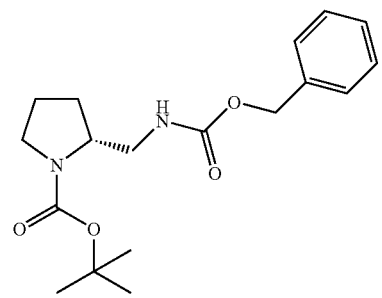

To a solution of (R)-2-(Aminomethyl)-1-N-Boc-pyrrolidine (1.6 g, 8 mmol) in 25 mL of dichloromethane was added DIPEA (2.09 mL, 12 mmol) and at 0° C. Benzyl Chloroformate (1.36 mL, 9.6 mmol). The reaction mixture was warmed-up to r.t. and then it was stirred for 3 hrs at this temperature.

Brine was added to the reaction mixture, the aqueous phase was extracted with dichloromethane and the combined organic phases were dried and evaporated to dryness. The crude was purified by chromatography (silica cartridge, cyclohexane:EtOAc 9:1) to give the title compound (2.07 g, y=77%).

MS: m/z=357 (M+Na) and 235 (M-BOC+1).

1H NMR (400 MHz, DMSO-$d_6$) δ ppm 6.98-7.49 (m, 6H) 4.88-5.15 (m, 2H) 3.58-3.83 (m, 1H) 3.05-3.32 (m, 3H) 2.75-3.04 (m, 1H) 1.52-1.98 (m, 4H) 1.20-1.49 (m, 9H)

Description 109 phenylmethyl [(2R)-2-pyrrolidinylmethyl]carbamate (D109)

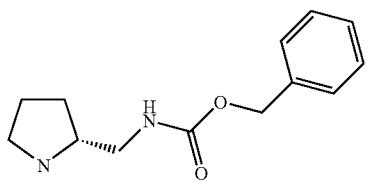

To a solution of 1,1-dimethylethyl (2R)-2-[({[(phenylmethyl)oxy]carbonyl}amino)methyl]-1-pyrrolidinecarboxylate (D108, 2.07 g, 6.1 mmol) in 16 ml of dichloromethane, cooled to 0° C., were added 4 ml of TFA. The reaction mixture was allowed to warm-up to r.t. and then it was stirred at this temperature for 30 mins. The title compound (1.06 g, y=88%) was isolated after purification by SCX.

1H NMR (400 MHz, DMSO-$d_6$) δ ppm 7.00-7.66 (m, 5H) 4.90-5.20 (m, 2H) 3.12-3.24 (m, 1H) 2.97-3.09 (m, 1H) 2.84-2.97 (m, 2H) 2.61-2.82 (m, 2H) 1.44-1.83 (m, 3H) 1.14-1.40 (m, 1H)

Description 110 diethyl {(2R)-2-[({[(phenylmethyl)oxy]carbonyl}amino)methyl]-1-pyrrolidinyl}propanedioate (D110)

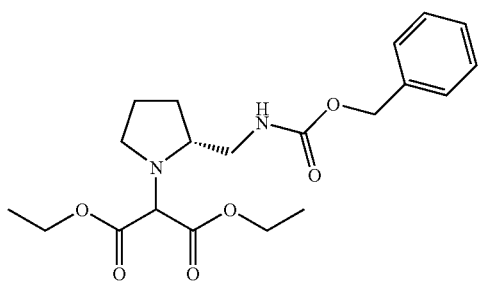

To a mixture of phenylmethyl [(2R)-2-pyrrolidinylmethyl]carbamate (D109, 1.26 g, 5.38 mmol) and $K_2CO_3$ (1.48 g, 10.76 mmol) in acetonitrile (20 ml), cooled to 0° C., was added dropwise diethyl bromomalonate (1.08 ml, 6.46 mmol) in a 2-3 mins time. Then the reaction mixture was allowed to warm-up to r.t. and it was stirred at this temperature for 2.5 hrs. Further diethyl bromomalonate (1.08 ml, 1.6 mmol) was added and the reaction mixture was stirred for one more hour.

The solvent was removed, water was added and it was extracted with EtOAc. The crude was purified by chromatography (silica cartridge, cyclohexane:EtOAc 95:5) to give the title compound (1.07 g).

MS: m/z=393 (M+1) and 415 (M+Na)

UPLC/MS: m/z=393 (M+1) @ t=0.79 min

1H NMR (400 MHz, DMSO-$d_6$) δ ppm 7.25-7.45 (m, 5H) 7.08-7.23 (m, 1H) 4.91-5.06 (m, 2H) 4.40-4.50 (m, 1H) 3.93-4.23 (m, 4H) 2.94-3.14 (m, 3H) 2.70-2.90 (m, 2H) 1.45-1.89 (m, 4H) 1.07-1.28 (m, 6H)

Description 111 ethyl (8aR)-3-oxooctahydropyrrolo[1,2-a]pyrazine-4-carboxylate (D111)

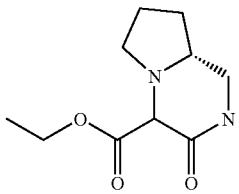

The solution of diethyl {(2R)-2-[({[(phenylmethyl)oxy]carbonyl}amino)methyl]-1-pyrrolidinyl}propanedioate (D110, 1.07 g, 2.72 mmol) in EtOH (ca. 20 ml) was degassed, (10%) Pd/C (580 mg) was added and the reaction mixture was stirred under a $H_2$ atmosphere for 2.5 hrs. The catalyst was filtered off and the volume of the filtrated solution was reduced in vacuo. The solution was warmed-up to 50° C. and it was stirred at this temperature for 6 hrs and at room temperature for 12 hrs. The solvent was evaporated to dryness to give the title compound (617 mg) as a mixture of diastereoisomers (ratio ca. 70:30). This crude was used in the next step without further purification.

MS: m/z=213 (M+1)

1H NMR (400 MHz, DMSO-$d_6$) δ ppm 7.93-8.12 (m, 1H) 4.03-4.27 (m, 3H) 3.15-3.30 (m, 1H) 2.91-3.07 (m, 1H) 2.77-2.93 (m, 1H) 2.37-2.47 (m, 1H) 2.03-2.15 (m, 1H) 1.63-1.94 (m, 3H) 1.26-1.50 (m, 1H) 1.04-1.28 (m, 3H)

The ratio between the two diastereoisomers was determined on the basis of the integral ratio of diagnostic peaks such as the N—H lactam signals found in 7.93-8.12 range.

Description 112

(8aR)-octahydropyrrolo[1,2-a]pyrazin-4-ylmethanol (D112)

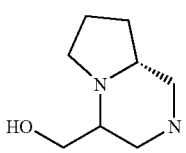

To a solution of ethyl (8aR)-3-oxooctahydropyrrolo[1,2-a]pyrazine-4-carboxylate (D111, 207 mg, 0.976 mmol) in THF (0.5 ml) was added 2M LiBH$_4$ in THF (1.46 ml) and the reaction mixture was refluxed for 17 hrs. The reaction mixture was cooled down to r.t., 9.7 ml of 1M BH$_3$-THF were added and the mixture was refluxed for 2 hrs.

The reaction mixture was cooled down to 0° C. and 4 ml of MeOH were added. Then 1.5 ml of conc. HCl were added at 0° C. and the reaction mixture was refluxed for 1 hr. The solvent was evaporated to dryness and the crude was purified by SCX cartridge and then by chromatography (silica, CH$_2$Cl$_2$: 2M NH$_3$ in MeOH 9:1 to 8:2) to give the title compound (73 mg) as a mixture of diastereoisomers.

MS: m/z=157 (M+1)

1H NMR (300 MHz, DMSO-d$_6$) δ ppm 4.2-4.4 (m, 1H) 3.44-3.63 (m, 1H) 3.04-3.22 (m, 2H) 2.54-2.97 (m, 4H) 2.05-2.31 (m, 1H) 1.84-2.03 (m, 1H) 1.40-1.85 (m, 3H) 0.99-1.32 (m, 1H)

Description 113

1,1-dimethylethyl (2S)-2-[({[(phenylmethyl)oxy]carbonyl}amino)methyl]-1-pyrrolidinecarboxylate (D113)

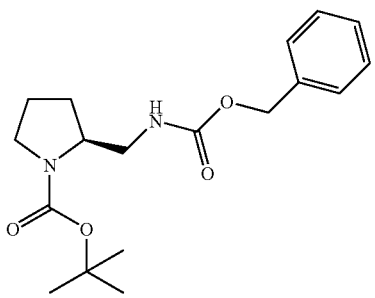

To a solution of (S)-2-(Aminomethyl)-1-N-Boc-pyrrolidine (1.65 g, 8.25 mmol) in 25 mL of dichloromethane was added DIPEA (2.15 mL, 12.3 mmol) and at 0° C. Benzyl Chloroformate (1.41 mL, 9.9 mmol). The reaction mixture was warmed-up to r.t. and then it was stirred for 3 hrs at this temperature.

Brine was added to the reaction mixture, the aqueous layer was extracted with dichloromethane and the combined organic phases were dried and evaporated to dryness. The crude was purified by chromatography (silica cartridge, cyclohexane:EtOAc 9:1) to give the title compound (2.23 g, y=80%).

MS: m/z=235 (M-BOC+1)

UPLC/MS: m/z=235 (M-BOC+1); 335 (M+1) @ t=0.8 min

1H NMR (400 MHz, DMSO-d$_6$) δ ppm 6.98-7.49 (m, 6H) 4.88-5.15 (m, 2H) 3.58-3.83 (m, 1H) 3.05-3.32 (m, 3H) 2.75-3.04 (m, 1H) 1.52-1.98 (m, 4H) 1.20-1.49 (m, 9H)

Description 114 phenylmethyl [(2S)-2-pyrrolidinylmethyl]carbamate (D114)

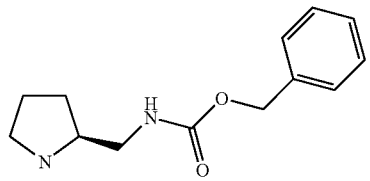

To a solution of 1,1-dimethylethyl (2S)-2-[({[(phenylmethyl)oxy]carbonyl}amino)methyl]-1-pyrrolidinecarboxylate (D113, 2.23 g, 6.67 mmol) in 16 mL of dichloromethane, cooled to 0° C., were added 4 mL of TFA. The reaction mixture was allowed to warm-up to r.t. and then it was stirred at this temperature for 30 mins. The title compound was isolated as a colourless oil after purification by SCX (1.36 g).

MS: m/z=235 (M-BOC+1)

1H NMR (400 MHz, DMSO-d$_6$) δ ppm 7.04-7.47 (m, 6H) 4.82-5.16 (m, 2H) 3.11-3.46 (m, 1H) 2.97-3.09 (m, 1H) 2.84-2.97 (m, 2H) 2.61-2.82 (m, 2H) 1.40-1.83 (m, 3H) 1.10-1.37 (m, 1H)

Description 115 diethyl {(2S)-2-[({[(phenylmethyl)oxy]carbonyl}amino)methyl]-1-pyrrolidinyl}propanedioate (D115)

To a mixture of phenylmethyl [(2S)-2-pyrrolidinylmethyl]carbamate (D114, 1.36 g, 5.81 mmol) and K$_2$CO$_3$ (1.6 g, 11.62 mmol) in acetonitrile (20 ml), cooled to 0° C., was added dropwise diethyl bromomalonate (1.37 ml, 6.97 mmol) in a 2-3 mins time. Then the reaction mixture was allowed to warm-up to room temperature and it was stirred for 4 hrs.

The volume of the solvent was reduced, brine was added and it was extracted with dichloromethane. The combined organic phases were dried and evaporated to dryness. The crude was purified by chromatography (silica cartridge, cyclohexane:EtOAc 95:5 to 7:3) to give the title compound as a colourless oil (1.40 g, y=61%).

1H NMR (400 MHz, DMSO-d$_6$) δ ppm 7.23-7.48 (m, 5H) 7.09-7.21 (m, 1H) 4.87-5.08 (m, 2H) 4.40-4.50 (m, 1H) 3.98-4.23 (m, 4H) 2.93-3.16 (m, 3H) 2.62-2.91 (m, 2H) 1.43-1.92 (m, 4H) 1.00-1.30 (m, 6H)

Description 116 ethyl (8aS)-3-oxooctahydropyrrolo[1,2-a]pyrazine-4-carboxylate (D116)

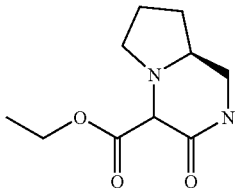

The solution of diethyl {(2S)-2-[({[(phenylmethyl)oxy]carbonyl}amino)methyl]-1-pyrrolidinyl}propanedioate (D115, 1.40 g, 3.67 mmol) in EtOH (ca. 20 ml) was degassed, (10%) Pd/C (778 mg, 0.734 mmol) was added and the reaction mixture was stirred under a $H_2$ atmosphere for 2.5 hrs. The catalyst was filtered off and the volume of the filtrated solution was reduced in vacuo. The solution was warmed-up to 50° C. and it was stirred at this temperature for 7 hrs. The solvent was evaporated to dryness to give the title compound as a yellowish oil (793 mg) as a mixture of diastereoisomers. This crude was used in the next step without further purification.

MS: m/z=213 (M+1)

1H NMR (400 MHz, DMSO-$d_6$) δ ppm 7.90-8.11 (m, 1H) 4.02-4.43 (m, 3H) 3.15-3.30 (m, 1H) 2.79-3.07 (m, 2H) 2.36-2.56 (m, 1H) 2.0-2.2 (m, 1H) 1.63-2.18 (m, 3H) 1.26-1.51 (m, 1H) 1.13-1.27 (m, 3H)

Description 117

(8aS)-octahydropyrrolo[1,2-a]pyrazin-4-ylmethanol (117)

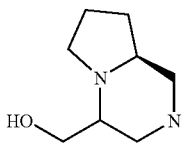

To a solution of ethyl (8aS)-3-oxooctahydropyrrolo[1,2-a]pyrazine-4-carboxylate (D116, 403 mg, 1.88 mmol) in THF (ca. 3 ml) was added 2M $LiBH_4$ in THF (1.41 ml, 2.83 mmol) and the reaction mixture was refluxed overnight. The reaction mixture was cooled down to r.t., 18.8 ml of 1M $BH_3$-THF were added and the mixture was refluxed for 2 hrs.

The reaction mixture was cooled down to 0° C. and 8 ml of MeOH were added. Then 3 ml of conc. HCl were added and the reaction mixture was refluxed for ca. 2 hrs. The solvents were evaporated to dryness and the crude was purified by SCX to give the title compound as a colourless oil (220 mg). It's a mixture of diastereoisomers.

MS: m/z=157 (M+1)

1H NMR (400 MHz, DMSO-$d_6$) δ ppm 4.29-4.47 (m, 1H) 3.46-3.64 (m, 1H) 3.10-3.45 (m, 2H) 2.82-2.96 (m, 1H) 2.50-2.81 (m, 3H) 1.44-2.38 (m, 5H) 1.01-1.31 (m, 1H)

Description 118

1,1-dimethylethyl 3-({[(1S)-1-(hydroxymethyl)-2-(methyloxy)-2-oxoethyl]amino}carbonyl)-4-thiomorpholinecarboxylate (D118)

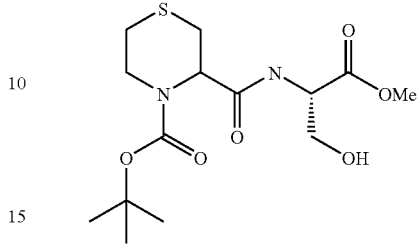

To a solution of N-Boc thiomorpholine carboxylic acid (1.36 g, 5.51 mmol) in dichloromethane (13.6 ml) were added under $N_2$, at r.t., TBTU (1.95 g, 6.06 mmol) and DIPEA (1.92 ml, 11.02 mmol) and the solution was stirred for 30 mins. To a suspension of L-serine methyl ester hydrochloride (1.71 g, 11.02 mmol) in dichloromethane (13.6 ml) was added DIPEA (1.92 ml, 11.02 mmol) and the resulting solution was stirred for 30 mins. Then the solution containing the serine free base was added to the reaction mixture and it was left stirring for 16 hrs. Water was added to the reaction mixture and the aqueous layer was extracted with dichloromethane (×3) and the combined organic phases were dried ($Na_2SO_4$) and evaporated to dryness. The crude title compound (3.87 g) was used in the next step without further purification.

UPLC/MS: m/z=371 (M+Na); 349 (M+1); 293 (M-tBu); 249 (M-BOC+1) @ t=0.59 min

Description 119

(7S)-7-(hydroxymethyl)hexahydropyrazino[2,1-c][1,4]thiazine-6,9-dione (D119)

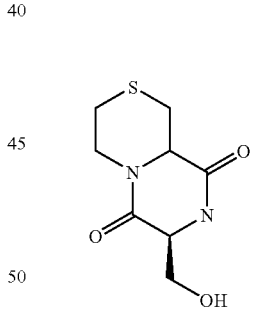

To a solution of the crude 1,1-dimethylethyl 3-({[(1S)-1-(hydroxymethyl)-2-(methyloxy)-2-oxoethyl]amino}carbonyl)-4-thiomorpholinecarboxylate (D118, 3.87 g) in 44 ml of dichloromethane were added under $N_2$, at r.t., 22 ml of TFA. The reaction mixture was stirred at room temperature for 3 hrs. The solvents were removed under reduced pressure and the residue was purified on a SCX cartridge. The fraction eluted with 2M methanolic ammonia was evaporated to dryness and the residue was dissolved in MeOH and refluxed for 20 hrs.

The reaction mixture was evaporated to dryness and the desired product was purified by SCX, eluting with MeOH. The title compound (1.1 g, y=92% over 2 steps) was isolated as a mixture of diastereoisomers (ratio ~50/50).

UPLC/MS: 1st peak m/z=217 (M+1) @ t=0.35 min; 2nd peak m/z=217 (M+1) @ t=0.36 min 1H NMR (400 MHz, DMSO-$d_6$) δ ppm 8.07-8.31 (m, 1H) 4.62-4.82 (m, 1H) 3.95-4.18 (m, 1H) 3.69-3.95 (m, 2H) 3.30-3.66 (m, 2H) 2.85-3.02 (m, 1H) 2.69-2.86 (m, 2H) 2.52-2.68 (m, 1H).

The ratio between the two diastereoisomers was determined on the basis of the integral ratio of diagnostic peaks such as the N—H lactam signals found in 8.07-8.31 range.

Description 120

(7S)-7-(hydroxymethyl)hexahydropyrazino[2,1-c][1,4]thiazine-6,9-dione 2,2-dioxide (D120)

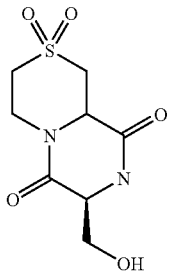

To a suspension of (7S)-7-(hydroxymethyl)hexahydropyrazino[2,1-c][1,4]thiazine-6,9-dione (D119, 1.1 g, 5.09 mmol) in dichloromethane (22 ml) was added at r.t. 77% m-CPBA (2.85 g, 12.73 mmol) and the reaction mixture was stirred at room temperature for 2 hrs. The solvent was removed under reduced pressure and the crude was purified by chromatography (silica, $CH_2Cl_2$: 2M $NH_3$ in MeOH 98:2 to 8:2) to give the title compound as a white solid (900 mg, y=71%) as a mixture of diastereoisomers (ratio ~60/40).

MS: m/z=249 (M+1) and 271 (M+Na)

1H NMR (500 MHz, DMSO-$d_6$) δ ppm 8.29-8.54 (m, 1H) 5.02-5.59 (m, 1H) 4.59-4.89 (m, 1H) 4.16-4.47 (m, 1H) 3.86-3.99 (m, 1H) 3.69-3.86 (m, 1H) 3.50-3.68 (m, 1H) 3.21-3.48 (m, 3H) 2.91-3.20 (m, 2H)

The ratio between the two diastereoisomers was determined on the basis of the integral ratio of diagnostic peaks such as the O—H alcohol signals found in 5.02-5.59 range.

Description 121

[(7R)-2,2-dioxidooctahydropyrazino[2,1-c][1,4]thiazin-7-yl]methanol (D121)

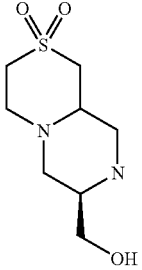

To a suspension of (7S)-7-(hydroxymethyl)hexahydropyrazino[2,1-c][1,4]thiazine-6,9-dione 2,2-dioxide (D120, 900 mg, 3.63 mmol) in THF (10 ml) were added under $N_2$, at r.t., 36.3 ml of 1M $BH_3$-THF solution. The reaction mixture was refluxed for 16 hrs.

6 N HCl (20 ml) was added to the reaction mixture, cooled to 0° C., and the resulting mixture was refluxed for 2 hrs. Then the reaction mixture was evaporated to dryness and the crude was purified by SCX to give the title compound as a white foam (753 mg, y=94%)

MS: m/z=221 (M+1) and 243 (M+Na)

1H NMR (300 MHz, DMSO-$d_6$) δ ppm 4.40-4.63 (m, 1H) 3.33-3.48 (m, 1H) 2.95-3.27 (m, 4H) 2.72-2.95 (m, 3H) 2.53-2.72 (m, 2H) 2.20-2.41 (m, 2H) 1.98-2.18 (m, 1H) 1.65-1.85 (m, 1H).

Description 122 and 123

(7R,9aR or 9aS)-7-({[(1,1-dimethylethyl)(dimethyl)silyl]oxy}methyl)octahydropyrazino[2,1-c][1,4]thiazine 2,2-dioxide (Description 122—Diastereoisomer 1) and (7R,9aS or 9aR)-7-({[(1,1-dimethylethyl)(dimethyl)silyl]oxy}methyl)octahydropyrazino[2,1-c][1,4]thiazine 2,2-dioxide (Description 123—Diastereisomer 2)

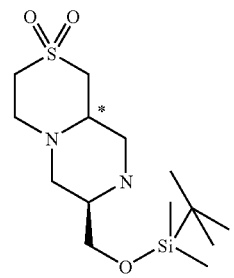

To a suspension of [(7R)-2,2-dioxidooctahydropyrazino[2,1-c][1,4]thiazin-7-yl]methanol (D121, 753 mg, 3.42 mmol) in dichloromethane (30 ml) were added at r.t. $Et_3N$ (1.9 ml, 13.68 mmol) and TDBMSCl (1.5 g, 10.3 mmol). The reaction mixture was stirred for 16 hrs at r.t.

Sat. $NaHCO_3$ was added and the aqueous phase was extracted with dichloromethane (×3) and the combined organic phases were dried and evaporated to dryness. The crude was purified by chromatography (silica, $CH_2Cl_2$: MeOH 1:0 to 97:3) to the title compounds:

D122—Diastereoisomer 1 (566 mg, colourless oil):

MS: m/z=335 (M+1)

1H NMR (500 MHz, DMSO-$d_6$) δ ppm 3.47-3.66 (m, 2H) 2.99-3.27 (m, 3H) 2.80-2.95 (m, 3H) 2.67-2.80 (m, 3H) 2.56-2.66 (m, 2H) 2.21-2.34 (m, 1H) 0.55-1.11 (s, 9H) −0.23-0.26 (s, 6H)

D123—Diastereoisomer 2 (382 mg, white solid):

MS: m/z=335 (M+1)

1H NMR (500 MHz, DMSO-$d_6$) δ ppm 3.39-3.48 (m, 1H) 3.31-3.40 (m, 1H) 3.13 (t, 1H) 2.91-3.09 (m, 3H) 2.70-2.85 (m, 3H) 2.56-2.65 (m, 1H) 2.42-2.51 (m, 1H) 2.19-2.36 (m, 2H) 1.91-2.06 (m, 1H) 1.74 (t, 1H) 0.80 (s, 9H)-0.02 (s, 6 H)

Description 124

2-[3,5-bis(trifluoromethyl)phenyl]-N-[6-[(7R,9aR or 9aS)-7-({[(1,1-dimethylethyl)(dimethyl)silyl]oxy}methyl)-2,2-dioxidohexahydropyrazino[2,1-c][1,4]thiazin-8(1H)-yl]-4-(4-fluoro-2-methylphenyl)-3-pyridinyl]-N,2-dimethylpropanamide (D124—Diastereoisomer 1)

Description 125

2-[3,5-bis(trifluoromethyl)phenyl]-N-[6-[(7R,9aS or 9aR)-7-({[(1,1-dimethylethyl)(dimethyl)silyl]oxy}methyl)-2,2-dioxidohexahydropyrazino[2,1-c][1,4]thiazin-8(1H)-yl]-4-(4-fluoro-2-methylphenyl)-3-pyridinyl]-N,2-dimethylpropanamide (D125—Diastereoisomer 2)

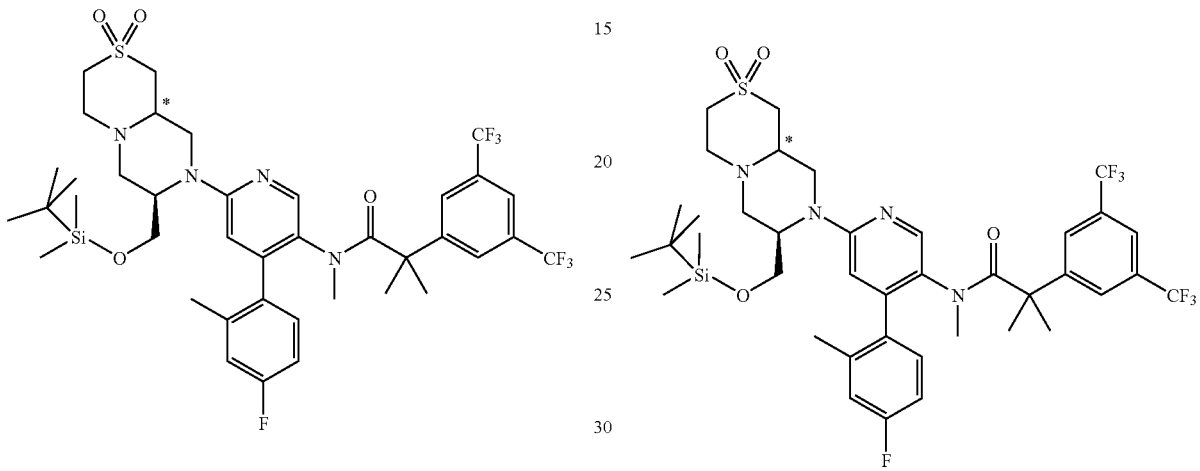

To a solution of (7R,9aR or 9aS)-7-({[(1,1-dimethylethyl)(dimethyl)silyl]oxy}methyl)octahydropyrazino[2,1-c][1,4]thiazine 2,2-dioxide (D122, 120 mg, 0.36 mmol) in 2.2 ml of toluene were added 2-[3,5-bis(trifluoromethyl)phenyl]-N-[6-chloro-4-(4-fluoro-2-methylphenyl)-3-pyridinyl]-N,2-dimethylpropanamide [WO 2005/002577] (147 mg, 0.28 mmol), bis-tri-tert-butylphosphine palladium (29 mg), hexadecyltrimethylammonium chloride (17.8 μL of a 25% aqueous solution) and sodium hydroxide solution (36 μL 50% aqueous solution). The reaction mixture was degassed by freeze-pump-thaw cycles and then it was stirred at 90° C. for 4 hrs.

EtOAc and sat. NaHCO₃ aq. were added to the reaction mixture and the aqueous phase was extracted with EtOAc (×3). The combined organic phases were dried and evaporated to dryness. The crude was purified by chromatography (silica, cyclohexane:EtOAc 7:3 to 0:1) to give the title compound as a white solid (201 mg).

HPLC/MS: m/z=831 (M+1) @ t=4.56 min

MS: m/z=831 (M+1)

1H NMR (500 MHz, DMSO-d$_6$) δ ppm 8.02 (s, 1H) 7.86 (s, 1H) 7.63-7.81 (m, 2H) 6.95-7.21 (m, 3H) 6.64 (s, 1H) 4.29-4.66 (m, 1H) 3.99-4.24 (m, 1H) 3.78-3.95 (m, 1H) 3.59-3.81 (m, 1H) 3.08-3.26 (m, 3H) 2.91-3.16 (m, 3H) 2.63-2.87 (m, 1H) 2.48 (s, 3H) 2.37-2.60 (m, 2H) 2.08-2.33 (m, 1H) 2.09 (s, 3H) 1.37 (s, 6H) 0.77 (s, 9H) 0.01 (s, 6H)

To a solution of (7R,9aS or 9aR)-7-({[(1,1-dimethylethyl)(dimethyl)silyl]oxy}methyl)octahydropyrazino[2,1-c][1,4]thiazine 2,2-dioxide (D123, 120 mg, 0.36 mmol) in 2.2 ml of toluene were added 2-[3,5-bis(trifluoromethyl)phenyl]-N-[6-chloro-4-(4-fluoro-2-methylphenyl)-3-pyridinyl]-N,2-dimethylpropanamide [WO 2005/002577] (147 mg, 0.28 mmol), bis-tri-tert-butylphosphine palladium (29 mg), hexadecyltrimethylammonium chloride (18 μL of a 25% aqueous solution) and sodium hydroxide solution (36 μL of a 50% aqueous solution). The reaction mixture was degassed by freeze-pump-thaw cycles and it was stirred at 90° C. for 5 hrs. Then further bis-tri-tert-butylphosphine palladium (29 mg) was added and the reaction mixture was stirred at 90° C. for one more hour and was left in freezer overnight.

EtOAc and sat. NaHCO₃ aq. were added to the reaction mixture and the aqueous phase was extracted with EtOAc (×3). The combined organic phases were dried and evaporated to dryness. The crude was purified by chromatography (silica, cyclohexane:EtOAc 7:3 to 0:1) to give the title compound as a white solid (127.4 mg, y=55%).

MS: m/z=831 (M+1)

1H NMR (500 MHz, DMSO-d$_6$) δ ppm 8.01 (s, 1H) 7.86 (s, 1H) 7.60-7.82 (m, 2H) 7.16 (d, 1H) 6.98-7.14 (m, 2H) 6.67 (s, 1H) 4.36-4.54 (m, 1H) 3.91-4.12 (m, 1H) 3.80-3.94 (m, 1H) 3.58-3.73 (m, 1H) 3.08-3.47 (m, 5H) 2.87-3.00 (m, 1H) 2.72-2.82 (m, 1H) 2.42-2.67 (m, 6H) 2.13-2.25 (m, 5H) 1.26-1.54 (m, 4H) 0.78 (s, 9H) 0.00 (s, 6H)

Description 126

(7S,9aS)-7-({[(1,1-dimethylethyl)(dimethyl)silyl]oxy}methyl)-8-(phenylmethyl)octahydropyrazino[2,1-c][1,4]oxazine (D126)

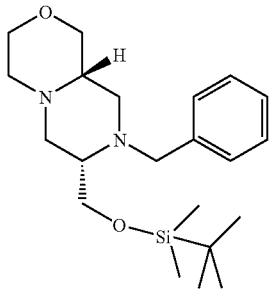

To a solution of (7S,9aS)-7-({[(1,1-dimethylethyl)(dimethyl)silyl]oxy}methyl)octahydropyrazino[2,1-c][1,4]oxazine (D22, 200 mg, 0.7 mmol) in dichloroethane (3 ml) were added under $N_2$, at r.t., PhCHO (0.142 ml, 1.4 mmol) and AcOH (79 μl, 1.4 mmol) and the reaction mixture was stirred for 30 mins. Sodium triacetoxyborohydride (295 mg, 1.4 mmol) was added and the reaction mixture was stirred for 3.5 hrs.

$NaHCO_3$ aq. was added to the reaction mixture and the two phases were separated. The aqueous phase was extracted with dichloromethane (3×) and the combined organic phases were dried and evaporated to dryness. The crude was purified by SCX and by chromatography (silica, $CH_2Cl_2$: 2M $NH_3$ in MeOH 1:0 to 95:5) to give 276 mg of the title compound as a colourless oil (276 mg, y=quantitative)

UPLC/MS: m/z=377 (M+1) @ t=0.69 min

1H NMR (500 MHz, DMSO-$d_6$) δ ppm 7.27-7.32 (m, 4H) 7.18-7.24 (m, 1H) 3.94 (t, 1H) 3.83 (d, 1H) 3.78-3.89 (m, 1H) 3.68-3.75 (m, 1H) 3.65 (d, 1H) 3.42-3.54 (m, 2H) 3.02 (t, 1H) 2.74 (dd, 2H) 2.45-2.50 (m, 1H) 2.18-2.32 (m, 3H) 2.08-2.18 (m, 2H) 0.84 (s, 9H) 0.02 (s, 3H) 0.00 (s, 3H)

Description 127

[(7S,9aS)-8-(phenylmethyl)octahydropyrazino[2,1-c][1,4]oxazin-7-yl]methanol (D127)

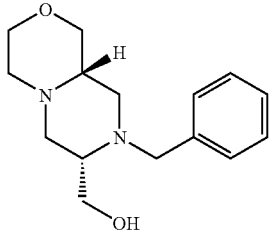

To a solution of (7S,9aS)-7-({[(1,1-dimethylethyl)(dimethyl)silyl]oxy}methyl)-8-(phenylmethyl)octahydropyrazino[2,1-c][1,4]oxazine (D126, 276 mg, 0.73 mmol) in MeOH (24 ml), cooled to 0° C., was added dropwise 12 N HCl (1.4 mL). The reaction mixture was stirred for 2 hrs at r.t., then it was put in the freezer for 12 hrs. The reaction mixture was warmed-up to r.t., further HCl was added (0.7 ml) and the reaction mixture was stirred for 2 more hrs. The mixture was filtered on a SCX cartridge washing with methanol and then with 2M methanolic ammonia. The fractions eluted with ammonia were combined and evaporated to dryness to give the title compound as a colourless oil (150 mg, y=78%).

UPLC/MS: m/z=263 (M+1) @ t=0.41 min

1H NMR (500 MHz, DMSO-$d_6$) δ ppm 7.26-7.33 (m, 4H) 7.19-7.24 (m, 1H) 4.42 (br. s., 1H) 3.81 (d, 1H) 3.74-3.83 (m, 2H) 3.60-3.72 (m, 2H) 3.43-3.52 (m, 2H) 3.02 (t, 1H) 2.78 (d, 1H) 2.64-2.72 (m, 1H) 2.53 (dd, 1H) 2.18-2.29 (m, 3H) 2.08-2.17 (m, 2H)

Description 128

(7S,9aS)-7-(fluoromethyl)-8-(phenylmethyl)octahydropyrazino[2,1-c][1,4]oxazine (D128)

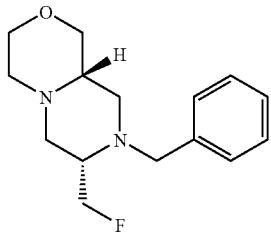

To a solution of [(7S,9aS)-8-(phenylmethyl)octahydropyrazino[2,1-c][1,4]oxazin-7-yl]methanol (D127, 125 mg, 0.477 mmol) in dichloromethane (5 ml), cooled to −78° C., was added DAST (0.187 ml, 1.431 mmol) dropwise and the reaction mixture was stirred for 16 hrs allowing the temperature to increase to r.t.

Water was added to the reaction mixture and the two phases were separated. The aqueous phase was extracted with dichloromethane (3×) and the combined organic phases were dried and evaporated to dryness. The crude was purified by chromatography (silica, $CH_2Cl_2$:MeOH 1:0 to 96:4) to give the title compound (106 mg).

MS: m/z=265 (M+1)

UPLC/MS: m/z=265 (M+1) @ t=0.47 min

1H NMR (500 MHz, DMSO-$d_6$) δ ppm 7.26-7.34 (m, 4H) 7.19-7.26 (m, 1H) 4.82-4.99 (m, 1H) 4.59-4.76 (m, 1H) 3.85 (d, 1H) 3.70 (dd, 1H) 3.63 (d, 1H) 3.50 (dd, 1H) 3.43-3.51 (m, 1H) 3.02-3.09 (m, 1H) 3.03 (t, 1H) 2.68 (d, 1H) 2.54 (d, 1H) 2.29-2.36 (m, 2H) 2.24 (t, 1H) 2.08-2.16 (m, 2H)

Description 129

(7S,9aS)-7-(fluoromethyl)octahydropyrazino[2,1-c][1,4]oxazine (D129)

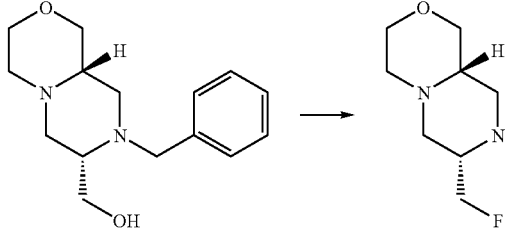

To a solution of (7S,9aS)-7-(fluoromethyl)-8-(phenylmethyl)octahydropyrazino[2,1-c][1,4]oxazine (D128, 30 mg, 0.11 mmol) in AcOH (30 ml) was added Pd-black (12 mg, 0.11 mmol) and the reaction mixture was stirred under a $H_2$ atmosphere (5 atm.) for 1.5 hrs. The reaction mixture was filtered on a SCX cartridge washing with methanol and then with 2M methanolic ammonia. The fractions eluted with ammonia were combined and evaporated to dryness. The crude was purified by chromatography (silica, $CH_2Cl_2$:MeOH 1:0 to 8:2) to give the title compound (14.9 mg, y=78%).

1H NMR (400 MHz, DMSO-$d_6$) δ ppm 4.55-4.65 (m, 1H) 4.42-4.53 (m, 1H) 3.65 (dd, 1H) 3.38-3.53 (m, 2H) 2.99 (t, 1H) 2.93-3.01 (m, 1H) 2.58 (dd, 1H) 2.42-2.45 (m, 1H) 2.37 (dd, 1H) 2.28-2.37 (m, 1H) 2.12-2.20 (m, 1H) 2.02-2.11 (m, 1H) 1.92-2.00 (m, 1H)

Description 130

(7S)-7-(hydroxymethyl)hexahydropyrazino[2,1-c][1,4]oxazine-6,9-dione (D130)

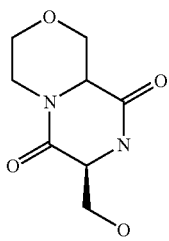

N-Boc-3-morpholinecarboxylic acid (1.038 g, 4.49 mmol) was suspended in anhydrous dichloromethane (20 mL). To it was added EDC (1.3 g, 6.78 mmol) and HOBt (607 mg, 4.49 mmol) and stirred for 30 minutes at R.T., at which time complete dissolution of the starting material was observed. A solution of L-Ser-Methylester hydrochloride (1.10 g, 17.07 mmol), and DIPEA (1.23 mL, 7.07 mmol) in dry dichloromethane (10 mL) was added. The resulting mixture was stirred overnight. Diluted with dichloromethane (50 mL), washed with sat NaHCO$_3$ solution (2×50 mL) and brine (50 mL). Dried (Na$_2$SO$_4$) and solvent removed under reduced pressure to afford a crude used in the next step.

It was dissolved in 20 mL of dichloromethane and treated with 10 mL of TFA. The reaction was stopped after 4 h. The mixture was passed through a SCX column. The basic components were eluted with 1M methanolic ammonia. The solvent was removed leaving an oily residue, which was re-dissolved in MeOH and heated to remove the solvent. A precipitate formed, which was collected by filtration as a white solid, corresponding to the title compound, with a 70:30 diastereomeric excess.

MS (direct): m/z=201 (M+1)

1H NMR (500 MHz, DMSO-d$_6$) d ppm 8.15 (br. s., 1H) 5.16 (t, 1H) 4.22 (dd, 1H) 4.08-4.13 (m, 1H) 4.00 (dd, 1H) 3.84-3.88 (m, 1H) 3.77-3.83 (m, 1H) 3.71-3.80 (m, 1H) 3.44-3.51 (m, 1H) 3.41 (t, 1H) 3.30 (t, 1H) 2.77 (td, 1H) (mixture of diastereoisomers, ratio about 70:30)

Description 131

(7R)-octahydropyrazino[2,1-c][1,4]oxazin-7-yl-methanol (D131)

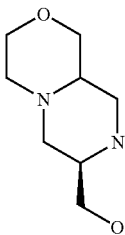

(7S)-7-(hydroxymethyl)hexahydropyrazino[2,1-c][1,4] oxazine-6,9-dione (D130, 151 mg, 0.75 mmol) was suspended in 1M borane THF complex solution (7.5 mL) and heated at reflux for 24 hours. Checked by MS, which showed only the product at m/z=173 (M+1). The reaction was cooled to 0° C., MeOH (5 mL) added dropwise followed by conc.HCl solution (1 mL). The resulting mixture was heated at 50° C. for 4 hours. The solvent was removed and the residue loaded on a SCX column, washed with MeOH before eluting the compound with 1M NH$_3$ in MeOH. Solvent evaporated under reduced pressure to afford the title compound as a colourless oil (125 mg).

1H NMR (500 MHz, DMSO-d$_6$) d ppm 4.43 (t, 1H) 3.68 (dd, 1H) 3.62 (t, 1H) 3.40-3.58 (m, 4H) 3.02 (t, 1H) 2.66-2.74 (m, 1H) 2.62 (d, 1H) 2.42-2.51 (m, 1H) 2.31-2.39 (m, 1H) 2.15 (dd, 1H) 2.09 (td, 1H) 1.92-2.03 (m, 1H)

Description 132

(7R,9aR)-7-({[(1,1-dimethylethyl)(dimethyl)silyl]oxy}methyl)octahydropyrazino[2,1-c][1,4]oxazine (D132)

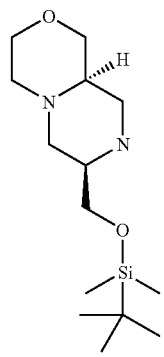

(7R)-octahydropyrazino[2,1-c][1,4]oxazin-7-ylmethanol (D131, 93 mg, 0.54 mmol, a sample recovered from a failed attempt at silylating the preparation of Dnn) was dissolved in dry dichloromethane (2 mL) and treated with Et$_3$N (0.15 mL, 1.08 mmol), and TBDMS-Cl (122 mg, 0.81 mmol). The resulting reaction mixture was stirred overnight at R.T. It was checked by direct MS, showing no starting material, replaced by the expected peak at m/z=287 (M+1 of the product). It was diluted with dichloromethane (20 mL) and washed with sat NaHCO$_3$ solution (2×20 mL), dried (Na$_2$SO$_4$) and the solvent was removed. The residue was purified by flash chromatography (silica, dichloromethane to dichloromethane:MeOH 90:10), leaving the product as a clear oil.

MS (direct): m/z=287 (M+1)

1H NMR (500 MHz, DMSO-d$_6$) d ppm 7.48 (br. s., 1H) 7.07 (br. s., 1H) 3.82 (dd, 1H) 3.75 (dd, 1H) 3.69 (dd, 1H) 3.55 (dd, 1H) 3.42-3.49 (m, 1H) 3.03 (t, 1H) 2.86-2.93 (m, 1H) 2.68 (dd, 1H) 2.50-2.54 (m, 1H) 2.33-2.46 (m, 2H) 2.21 (dd, 1H) 2.04-2.16 (m, 2H) 0.86 (s, 9H) 0.04 (s, 6H)—protonated form.

The whole ROESY cross peak pattern is in accordance with a syn relative stereochemistry.

Example 1

2-[3,5-Bis(trifluoromethyl)phenyl]-N-[6-(1,1-dioxidohexahydro-5H-isothiazolo[2,3-a]pyrazin-5-yl)-4-(4-fluoro-2-methylphenyl)pyridin-3-yl]-N,2-dimethylpropanamide (E1)

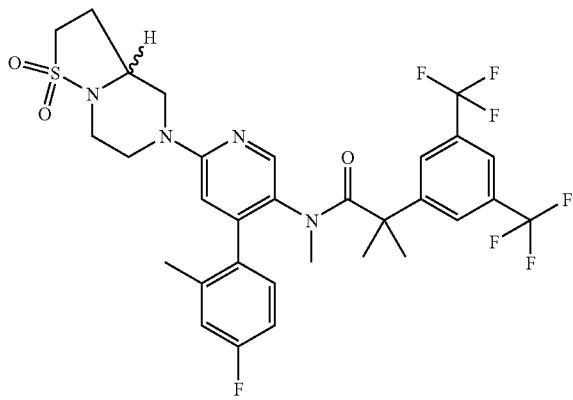

A 8 ml sealed vial was charged with 100 mg (0.187 mmol) of 2-[3,5-bis(trifluoromethyl)phenyl]-N-[6-chloro-4-(4-fluoro-2-methylphenyl)-3-pyridinyl]-N,2-dimethylpropanamide (WO 2005/002577), 98 mg (0.561 mmol) of hexahydro-2H-isothiazolo[2,3-a]pyrazine 1,1-dioxide (D10), 52 mg (0.374 mmol) of potassium carbonate; the reagents were dissolved in 0.8 ml of DMSO. The reaction mixture was heated at 180° C. for 36-48 hrs and then added to a saturated NH$_4$Cl solution and back extracted with dichloromethane; the crude material was purified on SPE cartridge (Silica) eluting with a gradient from cyclohexane/ethyl acetate 9:1, to cyclohexane/ethyl acetate 1:1 and affording 44 mg (0.065 mmol) of the title compound as pale yellow solid.

MS (ES/+): 673 [M+H]$^+$

NMR (DMSO-d$_6$): δ (ppm) 8.01 (s, 1H); 7.78 (s, 1H); 7.65 (s, 2H); 7.08-6.85 (m, 3H); 6.53 (s, 1H); 4.81-4.53 (m, 1H); 4.35-4.09 (m, 1H); 3.53-3.50 (m, 2H); 3.38-3.25 (m, 1H); 3.16-3.09 (m, 1H); 2.96 (t, 1H); 2.83 (t, 1H); 2.70-1.98 (m, 10H); 1.79-1.47 (m, 3H); 1.46-1.33 (s, 3H).

Example 2

2-[3,5-Bis(trifluoromethyl)phenyl]-N-{4-(4-fluoro-2-methylphenyl)-6-[(8aS)-6-oxohexahydropyrrolo[1,2-a]pyrazin-2(1H)-yl]-3-pyridinyl}-N,2-dimethyl-propanamide (E2)

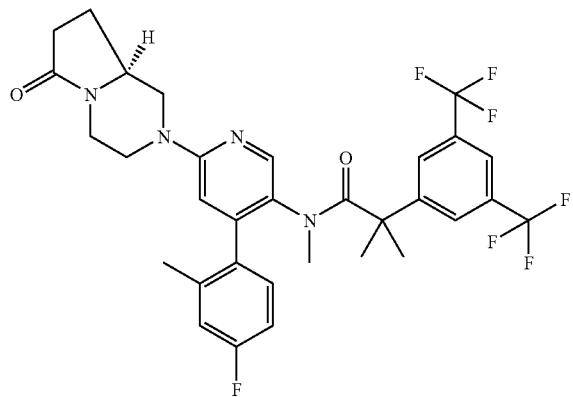

A 8 ml sealed vial was charged with 100 mg (0.187 mmol) of 2-[3,5-bis(trifluoromethyl)phenyl]-N-[6-chloro-4-(4-fluoro-2-methylphenyl)-3-pyridinyl]-N,2-dimethylpropanamide (WO 2005/002577), 78.6 mg (0.561 mmol) of (8aS)-hexahydropyrrolo[1,2-a]pyrazin-6(2H)-one (WO 2003/066635), 52 mg (0.374 mmol) of potassium carbonate; the reagents were dissolved in 0.8 ml of DMSO. The reaction mixture was heated at 180° C. for 36-48 hrs and then added to a saturated NH$_4$Cl solution and back extracted with dichloromethane; the crude material was purified on SPE cartridge (Silica) eluting with a gradient from cyclohexane/ethyl acetate 9:1, to ethyl acetate 100% and affording 52 mg of the title compound as pale yellow solid.

MS (ES/+): 637 [M+H]$^+$

NMR (DMSO-d$_6$): δ (ppm) 8.01 (s, 1H); 7.78 (s, 1H); 7.65 (s, 2H); 7.05-6.87 (m, 3H); 6.52 (s, 1H); 4.67-4.52 (m, 1H); 4.32-4.19 (m, 1H); 4.14-4.10 (d, 1H); 3.77-3.64 (m, 1H); 3.02-2.84 (m, 2H); 2.61 (t, 1H); 2.48-2.44 (dd, 2H); 2.41-2.33 (s, 3H); 2.30-2.22 (m, 1H); 2.13 (s, 3H); 1.79-1.65 (m, 1H); 1.53 (s, 3H); 1.38 (s, 3H).

Example 3

2-[3,5-Bis(trifluoromethyl)phenyl]-N-[4-(4-fluoro-2-methylphenyl)-6-(6-oxohexahydropyrrolo[1,2-a]pyrazin-2(1H)-yl)-3-pyridinyl]-N,2-dimethylpropanamide (E3)

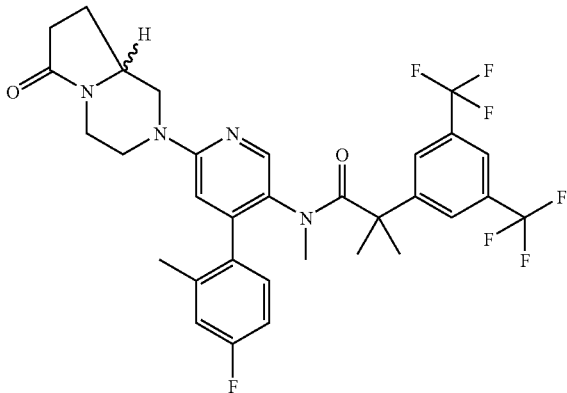

A 8 ml sealed vial was charged with 100 mg (0.187 mmoles) of 2-[3,5-bis(trifluoromethyl)phenyl]-N-[6-chloro-4-(4-fluoro-2-methylphenyl)-3-pyridinyl]-N,2-dimethylpropanamide (WO 2005/002577), 78.6 mg (0.561 mmol) of hexahydropyrrolo[1,2-a]pyrazin-6(2H)-one (WO 2003/066635), 52 mg (0.374 mmol) of potassium carbonate; the reagents were dissolved in 0.8 ml of DMSO. The reaction mixture was heated at 180° C. for 36-48 hrs and then added to a saturated NH$_4$Cl solution and back extracted with dichloromethane; the crude material was purified on SPE cartridge (Silica) eluting with a gradient from cyclohexane/ethyl acetate 9:1, to ethyl acetate 100% and affording 71 mg of the title compound as pale yellow solid.

MS (ES/+): 637 [M+H]$^+$

NMR (DMSO-d$_6$): δ (ppm) 8.01 (s, 1H); 7.78 (s, 1H); 7.65 (s, 2H); 7.05-6.87 (m, 3H); 6.52 (s, 1H); 4.67-4.52 (m, 1H); 4.32-4.19 (m, 1H); 4.14-4.10 (d, 1H); 3.77-3.64 (m, 1H); 3.02-2.84 (m, 2H); 2.61 (t, 1H); 2.48-2.44 (dd, 2H); 2.41-2.33 (s, 3H); 2.30-2.22 (m, 1H); 2.13 (s, 3H); 1.79-1.65 (m, 1H); 1.53 (s, 3H); 1.38 (s, 3H)

Example 4

2-[3,5-Bis(trifluoromethyl)phenyl]-N,2-dimethyl-N-{4-(2-methylphenyl)-6-[(8aS)-6-oxohexahydropyrrolo[1,2-a]pyrazin-2(1H)-yl]-3-pyridinyl}propanamide (E4)

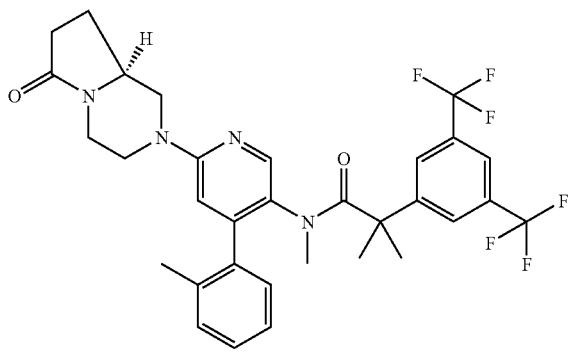

A 8 ml sealed vial was charged with 100 mg (0.161 mmoles) of 2-[3,5-bis(trifluoromethyl)phenyl]-N-[6-chloro-4-(2-methylphenyl)-3-pyridinyl]-N,2-dimethylpropanamide (WO 2005/002577), 67 mg (0.483 mmol) of (8aS)-hexahydropyrrolo[1,2-a]pyrazin-6(2H)-one (WO 2003/066635), 44.5 mg (0.322 mmol) of potassium carbonate; the reagents were dissolved in 0.8 ml of DMSO. The reaction mixture was heated at 180° C. for 36-48 hrs and then added to a saturated NH$_4$Cl solution and back extracted with DCM; the crude material was purified on SPE cartridge (Silica) eluting with a gradient from cyclohexane/ethyl acetate 9:1, to ethyl acetate 100% and affording 56 mg of the title compound as pale yellow solid.

MS (ES/+): 619 [M+H]$^+$

NMR (DMSO-d$_6$): δ (ppm) 8.07-8.00 (m, 1H); 7.81-7.77 (m, 1H); 7.73-7.63 (m, 2H); 7.37-7.21 (m, 4H); 6.61-6.56 (m, 1H); 4.68-4.54 (m, 1H); 4.33-4.19 (m, 1H); 4.18-4.08 (d, 1H); 3.78-3.67 (m, 1H); 3.04-2.85 (m, 2H); 2.69-2.54 (t, 1H); 2.53-2.42 9 dd, 1H); 2.42-2.33 (m, 3H); 2.33-2.23 (m, 1H); 2.21-2.10 (m, 3H); 1.78-1.66 (m, 1H); 1.57-1.48 (m, 3H); 1.42-1.32 (m, 3H).

Example 5

2-[3,5-Bis(trifluoromethyl)phenyl]-N,2-dimethyl-N-[4-(2-methylphenyl)-6-(6-oxohexahydropyrrolo[1,2-a]pyrazin-2(1H)-yl)-3-pyridinyl]propanamide (E5)

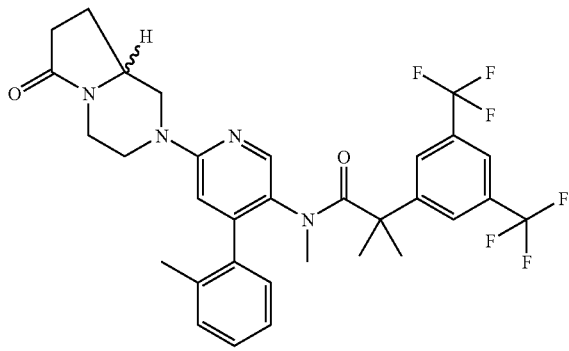

A 8 ml sealed vial was charged with 100 mg (0.161 mmoles) of 2-[3,5-bis(trifluoromethyl)phenyl]-N-[6-chloro-4-(2-methylphenyl)-3-pyridinyl]-N,2-dimethylpropanamide (WO 2005/002577), 67 mg (0.483 mmol) of hexahydropyrrolo[1,2-a]pyrazin-6(2H)-one (WO 2003/066635), 44.5 mg (0.322 mmol) of potassium carbonate; the reagents were dissolved in 0.8 ml of DMSO. The reaction mixture was heated at 180° C. for 36-48 hrs and then added to a saturated NH$_4$Cl solution and back extracted with DCM; the crude material was purified on SPE cartridge (Silica) eluting with a gradient from cyclohexane/ethyl acetate 9:1, to ethyl acetate 100% and affording 45 mg of the title compound as pale yellow solid.

MS (ES/+): 619 [M+H]$^+$

NMR (DMSO-d$_6$): δ (ppm) 8.07-8.00 (m, 1H); 7.81-7.77 (m, 1H); 7.73-7.63 (m, 2H); 7.37-7.21 (m, 4H); 6.61-6.56 (m, 1H); 4.68-4.54 (m, 1H); 4.33-4.19 (m, 1H); 4.18-4.08 (d, 1H); 3.78-3.67 (m, 1H); 3.04-2.85 (m, 2H); 2.69-2.54 (t, 1H); 2.53-2.42 9 dd, 1H); 2.42-2.33 (m, 3H); 2.33-2.23 (m, 1H); 2.21-2.10 (m, 3H); 1.78-1.66 (m, 1H); 1.57-1.48 (m, 3H); 1.42-1.32 (m, 3H).

Example 6

2-[3,5-Bis(trifluoromethyl)phenyl]-N-[6-(1,1-dioxidohexahydro-5H-isothiazolo[2,3-a]pyrazin-5-yl)-4-(2-methylphenyl)-3-pyridinyl]-N,2-dimethylpropanamide (E6)

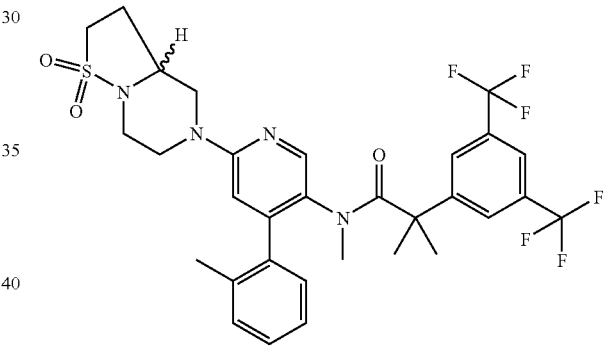

The title compound was prepared starting from 100 mg (0.161 mmoles) of 2-[3,5-bis(trifluoromethyl)phenyl]-N-[6-chloro-4-(2-methylphenyl)-3-pyridinyl]-N,2-dimethylpropanamide (WO 2005/002577), 85 mg (0.483 mmol) of hexahydro-2H-isothiazolo[2,3-a]pyrazine 1,1-dioxide (D10), 44.5 mg (0.322 mmol) of potassium carbonate; the reagents were dissolved in 0.8 ml of DMSO. The reaction mixture was heated at 180° C. for 36-48 hrs and then added to a saturated NH$_4$Cl solution and back extracted with DCM; the crude material was purified on SPE cartridge (Silica) eluting with a gradient from cyclohexane/ethyl acetate 9:1, to cyclohexane/ethyl acetate 1:1 and affording 80 mg of the title compound as pale yellow solid.

MS (ES/+): 655 [M+H]$^+$

NMR (DMSO-d$_6$): δ (ppm) 8.08-8.00 (m, 1H), 7.82-7.76 (m, 1H); 7.71-7.64 (m, 2H); 7.37-7.22 (m, 4H); 6.62-6.57 (m, 1H); 4.80-4.60 (m, 1H); 4.36-4.12 (m, 1H); 3.58-3.46 (m, 1H); 3.39-3.27 (m, 1H); 3.25-3.16 (m, 1H); 3.17-3.08 (t, 1H); 3.05-2.91 (t, 1H); 2.90-2.78 (t, 1H); 2.54-2.44 (m, 3H); 2.44-2.31 (m, 2H); 2.20-2.12 (m, 3H); 2.31-2.01 (m, 1H); 1.58-1.50 (m, 3H); 1.44-1.31 (m, 3H)

Example 7

1-[3,5-Bis(trifluoromethyl)phenyl]-N-{4-(4-fluoro-2-methylphenyl)-6-[(8aS)-hexahydropyrrolo[1,2-a]pyrazin-2(1H)-yl]-3-pyridinyl}-N-methylcyclopropanecarboxamide (E7)

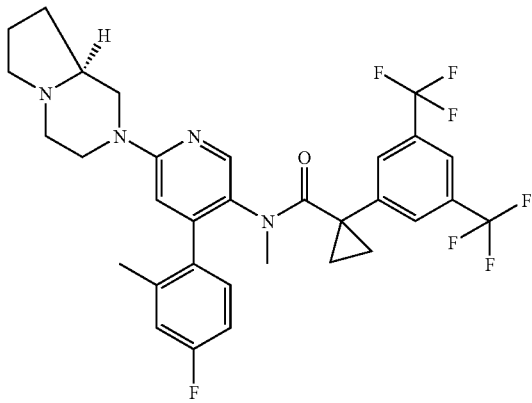

The title compound was prepared starting from 100 mg (0.188 mmoles) of 1-[3,5-bis(trifluoromethyl)phenyl]-N-[6-chloro-4-(4-fluoro-2-methylphenyl)-3-pyridinyl]cyclopropanecarboxamide (D2), 70 mg (0.554 mmol) of (8aS)-octahydropyrrolo[1,2-a]pyrazine, 52.2 mg (0.377 mmol) of potassium carbonate; the reagents were dissolved in 0.8 ml of DMSO. The reaction mixture was heated at 150° C. overnight and then added to a saturated NH$_4$Cl solution and back extracted with dichloromethane; the crude material was purified on SPE cartridge (Silica) eluting with a gradient from cyclohexane/ethyl acetate 1:1, to ethyl acetate 100%, affording 72 mg of the title compound as pale yellow solid.

MS (ES/+): 621 [M+H]$^+$

NMR (DMSO-d$_6$): δ (ppm) 7.93-7.89 (s, 1H); 7.86-7.82 (s, 1H); 7.67-7.62 (s, 2H); 7.06-7.01 (d, 1H); 6.89-6.77 (m, 2H); 6.57-6.52 (m, 1H); 4.38-4.34 (d, 1H); 4.21-4.17 (d, 1H); 3.10-2.87 (m, 2H); 2.88-2.84 (s, 3H); 2.62-2.50 (m, 1H); 2.26-2.06 (m, 2H); 2.17-2.10 (s, 3H); 2.06-1.94 (s, 1H); 1.90-1.61 (m, 3H); 1.46-1.10 (m, 6H)

Example 8

1-[3,5-Bis(trifluoromethyl)phenyl]-N-{4-(4-fluoro-2-methylphenyl)-6-[(8aR)-hexahydropyrrolo[1,2-a]pyrazin-2(1H)-yl]-3-pyridinyl}-N-methylcyclopropanecarboxamide (E8)

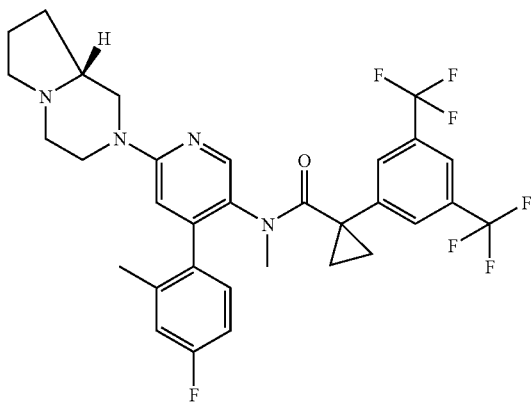

The title compound was prepared starting from 100 mg (0.188 mmoles) of 1-[3,5-bis(trifluoromethyl)phenyl]-N-[6-chloro-4-(4-fluoro-2-methylphenyl)-3-pyridinyl]cyclopropanecarboxamide (D2), 70 mg (0.554 mmol) of (8aR)-octahydropyrrolo[1,2-a]pyrazine, 52.2 mg (0.377 mmol) of potassium carbonate; the reagents were dissolved in 0.8 ml of DMSO. The reaction mixture was heated at 150° C. overnight and then added to a saturated NH$_4$Cl solution and back extracted with DCM; the crude material was purified on SPE cartridge (Silica) eluting with a gradient from cyclohexane/ethyl acetate 1:1, to ethyl acetate 100% and affording 70 mg of the title compound as pale yellow solid.

MS (ES/+): 621 [M+H]$^+$

NMR (DMSO-d$_6$): δ (ppm) 7.93-7.89 (s, 1H); 7.86-7.82 (s, 1H); 7.67-7.62 (s, 2H); 7.06-7.01 (d, 1H); 6.89-6.77 (m, 2H); 6.57-6.52 (m, 1H); 4.38-4.34 (d, 1H); 4.21-4.17 (d, 1H); 3.10-2.87 (m, 2H); 2.88-2.84 (s, 3H); 2.62-2.50 (m, 1H); 2.26-2.06 (m, 2H); 2.17-2.10 (s, 3H); 2.06-1.94 (s, 1H); 1.90-1.61 (m, 3H); 1.46-1.10 (m, 6H)

Example 9

1-[3,5-Bis(trifluoromethyl)phenyl]-N-{4-(4-fluoro-2-methylphenyl)-6-[(8aS)-6-oxohexahydropyrrolo[1,2-a]pyrazin-2(1H)-yl]-3-pyridinyl}-N-methylcyclopropanecarboxamide (E9)

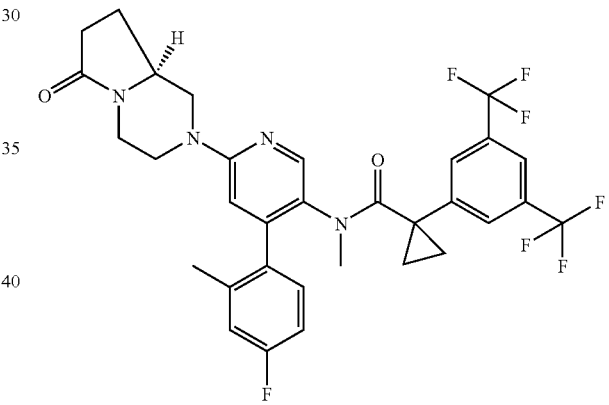

The title compound was prepared starting from 50 mg (0.094 mmoles) of 1-[3,5-bis(trifluoromethyl)phenyl]-N-[6-chloro-4-(4-fluoro-2-methylphenyl)-3-pyridinyl]cyclopropanecarboxamide (D2), 39 mg (0.278 mmol) of (8aS)-hexahydropyrrolo[1,2-a]pyrazin-6(2H)-one (WO 2003/066635), 26.2 mg (0.189 mmol) of potassium carbonate; the reagents were dissolved in 0.4 ml of DMSO. The reaction mixture was heated at 150° C. overnight and then added to a saturated NH$_4$Cl solution and back extracted with DCM; the crude material was purified on SPE cartridge (Silica) eluting with a gradient from cyclohexane/ethyl acetate 1:1, to ethyl acetate 100% and affording 26 mg of the title compound as pale yellow solid.

MS (ES/+): 635 [M+H]$^+$

NMR (DMSO-d$_6$): δ (ppm) 8.03-7.99 (m, 1H); 7.99-7.95 (m, 1H); 7.74-7.69 (m, 2H);
7.20-7.10 (m, 1H); 7.06-6.93 (m, 1H); 6.92-6.83 (m, 1H); 6.81-6.74 (m, 1H); 4.55-4.47 (d, 1H); 4.44-4.37 (d, 1H); 3.88-3.78 (d, 1H); 3.60-3.50 (d, 1H); 2.84-2.66 (m, 4H); 2.59-2.38 (m, 2H); 2.32-2.18 (m, 2H); 2.15-2.09 (m, 3H); 2.17-2.06 (m, 1H); 1.64-1.53 (m, 1H); 1.32-1.19 (m, 2H); 1.15-1.02 (m, 1H); 0.96-0.78 (1, H).

Example 10

1-[3,5-Bis(trifluoromethyl)phenyl]-N-{4-(4-fluoro-2-methylphenyl)-6-[(8aR)-6-oxohexahydropyrrolo[1,2-a]pyrazin-2(1H)-yl]-3-pyridinyl}-N-methylcyclopropanecarboxamide (E10)

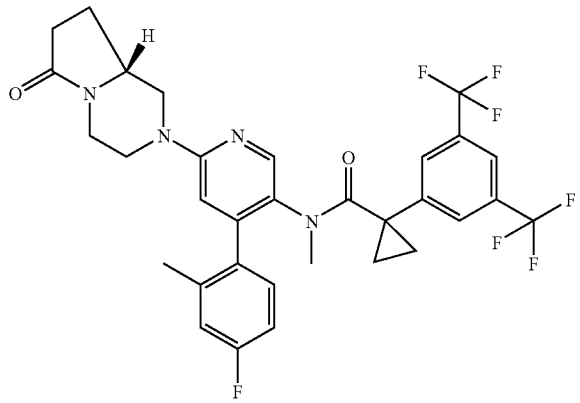

The title compound was prepared from 50 mg (0.094 mmoles) of 1-[3,5-bis(trifluoromethyl)phenyl]-N-[6-chloro-4-(4-fluoro-2-methylphenyl)-3-pyridinyl]cyclopropanecarboxamide (D2), 39 mg (0.278 mmol) of (8aR)-hexahydropyrrolo[1,2-a]pyrazin-6(2H)-one (WO 2003/066635), 26.2 mg (0.189 mmol) of potassium carbonate; the reagents were dissolved in 0.4 ml of DMSO. The reaction mixture was heated at 150° C. overnight and then added to a saturated NH$_4$Cl solution and back extracted with DCM; the crude material was purified on SPE cartridge (Silica) eluting with a gradient from cyclohexane/ethyl acetate 1:1, to ethyl acetate 100% and affording 12 mg of the title compound as pale yellow solid.

MS (ES/+): 635 [M+H]$^+$

NMR (DMSO-d$_6$): δ (ppm) 8.03-7.99 (m, 1H); 7.99-7.95 (m, 1H); 7.74-7.69 (m, 2H); 7.20-7.10 (m, 1H); 7.06-6.93 (m, 1H); 6.92-6.83 (m, 1H); 6.81-6.74 (m, 1H); 4.55-4.47 (d, 1H); 4.44-4.37 (d, 1H); 3.88-3.78 (d, 1H); 3.60-3.50 (d, 1H); 2.84-2.66 (m, 4H); 2.59-2.38 (m, 2H); 2.32-2.18 (m, 2H); 2.15-2.09 (m, 3H); 2.17-2.06 (m, 1H); 1.64-1.53 (m, 1H); 1.32-1.19 (m, 2H); 1.15-1.02 (m, 1H); 0.96-0.78 (1, H).

Example 11

2-[3,5-Bis(trifluoromethyl)phenyl]-N-{4-(4-fluoro-2-methylphenyl)-6-[(8aS)-3-oxohexahydropyrrolo[1,2-a]pyrazin-2(1H)-yl]-3-pyridinyl}-N,2-dimethylpropanamide (E11)

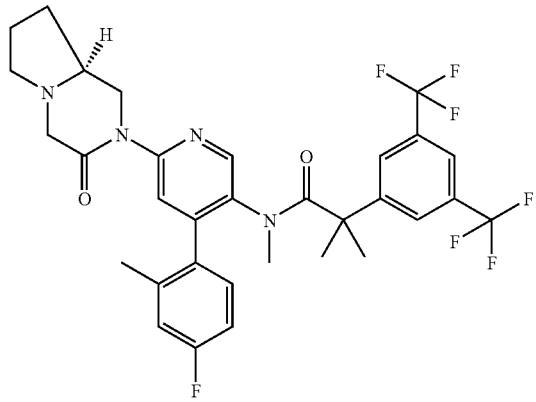

The title compound was prepared starting from 100 mg (0.187 mmoles) of 2-[3,5-bis(trifluoromethyl)phenyl]-N-[6-chloro-4-(4-fluoro-2-methylphenyl)-3-pyridinyl]-N,2-dimethylpropanamide (WO 2005/002577), 79 mg (0.563 mmol) of (8aS)-hexahydropyrrolo[1,2-a]pyrazin-3(4H)-one (D12), 72 mg of copper iodide (0.378 mmol), 40 μl (0.375 mmol) of N,N-dimethylmethanediamine, 112.4 mg (0.375 mmol) of cesium carbonate; the reagents were dissolved in 4 ml of dioxane and heated at 80° C. for 4 h and then at 120° C. overnight. The crude material was purified on SPE cartridge (Silica) eluting with a gradient from cyclohexane/ethyl acetate 9:1, to ethyl acetate 100% and affording 54 mg of the title compound as pale yellow solid.

MS (ES/+): 637 [M+H]$^+$

NMR (DMSO-d$_6$): δ (ppm) 8.39-8.23 (br. s, 1H), 8.09-7.97 (s, 1H), 7.87-7.64 (m, 3H), 7.21 (d, 1H), 7.17-7.06 (m, 2H), 4.62-4.15 (m, 2H), 4.09-3.65 (m, 2H), 3.19-3.00 (m, 1H), 2.87-2.53 (m, 2H), 2.42-2.24 (m, 1H), 2.20-2.04 (m, 6H), 2.00-1.88 (m, 1H), 1.88-1.76 (m, 1H), 1.75-1.59 (m, 1H), 1.59-1.47 (m, 1H), 1.46-1.23 (m, 6H)

Example 12

2-[3,5-Bis(trifluoromethyl)phenyl]-N-{4-(4-fluoro-2-methylphenyl)-6-[(8aR)-3-oxohexahydropyrrolo[1,2-a]pyrazin-2(1H)-yl]-3-pyridinyl}-N,2-dimethylpropanamide (E12)

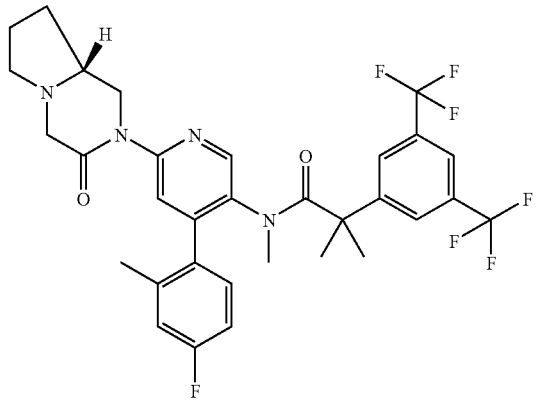

The title compound was prepared starting from 100 mg (0.187 mmoles) of 2-[3,5-bis(trifluoromethyl)phenyl]-N-[6-chloro-4-(4-fluoro-2-methylphenyl)-3-pyridinyl]-N,2-dimethylpropanamide (WO 2005/002577), 79 mg (0.563 mmol) of (8aR)-hexahydropyrrolo[1,2-a]pyrazin-3(4H)-one (D14), 72 mg of copper iodide (0.378 mmol), 40 μl (0.375 mmol) of N,N-dimethylmethanediamine, 112.4 mg (0.375 mmol) of cesium carbonate; the reagents were dissolved in 4 ml of dioxane and heated at 80° C. for 4 h and then at 120° C. overnight. The crude material was purified on SPE cartridge (Silica) eluting with a gradient from cyclohexane/ethyl acetate 9:1, to ethyl acetate 100% and affording 60 mg of the title compound as pale yellow solid.

MS (ES/+): 637 [M+H]$^+$

NMR (DMSO-d$_6$): δ (ppm) 8.39-8.23 (br. s, 1H), 8.09-7.97 (s, 1H), 7.87-7.64 (m, 3H), 7.21 (d, 1H), 7.17-7.06 (m, 2H), 4.62-4.15 (m, 2H), 4.09-3.65 (m, 2H), 3.19-3.00 (m, 1H), 2.87-2.53 (m, 2H), 2.42-2.24 (m, 1H), 2.20-2.04 (m, 6H), 2.00-1.88 (m, 1H), 1.88-1.76 (m, 1H), 1.75-1.59 (m, 1H), 1.59-1.47 (m, 1H), 1.46-1.23 (m, 6H).

Example 13

2-[3,5-Bis(trifluoromethyl)phenyl]-N-{4-(4-fluoro-2-methylphenyl)-6-[(8aR)-4-oxohexahydropyrrolo[1,2-a]pyrazin-2(1H)-yl]-3-pyridinyl}-N,2-dimethylpropanamide (E13)

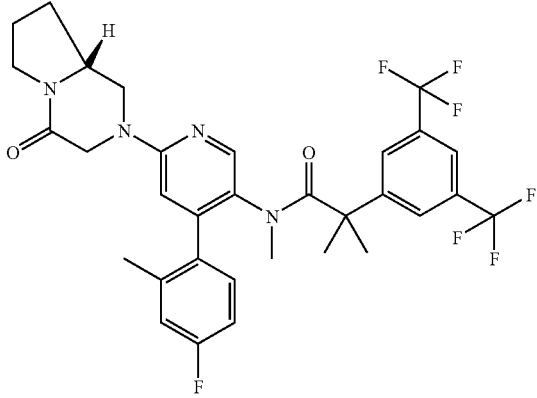

The title compound was prepared starting from 250 mg (0.47 mmole) of 2-[3,5-bis(trifluoromethyl)phenyl]-N-[6-chloro-4-(4-fluoro-2-methylphenyl)-3-pyridinyl]-N,2-dimethylpropanamide (WO 2005/002577), (8aR)-hexahydropyrrolo[1,2-a]pyrazin-4(1H)-one (D4), 164.4 mg (1.17 mmol), 130 mg of potassium carbonate (0.94 mmol); the reagents were dissolved in 1.5 ml of DMSO. The reaction mixture was heated at 150° C. overnight and then added to a saturated NH₄Cl solution and back extracted with DCM; the crude material was purified on SPE cartridge (Silica) eluting with a gradient cyclohexane/ethyl acetate 9:1, to ethyl acetate 100% and affording 115 mg of the title compound as pale yellow solid.

MS (ES/+): 637 [M+H]$^+$

NMR (DMSO-d$_6$): δ (ppm) 8.05-7.98 (s, 1H); 7.95-7.89 (s, 1H); 7.80-7.69 (br.s, 2H); 7.74-7.64 (br.s, 1H); 7.19-7.11 (d, 1H); 6.71-6.65 (s, 1H); 4.77-4.64 (d, 1H); 4.45-4.32 (d, 1H); 3.72-3.59 (m, 1H); 3.52-3.41 (dd, 1H); 3.39-3.31 (m, 1H); 2.83-2.73 (t, 1H); 2.60-2.50 (m, 1H); 2.31-2.17 (s, 3H); 2.21-2.15 (m, 1H); 2.15-2.05 (s, 3H); 1.97-1.88 (m, 1H); 1.82-1.71 (m, 1H); 1.71-1.58 (m, 1H); 1.55-1.42 (s, 3H); 1.41-1.27 (s, 3H).

Example 14

2-[3,5-Bis(trifluoromethyl)phenyl]-N-{4-(4-fluoro-2-methylphenyl)-6-[(8aR)-4-oxohexahydropyrrolo[1,2-a]pyrazin-2(1H)-yl]-3-pyridinyl}-N,2-dimethylpropanamide (E14)

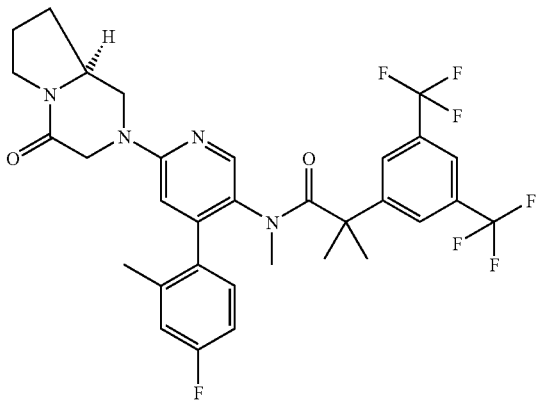

The title compound was prepared starting from 135 mg (0.253 mmoles) of 2-[3,5-bis(trifluoromethyl)phenyl]-N-[6-chloro-4-(4-fluoro-2-methylphenyl)-3-pyridinyl]-N,2-dimethylpropanamide (WO 2005/002577), 70 mg (0.5 mmol) of (8aS)-hexahydropyrrolo[1,2-a]pyrazin-4(1H)-one (EP 300189), 70 mg (0.5 mmol) of potassium carbonate; the reagents were dissolved in 0.8 ml of DMSO. The reaction mixture was heated at 150° C. overnight and then added to a saturated NH₄Cl solution and back extracted with DCM; the crude material was purified on SPE cartridge (Silica) eluting with a gradient cyclohexane/ethyl acetate 9:1, to ethyl acetate 100% and affording 24 mg of the title compound as pale yellow solid.

MS (ES/+): 637 [M+H]$^+$

NMR (DMSO-d$_6$): δ (ppm) 8.05-7.98 (s, 1H); 7.95-7.89 (s, 1H); 7.80-7.69 (br.s, 2H); 7.74-7.64 (br.s, 1H); 7.19-7.11 (d, 1H); 6.71-6.65 (s, 1H); 4.77-4.64 (d, 1H); 4.45-4.32 (d, 1H); 3.72-3.59 (m, 1H); 3.52-3.41 (dd, 1H); 3.39-3.31 (m, 1H); 2.83-2.73 (t, 1H); 2.60-2.50 (m, 1H); 2.31-2.17 (s, 3H); 2.21-2.15 (m, 1H); 2.15-2.05 (s, 3H); 1.97-1.88 (m, 1H); 1.82-1.71 (m, 1H); 1.71-1.58 (m, 1H); 1.55-1.42 (s, 3H); 1.41-1.27 (s, 3H).

Example 15

2-[3,5-Bis(trifluoromethyl)phenyl]-N-{4-(4-fluoro-2-methylphenyl)-6-[(9aS)-octahydro-3H-pyrrolo[1,2-d][1,4]diazepin-3-yl]-3-pyridinyl}-N,2-dimethylpropanamide (E15)

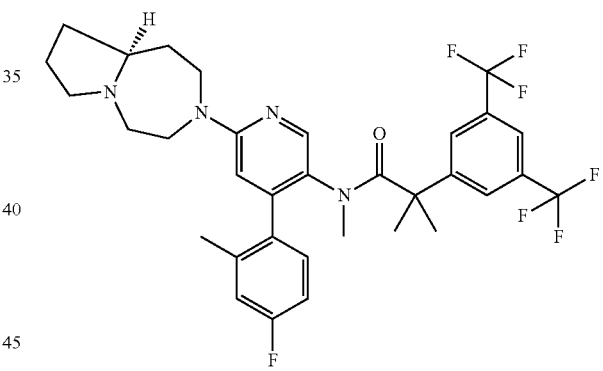

A 8 ml sealed vial was charged with 60 mg (0.112 mmoles) of 2-[3,5-bis(trifluoromethyl)phenyl]-N-[6-chloro-4-(4-fluoro-2-methylphenyl)-3-pyridinyl]-N,2-dimethylpropanamide (WO 2005/002577), 47 mg (0.335 mmol) of (9aS)-octahydro-1H-pyrrolo[1,2-d][1,4]diazepine (D6), 31 mg of potassium carbonate (0.224 mmol); the reagents were dissolved in 0.5 ml of DMSO. The reaction mixture was heated at 150° C. overnight and then added to a saturated NH₄Cl solution and back extracted with DCM; the crude material was purified on SPE cartridge (Silica) eluting with a gradient from cyclohexane/ethyl acetate 1:1, to ethyl acetate 100% and affording 32 mg of the title compound as pale yellow solid.

MS (ES/+): 637 [M+H]$^+$

NMR (DMSO-d$_6$): 8.02 (s, 1H), 7.93-7.82 (br.s, 1H), 7.79-7.70 (br.s, 2H), 7.73-7.64 (br.s, 1H), 7.15 (t, 1H), 7.13-7.03 (br. s, 1H), 6.66-6.52 (br. s, 1H), 4.28-3.98 (br. s, 1H0, 3.80-3.51 (br. s, 4H), 3.51-3.39 (br. s, 1H), 3.26-3.03 (br. s, 1H), 2.60-2.45 (br. s, 1H), 2.22 (s, 3H), 2.12 (s, 3H), 2.07-1.77 (br. s, 3H), 1.48 (s, 3H), 1.55-1.24 (m, 2H), 1.33 (s, 3H), 1.26-1.14 (m, 1H).

Example 16

2-[3,5-Bis(trifluoromethyl)phenyl]-N-[4-(4-fluoro-2-methylphenyl)-6-(9-oxohexahydropyrazino[2,1-c][1,4]oxazin-8(1H)-yl)-3-pyridinyl]-N,2-dimethylpropanamide (E16)

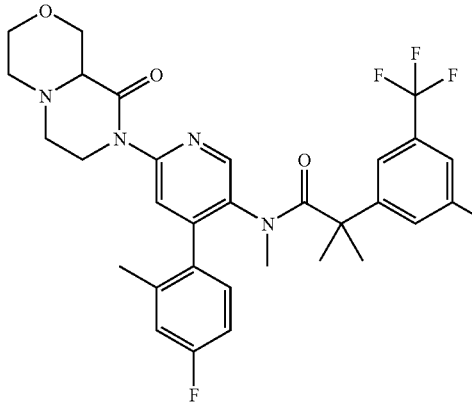

A 8 ml sealed vial was charged with 150 mg (0.281 mmol) of 2-[3,5-bis(trifluoromethyl)phenyl]-N-[6-chloro-4-(4-fluoro-2-methylphenyl)-3-pyridinyl]-N,2-dimethylpropanamide (WO 2005/002577), 120 mg (0.768 mmol) of hexahydropyrazino[2,1-c][1,4]oxazin-9(6H)-one (D7), 60 µL (0.563 mmol) of N,N'-dimethylethylenediamine, 110 mg (0.578 mmol) of copper iodide, 183 mg (0.562 mmol) of cesium carbonate; the reagents were dissolved in 4.5 ml of dioxane. The reaction mixture is stirred overnight at 150° C. The crude was purified by chromatography (silica, cyclohexane/EtOAc 90/10-30/70) affording the title compound as a white solid: 73 mg, 0.111 mmol, 40% yield.

Rf: 0.55 (EtOAc)

MS (ES/+): 653 [M+H]$^+$

NMR (DMSO-d$_6$): δ (ppm) 8.34-8.26 (s, 1H); 8.06-7.99 (s, 1H); 7.81-7.69 (br.s, 2H); 7.72-7.65 (br.s, 1H); 7.21-7.15 (d, 1H); 7.15-7.08 (s, 1H); 4.13-4.05 (dd, 1H); 4.03-3.82 (br.s, 2H); 3.80-3.72 (dd, 1H); 3.54-3.46 (dd, 1H); 3.40-3.31 (m, 1H); 3.14-3.06 (dd, 1H); 3.02-2.95 (dd, 1H); 2.86-2.80 (dd, 1H); 2.72-2.61 (m, 2H); 2.36-2.28 (t, 1H); 2.39-2.22 (br.s, 3H); 2.19-2.04 (br.s, 3H); 1.61-1.44 (br.s, 3H); 1.45-1.30 (br.s, 3H).

Example 17

2-[3,5-Bis(trifluoromethyl)phenyl]-N-[4-(4-fluoro-2-methylphenyl)-6-(9-oxohexahydropyrazino[2,1-c][1,4]oxazin-8(1H)-yl)-3-pyridinyl]-N,2-dimethylpropanamide (E17) Enantiomer 1 of E16

ENANTIOMER 1

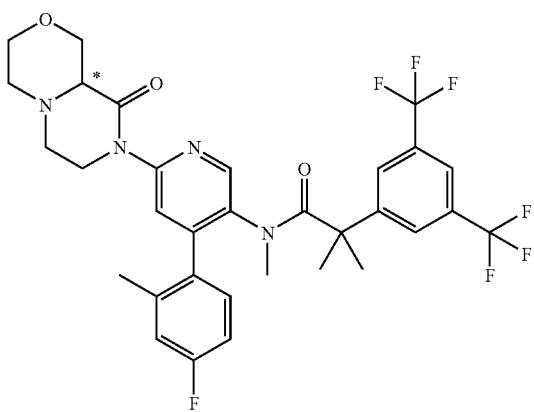

2-[3,5-Bis(trifluoromethyl)phenyl]-N-[4-(4-fluoro-2-methylphenyl)-6-(9-oxohexahydropyrazino[2,1-c][1,4]oxazin-8(1H)-yl)-3-pyridinyl]-N,2-dimethylpropanamide (E16; 42 mg) was submitted for chiral separation to isolate its enantiomers. The enantiomer labeled 1, of unknown but single stereochemistry was isolated using the following conditions (20 mg, 100% e.e.)

Preparative Conditions:

| | |
|---|---|
| Amount supplied | 42 mg |
| Chiral Column | CHIRALCEL OD, (25 × 2) cm |
| Mobile phase | n-Hexane/2-propanol 94/6% v/v |
| Flow rate | 18 ml/min |
| Detection | UV at 225 nm |
| Run Time | 17 min |

MS (ES/+): 653 [M+H]$^+$

NMR (DMSO-d$_6$): δ (ppm) 8.34-8.26 (s, 1H); 8.06-7.99 (s, 1H); 7.81-7.69 (br.s, 2H); 7.72-7.65 (br.s, 1H); 7.21-7.15 (d, 1H); 7.15-7.08 (s, 1H); 4.13-4.05 (dd, 1H); 4.03-3.82 (br.s, 2H); 3.80-3.72 (dd, 1H); 3.54-3.46 (dd, 1H); 3.40-3.31 (m, 1H); 3.14-3.06 (dd, 1H); 3.02-2.95 (dd, 1H); 2.86-2.80 (dd, 1H); 2.72-2.61 (m, 2H); 2.36-2.28 (t, 1H); 2.39-2.22 (br.s, 3H); 2.19-2.04 (br.s, 3H); 1.61-1.44 (br.s, 3H); 1.45-1.30 (br.s, 3H).

Example 18

2-[3,5-Bis(trifluoromethyl)phenyl]-N-[4-(4-fluoro-2-methylphenyl)-6-(9-oxohexahydropyrazino[2,1-c][1,4]oxazin-8(1H)-yl)-3-pyridinyl]-N,2-dimethylpropanamide (E18) Enantiomer 2 of E16

ENANTIOMER 2

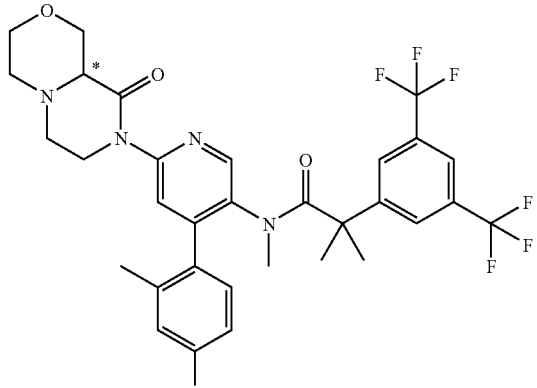

The title compound was isolated using the same conditions as E17, obtaining 17 mg, 100% e.e.

MS (ES/+): 653 [M+H]$^+$

NMR (DMSO-d$_6$): δ (ppm) 8.34-8.26 (s, 1H); 8.06-7.99 (s, 1H); 7.81-7.69 (br.s, 2H); 7.72-7.65 (br.s, 1H); 7.21-7.15 (d, 1H); 7.15-7.08 (s, 1H); 4.03-3.82 (br.s, 2H); 3.80-3.72 (dd, 1H); 3.54-3.46 (dd, 1H); 3.40-3.31 (m, 1H); 3.14-3.06 (dd, 1H); 3.02-2.95 (dd, 1H); 2.86-2.80 (dd, 1H); 2.72-2.61 (m, 2H); 2.36-2.28 (t, 1H); 2.39-2.22 (br.s, 3H); 2.19-2.04 (br.s, 3H); 1.61-1.44 (br.s, 3H); 1.45-1.30 (br.s, 3H).

Example 19

2-[3,5-Bis(trifluoromethyl)phenyl]-N-[4-(4-fluoro-2-methylphenyl)-6-(hexahydropyrazino[2,1-c][1,4]oxazin-8(1H)-yl)-3-pyridinyl]-N,2-dimethylpropanamide (E19)

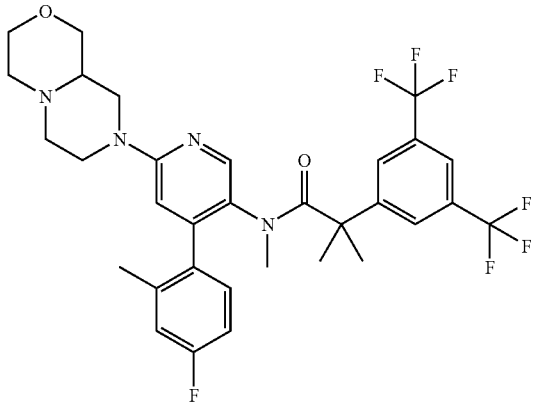

A 8 ml sealed vial was charged with 124 mg (0.233 mmol) of 2-[3,5-bis(trifluoromethyl)phenyl]-N-[6-chloro-4-(4-fluoro-2-methylphenyl)-3-pyridinyl]-N,2-dimethylpropanamide (WO 2005/002577); 83 mg (0.584 mmol) of octahydropyrazino[2,1-c][1,4]oxazine (EP 472826), 90 mg (0.701 mmol) of potassium carbonate; the reagents were dissolved in 0.5 ml of DMSO. The crude product was purified by flash chromatography (silica, cyclohexane/EtOAc 90/10-30/70) affording the title compound as a white solid 85 mg (0.133 mmol).

Rf: 0.4 (EtOAc)
MS (ES/+): 639 [M+H]$^+$.
NMR (DMSO-d$_6$): δ (ppm) 8.05-7.98 (s, 1H); 7.91-7.85 (s, 1H); 7.79-7.68 (m, 2H); 7.73-7.65 (br.s, 1H); 7.18-7.12 (d, 1H); 7.13-7.06 (br.s, 1H); 6.73-6.64 (s, 1H); 4.29-4.18 (d, 1H); 4.13-4.03 (d, 1H); 3.78-3.68 (t, 2H); 3.56-3.48 (t, 1H); 3.18-3.09 (t, 1H); 2.92-2.80 (t, 1H); 2.82-2.74 (d, 1H); 2.70-2.62 (d, 1H); 2.44-2.34 (t, 1H); 2.21-2.15 (s, 3H); 2.28-2.06 (m, 3H); 2.14-2.07 (s, 3H); 1.55-1.41 (s, 3H); 1.40-1.28 (s, 3H).

Example 20

2-[3,5-Bis(trifluoromethyl)phenyl]-N-[4-(4-fluoro-2-methylphenyl)-6-(hexahydropyrazino[2,1-c][1,4]oxazin-8(1H)-yl)-3-pyridinyl]-N,2-dimethylpropanamide (E20) Enantiomer 1 of E19

[[α]$_D$=1.8, c=1.0, MeOH]

ENANTIOMER 1

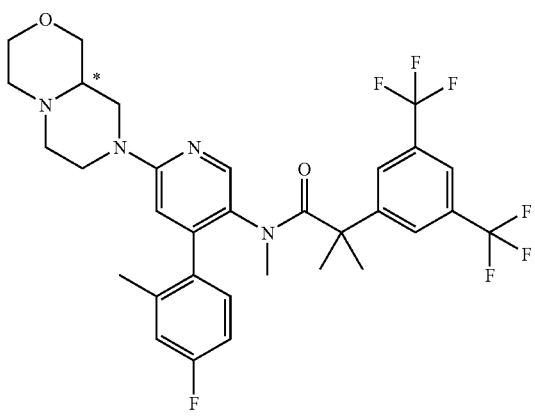

Example 19 (15 mg) was submitted for chiral separation to isolate its enantiomers. The enantiomer labeled 1, of unknown but single stereochemistry was isolated using the following conditions (5 mg, 97.2% e.e.)

Preparative Conditions:

| | |
|---|---|
| Amount supplied | 15 mg |
| Chiral Column | CHIRALCEL OD, (25 × 2) cm |
| Mobile phase | n-Hexane/2-propanol 94/6% v/v |
| Flow rate | 18 ml/min |
| Detection | UV at 225 nm |
| Run Time | 17 min |

MS (ES/+): 639 [M+H]$^+$
NMR (DMSO-d$_6$): δ (ppm) 8.05-7.98 (s, 1H); 7.91-7.85 (s, 1H); 7.79-7.68 (m, 2H); 7.73-7.65 (br.s, 1H); 7.18-7.12 (d, 1H); 7.13-7.06 (br.s, 1H); 6.73-6.64 (s, 1H); 4.29-4.18 (d, 1H); 4.13-4.03 (d, 1H); 3.78-3.68 (t, 2H); 3.56-3.48 (t, 1H); 3.18-3.09 (t, 1H); 2.92-2.80 (t, 1H); 2.82-2.74 (d, 1H); 2.70-2.62 (d, 1H); 2.44-2.34 (t, 1H); 2.21-2.15 (s, 3H); 2.28-2.06 (m, 3H); 2.14-2.07 (s, 3H); 1.55-1.41 (s, 3H); 1.40-1.28 (s, 3H).

Example 21

2-[3,5-Bis(trifluoromethyl)phenyl]-N-[4-(4-fluoro-2-methylphenyl)-6-(hexahydropyrazino[2,1-c][1,4]oxazin-8(1H)-yl)-3-pyridinyl]-N,2-dimethylpropanamide (E21) Enantiomer 2 of E19 [[α]$_D$=−1.0]

ENANTIOMER 2

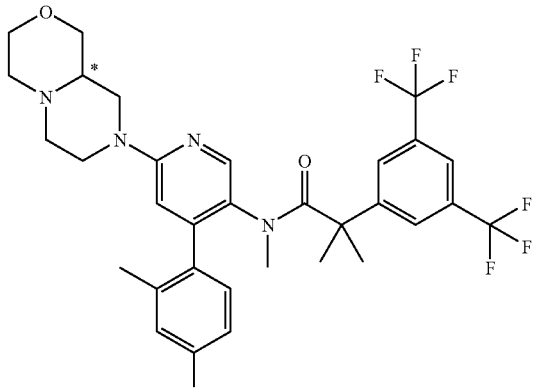

The title compound was isolated using the same conditions as E20, obtaining 5 mg, 99.8% e.e.

MS (ES/+): 639 [M+H]$^+$.
NMR (DMSO-d$_6$): δ (ppm) 8.05-7.98 (s, 1H); 7.91-7.85 (s, 1H); 7.79-7.68 (m, 2H); 7.73-7.65 (br.s, 1H); 7.18-7.12 (d, 1H); 7.13-7.06 (br.s, 1H); 6.73-6.64 (s, 1H); 4.29-4.18 (d, 1H); 4.13-4.03 (d, 1H); 3.78-3.68 (t, 2H); 3.56-3.48 (t, 1H); 3.18-3.09 (t, 1H); 2.92-2.80 (t, 1H); 2.82-2.74 (d, 1H); 2.70-2.62 (d, 1H); 2.44-2.34 (t, 1H); 2.21-2.15 (s, 3H); 2.28-2.06 (m, 3H); 2.14-2.07 (s, 3H); 1.55-1.41 (s, 3H); 1.40-1.28 (s, 3H).

Example 22

2-[3,5-Bis(trifluoromethyl)phenyl]-N-[6-(1,1-dioxi-dohexahydro-5H-isothiazolo[2,3-a]pyrazin-5-yl)-4-(4-fluoro-2-methylphenyl)-3-pyridinyl]-N,2-dimethylpropanamide (E22) Enantiomer 1 of E1

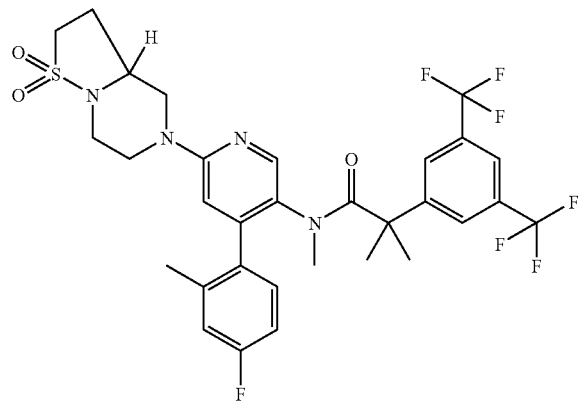

Preparative Conditions:
Amount supplied 37 mg

| Chiral Column | CHIRALPAK AD-H, (25 × 2) cm |
|---|---|
| Mobile phase | n-Hexane/Ethanol + 0.1% isopropylamine 25/75% v/v |
| Flow rate | 15 ml/min |
| Detection | UV at 225 nm |

Isolated: 4 mg; purity of enantiomer 1 resulted to be 100%
MS (ES/+): 673 [M+H]$^+$
NMR (DMSO-d$_6$): δ (ppm) 8.01 (s, 1H); 7.78 (s, 1H); 7.65 (s, 2H); 7.08-6.85 (m, 3H); 6.53 (s, 1H); 4.81-4.53 (m, 1H); 4.35-4.09 (m, 1H); 3.53-3.50 (m, 1H); 3.38-3.25 (m, 1H); 3.16-3.09 (m, 1H); 2.96 (t, 1H); 2.83 (t, 1H); 2.70-1.98 (m, 10H); 1.79-1.47 (m, 3H); 1.46-1.33 (s, 3H).

Example 23

2-[3,5-Bis(trifluoromethyl)phenyl]-N-[6-(1,1-dioxi-dohexahydro-5H-isothiazolo[2,3-a]pyrazin-5-yl)-4-(4-fluoro-2-methylphenyl)-3-pyridinyl]-N,2-dimethylpropanamide (E23) Enantiomer 2 of E1

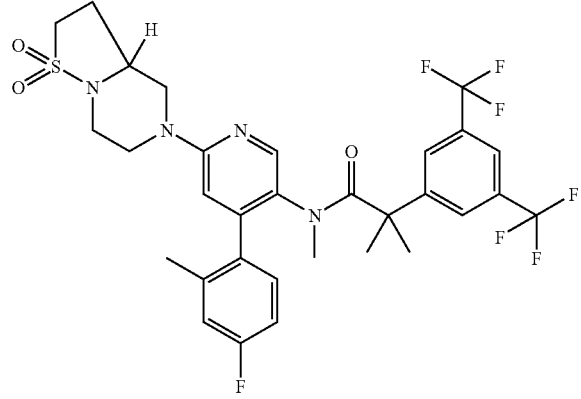

Preparative Conditions:

| Chiral Column | CHIRALPAK AD-H, (25 × 2) cm |
|---|---|
| Mobile phase | n-Hexane/Ethanol + 0.1% isopropylamine 25/75% v/v |
| Flow rate | 15 ml/min |
| Detection | UV at 225 nm |

Isolated: 6 mg; purity of enantiomer 2 was 98.8% by UV
MS (ES/+): 673 [M+H]$^+$
NMR (DMSO-d$_6$): δ (ppm) 8.01 (s, 1H); 7.78 (s, 1H); 7.65 (s, 2H); 7.08-6.85 (m, 3H); 6.53 (s, 1H); 4.81-4.53 (m, 1H); 4.35-4.09 (m, 1H); 3.53-3.50 (m, 1H); 3.38-3.25 (m, 1H); 3.16-3.09 (m, 1H); 2.96 (t, 1H); 2.83 (t, 1H); 2.70-1.98 (m, 10H); 1.79-1.47 (m, 3H); 1.46-1.33 (s, 3H).

Example 24

2-[3,5-Bis(trifluoromethyl)phenyl]-N-{4-(4-fluoro-2-methylphenyl)-6-[(8aS)-hexahydropyrrolo[1,2-a]pyrazin-2(1H)-yl]-3-pyridinyl}-N,2-dimethylpropanamide (E24)

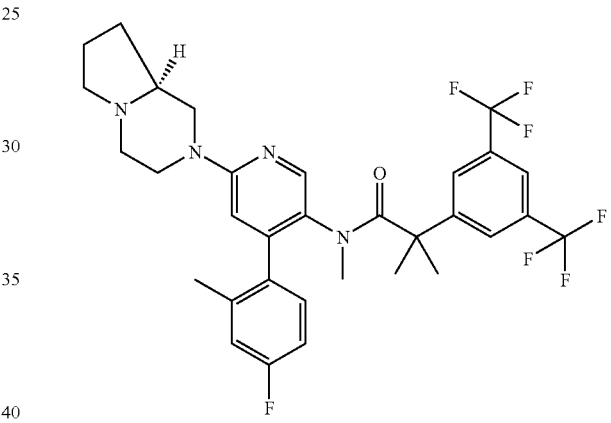

A 10 ml microwave tube was charged with 80 mg (0.150 mmol) of 2-[3,5-bis(trifluoromethyl)phenyl]-N-[6-chloro-4-(4-fluoro-2-methylphenyl)-3-pyridinyl]-N,2-dimethylpropanamide (WO 2005/002577), 47.4 mg (0.375 mmol) of (8aS)-octahydropyrrolo[1,2-a]pyrazine, 62.2 mg (0.450 mmol) of potassium carbonate; the reagents were dissolved in 0.6 ml of DMSO. The reaction mixture was irradiated in a microwave oven (180° C., 300 W) for 1 hour and then the crude is purified by a Mass Directed Preparative Instrument by Waters (System Fraction Lynx™) performed on a X Terra Prep MS C18 (30×150 mm; 10 μm) (mobile phase: from 99% [water+0.1% HCO$_2$H] and 1% [CH$_3$CN+0.1% HCO$_2$H] to 100% [CH$_3$CN+0.1% HCO$_2$H] in 8 min and 30"; 100% [CH$_3$CN+0.1% HCO$_2$H] for 6 min; from 100% [CH$_3$CN+0.1% HCO$_2$H] to 99% [water+0.1% HCO$_2$H] and 1% [CH$_3$CN+0.1% HCO$_2$H] in 30"; 99% [water+0.1% HCO$_2$H] and 1% [CH$_3$CN+0.1% HCO$_2$H] for 12"); T=rt; flow rate=40 ml/min; UV Detection: 210-400 nm; MS Detection Mode: ES (+)/ES (−), Mass Range: 100-900] to afford 45 mg of the target compound as pale yellow solid.

R$_F$=0.2 (Ethyl Acetate)
MS (ES/+): 623 [M+H]$^+$
NMR (CDCl$_3$): δ (ppm) 8.00 (s, 1H), 7.78 (s, 1H), 7.71-7.60 (br. s, 2H), 7.27-7.22 (br. s, 1H), 7.05-6.85 (br. s, 2H), 6.52-6.45 (s, 1H), 4.63-3.98 (m, 2H), 3.74-2.94 (m, 4H), 2.42-2.29 (s, 3H), 2.67-1.86 (m, 3H), 2.17-2.07 (s, 3H), 1.56-1.48 (s, 3H), 1.81-1.12 (m, 4H), 1.41-1.33 (s, 3H).

Example 25

2-[3,5-Bis(trifluoromethyl)phenyl]-N-{4-(4-fluoro-2-methylphenyl)-6-[(8aR)-hexahydropyrrolo[1,2-a]pyrazin-2(1H)-yl]-3-pyridinyl}-N,2-dimethylpropanamide (E25)

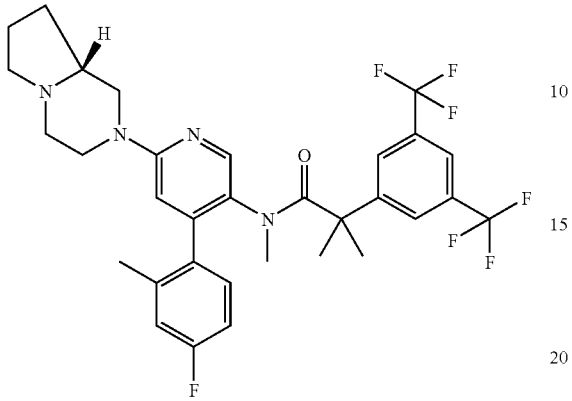

The title compound was prepared starting from 100 mg (0.187 mmole) of 2-[3,5-bis(trifluoromethyl)phenyl]-N-[6-chloro-4-(4-fluoro-2-methylphenyl)-3-pyridinyl]-N,2-dimethylpropanamide (WO 2005/002577), 70 mg (0.554 mmol) of (8aR)-octahydropyrrolo[1,2-a]pyrazine, 52.2 mg of potassium carbonate (0.377 mmol); the reagents were dissolved in 0.6 ml of DMSO and the reaction mixture was heated at 150° C. overnight. Obtained after flash chromatography 52 mg of the desired compound.

MS (ES/+): 623 [M+H]$^+$

NMR (DMSO-d$_6$): δ (ppm) 8.00 (s, 1H), 7.78 (s, 1H), 7.71-7.60 (br. s, 2H), 7.27-7.22 (br. s, 1H), 7.05-6.85 (br. s, 2H), 6.52-6.45 (s, 1H), 4.63-3.98 (m, 2H), 3.74-2.94 (m, 4H), 2.42-2.29 (s, 3H), 2.67-1.86 (m, 3H), 2.17-2.07 (s, 3H), 1.56-1.48 (s, 3H), 1.81-1.12 (m, 4H), 1.41-1.33 (s, 3H).

Example 26

2-[3,5-Bis(trifluoromethyl)phenyl]-N-{4-(4-fluoro-2-methylphenyl)-6-[(8aR)-hexahydropyrrolo[1,2-a]pyrazin-2(1H)-yl]-3-pyridinyl}-N,2-dimethylpropanamide hydrochloride (E26)

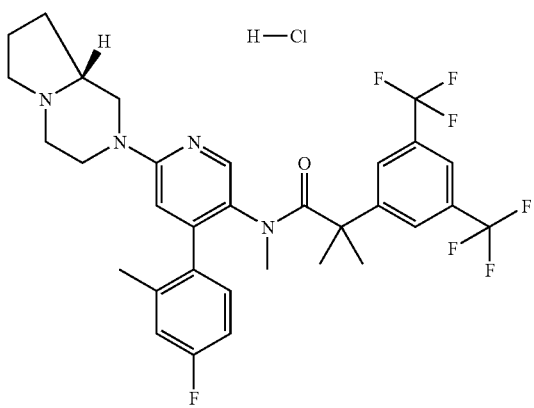

2-[3,5-Bis(trifluoromethyl)phenyl]-N-{4-(4-fluoro-2-methylphenyl)-6-[(8aR)-hexahydropyrrolo[1,2-a]pyrazin-2(1H)-yl]-3-pyridinyl}-N,2-dimethylpropanamide (E25; 39 mg, 0.063 mmol) was dissolved in DCM and the temperature was lowered at 0° C.;

HCl (1M soln. in Et$_2$O) 75 μl (0.075 mmol) was slowly added and, afterwards, the reaction mixture was stirred at this temperature for 30 min. Then, the solvent was removed and, the solid obtained was triturated with pentane.

Obtained 41 mg of the desired compound as pale yellow solid.

MS (ES/+): 623 [M+H]$^+$

NMR (DMSO-d$_6$): δ (ppm) 10.63 (s, 1H), 8.02 (s, 1H), 7.96 (s, 1H), 7.81-7.65 (m, 2H), 7.17 (d, 1H), 7.15-7.07 (m, 1H), 6.90-6.84 (s, 1H), 4.88-4.66 m, 1H), 4.12-1.08 (m, 24H).

Example 27

2-[3,5-Bis(trifluoromethyl)phenyl]-N-{4-(4-fluoro-2-methylphenyl)-6-[(8aR)-6-oxohexahydropyrrolo[1,2-a]pyrazin-2(1H)-yl]-3-pyridinyl}-N,2-dimethylpropanamide (E27)

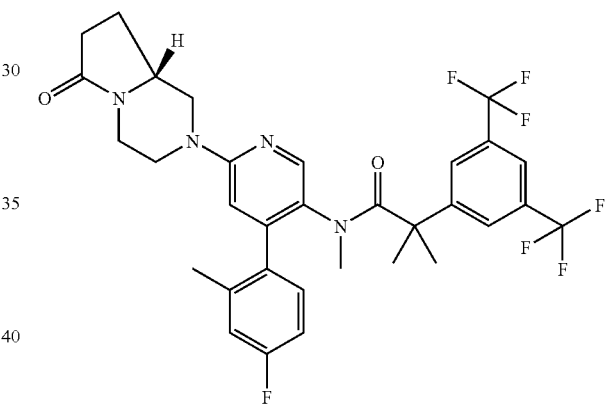

A 8 ml sealed vial was charged with 100 mg (0.187 mmol) of 2-[3,5-bis(trifluoromethyl)phenyl]-N-[6-chloro-4-(4-fluoro-2-methylphenyl)-3-pyridinyl]-N,2-dimethylpropanamide (WO 2005/002577), 78.6 mg (0.561 mmol) of (8aS)-hexahydropyrrolo[1,2-a]pyrazin-6(2H)-one (WO 2003/066635), 52 mg (0.374 mmol) of potassium carbonate; the reagents were dissolved in 0.8 ml of DMSO. The reaction mixture was heated at 180° C. for 36-48 hrs and then added to a saturated NH$_4$Cl solution and back extracted with DCM; the crude material was purified on SPE cartridge (Silica) eluting with a gradient from cyclohexane/ethyl acetate 9:1, to ethyl acetate 100% and affording 23 mg of the desired compound.

MS (ES/+): 637 [M+H]$^+$

NMR (DMSO-d$_6$): δ (ppm) 8.01 (s, 1H); 7.78 (s, 1H); 7.65 (s, 2H); 7.05-6.87 (m, 3H); 6.52 (s, 1H); 4.67-4.52 (m, 1H); 4.32-4.19 (m, 1H); 4.14-4.10 (d, 1H); 3.77-3.64 (m, 1H); 3.02-2.84 (m, 2H); 2.61 (t, 1H); 2.48-2.44 (dd, 2H); 2.41-2.33 (s, 3H); 2.30-2.22 (m, 1H); 2.13 (s, 3H); 1.79-1.65 (m, 1H); 1.53 (s, 3H); 1.38 (s, 3H).

Example 28

2-[3,5-Bis(trifluoromethyl)-phenyl]-N-{4-(2-chlorophenyl)-6-[(8aS)-hexahydropyrrolo[1,2-a]pyrazin-2(1H)-yl]-3-pyridinyl}-N,2-dimethylpropanamide (E28)

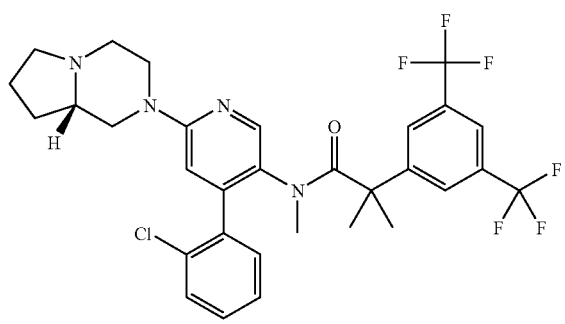

To a solution of 2-[3,5-bis(trifluoromethyl)phenyl]-N-[6-chloro-4-(2-chlorophenyl)-3-pyridinyl]-N,2-dimethylpropanamide (WO 2005/002577; 0.11 mmol) in dry DMSO (1 ml) S-octahydropyrrolo[1,2-a]pyrazine, (0.22 mmol) and potassium carbonate (0.22 mmol) were added and the resulting mixture was shaken for 12 hours at 150° C. After cooling the dichloromethane was added (2 ml) and then isocyanate polymer bound was added (2.0 mmol), and the resulting mixture was shaken at room temperature overnight. Then the resin was filtered and the filtrate was concentrated under reduced pressure. Purifications were carried out using mass directed HPLC:

Preparative Chromatographic Conditions

Column: X Terra MS C18 5 μm, 100×19 mm

Mobile phase: A: $NH_4HCO_3$ sol. 10 mM, pH10; B: $CH_3CN$

Gradient: 30% (B) for 1 min, from 30% (B) to 95% (B) in 9 min, 95% (B) for 3 min Flow rate: 20 ml/min UV wavelength range: 210-350 nm Mass range: 100-900 amu Ionization: ES+

Analytical Chromatographic Conditions

Column: X Terra MS C18 5 μm, 50×4.6 mm

Mobile phase: A: $NH_4HCO_3$ sol. 10 mM, pH10; B: $CH_3CN$

Gradient: 30% (B) for 1 min, from 30% (B) to 95% (B) in 9 min, 95% (B) for 3 min Flow rate: 1 ml/min UV wavelength range: 210-350 nm Mass range: 100-900 amu Ionization: ES+

Obtained 44.6 mg of the desired compound.

NMR (CDCl$_3$): δ (ppm) 8.03 (s, 1H), 7.90 (s, 1H), 7.74 (s, 2H), 7.54 (2, 2H), 7.49-7.39 (m, 2H), 7.27 (d, 1H), 6.72 (s, 1H), 4.39 (d, 1H), 4.22 (d, 1H), 3.05-2.98 (m, 2H), 2.90-2.83 (t, 1H), 2.57-2.46 (m, 1H), 2.42 (s, 3H), 2.12 (t, 1H), 2.04 (q, 1H), 1.97-1.61 (m, 4H), 1.45-1.19 (m, 7H).

Example 29

2-[3,5-Bis(trifluoromethyl)-phenyl]-N-{4-(2-chlorophenyl)-6-[(8aR)-hexahydropyrrolo[1,2-a]pyrazin-2(1H)-yl]-3-pyridinyl}-N,2-dimethylpropanamide (E29)

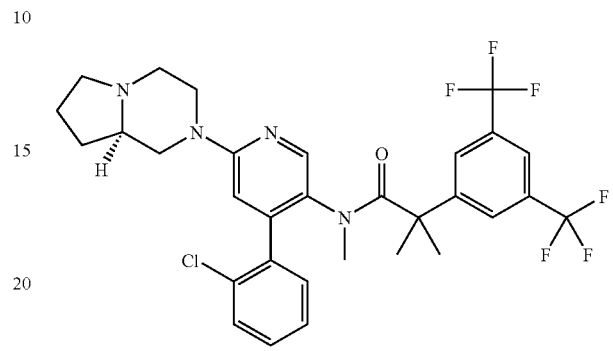

To a solution of 2-[3,5-bis(trifluoromethyl)phenyl]-N-[6-chloro-4-(2-chlorophenyl)-3-pyridinyl]-N,2-dimethylpropanamide (WO 2005/002577; 0.11 mmol) in dry DMSO (1 ml) R-octahydropyrrolo[1,2-a]pyrazine, (0.22 mmol) and potassium carbonate (0.22 mmol) were added and the resulting mixture was shaken for 12 hours at 150° C. After cooling the dichloromethane was added (2 ml) and then isocyanate polymer bound was added (2.0 mmol), and the resulting mixture was shaken at room temperature overnight. Then the resin was filtered and the filtrate was concentrated under reduced pressure. Purifications were carried out using mass directed HPLC:

Preparative Chromatographic Conditions

Column: X Terra MS C18 5 μm, 100×19 mm

Mobile phase: A: $NH_4HCO_3$ sol. 10 mM, pH10; B: $CH_3CN$

Gradient: 30% (B) for 1 min, from 30% (B) to 95% (B) in 9 min, 95% (B) for 3 min Flow rate: 20 ml/min UV wavelength range: 210-350 nm Mass range: 100-900 amu Ionization: ES+

Analytical Chromatographic Conditions

Column: X Terra MS C18 5 μm, 50×4.6 mm

Mobile phase: A: $NH_4HCO_3$ sol. 10 mM, pH10; B: $CH_3CN$

Gradient: 30% (B) for 1 min, from 30% (B) to 95% (B) in 9 min, 95% (B) for 3 min Flow rate: 1 ml/min UV wavelength range: 210-350 nm Mass range: 100-900 amu Ionization: ES+

Obtained 26.3 mg of the desired compound.

NMR (DMSO-d$_6$): δ (ppm) 8.03 (s, 1H), 7.90 (s, 1H), 7.74 (s, 2H), 7.54 (2, 2H), 7.49-7.39 (m, 2H), 7.27 (d, 1H), 6.72 (s, 1H), 4.39 (d, 1H), 4.22 (d, 1H), 3.05-2.98 (m, 2H), 2.90-2.83 (t, 1H), 2.57-2.46 (m, 1H), 2.42 (s, 3H), 2.12 (t, 1H), 2.04 (q, 1H), 1.97-1.61 (m, 4H), 1.45-1.19 (m, 7H).

Example 30

2-[3,5-Bis(trifluoromethyl)phenyl]-N-[4-(4-fluoro-2-methylphenyl)-6-(hexahydropyrazino[2,1-c][1,4]oxazin-8(1H)-yl)-3-pyridinyl]-N,2-dimethylpropanamide hydrochloride (E30) Enantiomer 1

ENANTIOMER 1

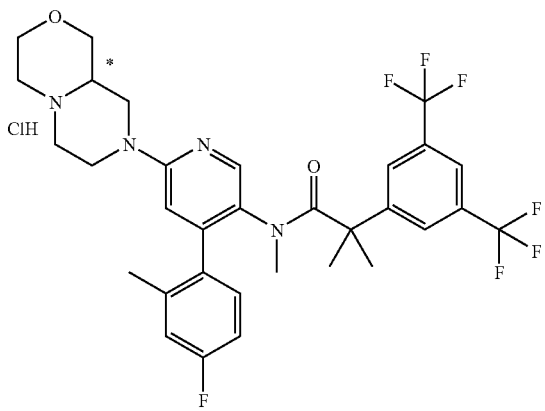

A sample of 2-[3,5-bis(trifluoromethyl)phenyl]-N-[4-(4-fluoro-2-methylphenyl)-6-(hexahydropyrazino[2,1-c][1,4]oxazin-8(1H)-yl)-3-pyridinyl]-N,2-dimethylpropanamide (E20, 42 mg, 66 μmol) was suspended in 1 ml of anhydrous diethyl ether and treated at 0° C. for 30 min with 79 μL of 1M HCl in diethyl ether. The solvent was removed under a stream of nitrogen and the product triturated with anhydrous pentane, to give, after filtration, the hydrochloride as a white solid (44 mg, quantitative).

MS (ES/+): 639 [M+H]$^+$

NMR (DMSO-d$_6$): δ (ppm) 10.99 (br. s, 1H), 8.04 (s, 1H), 7.95 9 s, 1H), 7.85-7.60 (m, 2H), 7.19 (d, 1H), 7.16-6.92 (m, 2H), 6.92-6.80 (s, 1H), 4.56 (d, 1H), 4.43 (d, 1H), 4.12-3.93 (m, 2H), 3.81 (t, 1H), 3.59 (t, 1H), 3.52-3.45 (m, 1H), 3.29-3.12 (m, 3H), 3.05-2.79 (m, 1H), 2.60-2.52 (m, 1H), 2.33-2.20 (br.s, 3H), 2.22-2.14 (m, 1H), 2.16-2.05 (br.s, 3H), 1.56-1.09 (m, 6H).

Example 31

2-[3,5-Bis(trifluoromethyl)phenyl]-N-[4-(4-fluoro-2-methylphenyl)-6-(hexahydropyrazino[2,1-c][1,4]oxazin-8(1H)-yl)-3-pyridinyl]-N,2-dimethylpropanamide hydrochloride (E31) Enantiomer 2

ENANTIOMER 2

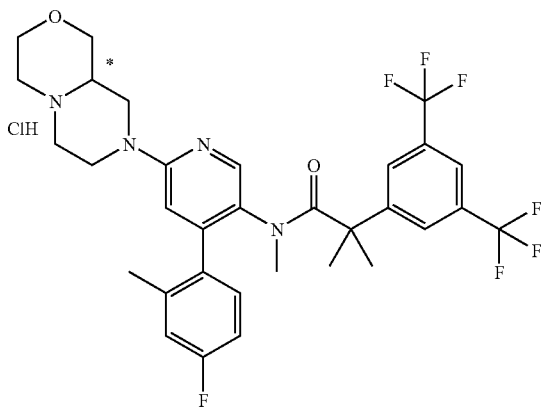

A sample of 2-[3,5-bis(trifluoromethyl)phenyl]-N-[4-(4-fluoro-2-methylphenyl)-6-(hexahydropyrazino[2,1-c][1,4]oxazin-8(1H)-yl)-3-pyridinyl]-N,2-dimethylpropanamide (E21; 39 mg, 61 μmol) was suspended in 1 ml of anhydrous diethyl ether and treated at 0° C. for 30 min with 73 μL of 1M HCl in diethyl ether. The solvent was removed under a stream of nitrogen and the product triturated with anhydrous pentane, to give, after filtration, the hydrochloride as a white solid 41 mg.

MS (ES/+): 639 [M+H]$^+$

NMR (DMSO-d$_6$): δ (ppm) 10.99 (br. s, 1H), 8.04 (s, 1H), 7.95 9 s, 1H), 7.85-7.60 (m, 2H), 7.19 (d, 1H), 7.16-6.92 (m, 2H), 6.92-6.80 (s, 1H), 4.56 (d, 1H), 4.43 (d, 1H), 4.12-3.93 (m, 2H), 3.81 (t, 1H), 3.59 (t, 1H), 3.52-3.45 (m, 1H), 3.29-3.12 (m, 3H), 3.05-2.79 (m, 1H), 2.60-2.52 (m, 1H), 2.33-2.20 (br. s, 3H), 2.22-2.14 (m, 1H), 2.16-2.05 (br. s, 3H), 1.56-1.09 (m, 6H).

Example 32

2-[3,5-Bis(trifluoromethyl)phenyl]-N-{4-(4-fluoro-2-methylphenyl)-6-[(3R,8aR)-3-(hydroxymethyl)hexahydropyrrolo[1,2-a]pyrazin-2(1H)-yl]-3-pyridinyl}-N,2-dimethylpropanamide (E32)

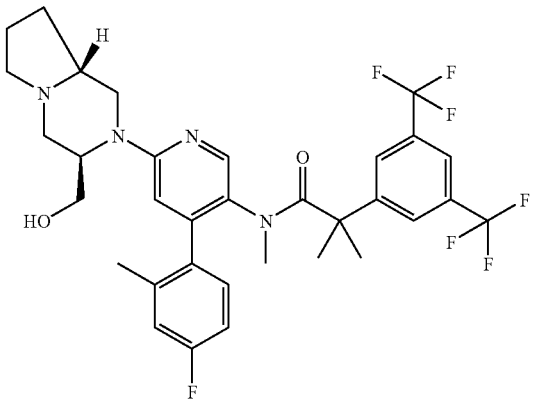

The title compound was prepared starting from 323 mg (0.608 mmoles) of 2-[3,5-bis(trifluoromethyl)phenyl]-N-[6-chloro-4-(4-fluoro-2-methylphenyl)-3-pyridinyl]-N,2-dimethylpropanamide (WO 2005/002577), 1.216 mg (0.160 mmol) of (3R,9aR)-octahydro-2H-pyrido[1,2-a]pyrazin-3-ylmethanol (Tetrahedron Asymmetry, 1996, 7(7), 1999-2005), 35 mg of bis(dibenzylideneacetone)palladium (0.061 mmol), 57 mg of 2-dicyclohexylphosphino-2'-(N,N-dimethylamino)biphenyl (0.145 mmol), 297 mg (0.912 mmol) of cesium carbonate; the reagents were dissolved in 10 ml of toluene and stirred at 140° C. in a closed vial for 4 hours. More dicyclohexylphosphino-2'-(N,N-dimethylamino)biphenyl (57 mg 0.145 mmol), and bis(dibenzylideneacetone)palladium (35 mg, 0.061 mmol) were added and the reaction kept at 140° C. for additional 4 hours. The crude material was loaded on a SCX cartridge, the neutral fractions were washed with methanol and the basic eluted with 2M ammonia in methanol and collected. The solvent was removed and the residue purified by chromatography (Silica) eluting with ethyl acetate, followed by a gradient from methylene chloride to methylene chloride:methanol 95:5. The cleanest fractions were purified further by chromatography on an NH$_2$ silica cartridge with a gradient cyclohexane to cyclohexane:ethyl acetate 70:30, affording 29 mg of the title compound as pale yellow solid.

MS (ES/+): 653 [M+H]$^+$

NMR (DMSO-d$_6$): δ (ppm) 7.89-7.86 (s, 1H); 7.80-7.76 (s, 1H); 7.70-7.66 (s, 2H); 7.12-7.03 (m, 2H); 7.00-6.92 (m, 1H); 6.50-6.47 (s, 1H); 4.06-3.97 (m, 1H); 3.66-3.54 (m, 3H); 3.49-3.39 (m, 1H); 3.27-3.12 (m, 1H); 3.11-3.00 (m, 1H); 2.89-2.77 (m, 2H); 2.44-2.38 (s, 3H); 2.17-2.07 (s, 3H); 2.07-1.41 (m, 5H); 1.38-1.31 (s, 3H); 1.26-1.20 (s, 3H).

Example 33

2-[3,5-Bis(trifluoromethyl)phenyl]-N-[6-(2,2-dioxidohexahydropyrazino[2,1-c][1,4]thiazin-8(1H)-yl)-4-(4-fluoro-2-methylphenyl)-3-pyridinyl]-N,2-dimethylpropanamide (E33)

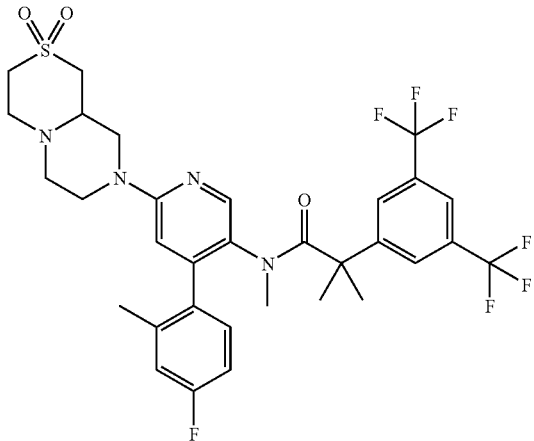

A 8 ml sealed vial was charged with 180 mg (0.31 mmol) of 2-[3,5-bis(trifluoromethyl)phenyl]N-[6-chloro-4-(4-fluoro-2-methylphenyl)-3-pyridinyl]-N,2-dimethylpropanamide (WO 2005/002577); 168 mg (0.62 mmol) of octahydropyrazino[2,1-c][1,4]thiazine 2,2-dioxide (D19), 128 mg (0.701 mmol) of potassium carbonate; the reagents were dissolved in 1 ml of DMSO and stirred at 150° C. for 18 h. The reaction mixture was diluted with water and ethyl acetate and the aqueous phase was extracted with ethyl acetate. The combined organic fractions were dried and the solvent was removed under reduced pressure. The crude product was purified by flash chromatography (silica, cyclohexane/EtOAc 50/50 to EtOAc) affording the title compound as a white solid 105 mg.

MS (ES/+): [M+Na]$^+$.

NMR (DMSO-d$_6$): δ (ppm) 8.07-7.99 (s, 1H), 7.97-7.86 (s, 1H), 7.82-7.62 (m, 2H), 7.22-7.12 (d, 1H), 7.15-6.98 (m, 2H), 6.79-6.69 (s, 1H), 4.32-4.13 (m, 2H), 3.31-3.07 (m, 5H), 3.04-2.84 (m, 3H), 2.73-2.55 (m, 2H), 2.57-2.43 (m, 3H), 2.36-2.18 (m, 1H), 2.29-2.05 (m, 3H); 1.60-1.27 (m, 6H).

Example 34

2-[3,5-Bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide (E34)

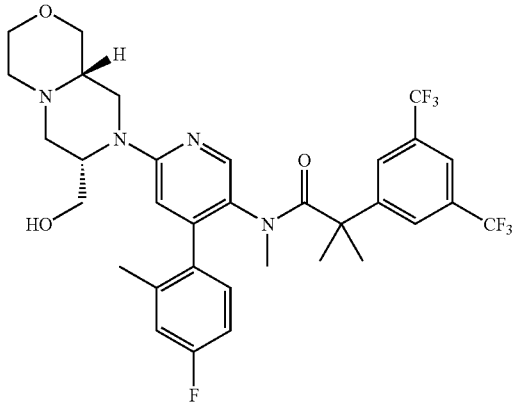

2-[3,5-bis(trifluoromethyl)phenyl]-N-[6-[(7S,9aS)-7-({[(1,1-dimethylethyl)(dimethyl)silyl]oxy}methyl)hexahydropyrazino[2,1-c][1,4]oxazin-8(1H)-yl]-4-(4-fluoro-2-methylphenyl)-3-pyridinyl]-N,2-dimethylpropanamide (D24) (390 mg, 0.498 mmol) was dissolved 17 mL of methanol. To this solution was added concentrated HCl (0.9 mL) at 0° C., and stirring was continued at room temperature for 3 h (complete conversion). The reaction mixture was loaded on a SCX cartridge and washed with MeOH. The product was eluted with 0.5 M methanolic ammonia. The product-containing fractions were evaporated, leaving the target compound as a white solid: 310 mg, 0.464 mmol, 93%.

UPLC/MS: m/z=669 (M+1).

$^1$H-NMR (DMSO-d$_6$): δ (ppm) 8.07-7.97 (s, 1H), 7.88-7.81 (s, 1H), 7.79-7.69 (br. s, 2H), 7.19-7.11 (d, 1H), 7.14-7.06 (br. s, 2H) 6.64-6.56 (s, 1H), 4.75-4.65 (m, 1H), 4.31-4.13 (br. S, 1H), 4.15-4.01 (br. s, 1H), 3.80-3.68 (m, 3H), 3.58-3.49 (t, 1H); 3.43-3.34 (m, 1H); 3.18-3.09 (t, 1H); 3.04-2.98 (d, 1H); 2.68-2.58 (d, 1H); 2.51-2.45 (s, 3H); 2.20-2.13 (s, 3H); 2.29-2.00 (m, 4H); 1.54-1.39 (s, 3H); 1.39-1.28 (s, 3H).

Example 35

2-[3,5-Bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide Hydrochloride (E35)

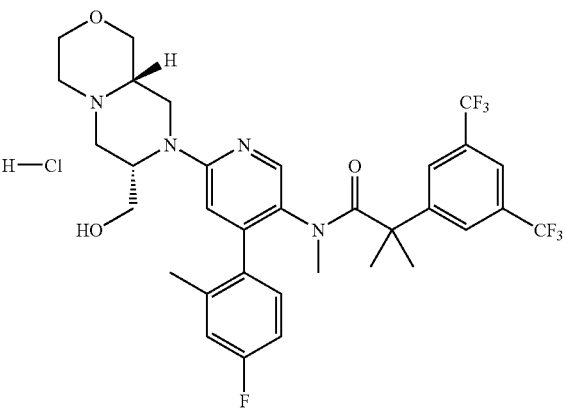

To a solution of 2-[3,5-bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide (E34) (300 mg, 0.449 mmol) in 2 mL of diethyl ether was added 0.6 mL of a 1M HCl solution in diethyl ether. A white precipitate formed. The solvent and excess HCl were removed under a stream of nitrogen and the residue was triturated with 1 mL of 1:1 pentane:Et$_2$O. The white solid was collected by filtration and left under high vacuum to give the title compound 280 mg, 0.397 mmol, 88% yield.

1H NMR (500 MHz, DMSO-d$_6$) δ ppm 10.24 (br. s., 1H) 8.03 (br. s., 1H) 7.90 (br. s., 1H) 7.55-7.82 (m, 2H) 6.89-7.24 (m, 3H) 6.77 (br. s., 1H) 4.65 (br. s., 1H) 4.45 (br. s., 1H) 3.92-4.15 (m, 2H) 3.76-3.90 (m, 2H) 3.34-3.55 (m, 2H) 3.09-3.36 (m, 2H) 2.84-3.04 (m, 1H) 2.49-2.62 (m, 2H) 2.01-2.30 (m, 6H) 1.10-1.58 (m, 8H).

α$_D$ (c=0.5 in MeOH)=−39.6 obtained using a polAAR 3000 polarimeter, =589.4 nm, cell volume=1.3 ml, path length, l=1 dm. (This value was determined on a different sample, spectroscopically the same as that described above and prepared in an analogous way).

Example 36

2-[3,5-Bis(trifluoromethyl)phenyl]-N-{4-(4-fluoro-2-methylphenyl)-6-[(7S,9aR)-7-(hydroxymethyl)hexahydropyrazino[2,1-c][1,4]oxazin-8(1H)-yl]-3-pyridinyl}-N,2-dimethylpropanamide (E36)

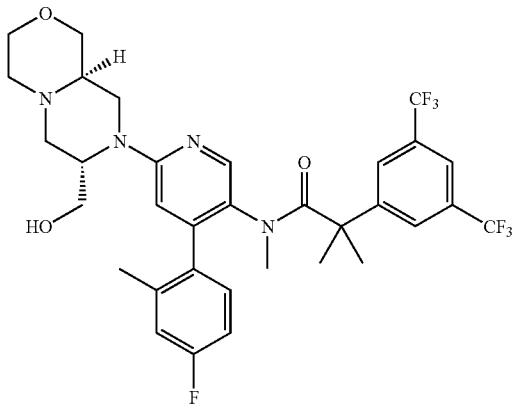

2-[3,5-bis(trifluoromethyl)phenyl]-N-[6-[(7S,9aR)-7-({[(1,1-dimethylethyl)(dimethyl)silyl]oxy}methyl)hexahydropyrazino[2,1-c][1,4]oxazin-8(1H)-yl]-4-(4-fluoro-2-methylphenyl)-3-pyridinyl]-N,2-dimethylpropanamide (D25) (87 mg, 0.111 mmol) was dissolved 4 mL of methanol. To this solution was added concentrated HCl (0.2 mL) at 0° C., and stirred at room temperature for 1 h (complete conversion). The reaction mixture was loaded on a SCX cartridge and washed with MeOH. The product was eluted with 0.5 M methanolic ammonia. The UV-active basic fractions were evaporated, leaving the target compound as a white solid: 69 mg, 0.103 mmol, 93%.

MS: m/z=669 (M+1).

$^1$H-NMR (DMSO-d$_6$): δ (ppm) 8.07-7.97 (m, 1H), 7.95-7.89 (br. s, 1H), 7.81-7.67 (br. s, 2H), 7.20-7.10 (d, 1H), 7.16-7.04 (br. s, 2H), 6.75-6.65 (br. s, 1H), 4.87-4.78 (br. s, 1H), 3.96-3.79 (br. s, 1H), 3.66-3.47 (m, 4H), 3.42-3.34 (m, 1H), 3.32-3.23 (m, 1H); 3.17-3.07 (dd, 1H); 2.71-2.63 (dd, 1H); 2.61-2.39 (m, 2H); 2.50-2.44 (s, 3H); 2.39-1.99 (m, 3H); 2.16-2.02 (br. s, 3H); 1.58-1.42 (s, 3H); 1.40-1.27 (s, 3H).

Example 37

2-[3,5-Bis(trifluoromethyl)phenyl]-N-{4-(4-fluoro-2-methylphenyl)-6-[(7S,9aR or 9aS)-7-(hydroxymethyl)-2,2-dioxidohexahydropyrazino[2,1-c][1,4]thiazin-8(1H)-yl]-3-pyridinyl}-N,2-dimethylpropanamide (E37)—Diastereoisomer 1

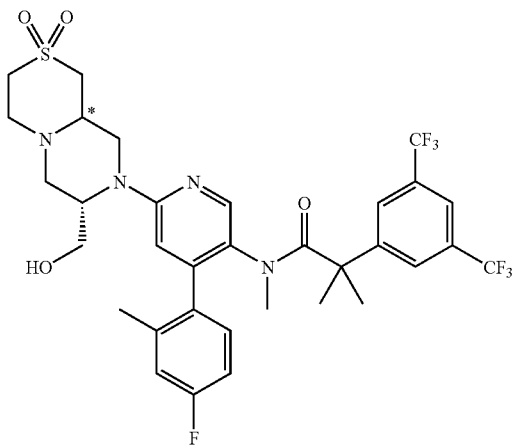

To a solution of 2-[3,5-bis(trifluoromethyl)phenyl]-N-[6-[(7S,9aR or 9aS)-7-({[(1,1-dimethylethyl)(dimethyl)silyl]oxy}methyl)-2,2-dioxidohexahydropyrazino[2,1-c][1,4]thiazin-8(1H)-yl]-4-(4-fluoro-2-methylphenyl)-3-pyridinyl]-N,2-dimethylpropanamide (D31) (170 mg, 0.2 mmol) in 8 mL of methanol was added dropwise HCl 12 N (0.4 mL) at 0° C. The reaction mixture was stirred at room temperature for 1.5 hrs, then it was purified by SCX cartridge to give the title compound as a white solid (120 mg, yield=81%).

HPLC: peak @ t=5.54 min

1H NMR (500 MHz, DMSO-d$_6$) δ ppm 8.01 (s, 1H) 7.85 (s, 1H) 7.63-7.81 (m, 2H) 7.16 (d, 1H) 7.03-7.17 (m, 2H) 6.67 (s, 1H) 4.71 (t, 1H) 4.19-4.36 (m, 1H) 4.02-4.19 (m, 1H) 3.65-3.80 (m, 1H) 3.36-3.53 (m, 1H) 3.24-3.36 (m, 2H) 3.15-3.29 (m, 2H) 3.10 (d, 1H) 2.86-3.01 (m, 1H) 2.72-2.84 (m, 1H) 2.65 (d, 1H) 2.49 (s, 3H) 2.42-2.56 (m, 2H) 2.20 (s, 3H) 1.49 (s, 3H) 1.34 (s, 3H).

Example 38

2-[3,5-Bis(trifluoromethyl)phenyl]-N-{4-(4-fluoro-2-methylphenyl)-6-[(7S,9aS or R)-7-(hydroxymethyl)-2,2-dioxidohexahydropyrazino[2,1-c][1,4]thiazin-8(1H)-yl]-3-pyridinyl}-N,2-dimethylpropanamide (E38)—Diastereomer 2

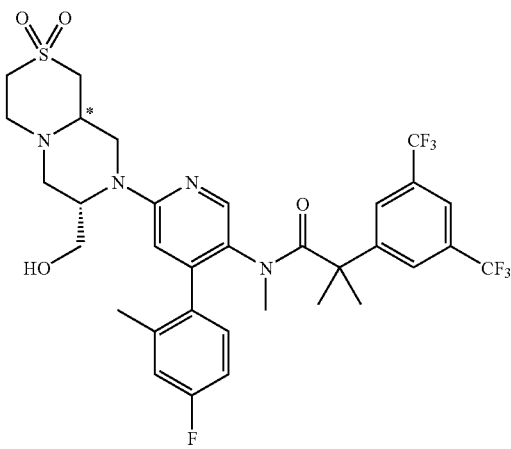

2-[3,5-Bis(trifluoromethyl)phenyl]-N-[6-[(7S,9aS or R)-7-({[(1,1-dimethylethyl)(dimethyl)silyl]oxy}methyl)-2,2-dioxidohexahydropyrazino[2,1-c][1,4]thiazin-8(1H)-yl]-4-(4-fluoro-2-methylphenyl)-3-pyridinyl]-N,2-dimethylpropanamide (D36) (158 mg, 0.190 mmol) was dissolved 10 mL of methanol. To this solution was added dropwise concentrated HCl (0.4 mL) at 0° C., and stirred at room temperature for 1.5 h (complete conversion by UPLC/MS, peak at 0.87 min., m/z=717 (M+1), 359 (M/2+1). The reaction mixture was purified by SCX cartridge, leaving the target compound as a solid: 107 mg, 0.149 mmol, 78%.

MS: m/z=669 (M+1).

1H NMR (500 MHz, DMSO-d$_6$) δ ppm 7.97-8.07 (m, 1H) 7.81-7.93 (m, 1H) 7.62-7.81 (m, 2H) 6.90-7.24 (m, 3H) 6.57-6.71 (m, 1H) 4.65-4.76 (m, 1H) 4.09-4.38 (m, 1H) 3.65-3.79 (m, 1H) 3.30-3.49 (m, 2H) 3.05-3.28 (m, 5H) 3.00 (t, 1H) 2.65-2.79 (m, 1H) 2.37-2.50 (m, 1H) 2.01-2.33 (m, 7H) 1.10-1.55 (m, 6H).

Example 39

N-[6-[(3S,9aR or S)-8-acetyl-3-(hydroxymethyl) octahydro-2H-pyrazino[1,2-a]pyrazin-2-yl]-4-(4-fluoro-2-methylphenyl)-3-pyridinyl]-2-[3,5-bis(trifluoromethyl)phenyl]-N,2-dimethylpropanamide (E39)—Diastereoisomer 1

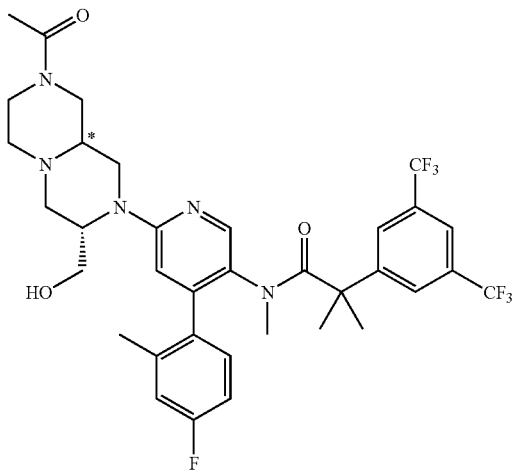

N-[6-[(3S,9aR or S)-8-acetyl-3-({[(1,1-dimethylethyl)(dimethyl)silyl]oxy}methyl)octahydro-2H-pyrazino[1,2-a]pyrazin-2-yl]-4-(4-fluoro-2-methylphenyl)-3-pyridinyl]-2-[3,5-bis(trifluoromethyl)phenyl]-N,2-dimethylpropanamide (D41) (1.168 g, 1.42 mmol) was dissolved in 40 mL of methanol. To this solution was added concentrated HCl (2.5 mL) at 0° C., and stirred at room temperature for 1 h. UPLC/MS analysis showed complete conversion to the expected product (peak at 0.75 min, m/z=710 (M+1), 355.7 (M/2+1)). The reaction mixture was purified by SCX cartridge, followed by flash chromatography (CH$_2$Cl$_2$→CH$_2$Cl$_2$:MeOH 92.5:7.5), to give target compound as a solid: 483 mg, -mmol, 78%.

1H NMR (500 MHz, DMSO-d$_6$) δ ppm 7.97-8.06 (m, 1H) 7.80-7.89 (m, 1H) 7.60-7.80 (m, 2H) 6.90-7.24 (m, 3H) 6.54-6.76 (m, 1H) 4.66-4.74 (m, 1H) 4.04-4.43 (m, 2H) 3.67-3.91 (m, 2H) 3.32-3.47 (m, 1H) 3.13-3.23 (m, 1H) 3.00-3.10 (m, 1H) 2.68-2.87 (m, 2H) 2.55-2.69 (m, 2H) 1.78-2.40 (m, 12H) 1.11-1.58 (m, 6H)

Example 40

N-[6-[(3S,9aS or R)-8-acetyl-3-(hydroxymethyl) octahydro-2H-pyrazino[1,2-a]pyrazin-2-yl]-4-(4-fluoro-2-methylphenyl)-3-pyridinyl]-2-[3,5-bis(trifluoromethyl)phenyl]-N,2-dimethylpropanamide (E40)—Diastereoisomer 2

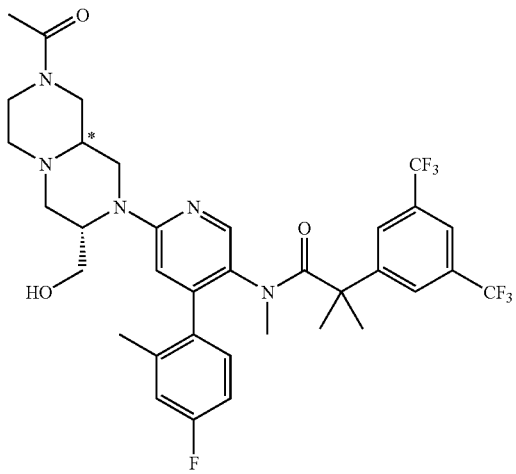

N-[6-[(3S,9aS or R)-8-acetyl-3-({[(1,1-dimethylethyl)(dimethyl)silyl]oxy}methyl)octahydro-2H-pyrazino[1,2-a]pyrazin-2-yl]-4-(4-fluoro-2-methylphenyl)-3-pyridinyl]-2-[3,5-bis(trifluoromethyl)phenyl]-N,2-dimethylpropanamide (D42) was treated as described for N-[6-[(3S,9aR or S)-8-acetyl-3-({[(1,1-dimethylethyl)(dimethyl)silyl]oxy}methyl)octahydro-2H-pyrazino[1,2-a]pyrazin-2-yl]-4-(4-fluoro-2-methylphenyl)-3-pyridinyl]-2-[3,5-bis(trifluoromethyl)phenyl]-N,2-dimethylpropanamide (D41) above. UPLC/MS analysis showed complete conversion to the expected product (peak at 0.71 min, m/z=710 (M+1), 355.7 (M/2+1)). The product was purified in the same way, yielding 700 mg.

1H NMR (500 MHz, DMSO-d$_6$) δ ppm 7.97-8.06 (m, 1H) 7.86-7.94 (m, 1H) 7.61-7.82 (m, 2H) 6.92-7.21 (m, 3H) 6.64-6.79 (m, 1H) 4.75-4.84 (m, 1H) 4.05-4.17 (m, 1H) 3.90-4.05 (m, 1H) 3.45-3.69 (m, 4H) 3.33-3.45 (m, 1H) 3.18-3.30 (m, 1H) 3.05-3.18 (m, 2H) 2.69-2.83 (m, 1H) 2.51-2.64 (m, 2H) 2.32-2.45 (m, 2H) 2.05-2.29 (m, 5H) 1.93-2.01 (m, 3H) 1.09-1.56 (m, 6H).

Example 41

2-[3,5-bis(trifluoromethyl)phenyl]-N-{6'-[(7S,9aS)-7-(hydroxymethyl)hexahydropyrazino[2,1-c][1,4]oxazin-8(1H)-yl]-4-methyl-3,4'-bipyridin-3'-yl}-N,2-dimethylpropanamide (E41)

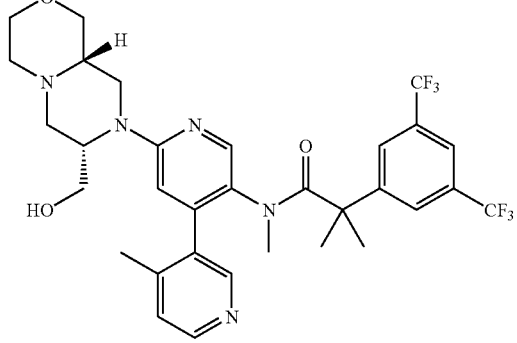

2-[3,5-bis(trifluoromethyl)phenyl]-N-{6'-[(7S,9aS)-7-({[(1,1-dimethylethyl)(dimethyl)silyl]oxy}methyl)hexahydropyrazino[2,1-c][1,4]oxazin-8(1H)-yl]-4-methyl-3,4'-bipyridin-3'-yl}-N,2-dimethylpropanamide (D53, 86 mg) was dissolved in dry MeOH (4 mL), cooled in an ice/salt bath to ~0° C. before adding c.HCl solution. The mixture was stirred at ~0° C. for 45 mins before allowing to warm up to R.T. and stirring for a further 2 hrs. Placed on a 5 g SCX column, washed with MeOH ×3, before eluting compound off with NH3 in MeOH. Solvent evaporated. Residue purified on a 5 g sek pak column eluting with Pent to EtOAc to 10% MeOH/EtOAc. Solvent evaporated to dryness in vacuo to afford a colourless gum of the title compound.

NMR (DMSO-d6) δ 8.44 (1H, d), 8.21 (1H, s), 8.04 (1H, s), 7.89 (1H, s), 7.73 (2H, s), 7.33 (1H, d), 6.70 (1H, s), 4.71 (1H, br t), 4.23 (1H, br s), 4.10 (1 h, br s), 3.76 (3H, m), 3.55 (1H, t), 3.41 (2H, m), 3.16 (1H, t), 3.02 (1H, d), 2.66 (1H, m), 2.33-2.05 (7H, m), 1.47-1.17 (6H, br m)

MS (API+): m/z 652.1 (MH+; 20%).

Example 42

2-[3,5-bis(trifluoromethyl)phenyl]-N-{6'-[(7S,9aS)-7-(hydroxymethyl)hexahydropyrazino[2,1-c][1,4]oxazin-8(1H)-yl]-4-methyl-3,4'-bipyridin-3'-yl}-N,2-dimethylpropanamide hydrochloride (E42)

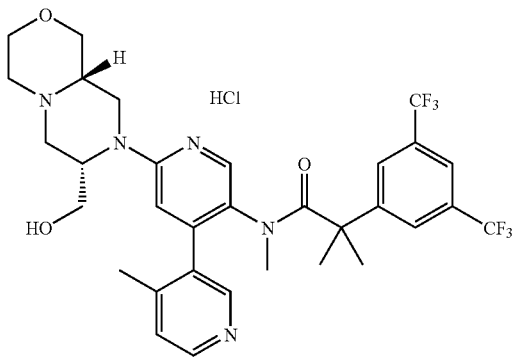

Title compound was made by dissolving 2-[3,5-bis(trifluoromethyl)phenyl]-N-{6'-[(7S,9aS)-7-(hydroxymethyl)hexahydropyrazino[2,1-c][1,4]oxazin-8(1H)-yl]-4-methyl-3,4'-bipyridin-3'-yl}-N,2-dimethylpropanamide (E41, 33.8 mg) in minimum of DCM, adding 1M HCl solution in Et2O, adding Et2O, triturating till a solid precipitates out. Liquors removed. More Et2O added triturated again. Solvent blown dry to afford a white solid.

MS (API+): m/z=652.3 (MH+; 20%)

Example 43

2-[3,5-bis(trifluoromethyl)phenyl]-N-{6-fluoro-6'-[(7S,9aS)-7-(hydroxymethyl)hexahydropyrazino[2,1-c][1,4]oxazin-8(1H)-yl]-2-methyl-3,4'-bipyridin-3'-yl}-N,2-dimethylpropanamide (E43)

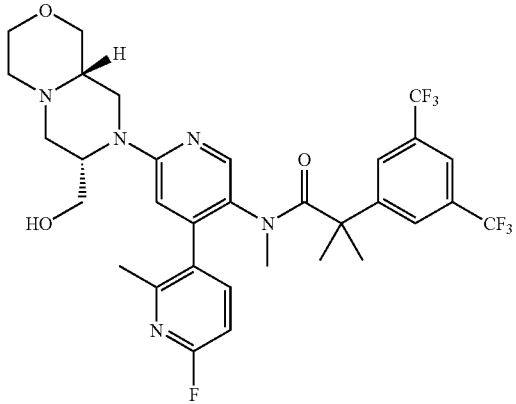

2-[3,5-bis(trifluoromethyl)phenyl]-N-(6'-chloro-6-fluoro-2-methyl-3,4'-bipyridin-3'-yl)-N,2-dimethylpropanamide (D54, 53.5 mg, 0.1 mmol), (7S,9aS)-7-({[(1,1-dimethylethyl)(dimethyl)silyl]oxy}methyl)octahydropyrazino[2,1-c][1,4]oxazine (D51, 37 mg, 0.13 mmol) were dissolved in toluene (1.5 mL). Bis tritertbutylphosphine palladium (13 mg, 0.026 mmol), followed by hexadecyltrimethylammoium chloride (10 µL, 25% aq sol), and finally sodium hydroxide solution (0.13 mL, 50% aq sol). The mixture was degassed for 5 minutes before heating at 90° C. for 4.5 hours. Cooled to R.T., diluted with EtOAc, washed with sat. NaHCO3 solution, dried (MgSO4). Filtered. Solvent evaporated. Residue purified by SCX column, washing with MeOH before eluting with NH3 in MeOH. Solvent evaporated. Residue purified by column chromatography eluting with Pent to EtOAc to 10% MeOH/EtOAc. Solvent evaporated under reduced pressure to afford a colourless solid of the title compound (11 mg).

NMR (400 MHz, CDCl3) δ 7.98 (1H, s), 7.79 (1H, s), 7.73-7.70 (1H, br m), 7.64 (1H, s), 6.82 (1H, s), 6.43 (1H, s), 4.55 (1H, d), 4.02 (2H, s), 3.90 (1H, d), 3.81 (2H, t), 3.67 (1H, m), 3.33 (1H, t), 3.12-3.06 (2H, m), 2.77 (1H, d), 2.54-2.30 (10H, m), 1.49 (3H,$), 1.35 (3H, s)

MS (API+): m/z 670.3 (MH+; 100%)

Example 44

2-[3,5-bis(trifluoromethyl)phenyl]-N-{6-fluoro-6'-[(7S,9aS)-7-(hydroxymethyl)hexahydropyrazino[2,1-c][1,4]oxazin-8(1H)-yl]-2-methyl-3,4'-bipyridin-3'-yl}-N,2-dimethylpropanamide hydrochloride (E44)

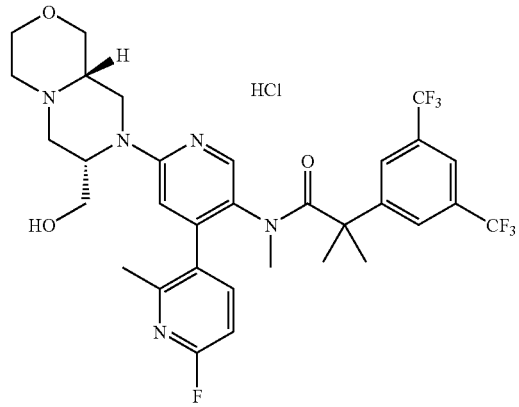

HCl salt made as described in example 41 starting from 2-[3,5-bis(trifluoromethyl)phenyl]-N-{6-fluoro-6'-[(7S,9aS)-7-(hydroxymethyl)hexahydropyrazino[2,1-c][1,4]oxazin-8(1H)-yl]-2-methyl-3,4'-bipyridin-3'-yl}-N,2-dimethylpropanamide (E43, 11.3 mg) to afford an off white solid.

MS (API+): m/z 670.3 (MH+; 100%)

Example 45

2-[3,5-bis(trifluoromethyl)phenyl]-N-{4-(5-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide (E45)

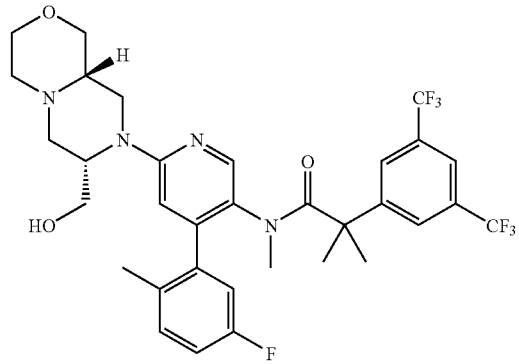

2-[3,5-bis(trifluoromethyl)phenyl]-N-[6-[(7S,9aS)-7-({[(1,1-dimethylethyl)(dimethyl)silyl]oxy}methyl)hexahydropyrazino[2,1-c][1,4]oxazin-8(1H)-yl]-4-(5-fluoro-2-methylphenyl)-3-pyridinyl]-N,2-dimethylpropanamide (D56, 110 mg) was dissolved in dry MeOH (2 mL), cooled in an ice-salt bath before adding cHCl solution (0.2 mL), and stirring at R.T. for 2 hours. Poured directly onto a 5 g SCX column. Washed with MeOH (2×10 mL), before eluting the compound with NH₃ in MeOH 94×10 mL). Solvent evaporated. Residue purified on a 5 g sek-pak column eluting with Pent to EtOAc to 10% MeOH/EtOAc. Solvent evaporated to afford the title compound as a white solid.

NMR (400 MHz; CDCl3) δ 7.98 (1H, br s), 7.77 (1H, s), 7.67 (2H, s), 7.21 (1H, br s), 7.00 (2H, m), 6.44 (1H, s), 4.57 (1H, br s), 4.20-4.08 (1H, br m), 4.02 (2H, s), 3.89 (1H, dd), 3.81 (2H, d), 3.70 (1H, m), 3.33 (1H, t), 3.11-3.05 (2H, m), 2.76 (1H, d), 3.63 (1H, d), 2.42-2.30 (4H, m), 2.29-2.05 (4H, m), 1.51-1.32 (6H, m)

MS (API+): m/z 669.3 (MH+; 100%)

Example 46

2-[3,5-bis(trifluoromethyl)phenyl]-N-{4-(5-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide hydrochloride (E46)

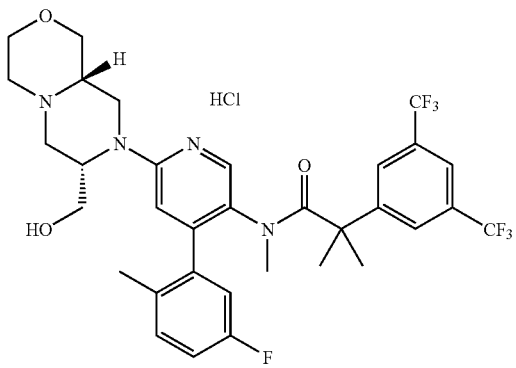

HCl salt made according to method described in Example 41 starting from 2-[3,5-bis(trifluoromethyl)phenyl]-N-{4-(5-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide (E45, 11.5 mg) to afford a pale yellow solid MS (API+): m/z 669.3 (MH+; 100%)

Example 47

2-[3,5-bis(trifluoromethyl)phenyl]-N-{4-(2-chloro-4-fluorophenyl)-6-[(7S,9aS)-7-(hydroxymethyl)hexahydropyrazino[2,1-c][1,4]oxazin-8(1H)-yl]-3-pyridinyl}-N,2-dimethylpropanamide (E47)

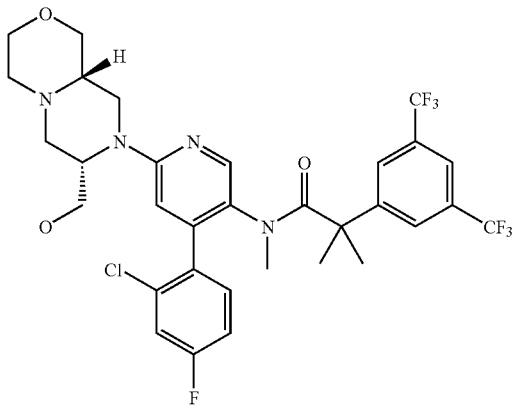

2-[3,5-bis(trifluoromethyl)phenyl]-N-{4-(2-chloro-4-fluorophenyl)-6-[(7S,9aS)-7-({[(1,1-dimethylethyl)(dimethyl)silyl]oxy}methyl)hexahydropyrazino[2,1-c][1,4]oxazin-8(1H)-yl]-3-pyridinyl}-N,2-dimethylpropanamide (D58, 22 mg, 0.027 mmol) was dissolved in dry MeOH (2 mL), cooled in an ice-salt bath to ~0° C. before adding c.HCl solution (~0.1 mL), slowly. The reaction mixture was stirred at ~0° C. for 1 hour before warming up and stirring at R.T. for 2 hours. Placed directly onto a 2 g SCX column, washing with MeOH (2×5 mL) before eluting the compound off with NH₃ in MeOH (4×5 mL). Solvent evaporated under reduced pressure to afford the title compound as an off white solid. (10 mg)

NMR (400 MHz, DMSO-d6) δ 8.03 (1H, s), 7.89 (1H, s), 7.71 (2H, s), 7.55 (1H, d), 7.34 (2H, m), 6.65 (1H, s), 4.71 (1H, t), 4.22 (1H, br m), 4.07 (1H, br m), 3.76 (2H, m), 3.55 (1H, t), 3.15 (1H, t), 3.03 (1H, m), 2.68-2.60 (2H, m), 2.50-2.40 (3H, m), 2.18-2.05 (3H, m), 1.45 (3H, s), 1.31 (3H, s)

MS (API+): m/z 689.3 (MH+; 100%)

Example 48

2-[3,5-bis(trifluoromethyl)phenyl]-N-{4-(2-chloro-4-fluorophenyl)-6-[(7S,9aS)-7-(hydroxymethyl)hexahydropyrazino[2,1-c][1,4]oxazin-8(1H)-yl]-3-pyridinyl}-N,2-dimethylpropanamide hydrochloride (E48)

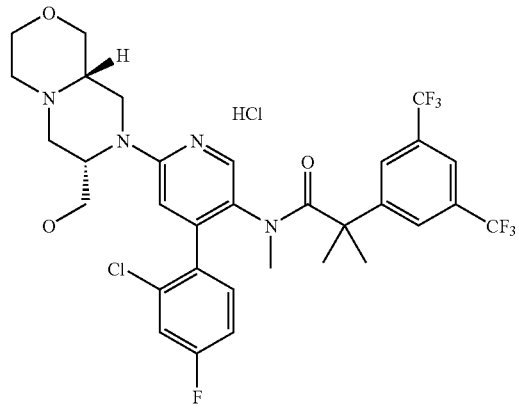

HCl salt made according to method described in Example 41 starting from 2-[3,5-bis(trifluoromethyl)phenyl]-N-{4-(2-chloro-4-fluorophenyl)-6-[(7S,9aS)-7-(hydroxymethyl)hexahydropyrazino[2,1-c][1,4]oxazin-8(1H)-yl]-3-pyridinyl}-N,2-dimethylpropanamide (E47, 10 mg) to afford a pale yellow solid.

MS (API+): m/z 689.2 (MH+; 100%)

Example 49

2-[3,5-bis(trifluoromethyl)phenyl]-N-{6-[(7S,9aS)-7-(hydroxymethyl)hexahydropyrazino[2,1-c][1,4]oxazin-8(1H)-yl]-4-[2-(hydroxymethyl)phenyl]-3-pyridinyl}-N,2-dimethylpropanamide (E49)

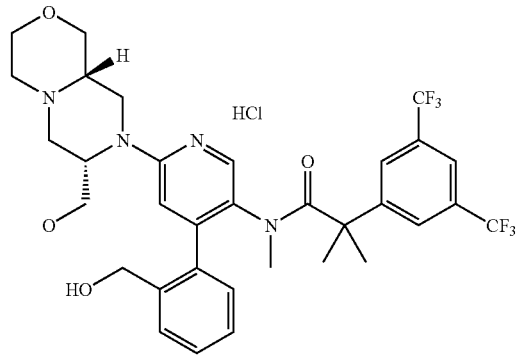

2-[3,5-bis(trifluoromethyl)phenyl]-N-{6-[(7S,9aS)-7-({[(1,1-dimethylethyl)(dimethyl)silyl]oxy}methyl)hexahydropyrazino[2,1-c][1,4]oxazin-8(1H)-yl]-4-[2-(hydroxymethyl)phenyl]-3-pyridinyl}-N,2-dimethylpropanamide (D61, 24.6 mg, 0.0315 mmol) was suspended in dry MeOH (1 mL) before adding c.HCl solution (5 drops). The reaction mixture was then stirred at R.T. for 3 hours. Poured directly onto a 5 g SCX column, washing with MeOH (2×10 mL) before eluting the compound off with $NH_3$ in MeOH (4×10 mL). Solvent evaporated. Residue purified on a 5 g sek pak column eluting with 0-100% EtOAc/Pent followed by 0-10% MeOH/EtOAc. Solvent evaporated to afford the title compound as a colourless gum.

NMR (400 MHz, CDCl3) δ 7.94 (1H, d), 7.78 (1H, s), 7.66-7.59 (3H, m), 7.43 (1H, t), 7.28 (1H, m), 7.00-6.96 (1H, m), 6.46 (1H, d), 4.67 (1H, m), 4.53 (1H, d), 4.42-4.34 (1H, m), 4.05-3.98 (2H, m), 3.90-3.67 (6H, m), 3.35-3.30 (1H, m), 3.09-3.00 (2H, m), 2.72 (3H, d), 2.63 (1H, dd), 2.45-2.30 (3H, m), 1.30 (6H, s)

MS (API+): m/z 667.3 (MH+; 100%)

Example 50

2-[3,5-bis(trifluoromethyl)phenyl]-N-{6-[(7S,9aS)-7-(hydroxymethyl)hexahydropyrazino[2,1-c][1,4]oxazin-8(1H)-yl]-4-[2-(hydroxymethyl)phenyl]-3-pyridinyl}-N,2-dimethylpropanamide hydrochloride (E50)

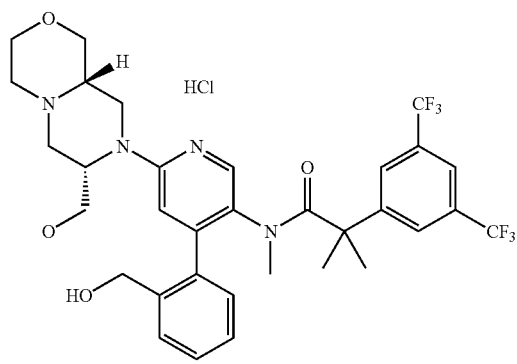

HCl salt made according to method described in Example 41 starting from 2-[3,5-bis(trifluoromethyl)phenyl]-N-{6-[(7S,9aS)-7-(hydroxymethyl)hexahydropyrazino[2,1-c][1,4]oxazin-8(1H)-yl]-4-[2-(hydroxymethyl)phenyl]-3-pyridinyl}-N,2-dimethylpropanamide (E49, 10.2 mg) to afford a yellow solid.

MS (API+): 667.3 (MH+; 100%)

Example 51

2-[3,5-bis(trifluoromethyl)phenyl]-N-[6-[(9aR or 9aS)-2,2-dioxidohexahydropyrazino[2,1-c][1,4]thiazin-8(1H)-yl]-4-(4-fluoro-2-methylphenyl)-3-pyridinyl]-N,2-dimethylpropanamide (E51—Enantiomer 1)

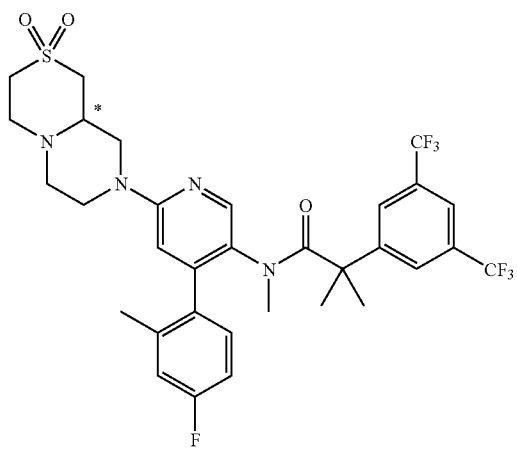

N-[6-(8-acetyloctahydro-2H-pyrazino[1,2-a]pyrazin-2-yl)-4-(4-fluoro-2-methyl phenyl)-3-pyridinyl]-2-[3,5-bis(trifluoromethyl)phenyl]-N,2-dimethylpropanamide (E33, 101 mg) was submitted for chiral separation to isolate its enantiomers. The Enantiomer labeled 1, of unknown but single stereochemistry was isolated using preparative conditions described below (obtained 12 mg of title compound, >95% e.e., analytical retention time 10.23 min).

Semipreparative SFC (Gilson) Conditions:

| | |
|---|---|
| Amount supplied | 101 mg |
| Chiral Column | CHIRALCEL OD-H, (25 × 2) cm |
| Mobile phase | n-Hexane/2-propanol 94/6% v/v |
| Flow rate | 18 ml/min |
| Detection | UV at 225 nm |

Analytical SFC (Berger) Conditions:

| | |
|---|---|
| Chiral Column | CHIRALCEL OD-H, (25 × 0.46) cm |
| Mobile phase | n-Hexane/ethanol 70/30% v/v |
| Flow rate | 0.8 ml/min |
| Detection | UV at 225 nm |

1H NMR (500 MHz, DMSO-$d_6$) δ ppm 8.02 (br. s., 1H) 7.89 (br. s., 1H) 7.61-7.84 (m, 2H) 7.16 (d, 1H) 6.90-7.14 (m, 2H) 6.72 (br. s., 1H) 4.12-4.31 (m, 2H) 3.08-3.32 (m, 5H) 2.85-3.03 (m, 3H) 2.52-2.73 (m, 2H) 2.01-2.32 (m, 7H) 1.13-1.59 (m, 6H)

MS (direct): 687 (M+1)

Example 52

2-[3,5-bis(trifluoromethyl)phenyl]-N-[6-[(9aS or 9aR)-2,2-dioxidohexahydropyrazino[2,1-c][1,4]thiazin-8(1H)-yl]-4-(4-fluoro-2-methylphenyl)-3-pyridinyl]-N,2-dimethylpropanamide (E52—Enantiomer 2)

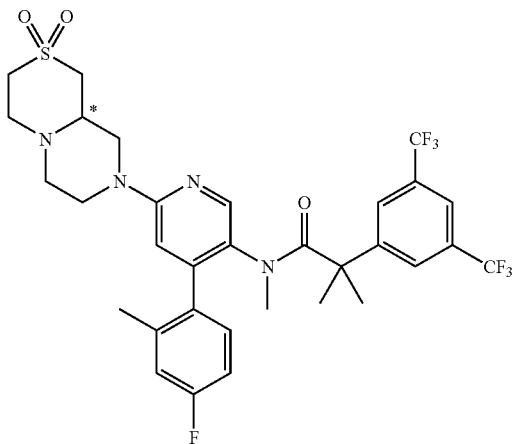

The title compound was obtained as the second compound, labeled Enantiomer 2, from the chiral separation performed on 2-[3,5-Bis(trifluoromethyl)phenyl]-N-[6-(2,2-dioxidohexahydropyrazino[2,1-c][1,4]thiazin-8(1H)-yl]-4-(4-fluoro-2-methylphenyl)-3-pyridinyl]-N,2-dimethylpropanamide (E33) as reported for 2-[3,5-bis(trifluoromethyl)phenyl]-N-[6-[(9aR or 9aS)-2,2-dioxidohexahydropyrazino[2,1-c][1,4]thiazin-8(1H)-yl]-4-(4-fluoro-2-methylphenyl)-3-pyridinyl]-N,2-dimethylpropanamide (E51)(obtained 70 mg, >95.5% e.e., analytical retention time 14.56 min).

1H NMR (500 MHz, DMSO-$d_6$) δ ppm 8.02 (br. s., 1H) 7.89 (br. s., 1H) 7.61-7.84 (m, 2H) 7.16 (d, 1H) 6.90-7.14 (m, 2H) 6.72 (br. s., 1H) 4.12-4.31 (m, 2H) 3.08-3.32 (m, 5H) 2.85-3.03 (m, 3H) 2.52-2.73 (m, 2H) 2.01-2.32 (m, 7H) 1.13-1.59 (m, 6H)

MS (direct): 687 (M+1)

Example 53

2-[3,5-bis(trifluoromethyl)phenyl]-N-{4-(4-fluoro-2-methylphenyl)-6-[(7aS)-3-oxotetrahydro-1H-pyrrolo[1,2-c]imidazol-2(3H)-yl]-3-pyridinyl}-N,2-dimethylpropanamide (E53)

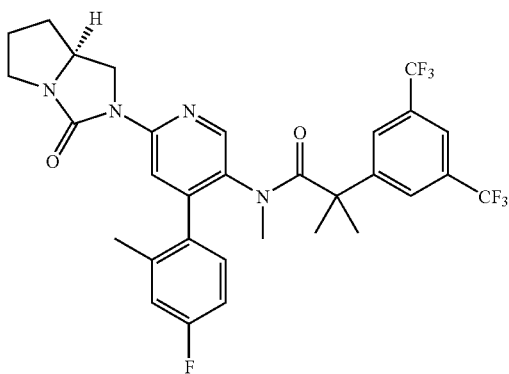

The starting 2-[3,5-bis(trifluoromethyl)phenyl]-N-(4-(4-fluoro-2-methylphenyl)-6-{[(2S)-2-pyrrolidinylmethyl] amino}-3-pyridinyl)-N,2-dimethylpropanamide (D62, 38 mg, 0.064 mmol) was dissolved in 1 mL of anhydrous dichloromethane and treated with triethylamine (20 µL, 0.143 mmol). The solution was brought to 0° C. and triphosgene (10 mg, 0.034 mmol) was added. The reaction was stirred at 0° C. for 15 min, then brought to room temperature. After 24 h, the reaction was diluted with dichloromethane (10 mL) and extracted with brine. The organics were collected and the solvent removed. The product was isolated by flash chromatography (silica, cyclohexane:EtOAc 80:20 to EtOAc). Thus were obtained 8 mg of the target compound.

HPLC/MS: m/z=623 (M+1),

1H NMR (400 MHz, DMSO-$d_6$) δ ppm 8.03 (s, 1H) 8.00 (s, 1H) 7.89 (s, 1H) 7.66-7.72 (m, 2H) 7.04-7.13 (m, 2H) 6.94-7.04 (m, 1H) 4.10 (t, 1H) 3.94 (dd, 1H) 3.74-3.84 (m, 1H) 3.47-3.59 (m, 1H) 2.90-3.08 (m, 1H) 2.43 (s, 3H) 2.09 (s, 3H) 1.97-2.10 (m, 1H) 1.74-1.98 (m, 2H) 1.47-1.73 (m, 1H) 1.36 (s, 6H)

Example 54

2-[3,5-bis(trifluoromethyl)phenyl]-N-{4-(4-fluoro-2-methylphenyl)-6-[(9aS)-1-oxohexahydro-1H-pyrrolo[1,2-a][1,4]diazepin-2(3H)-yl]-3-pyridinyl}-N,2-dimethylpropanamide (E54)

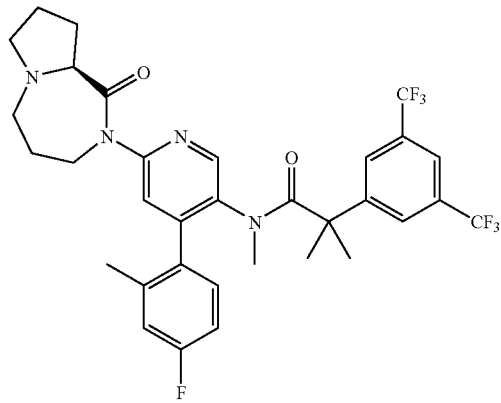

A solution of (9aS)-octahydro-1H-pyrrolo[1,2-a][1,4]diazepin-1-one (Polish Journal of Chemistry, 59(10-12), 1243-6; 1985) (31 mg, 0.201 mmol), 2-[3,5-bis(trifluoromethyl)phenyl]-N-[6-chloro-4-(4-fluoro-2-methylphenyl)-3-pyridinyl]-N,2-dimethylpropanamide [WO 2005/002577] (53 mg, 0.0996 mmol), N,N'-dimethyethylendiamine (224, 0.207 mmol), copper(I) iodide (38 mg, 0.200 mmol) and caesium carbonate (65 mg, 0.199 mmol) in 3 mL of dioxane was heated to 100° C. in a sealed vial overnight. Heating was continued for additional 2 days. It was diluted with 10 mL of EtOAc and extracted with water. The organics were dried (Na$_2$SO$_4$) and the solvent removed. The product was isolated by flash chromatography (silica, cyclohexane:EtOAc 90:10 to 30:70). Thus were obtained 14 mg of the target compound.

HPLC/MS: m/z=651 (M+1), >99% by UV.

1H NMR (500 MHz, DMSO-$d_6$) δ ppm 8.34 (s, 1H) 8.10 (s, 1H) 7.84 (br. s., 2H) 7.77 (br. s., 1H) 7.57 (s, 1H) 7.25 (d, 1H) 7.19 (br. s., 1H) 4.54 (br. s., 1H) 3.96 (t, 1H) 3.72 (dd, 1H) 3.25 (dd, 1H) 3.02-3.09 (m, 1H) 2.53-2.67 (m, 1H) 2.43 (s, 3H) 2.28-2.42 (m, 1H) 2.19 (s, 3H) 1.81-1.91 (m, 1H) 1.66-1.78 (m, 2H) 1.60 (s, 3H) 1.44 (s, 3H) 1.26-1.38 (m, 1H) 1.11-1.22 (m, 1H) 0.89-1.07 (m, 1H)

Example 55

2-[3,5-bis(trifluoromethyl)phenyl]-N-{4-(4-fluoro-2-methylphenyl)-6-[8a-(hydroxymethyl)hexahydropyrrolo[1,2-a]pyrazin-2(1H)-yl]-3-pyridinyl}-N,2-dimethylpropanamide (E55)

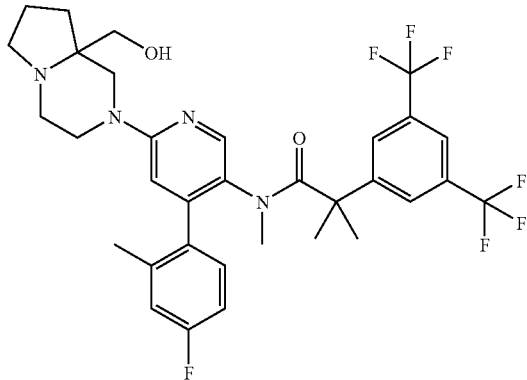

To a solution of hexahydropyrrolo[1,2-a]pyrazin-8a(6H)-ylmethanol (D67, 35 mg) in methyl sulfoxide (1.5 mL), 2-[3,5-bis(trifluoromethyl)phenyl]-N-[6-chloro-4-(4-fluoro-2-methylphenyl)-3-pyridinyl]-N,2-dimethylpropanamide [WO 2005/002577] (60 mg) and potassium carbonate (63 mg) were added. The resulting mixture was heated at 150° C. for 24 hours. The mixture was allowed to cool down to r.t and further D67 (17 mg) and potassium carbonate (15 mg) were added. The resulting mixture was heated at 150° C. for further 8 hours and then it was allowed to cool to r.t. and diluted with water (2 mL). The aqueous phase was extracted with ethyl acetate (3×2.5 mL). The combined organic extracts were dried and concentrated in vacuo to a residue which was purified twice by flash chromatography (first purification: EtOAc/Cycl from 80/20 to 100:0 then DCM/MeOH 95:5. Second purification: DCM/MeOH 98:2) to give the desired compound (7.7 mg) as yellow foam.

T.l.c.: DCM/MeOH 9:1, Rf=0.29.
UPLC/MS: peak at Rt=0.673 min with m/z=653 [M+H]⁺.
1H NMR (300 MHz, DMSO-d₆) δ ppm 7.94 (s, 1H) 7.82 (br. s., 1H) 7.73 (s, 2H) 7.07-7.20 (m, 2H) 6.96-7.07 (m, 1H) 6.46 (s, 1H) 3.90 (d, 1H) 3.37-3.60 (m, 3H) 3.11-3.32 (m, 4H) 2.80-2.95 (m, 2H) 2.47 (s, 3H) 2.18 (s, 3H) 1.61-1.82 (m, 2H) 1.40 (s, 6H) 1.32-1.54 (m, 2H).

Example 56

2-[3,5-bis(trifluoromethyl)phenyl]-N-{4-(4-fluoro-2-methylphenyl)-6-[(8S)-8-hydroxyhexahydropyrrolo[1,2-a]pyrazin-2(1H)-yl]-3-pyridinyl}-N,2-dimethylpropanamide (E56)

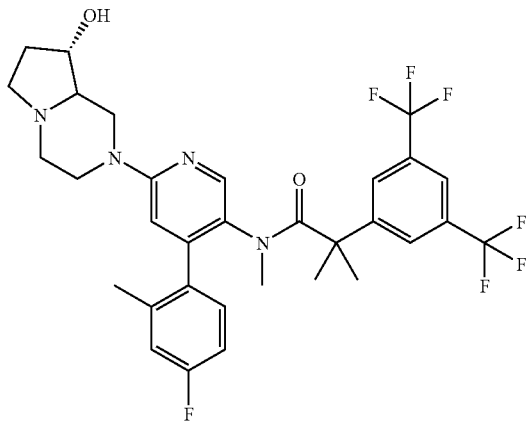

To a solution of (8S)-octahydropyrrolo[1,2-a]pyrazin-8-ol (D71, 32 mg) in methyl sulfoxide (1.2 mL), 2-[3,5-bis(trifluoromethyl)phenyl]-N-[6-chloro-4-(4-fluoro-2-methylphenyl)-3-pyridinyl]-N,2-dimethylpropanamide [WO 2005/002577] (60 mg) and potassium carbonate (63 mg) were added. The resulting mixture was heated at 150° C. for 24 hours. The mixture was allowed to cool down to r.t. and diluted with water (2 mL). The aqueous phase was extracted with ethyl acetate (3×2.5 mL). The combined organic extracts were dried and concentrated in vacuo to a residue which was purified by flash chromatography (DCM/MeOH from 100:0 to 95:5) to give the desired compound (18.8 mg) as yellow foam.

T.l.c.: DCM/MeOH 9:1, Rf=0.48.
UPLC/MS: peak at Rt=0.71 min with m/z=639 [M+H]⁺.
1H NMR (300 MHz, DMSO-d₆) δ ppm 7.95 (s, 1H) 7.86 (br. s., 1H) 7.74 (s, 2H) 7.07-7.20 (m, 2H) 6.98-7.08 (m, 1H) 6.59 (s, 1H) 4.12-4.35 (m, 3H) 2.82-2.99 (m, 3H) 2.48 (s, 3H) 2.43-2.66 (m, 2H) 2.24-2.39 (m, 1H) 2.18 (s, 3H) 2.06-2.24 (m, 1H) 1.91-2.03 (m, 1H) 1.77-1.89 (m, 1H) 1.51-1.70 (m, 1H) 1.41 (s, 6H)

Example 57 cis-2-[3,5-bis(trifluoromethyl)phenyl]-N-{4-(4-fluoro-2-methylphenyl)-6-[1-(hydroxymethyl)hexahydropyrrolo[1,2-a]pyrazin-2(1H)-yl]-3-pyridinyl}-N,2-dimethylpropanamide (E57)

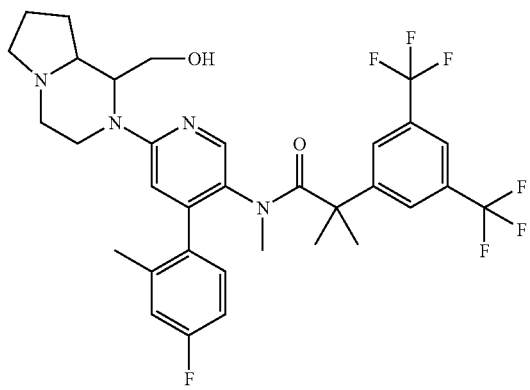

To a solution of cis-2-[3,5-bis(trifluoromethyl)phenyl]-N-[6-[1-({[(1,1-dimethylethyl)(dimethyl)silyl]oxy}methyl)hexahydropyrrolo[1,2-a]pyrazin-2(1H)-yl]-4-(4-fluoro-2-methylphenyl)-3-pyridinyl]-N,2-dimethylpropanamide (D74, 10.5 mg) in dry methanol (1 mL) at 0° C., one drop of concentrated HCl was added. The resulting mixture was stirred at 0° C. for 1.5 hours and then was allowed to reach rt and stirred at this temperature for 2 hours. The solution was then directly charged onto a SCX cartridge (eluting with MeOH and ammonia, 0.5N solution in methanol) to give the desired compound (4.5 mg) as yellow oil.

UPLC/MS: peak at Rt=0.73 min with m/z=653 [M+H]⁺.
The following examples were obtained through preparation analogous to the following one:
E58

A suspension of 2-[3,5-bis(trifluoromethyl)phenyl]-N-[6-chloro-4-(4-fluoro-2-methylphenyl)-3-pyridinyl]-N,2-dimethylpropanamide [WO 2005/002577] (100 mg), (8aS)-hexahydropyrrolo[1,2-a]pyrazin-1(2H)-one (D76, 79 mg, 3 eq), CuI (72 mg, 2 eq), N,N'-Dimethylethylenediamine (40 μl, 2 eq) and CsCO₃ (122.4 mg, 2 eq) in dioxane (3 ml) was heated in a sealed tube at 80° C. for 4 hrs and at 120° C.

overnight. The reaction mixture was taken up with dichloromethane and it was washed with NH₄Cl aq. The organic phase was evaporated to dryness and the crude was purified by chromatography (silica cartridge, cyclohexane:EtOAc 1:1 to 0:1) to give the title compound (39 mg).

Where prepared, the HCl salts were prepared according to the following experimental procedure:
E61

To a solution of 2-[3,5-bis(trifluoromethyl)phenyl]-N-{4-(4-fluoro-2-methylphenyl)-6-[(8aR)-1-oxohexahydropyrrolo[1,2-a]pyrazin-2(1H)-yl]-3-pyridinyl}-N,2-dimethyl-propanamide (E60, 47 mg, 0.074 mmol) in dichloromethane (1.9 ml), cooled to 0° C., was added dropwise 1N HCl in Et₂O (88 μl) and the reaction mixture was stirred at 0° C. for 30 mins. The solvent was evaporated and the solid was triturated with pentane to give title compound (50 mg).

| Example n° | Structure | Characterization | Monomer | Monomer Preparation |
|---|---|---|---|---|
| E58 | 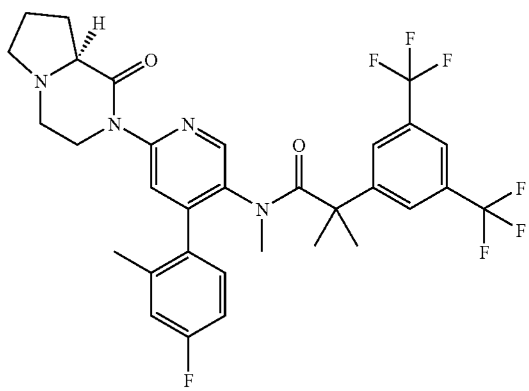 | | | Description 76 (8aS)-hexahydropyrrolo[1,2-a]pyrazin-1(2H)-one (D76) |
| E59 | 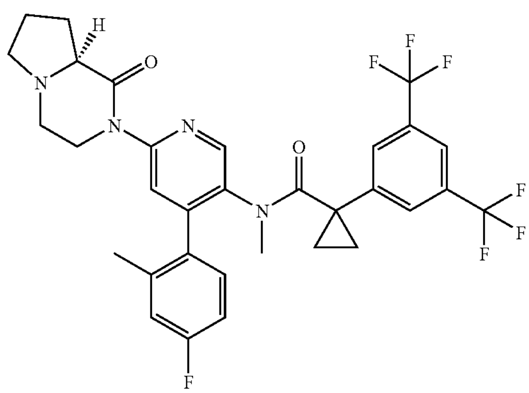 | | | The same as before |
| E60 | 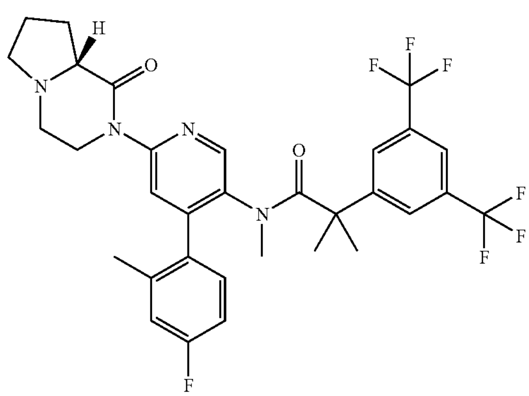 | | | Described in literature: Quinolinone compounds. Jpn. Kokai Tokkyo Koho (1985), 12 pp. CODEN: JKXXAF JP 60166681 A2 19850829 Showa. CAN 104:109495 AN 1986:109495 CAPLUS |

-continued
| Example n° | Structure | Characterization | Monomer | Monomer Preparation |
|---|---|---|---|---|
| E61 | 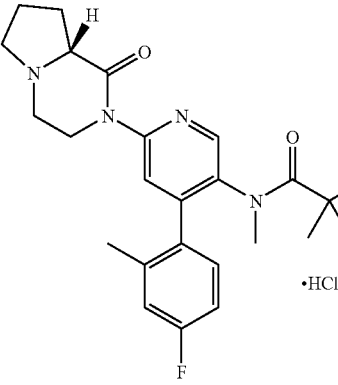 ·HCl | 1H NMR (500 MHz, DMSO-d$_6$) δ ppm 11.17 (br. s., 1 H) 8.35 (s, 1 H) 8.04 (s, 1 H) 7.83 (s, 1 H) 7.69-7.81 (m, 2 H) 7.22 (d, 1 H) 7.09-7.17 (m, 2 H) 3.09-4.75 (m, 7 H) 2.45-2.56 (m, 3 H) 2.13 (s, 3 H) 1.76-2.45 (m, 4 H) 1.11-1.71 (m, 6 H) | 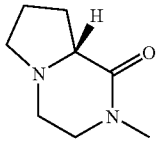 | The same as before |
| E62 | 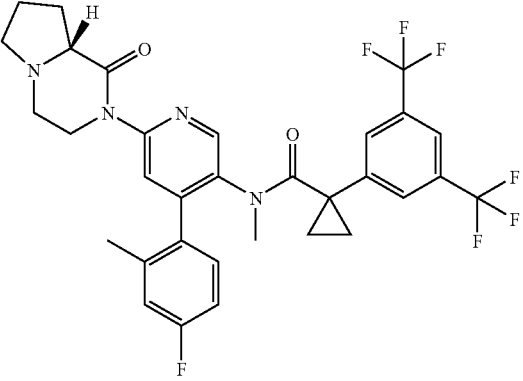 | | 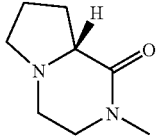 | The same as before |
| E63 | 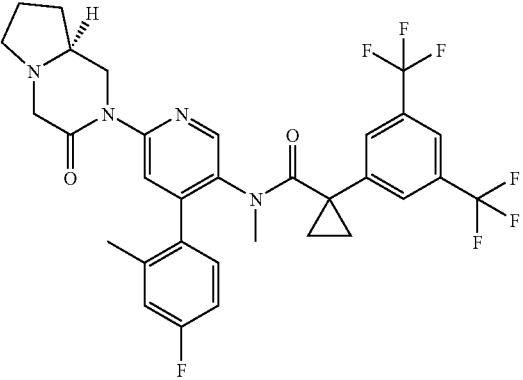 | | 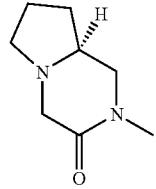 | Description 12 (8aS)-Hexahydropyrrolo [1,2-a]pyrazin-3(4H)-one (D12) |

| Example n° | Structure | Characterization | Monomer | Monomer Preparation |
|---|---|---|---|---|
| E64 | 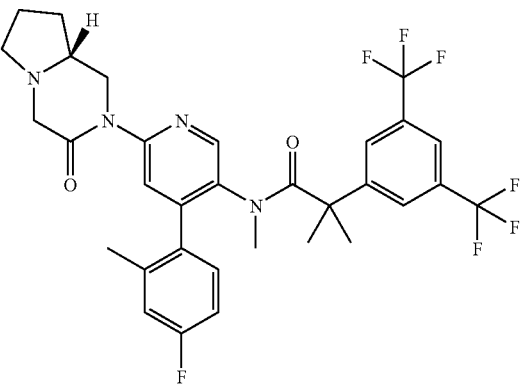 | | 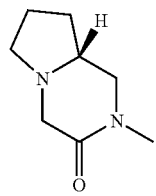 | Description 14 (8aR)-Hexahydropyrrolo[1,2-a]pyrazin-3(4H)-one (D14) |
| E65 | 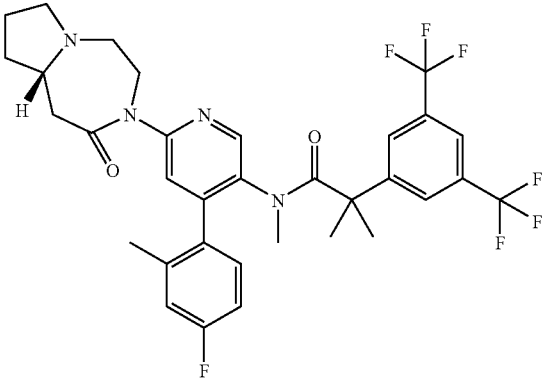 | | 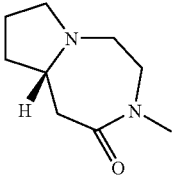 | Description 5 (9aS)-Hexahydro-1H-pyrrolo[1,2-d][1,4]diazepin-2(3H)-one (D5) |
| E66 | 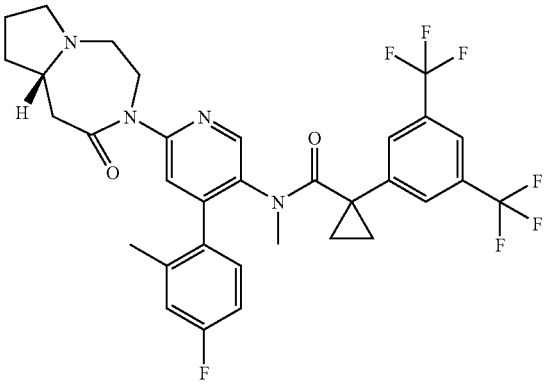 | | 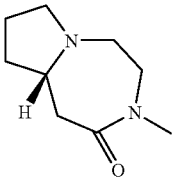 | Description 5 (9aS)-Hexahydro-1H-pyrrolo[1,2-d][1,4]diazepin-2(3H)-one (D5) |

Example 67

2-[3,5-bis(trifluoromethyl)phenyl]-N-[4-(4-fluoro-2-methylphenyl)-6-(9-oxooctahydro-2H-pyrazino[1,2-a]pyrazin-2-yl)-3-pyridinyl]-N,2-dimethylpropanamide (E67)

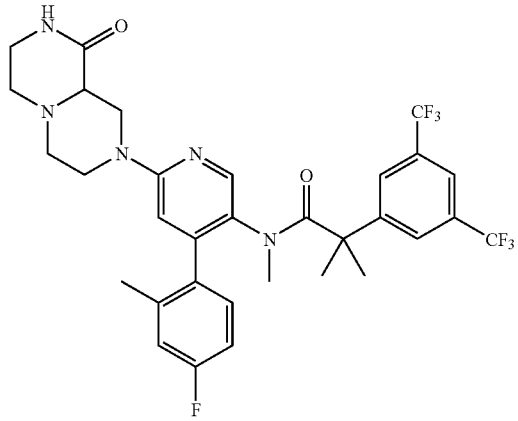

To a solution of 2-[3,5-bis(trifluoromethyl)phenyl]-N-[6-chloro-4-(4-fluoro-2-methylphenyl)-3-pyridinyl]-N,2-dimethylpropanamide [WO 2005/002577] (50 mg, 0.092 mmol) in 0.5 mL of DMSO was added hexahydro-2H-pyrazino[1,2-a]pyrazin-1(6H)-one (D78, 33 mg, 0.213 mmol) and potassium carbonate (39 mg, 0.28 mmol) and the reaction was left at 150° C. for 24 h. It was worked up by diluting with dichloromethane and extracting with brine. The organics were dried ($Na_2SO_4$), and the solvent removed. The product was purified by flash chromatography: silica, cyclohexane:EtOAc 50:50 to EtOAc. Obtained 37 mg of the title compound.

MS (direct): 652 (M+1)

1H NMR (500 MHz, DMSO-$d_6$) δ ppm 8.01 (s, 1H) 7.92 (s, 1H) 7.82 (d, 1H) 7.66-7.78 (m, 2H) 6.92-7.20 (m, 3H) 6.64 (br. s., 1H) 4.57-4.70 (m, 1H) 3.25-3.32 (m, 1H) 3.01-3.13 (m, 1H) 2.83-2.96 (m, 3H) 2.52-2.68 (m, 2H) 2.40 (dt, 1H) 2.01-2.31 (m, 8H) 1.14-1.59 (m, 6H)

Example 68

2-[3,5-bis(trifluoromethyl)phenyl]-N-{4-(4-fluoro-2-methylphenyl)-6-[(9aR or 9aS)-9-oxooctahydro-2H-pyrazino[1,2-a]pyrazin-2-yl]-3-pyridinyl}-N,2-dimethylpropanamide (E68—Enantiomer 1)

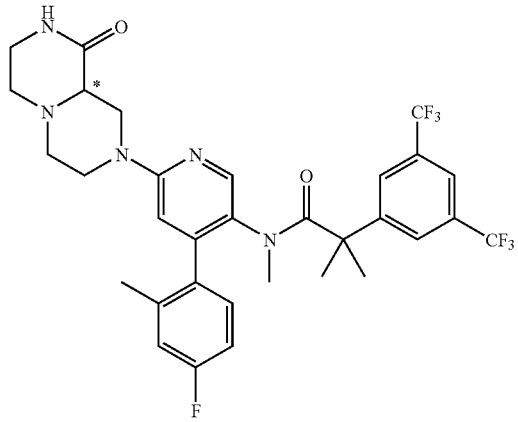

2-[3,5-bis(trifluoromethyl)phenyl]-N-[4-(4-fluoro-2-methyl phenyl)-6-(9-oxooctahydro-2H-pyrazino[1,2-a]pyrazin-2-yl)-3-pyridinyl]-N,2-dimethylpropanamide (E67, 30 mg) was submitted for chiral separation to isolate its enantiomers.

The enantiomer labeled 1, of unknown but single stereochemistry was isolated using the following conditions (obtained 8.3 mg, 75% e.e., analytical retention time 15.5 min)

Preparative Conditions:

| | |
|---|---|
| Amount supplied | 30 mg |
| Chiral Column | CHIRALCEL OD-H, (25 × 2.1) cm |
| Mobile phase | n-Hexane/2-propanol 87/13% v/v |
| Flow rate | 22 ml/min |
| P | 182 bar |
| T | 36 C. |
| Detection | UV at 220 nm |

Analytical SFC (Berger) Conditions:

| | |
|---|---|
| Chiral Column | CHIRALCEL OD-H, (25 × 0.46) cm |
| Mobile phase | n-Hexane/2-propanol 85/15% v/v |
| Flow rate | 1.5 ml/min |
| P | 180 bar |
| T | 35 C. |
| Detection | UV at 220 nm |

1H NMR (500 MHz, DMSO-$d_6$) δ ppm 8.03 (s, 1H) 7.92 (s, 1H) 7.82 (d, 1H) 7.50-7.78 (m, 2H) 6.90-7.21 (m, 3H) 6.66 (br. s., 1H) 4.48-4.78 (m, 1H) 4.05-4.21 (m, 1H) 3.21-3.46 (m, 1H) 3.04-3.11 (m, 1H) 2.79-2.96 (m, 3H) 2.55-2.67 (m, 2H) 2.38 (dd, 1H) 1.98-2.31 (m, 7H) 1.07-1.64 (m, 6H)

Example 69

2-[3,5-bis(trifluoromethyl)phenyl]-N-{4-(4-fluoro-2-methylphenyl)-6-[(9aS or 9aR)-9-oxooctahydro-2H-pyrazino[1,2-a]pyrazin-2-yl]-3-pyridinyl}-N,2-dimethylpropanamide (E69—Enantiomer 2)

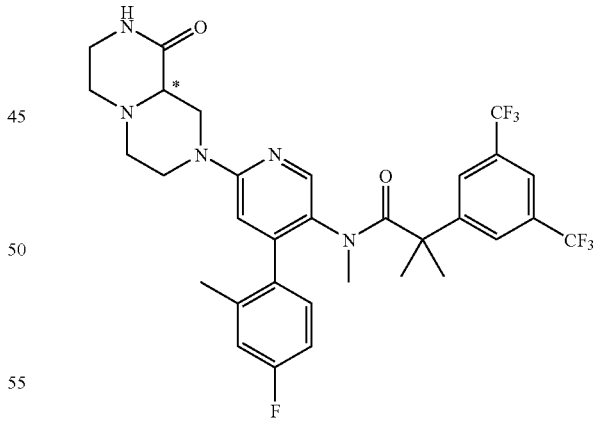

The title compound was obtained as Enantiomer labeled 2 from the chiral separation of 2-[3,5-bis(trifluoromethyl)phenyl]-N-[4-(4-fluoro-2-methylphenyl)-6-(9-oxooctahydro-2H-pyrazino[1,2-a]pyrazin-2-yl)-3-pyridinyl]-N,2-dimethylpropanamide (E67), as described for 2-[3,5-bis(trifluoromethyl)phenyl]-N-{4-(4-fluoro-2-methyl phenyl)-6-[(9aR or 9aS)-9-oxooctahydro-2H-pyrazino[1,2-a]pyrazin-2-yl]-3-pyridinyl}-N,2-dimethylpropanamide (E68—Enantiomer 1). Obtained 3.8 mg, >95.5% e.e., analytical retention time 17.7 min).

Example 70

N-[6-(8-acetyloctahydro-2H-pyrazino[1,2-a]pyrazin-2-yl)-4-(4-fluoro-2-methylphenyl)-3-pyridinyl]-2-[3,5-bis(trifluoromethyl)phenyl]-N,2-dimethylpropanamide (E70)

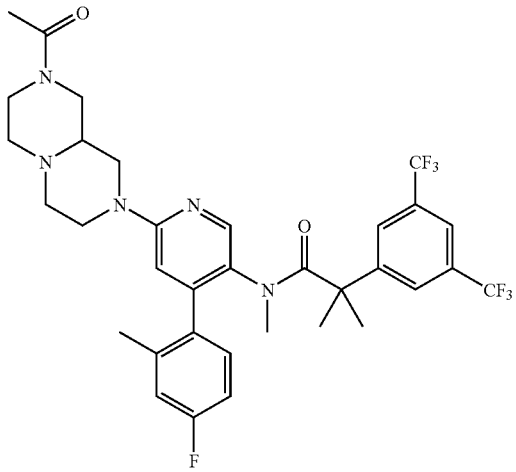

To a solution of crude 2-[3,5-bis(trifluoromethyl)phenyl]-N-[4-(4-fluoro-2-methyl phenyl)-6-(octahydro-2H-pyrazino[1,2-a]pyrazin-2-yl)-3-pyridinyl]-N,2-dimethylpropanamide (prepared with an analogous procedure to that described for D80, 89 mg, 0.14 mmol) in 5 mL of dichloromethane were added at 0° C. triethylamine (197 µL, 1.41 mmol) and acetyl chloride (75 µL, 1.0 mmol). The reaction was left at room temperature for 2 h. It was diluted with dichloromethane, extracted with sat NaHCO$_3$ solution, the organics dried (Na$_2$SO$_4$), and the solvent was removed. The product was purified by flash chromatography (silica, cyclohexane:EtOAc 50:50 to EtOAc). Obtained 60 mg.

1H NMR (500 MHz, DMSO-d$_6$) δ ppm 8.02 (s, 1H) 7.89 (s, 1H) 7.61-7.83 (m, 2H) 7.14 (d, 1H) 6.92-7.21 (m, 2H) 6.65-6.80 (m, 1H) 4.05-4.53 (m, 3H) 3.81 (dd, 1H) 2.72-2.97 (m, 4H) 2.59-2.70 (m, 2H) 2.50 (s, 3H) 1.99 (s, 3H) 1.78-2.37 (m, 6H) 1.01-1.56 (m, 6H)

MS (direct): m/z=680 (M+1), 340 (2M+2)$_{1-2}$.

Example 71

N-[6-[(9aR or 9aS)-8-acetyloctahydro-2H-pyrazino[1,2-a]pyrazin-2-yl]-4-(4-fluoro-2-methylphenyl)-3-pyridinyl]-2-[3,5-bis(trifluoromethyl)phenyl]-N,2-dimethylpropanamide (E71—Enantiomer 1)

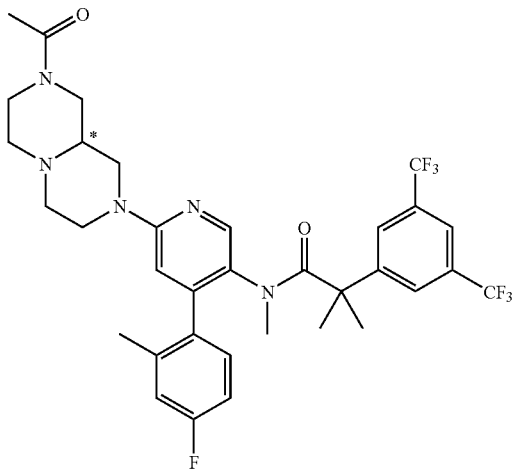

N-[6-(8-acetyloctahydro-2H-pyrazino[1,2-a]pyrazin-2-yl)-4-(4-fluoro-2-methylphenyl)-3-pyridinyl]-2-[3,5-bis(trifluoromethyl)phenyl]-N,2-dimethylpropanamide (E70, 44.5 mg) was submitted for chiral separation to isolate its enantiomers. The enantiomer labeled 1, of unknown but single stereochemistry was isolated using the following conditions (obtained 12.8 mg, >99.5% e.e., analytical retention time 13.1 min)

Preparative Conditions:

| | |
|---|---|
| Amount supplied | 44.5 mg |
| Chiral Column | CHIRALCEL OD-H, (25 × 2.1) cm |
| Mobile phase | n-Hexane/2-propanol 85/15% v/v |
| Flow rate | 22 ml/min |
| P | 182 bar |
| T | 36 C. |
| Detection | UV at 220 nm |

Analytical SFC (Berger) Conditions:

| | |
|---|---|
| Chiral Column | CHIRALCEL OD-H, (25 × 0.46) cm |
| Mobile phase | n-Hexane/2-propanol 85/15% v/v |
| Flow rate | 1.5 ml/min |
| P | 180 bar |
| T | 35 C. |
| Detection | UV at 220 nm |

1H NMR (500 MHz, DMSO-d$_6$) δ ppm 8.02 (s, 1H) 7.89 (s, 1H) 7.61-7.83 (m, 2H) 7.14 (d, 1H) 6.92-7.21 (m, 2H) 6.65-6.80 (m, 1H) 4.05-4.53 (m, 3H) 3.81 (dd, 1H) 2.72-2.97 (m, 4H) 2.59-2.70 (m, 2H) 2.50 (s, 3H) 1.99 (s, 3H) 1.78-2.37 (m, 6H) 1.01-1.56 (m, 6H)

Example 72

N-[6-[(9aS or 9aR)-8-acetyloctahydro-2H-pyrazino[1,2-a]pyrazin-2-yl]-4-(4-fluoro-2-methylphenyl)-3-pyridinyl]-2-[3,5-bis(trifluoromethyl)phenyl]-N,2-dimethylpropanamide (E72—Enantiomer 2)

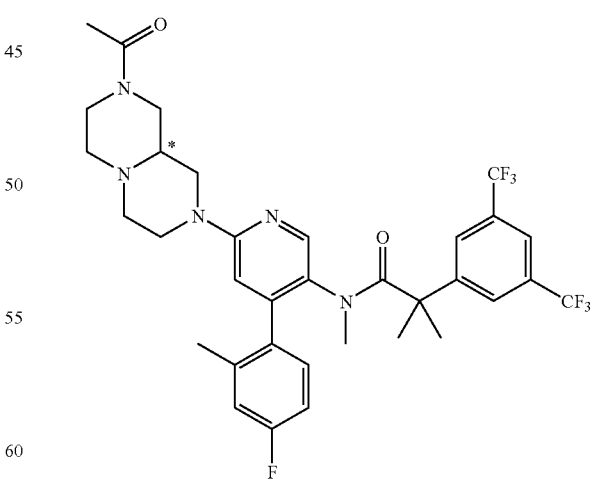

The title compound was obtained as Enantiomer labeled 2 from the chiral separation of N-[6-(8-acetyloctahydro-2H-pyrazino[1,2-a]pyrazin-2-yl)-4-(4-fluoro-2-methylphenyl)-3-pyridinyl]-2-[3,5-bis(trifluoromethyl)phenyl]-N,2-dimethylpropanamide (E70), as described for N-[6-[(9aR or 9aS)-8-acetyloctahydro-2H-pyrazino[1,2-a]pyrazin-2-yl]-4-(4-fluoro-2-methylphenyl)-3-pyridinyl]-2-[3,5-bis(trifluoromethyl)phenyl]-N,2-dimethylpropanamide (E71—Enantiomer 1). Obtained 11.6 mg, >95.5% e.e., analytical retention time 17.5 min)

1H NMR (500 MHz, DMSO-$d_6$) δ ppm 8.02 (s, 1H) 7.89 (s, 1H) 7.61-7.83 (m, 2H) 7.14 (d, 1H) 6.92-7.21 (m, 2H) 6.65-6.80 (m, 1H) 4.05-4.53 (m, 3H) 3.81 (dd, 1H) 2.72-2.97 (m, 4H) 2.59-2.70 (m, 2H) 2.50 (s, 3H) 1.99 (s, 3H) 1.78-2.37 (m, 6H) 1.01-1.56 (m, 6H)

Example 73

2-[3,5-bis(trifluoromethyl)phenyl]-N-{4-(4-fluoro-2-methylphenyl)-6-[8-(methylsulfonyl)octahydro-2H-pyrazino[1,2-a]pyrazin-2-yl]-3-pyridinyl}-N,2-dimethylpropanamide (E73)

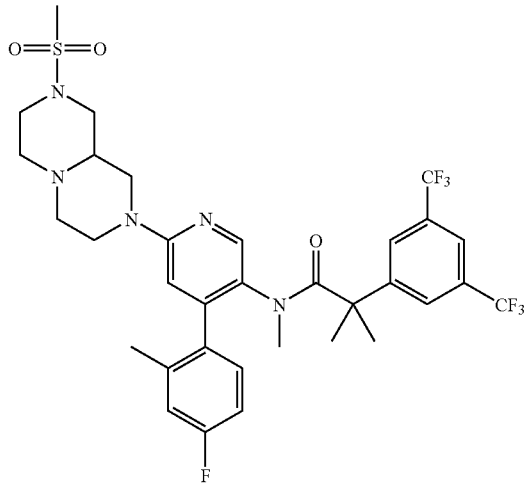

To a solution of crude 2-[3,5-bis(trifluoromethyl)phenyl]-N-4-[4-(4-fluoro-2-methylphenyl)-6-(octahydro-2H-pyrazino[1,2-a]pyrazin-2-yl)-3-pyridinyl]-N,2-dimethylpropanamide (D80, 100 mg, 0.16 mmol) in 5 mL of dichloromethane were added triethylamine (44 μL, 0.32 mmol, 2 eq.) and, at 0° C., methanesulfonyl chloride (18 μL, 0.24 mmol, 1.5 eq.). The reaction was left at room temperature overnight. Additional 3 eq. of methanesulfonyl chloride were added. It was then diluted with dichloromethane, extracted with sat. NaHCO$_3$, the organics dried (Na$_2$SO$_4$), and the solvent was removed. The product was purified by flash chromatography (silica, EtOAc). Obtained 60 mg of the title compound.

MS (direct): m/z=716 (M+1).

1H NMR (500 MHz, DMSO-$d_6$) δ ppm 8.02 (s, 1H) 7.89 (s, 1H) 7.63-7.81 (m, 2H) 6.92-7.22 (m, 3H) 6.77 (s, 1H) 4.25-4.41 (m, 1H) 4.13-4.31 (m, 1H) 3.51 (d, 1H) 3.45 (d, 1H) 2.88 (s, 3H) 2.81-2.92 (m, 2H) 2.50 (s, 3H) 2.40-2.62 (m, 3H) 2.18 (s, 3H) 2.05-2.28 (m, 4H) 1.49 (s, 3H) 1.35 (s, 3H)

Example 74

2-[3,5-bis(trifluoromethyl)phenyl]-N-{4-(4-fluoro-2-methylphenyl)-6-[(9aR or 9aS)-8-(methylsulfonyl)octahydro-2H-pyrazino[1,2-a]pyrazin-2-yl]-3-pyridinyl}-N,2-dimethylpropanamide (E74—Enantiomer 1)

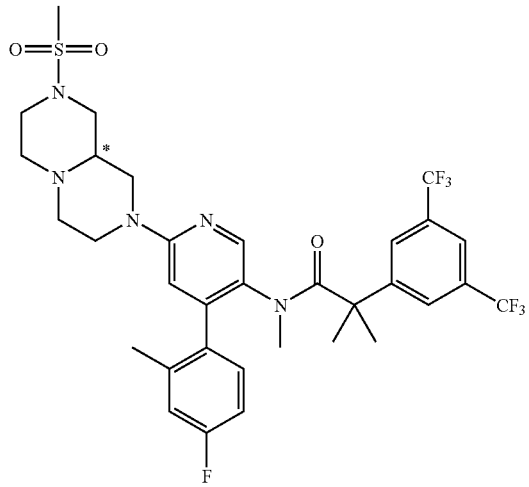

N-[6-(8-acetyloctahydro-2H-pyrazino[1,2-a]pyrazin-2-yl)-4-(4-fluoro-2-methylphenyl)-3-pyridinyl]-2-[3,5-bis(trifluoromethyl)phenyl]-N,2-dimethylpropanamide (E73, 55.5 mg) was submitted for chiral separation to isolate its enantiomers. The enantiomer labeled 1, of unknown but single stereochemistry was isolated using the following conditions (obtained 11.5 mg, >99.5% e.e., analytical retention time 8.16 min)

Preparative Conditions:

| | |
|---|---|
| Amount supplied | 55.5 mg |
| Chiral Column | Chiralpak AD-H, (25 × 2.1) cm |
| Mobile phase | n-Hexane/Ethanol 60/40% v/v |
| Flow rate | 13 ml/min |

Analytical Conditions:

| | |
|---|---|
| Chiral Column | Chiralpak AD-H, (25 × 0.46) cm |
| Mobile phase | n-Hexane/Ethanol 60/40% v/v + 1% isopropylamine |
| Flow rate | 0.8 ml/min |
| Detection | UV 200-400 nm |

1H NMR (500 MHz, DMSO-$d_6$) δ ppm 8.02 (s, 1H) 7.90 (s, 1H) 7.59-7.82 (m, 2H) 6.87-7.20 (m, 3H) 6.68-6.84 (m, 1H) 4.28-4.40 (m, 1H) 4.17-4.27 (m, 1H) 3.52 (d, 1H) 3.46 (d, 1H) 2.90 (s, 3H) 2.80-2.93 (m, 4H) 2.44-2.57 (m, 5H) 2.01-2.27 (m, 6H) 1.24-1.60 (m, 6H)

Example 75

2-[3,5-bis(trifluoromethyl)phenyl]-N-{4-(4-fluoro-2-methylphenyl)-6-[(9aS or 9aR)-8-(methylsulfonyl)octahydro-2H-pyrazino[1,2-a]pyrazin-2-yl]-3-pyridinyl}-N,2-dimethylpropanamide (E75—Enantiomer 2)

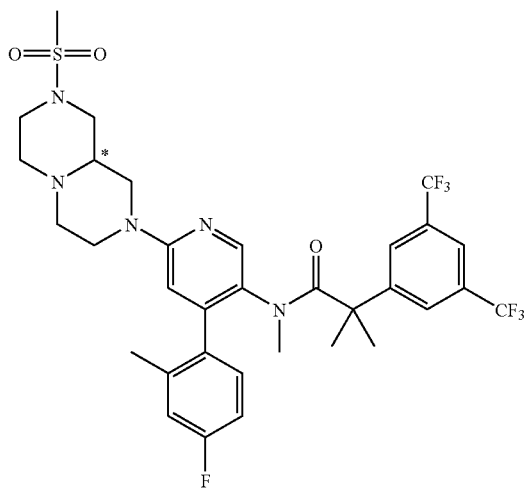

The title compound was obtained as Enantiomer labeled 2 from the chiral separation of 2-[3,5-bis(trifluoromethyl)phenyl]-N-{4-(4-fluoro-2-methylphenyl)-6-[8-(methylsulfonyl)octahydro-2H-pyrazino[1,2-a]pyrazin-2-yl]-3-pyridinyl}-N,2-dimethyl propanamide (E73), as described for 2-[3,5-bis(trifluoromethyl)phenyl]-N-{4-(4-fluoro-2-methylphenyl)-6-[(9aR or 9aS)-8-(methylsulfonyl)octahydro-2H-pyrazino[1,2-a]pyrazin-2-yl]-3-pyridinyl}-N,2-dimethylpropanamide (E74-Enantiomer 1). Obtained 12.6 mg, >95.5% e.e., analytical retention time 14.36 min)

1H NMR (500 MHz, DMSO-$d_6$) δ ppm 8.02 (s, 1H) 7.90 (s, 1H) 7.59-7.82 (m, 2H) 6.87-7.20 (m, 3H) 6.68-6.84 (m, 1H) 4.28-4.40 (m, 1H) 4.17-4.27 (m, 1H) 3.52 (d, 1H) 3.46 (d, 1H) 2.90 (s, 3H) 2.80-2.93 (m, 4H) 2.44-2.57 (m, 5H) 2.01-2.27 (m, 6H) 1.24-1.60 (m, 6H)

Example 76

2-[3,5-bis(trifluoromethyl)phenyl]-N-[4-(4-fluoro-2-methylphenyl)-6-(8-methyloctahydro-2H-pyrazino[1,2-a]pyrazin-2-yl)-3-pyridinyl]-N,2-dimethylpropanamide (E76)

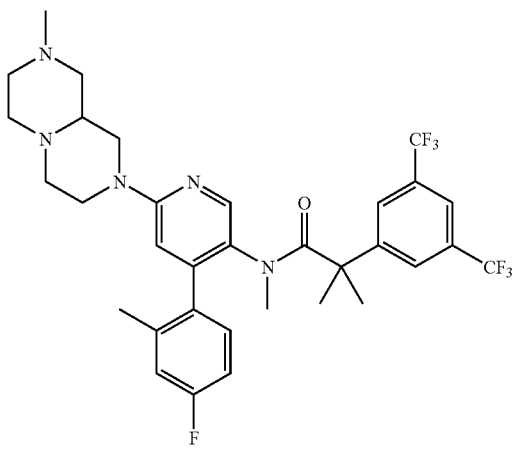

To a solution of crude 2-[3,5-bis(trifluoromethyl)phenyl]-N-[4-(4-fluoro-2-methylphenyl)-6-(octahydro-2H-pyrazino[1,2-a]pyrazin-2-yl)-3-pyridinyl]-N,2-dimethylpropanamide (D80, 100 mg, 0.16 mmol) in 5 mL of acetonitrile was added a 37% aqueous formaldehyde solution (24 µL, 0.32 mmol). The solution was stirred at room temperature for 30 min, and then sodium triacetoxyborohydride (50 mg, 0.24 mmol) was added and the reaction stirred at room temperature overnight. The solvent was evaporated and the residue dissolved in dichloromethane and extracted with water and brine. The product was purified by flash chromatography (silica, dichloromethane to dichloromethane: MeOH 95:5). Obtained 58 mg of the title compound.

MS (direct): m/z=652 (M+1).

1H NMR (500 MHz, DMSO-$d_6$) δ ppm 7.96-8.08 (m, 1H) 7.81-7.93 (m, 1H) 7.60-7.80 (m, 2H) 7.15 (d, 1H) 6.88-7.12 (m, 2H) 6.60-6.79 (m, 1H) 4.24 (d, 1H) 4.12 (d, 1H) 2.74-2.92 (m, 2H) 2.61-2.73 (m, 2H) 2.41-2.57 (m, 4H) 1.92-2.31 (m, 11H) 1.68 (t, 1H) 1.10-1.56 (m, 6H)

Example 77

2-[3,5-bis(trifluoromethyl)phenyl]-N-{4-(4-fluoro-2-methylphenyl)-6-[(9aS or 9aR)-8-methyloctahydro-2H-pyrazino[1,2-a]pyrazin-2-yl]-3-pyridinyl}-N,2-dimethylpropanamide (E77—Enantiomer 1)

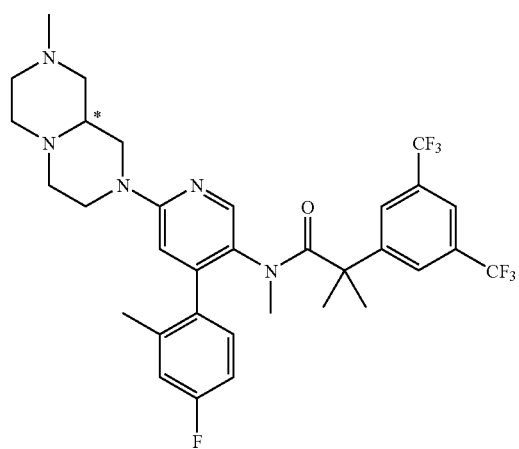

N-[6-(8-acetyloctahydro-2H-pyrazino[1,2-a]pyrazin-2-yl)-4-(4-fluoro-2-methylphenyl)-3-pyridinyl]-2-[3,5-bis(trifluoromethyl)phenyl]-N,2-dimethylpropanamide (E76, 50 mg) was submitted for chiral separation to isolate its enantiomers. The enantiomer labeled 1, of unknown but single stereochemistry was isolated using the following conditions (obtained 13 mg, 70% e.e., analytical retention time 10.7 min)

Semipreparative SFC (Gilson) Conditions:

| | |
|---|---|
| Amount supplied | 50 mg |
| Chiral Column | CHIRALCEL OD-H, (25 × 2.1) cm |
| Mobile phase | n-Hexane/(Ethanol + 0.1% isopropylamine) 95/5% v/v |
| Flow rate | 22 ml/min |
| P | 182 bar |
| T | 36 C. |
| Detection | UV at 220 nm |

Analytical SFC (Berger) Conditions:

| Chiral Column | CHIRALCEL OD-H, (25 × 0.46) cm |
|---|---|
| Mobile phase | n-Hexane/2-propanol 85/15% v/v |
| Flow rate | 1.5 ml/min |
| P | 180 bar |
| T | 35 C. |
| Detection | UV at 220 nm |

1H NMR (500 MHz, DMSO-$d_6$) δ ppm 7.96-8.07 (m, 1H) 7.84-7.91 (m, 1H) 7.61-7.81 (m, 2H) 7.16 (d, 1H) 6.99-7.13 (m, 2H) 6.65-6.73 (m, 1H) 4.24 (d, 1H) 4.13 (d, 1H) 2.73-2.94 (m, 2H) 2.62-2.75 (m, 2H) 2.37-2.58 (m, 4H) 1.95-2.33 (m, 11H) 1.69 (t, 1H) 1.25-1.56 (m, 6H)

Example 78

2-[3,5-bis(trifluoromethyl)phenyl]-N-{4-(4-fluoro-2-methylphenyl)-6-[(9aR or 9aS)-8-methyloctahydro-2H-pyrazino[1,2-a]pyrazin-2-yl]-3-pyridinyl}-N,2-dimethylpropanamide (E78—Enantiomer 2)

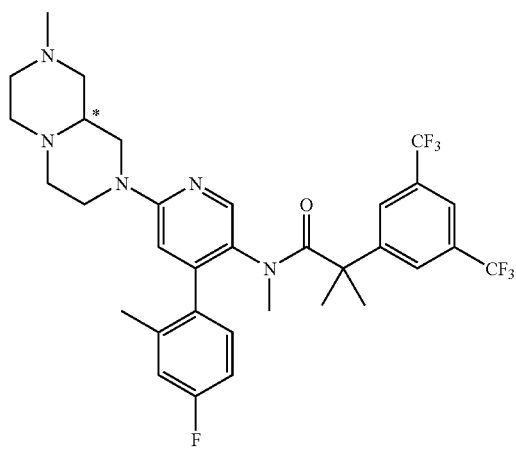

The title compound was obtained as Enantiomer labeled 2 from the chiral separation of 2-[3,5-bis(trifluoromethyl)phenyl]-N-[4-(4-fluoro-2-methylphenyl)-6-(8-methyloctahydro-2H-pyrazino[1,2-a]pyrazin-2-yl)-3-pyridinyl]-N,2-dimethylpropanamide (E76), as described for 2-[3,5-bis(trifluoromethyl)phenyl]-N-{4-(4-fluoro-2-methylphenyl)-6-[(9aS or 9aR)-8-methyloctahydro-2H-pyrazino[1,2-a]pyrazin-2-yl]-3-pyridinyl}-N,2-dimethylpropanamide (E77—Enantiomer 1). Obtained 12 mg, >95.5% e.e., analytical retention time 13.9 min).

1H NMR (500 MHz, DMSO-$d_6$) δ ppm 7.96-8.07 (m, 1H) 7.84-7.91 (m, 1H) 7.61-7.81 (m, 2H) 7.16 (d, 1H) 6.99-7.13 (m, 2H) 6.65-6.73 (m, 1H) 4.24 (d, 1H) 4.13 (d, 1H) 2.73-2.94 (m, 2H) 2.62-2.75 (m, 2H) 2.37-2.58 (m, 4H) 1.95-2.33 (m, 11H) 1.69 (t, 1H) 1.25-1.56 (m, 6H)

Example 79

2-[3,5-bis(trifluoromethyl)phenyl]-N-{4-(4-fluoro-2-methylphenyl)-6-[(3R,8aR)-3-(hydroxymethyl)hexahydropyrrolo[1,2-a]pyrazin-2(1H)-yl]-3-pyridinyl}-N,2-dimethylpropanamide (E79)

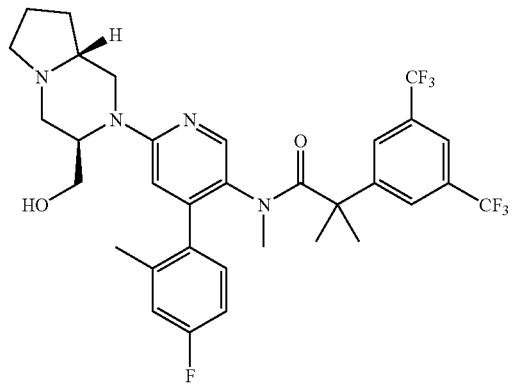

(3R,8aR)-octahydropyrrolo[1,2-a]pyrazin-3-ylmethanol (190 mg, 1.22 mmol, Tetrahedron Asymmetry, 1996, 7(7), 1999-2005) was dissolved in 10 mL of toluene, followed by the 2-[3,5-bis(trifluoromethyl)phenyl]-N-[6-chloro-4-(4-fluoro-2-methylphenyl)-3-pyridinyl]-N,2-dimethylpropanamide [WO 2005/002577] (323 mg, 0.607 mmol), 2-dicyclohexylphosphino-2'-(N,N-dimethylamino)biphenyl (ligand) (57 mg, 0.144 mmol), Pd(dba)$_2$ (35 mg, 0.061 mmol) and, at last, cesium carbonate (297 mg, 0.912 mmol). The mixture was stirred at 130° C. After 3.5 h, more ligand (55 mg, 0.139 mmol) and Pd(dba)$_2$ (35 mg, 0.061 mmol) were added and the reaction left overnight. It was let cool down to room temperature, diluted with 10 mL of MeOH, loaded on a 10 g SCX column, washed with MeOH and eluted with 1M methanolic ammonia. The sample coming from the SCX column was further purified by flash chromatography: 1$^{st}$ column: silica, cyclohexane:EtOAc 50:50 to 0:100; 2$^{nd}$ column, NH$_2$-modified silica, cyclohexane:EtOAc 100:0 to 0:100. Isolated 29 mg of the target material.

O.A.HPLC, peak @ 5.20 min, >99% purity (UV).

LC/MS (checked after 1$^{st}$ column): m/z=653.

1H NMR (500 MHz, DMSO-$d_6$) δ ppm 8.02 (s, 1H) 7.85 (s, 1H) 7.74 (br. s., 2H) 7.15 (d, 1H) 7.05-7.13 (m, 2H) 6.53 (s, 1H) 3.94-4.02 (m, 2H) 3.58-3.67 (m, 1H) 3.53-3.59 (m, 1H) 3.08-3.18 (m, 1H) 2.82-2.89 (m, 1H) 2.72-2.80 (m, 1H) 2.50-2.56 (m, 1H) 2.24 (s, 3H) 2.15-2.19 (m, 1H) 2.10 (s, 3H) 1.89 (s, 3H) 1.73-1.83 (m, 1H) 1.47 (s, 3H) 1.40-1.70 (m, 3H) 1.34 (s, 3H)

Example 80

2-[3,5-bis(trifluoromethyl)phenyl]-N-{4-(4-fluoro-2-methylphenyl)-6-[(3R,8aR)-3-(hydroxymethyl)hexahydropyrrolo[1,2-a]pyrazin-2(1H)-yl]-3-pyridinyl}-N,2-dimethylpropanamide Hydrochloride (E80)

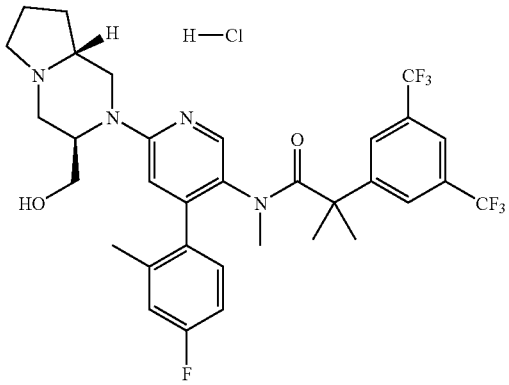

The starting free base (E79, 25 mg, 0.038 mmol) was dissolved in 0.3 mL of dichloromethane and 1M HCl in Et$_2$O (57 μL, 0.057 mmol) was added at 0° C. under a stream of nitrogen. The solution was stirred for 15 min. at 0° C. and the solvent was removed under a nitrogen stream. The solid was triturated with Et$_2$O and pentane, leaving the product as an off-white solid (25 mg).

O.A.HPLC, peak @ 5.20 min, >99% purity (UV).
1H NMR (500 MHz, DMSO-d$_6$) δ ppm 10.14 (br. s., 1H) 8.03 (s, 1H) 7.92 (s, 1H) 7.75 (br. s., 2H) 7.17 (d, 1H) 7.10 (br. s., 2H) 6.67 (s, 1H) 5.17 (br. s., 1H) 4.24-4.36 (m, 1H) 3.48-4.04 (m, 6H) 3.07-3.16 (m, 1H) 2.54-2.59 (m, 1H) 2.24 (s, 3H) 2.17 (s, 3H) 2.10 (s, 1H) 1.97-2.06 (m, 1H) 1.70-1.89 (m, 3H) 1.48 (s, 3H) 1.34 (s, 3H)

Example 81

2-[3,5-bis(trifluoromethyl)phenyl]-N-{4-(4-fluoro-2-methylphenyl)-6-[(3S,8aR)-3-(hydroxymethyl)hexahydropyrrolo[1,2-a]pyrazin-2(1H)-yl]-3-pyridinyl}-N,2-dimethylpropanamide (E81)

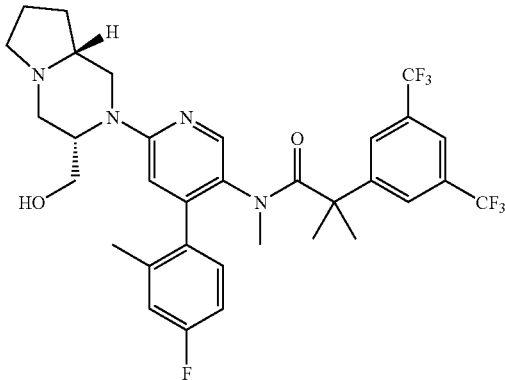

(3S,8aR)-Octahydropyrrolo[1,2-a]pyrazin-3-ylmethanol (Tetrahedron Asymmetry, 1996, 7(7), 1999-2005, 230 mg, 1.47 mmol) and 2-[3,5-bis(trifluoromethyl)phenyl]-N-[6-chloro-4-(4-fluoro-2-methylphenyl)-3-pyridinyl]-N,2-dimethylpropanamide [WO 2005/002577] (570 mg, 1.07 mmol) were dissolved in 12 mL of toluene. 2-Dicyclohexylphosphino-2'-(N,N-dimethylamino)biphenyl (ligand) (78 mg, 0.20 mmol), Pd(dba)$_2$ (45 mg, 0.08 mmol) and, at last, caesium carbonate (697 mg, 2.14 mmol) were added. The reaction vessel was sealed and nitrogen bubbled through the solution for 15 min. The reaction mixture was heated to 140° C. for 15 h. The mixture was diluted with 100 mL of EtOAc and extracted with water. The aqueous phase was extracted again with dichloromethane. The combined organics were dried and the solvent removed. Product purified by flash chromatography: silica, cyclohexane:EtOAc 50:50 to 0:100. Further purification by HPLC (prep. conditions: Column: Gemini C18 5 μm, 100×19 mm; Mobile phase: A: NH4HCO3 sol. 10 mM, pH10; B: CH3CN, Gradient: 50% (B) for 1 min, from 50% (B) to 65% (B) in 12 min, 95% (B) for 6 min; Flow rate: 17 ml/min; UV wavelength range: 210-350 nm; Mass range: 100-900 amu; Ionization: ES+. Isolated 31 mg of the title compound.

O.A.HPLC, peak @ 5.17 min, >99% purity (UV).
LC/MS: m/z=653 (analytical data from HPLC separation).
1H NMR (300 MHz, DMSO-d$_6$) δ ppm 7.90-8.02 (m, 1H) 7.82 (s, 1H) 7.70-7.77 (m, 2H) 7.07-7.23 (m, 2H) 7.03 (td, 1H) 6.58 (s, 1H) 4.42 (dd, 1H) 4.20-4.34 (m, 1H) 3.75 (t, 1H) 3.49 (dd, 1H) 3.31 (d, 1H) 2.97-3.17 (m, 1H) 2.70 (t, 1H) 2.47 (s, 3H) 2.17 (s, 3H) 2.12-2.21 (m, 1H) 1.95-2.14 (m, 1H) 1.86-2.07 (m, 1H) 1.61-1.99 (m, 4H) 1.41 (s, 6H).

Example 82

2-[3,5-bis(trifluoromethyl)phenyl]-N-{4-(4-fluoro-2-methylphenyl)-6-[(3S,8aR)-3-(hydroxymethyl)hexahydropyrrolo[1,2-a]pyrazin-2(1H)-yl]-3-pyridinyl}-N,2-dimethylpropanamide Hydrochloride (E82)

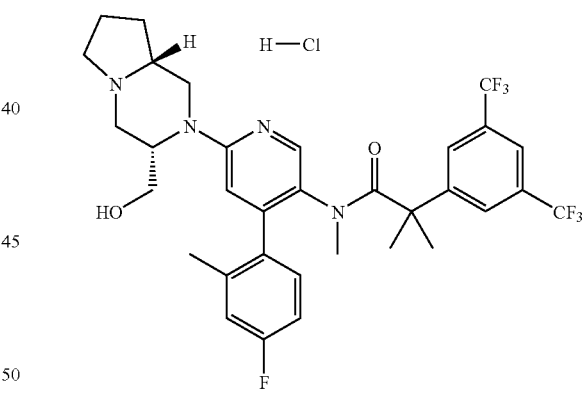

2-[3,5-bis(trifluoromethyl)phenyl]-N-{4-(4-fluoro-2-methylphenyl)-6-[(3S,8aR)-3-(hydroxymethyl)hexahydropyrrolo[1,2-a]pyrazin-2(1H)-yl]-3-pyridinyl}-N,2-dimethylpropanamide (E81, 25 mg, 0.038 mmol) was converted to its hydrochloride as reported above in the procedure for 2-[3,5-bis(trifluoromethyl)phenyl]-N-{4-(4-fluoro-2-methylphenyl)-6-[(3R,8aR)-3-(hydroxymethyl)hexahydropyrrolo[1,2-a]pyrazin-2(1H)-yl]-3-pyridinyl}-N,2-dimethylpropanamide Hydrochloride (E80). Obtained 26 mg of the title compound.

O.A.HPLC, peak @ 5.13 min, 98.6% purity (UV).
1H NMR (300 MHz, DMSO-d$_6$) δ ppm 10.31 (br. s., 1H) 8.07 (s, 1H) 7.90-7.98 (m, 1H) 7.63-7.87 (m, 2H) 6.97-7.31 (m, 3H) 6.74 (s, 1H) 4.48-4.95 (m, 2H) 4.02-4.32 (m, 1H) 2.92-4.01 (m, 4H) 2.27 (s, 3H) 2.12 (s, 3H) 1.38 (s, 6H) 0.66-2.76 (m, 7H).

Example 83

2-[3,5-bis(trifluoromethyl)phenyl]-N-{4-(4-fluoro-2-methylphenyl)-6-[(3R,8aS)-3-(hydroxymethyl)hexahydropyrrolo[1,2-a]pyrazin-2(1H)-yl]-3-pyridinyl}-N,2-dimethylpropanamide (E83)

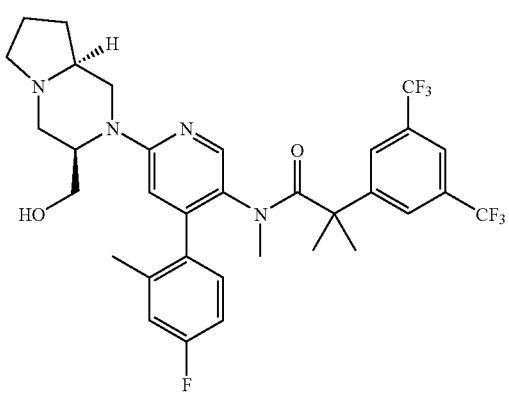

To a solution of (3R,8aS)-3-({[(1,1-dimethylethyl)(dimethyl)silyl]oxy}methyl)octahydropyrrolo[1,2-a]pyrazine (D81, 200 mg, 0.739 mmol) in 3 mL of toluene were added 2-[3,5-bis(trifluoromethyl)phenyl]-N-[6-chloro-4-(4-fluoro-2-methylphenyl)-3-pyridinyl]-N,2-dimethylpropanamide [WO 2005/002577] (304 mg, 0.569 mmol) (t-Bu$_3$P)$_2$Pd (58 mg, 0.114 mmol), a 25% aqueous solution of cetyltrimethylammonium chloride (35 µL), and, at last, 50% aqueous NaOH (68 µL). The reaction deoxygenated by two freeze-pump-thaw cycles and then heated to 90° C. overnight. The solution was diluted with EtOAc, washed with sat. NaHCO$_3$ and brine. The sample was purified by flash chromatography (silica, cyclohexane:EtOAc 95:5 to 60:40). Isolated 230 mg of O-TBDMS protected intermediate (UPLC/MS: pak @ 0.89 min, m/z=767 (M+1), 384 (M+2)/2).

The intermediate was dissolved in 10 mL of MeOH and 0.5 mL of conc. HCl were added. The reaction was left at room temperature for 1 h. The product was isolated by SCX cartridge. Isolated 133 mg of the title compound.

1H NMR (300 MHz, DMSO-d$_6$) δ ppm 7.90-8.02 (m, 1H) 7.82 (s, 1H) 7.70-7.77 (m, 2H) 7.07-7.23 (m, 2H) 7.03 (td, 1H) 6.58 (s, 1H) 4.42 (dd, 1H) 4.20-4.34 (m, 1H) 3.75 (t, 1H) 3.49 (dd, 1H) 3.31 (d, 1H) 2.97-3.17 (m, 1H) 2.70 (t, 1H) 2.47 (s, 3H) 2.17 (s, 3H) 2.12-2.21 (m, 1H) 1.95-2.14 (m, 1H) 1.86-2.07 (m, 1H) 1.61-1.99 (m, 4H) 1.41 (s, 6H).

UPLC/MS: peak @ 0.71 min, m/z=653 (M+1).

Example 84

2-[3,5-bis(trifluoromethyl)phenyl]-N-{4-(4-fluoro-2-methylphenyl)-6-[(3S,8aS)-3-(hydroxymethyl)hexahydropyrrolo[1,2-a]pyrazin-2(1H)-yl]-3-pyridinyl}-N,2-dimethylpropanamide (E84)

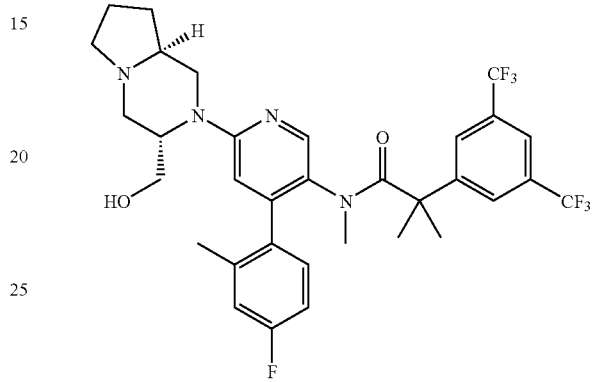

To a solution of (3S,8aS)-3-({[(1,1-dimethylethyl)(dimethyl)silyl]oxy}methyl)octahydropyrrolo[1,2-a]pyrazine (D82, 157 mg, 0.58 mmol) in 2.5 mL of toluene were added 2-[3,5-bis(trifluoromethyl)phenyl]-N-[6-chloro-4-(4-fluoro-2-methylphenyl)-3-pyridinyl]-N,2-dimethylpropanamide [WO 2005/002577] (238 mg, 0.45 mmol) (t-Bu$_3$P)$_2$Pd (46 mg, 0.09 mmol), a 25% aqueous solution of cetyltrimethylammonium chloride (26 µL), and, at last, 50% aqueous NaOH (54 µL). The reaction deoxygenated by freeze-pump-thaw cycles and then heated to 90° C. for 7 h. The reaction was checked by UPLC/MS, showing the expected product peak at 0.84 min, with m/z=767 (M+1) and 384 ((M+2)/2). The solution was diluted with EtOAc, washed with sat. NaHCO$_3$ and brine. The sample was purified by flash chromatography (silica, cyclohexane:EtOAc 90:10 to 0:100). Isolated 251 mg of O-TBDMS protected intermediate.

The intermediate was dissolved in 11 mL of MeOH and 0.55 mL of conc. HCl were added. The reaction was left at room temperature for 1 h. The product was isolated by SCX cartridge. Isolated 140 mg of the title compound.

1H NMR (500 MHz, DMSO-d$_6$) δ ppm 8.02 (s, 1H) 7.86 (s, 1H) 7.75 (br. s., 2H) 7.15 (d, 1H) 7.10 (br. s., 2H) 6.52 (s, 1H) 4.83 (br. s., 1H) 3.94-4.03 (m, 1H) 3.57-3.69 (m, 1H) 3.50-3.58 (m, 2H) 3.33-3.46 (m, 1H) 3.18-3.27 (m, 1H) 3.10-3.18 (m, 1H) 2.81-2.89 (m, 1H) 2.73-2.81 (m, 1H) 2.51-2.59 (m, 1H) 2.49 (s, 3H) 2.11 (s, 3H) 1.84-1.94 (m, 1H) 1.73-1.82 (m, 1H) 1.55-1.68 (m, 1H) 1.46 (s, 3H) 1.36-1.47 (m, 1H) 1.33 (s, 3H)

O.A. HPLC: peak @ 5.20 min, 98.9% purity (UV).

Example 85

2-[3,5-bis(trifluoromethyl)phenyl]-N-[6-(hexahydro-pyrazino[2,1-c][1,4]oxazin-8(1H)-yl)-4-(2-methylphenyl)-3-pyridinyl]-N,2-dimethylpropanamide (E85)

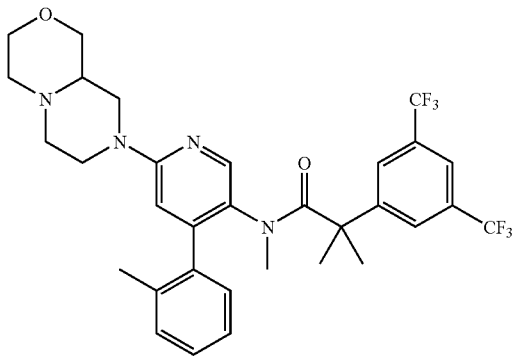

A solution of 2-[3,5-bis(trifluoromethyl)phenyl]-N-[6-chloro-4-(2-methylphenyl)-3-pyridinyl]-N,2-dimethylpropanamide [WO 2002/16324A1] (200 mg, 0.388 mmol), octahydropyrazino[2,1-c][1,4]oxazine (EP472826, 111 mg, 0.776 mmol), and potassium carbonate (161 mg, 1.165 mmol) in 1 mL of DMSO was heated to 150° C. for 47 h. It was worked up by diluting with dichloromethane and extracting with brine. The organics were dried ($Na_2SO_4$), and the solvent removed. The product was purified by flash chromatography: silica, dichloromethane to dichloromethane: MeOH 95:5. Obtained 92 mg of the title compound.

HPLC/MS: Peak @ 2.11 min, 621 (M+1)

1H NMR (400 MHz, DMSO-$d_6$) δ ppm 7.97 (s, 1H) 7.83 (s, 1H) 7.69 (br. s., 2H) 7.23 (s, 2H) 7.15 (br. s., 1H) 7.02 (br. s., 1H) 6.65 (s, 1H) 4.20 (d, 1H) 4.04 (d, 1H) 3.70 (t, 2H) 3.48 (t, 1H) 3.09 (t, 1H) 2.83 (t, 1H) 2.74 (d, 1H) 2.62 (d, 1H) 2.49 (s, 3H) 2.36 (t, 1H) 2.09-2.24 (m, 3H) 2.07 (s, 3H) 1.39 (s, 3H) 1.25 (s, 3 H).

Example 86

2-[3,5-bis(trifluoromethyl)phenyl]-N-[6-[(9aR or 9aS)-hexahydropyrazino[2,1-c][1,4]oxazin-8(1H)-yl]-4-(2-methylphenyl)-3-pyridinyl]-N,2-dimethyl-propanamide (E86—Enantiomer 1)

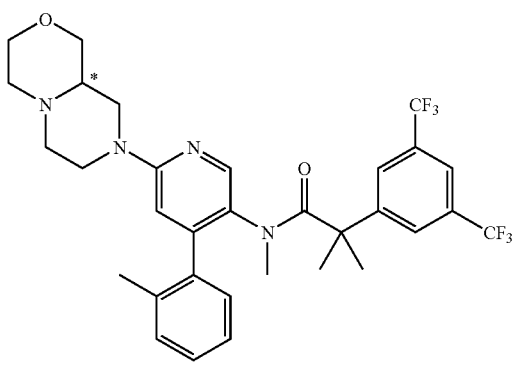

2-[3,5-bis(trifluoromethyl)phenyl]-N-[6-(hexahydropy-razino[2,1-c][1,4]oxazin-8(1H)-yl)-4-(2-methylphenyl)-3-pyridinyl]-N,2-dimethylpropanamide (E85, 87 mg) was submitted for chiral separation to isolate its enantiomers. The enantiomer labeled 1, of unknown but single stereochemistry was isolated using the following conditions (obtained 41 mg, >99.5% e.e., analytical retention time 5.84 min)

Preparative Conditions:

| | |
|---|---|
| Amount supplied | 87 mg |
| Chiral Column | CHIRALCEL OD-H, (25 × 2.1) cm |
| Mobile phase | n-Hexane/2-propanol 94/6% v/v |
| Flow rate | 18 ml/min |
| Detection | UV at 225 nm |

Analytical Conditions:

| | |
|---|---|
| Chiral Column | CHIRALCEL OD-H, (25 × 0.46) cm |
| Mobile phase | n-Hexane/2-propanol 85/15% v/v |
| Flow rate | 1.0 ml/min |
| P | 180 bar |
| T | 35 C. |
| Detection | UV at 225 nm |

1H NMR (500 MHz, DMSO-$d_6$) δ ppm 8.02 (s, 1H) 7.87 (s, 1H) 7.64-7.79 (m, 2H) 6.98-7.33 (m, 4H) 6.64-6.74 (m, 1H) 4.24 (d, 1H) 4.09 (d, 1H) 3.74 (t, 2H) 3.53 (t, 1H) 3.13 (t, 1H) 2.86 (t, 1H) 2.78 (d, 1H) 2.66 (d, 1H) 2.51 (s, 3H) 2.40 (t, 1H) 2.00-2.30 (m, 6H) 1.11-1.48 (m, 6H).

Example 87

2-[3,5-bis(trifluoromethyl)phenyl]-N-[6-[(9aS or 9aR)-hexahydropyrazino[2,1-c][1,4]oxazin-8(1H)-yl]-4-(2-methylphenyl)-3-pyridinyl]-N,2-dimethyl-propanamide (E87—Enantiomer 2)

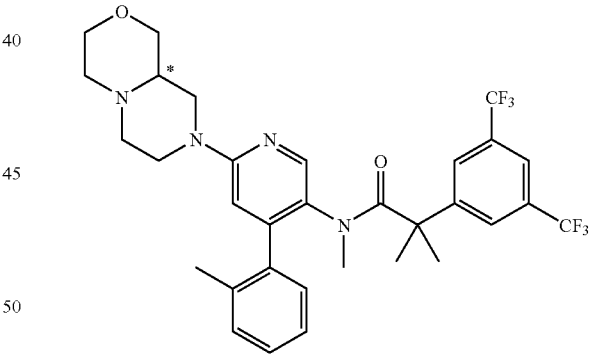

The title compound was obtained as Enantiomer labeled 2 from the chiral separation of 2-[3,5-bis(trifluoromethyl)phenyl]-N-[6-(hexahydropyrazino[2,1-c][1,4]oxazin-8(1H)-yl)-4-(2-methylphenyl)-3-pyridinyl]-N,2-dimethylpropanamide (E85), as described for 2-[3,5-bis(trifluoromethyl)phenyl]-N-[6-[(9aR or 9aS)-hexahydropyrazino[2,1-c][1,4]oxazin-8 (1H)-yl]-4-(2-methyl phenyl)-3-pyridinyl]-N,2-dimethyl-propanamide (E86—Enantiomer 1). Obtained 35 mg of the title compound, >95.5% e.e., analytical retention time 8.80 min.

1H NMR (500 MHz, DMSO-$d_6$) δ ppm 8.02 (s, 1H) 7.87 (s, 1H) 7.64-7.79 (m, 2H) 6.98-7.33 (m, 4H) 6.64-6.74 (m, 1H) 4.24 (d, 1H) 4.09 (d, 1H) 3.74 (t, 2H) 3.53 (t, 1H) 3.13 (t, 1H) 2.86 (t, 1H) 2.78 (d, 1H) 2.66 (d, 1H) 2.51 (s, 3H) 2.40 (t, 1H) 2.00-2.30 (m, 6H) 1.11-1.48 (m, 6H).

Example 88

N-[6-[(3R,9aR or 9aS)-8-acetyl-3-(hydroxymethyl) octahydro-2H-pyrazino[1,2-a]pyrazin-2-yl]-4-(4-fluoro-2-methylphenyl)-3-pyridinyl]-2-[3,5-bis(trifluoromethyl)phenyl]-N,2-dimethylpropanamide (E88—Diastereoisomer 1)

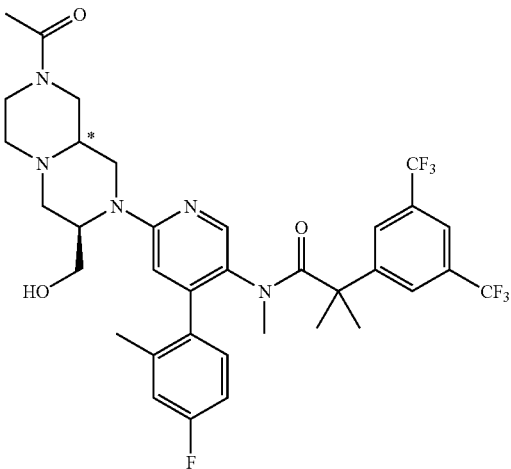

The N-[6-((3R,9aR or 9aS)-8-acetyl-3-{[(1,1-dimethylethyl)(dimethyl)silyl]methyl}octahydro-2H-pyrazino[1,2-a]pyrazin-2-yl)-4-(4-fluoro-2-methyl phenyl)-3-pyridinyl]-2-[3,5-bis(trifluoromethyl)phenyl]-N,2-dimethylpropanamide (D88, 148 mg) was dissolved 6 mL of $CH_2Cl_2$. To this solution was added concentrated HCl (0.3 mL) at 0° C., and stirred at room temperature for 30 min. UPLC/MS analysis showed complete conversion to the expected product (peak at 0.70 min, m/z=710 (M+1), 355.7 ((M+2)/2)). The reaction mixture was purified by SCX cartridge to give title compound as a solid: 106 mg.

1H NMR (400 MHz, DMSO-$d_6$) δ ppm 7.88 (s, 1H) 7.82 (s, 1H) 7.68 (s, 2H) 7.03-7.13 (m, 2H) 6.92-7.01 (m, 1H) 6.63 (s, 1H) 4.40-4.47 (m, 1H) 3.92-4.01 (m, 1H) 3.54-3.65 (m, 2H) 3.51 (dd, 1H) 3.41 (dd, 1H) 3.11 (dd, 1H) 2.72-2.81 (m, 1H) 2.47 (s, 3H) 2.34-2.53 (m, 7H) 2.11 (s, 3H) 1.94 (s, 3H) 1.35 (s, 6H).

Example 89

N-[6-[(3R,9aS or 9aR)-8-acetyl-3-(hydroxymethyl) octahydro-2H-pyrazino[1,2-a]pyrazin-2-yl]-4-(4-fluoro-2-methylphenyl)-3-pyridinyl]-2-[3,5-bis(trifluoromethyl)phenyl]-N,2-dimethylpropanamide (E89—Diastereoisomer 2)

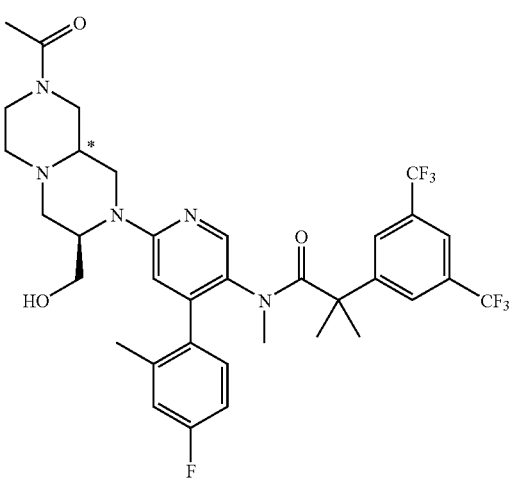

To a solution of the N-[6-((3R,9aS or 9aR)-8-acetyl-3-{[(1,1-dimethylethyl)(dimethyl)silyl]methyl}octahydro-2H-pyrazino[1,2-a]pyrazin-2-yl)-4-(4-fluoro-2-methyl phenyl)-3-pyridinyl]-2-[3,5-bis(trifluoromethyl)phenyl]-N,2-dimethylpropanamide (D92, 199 mg, 0.242 mmol) in 8 mL of MeOH were added dropwise 0.4 mL of conc. HCl. The reaction was stirred at room temperature for 3 h. UPLC/MS analysis showed conversion to the expected product (peak at 0.75 min, m/z=710 (M+1), 355.7 ((M+2)/2)). The reaction mixture was purified by SCX cartridge to give a solid that was purified further by flash chromatography (silica, dichloromethane to dichloromethane: (0.5 M NH3 in MeOH) 95:5). Obtained 121.6 mg of the title compound.

1H NMR (500 MHz, DMSO-$d_6$) δ ppm 8.02 (s, 1H) 7.85 (s, 1H) 7.74 (br. s., 2H) 7.15 (d, 1H) 7.10 (br. s., 2H) 6.61 (br. s., 1H) 4.67-4.73 (m, 1H) 4.33 (t, 1H) 4.22 (br. s., 2H) 3.71-3.87 (m, 2H) 3.37-3.45 (m, 1H) 2.98-3.11 (m, 1H) 2.70-2.85 (m, 2H) 2.53-2.69 (m, 2H) 2.49 (s, 3H) 2.11 (br. s., 3H) 2.04-2.24 (m, 2H) 1.99 (s, 3H) 1.84-1.96 (m, 1H) 1.48 (s, 3H) 1.33 (s, 3H).

Example 90

2-[3,5-bis(trifluoromethyl)phenyl]-N-{4-(4-fluoro-2-methylphenyl)-6-[(7R,9aR or 9aS)-7-methylhexahydropyrazino[2,1-c][1,4]oxazin-8(1H)-yl]-3-pyridinyl}-N,2-dimethylpropanamide (E90—Diastereoisomer 1)

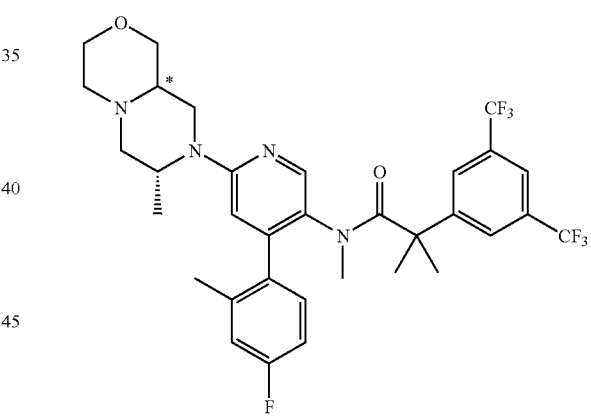

To a solution of (7R,9aR or 9aS)-7-methyloctahydropyrazino[2,1-c][1,4]oxazine (D94, 50 mg, 0.32 mmol) in 2.1 mL of toluene was added 2-[3,5-bis(trifluoromethyl)phenyl]-N-[6-chloro-4-(4-fluoro-2-methylphenyl)-3-pyridinyl]-N,2-dimethylpropanamide [WO 2005/002577] (131 mg, 0.246 mmol), bis-tri-tert-butylphosphine palladium (25 mg, 0.0492 mmol), hexadecyltrimethylammonium chloride (16 μL of a 25% aqueous solution) and, at last, sodium hydroxide solution (29.5 μL of a 50% aqueous solution). The solution was degassed by three freeze-pump-thaw cycles, then stirred at 90° C. for 2 h. It was checked by UPLC/MS, which showed peaks for the expected product at 0.75 min. (m/z=653 (M+1), 327 (M+2)/2). The solution was diluted with EtOAc, extracted with sat. $NaHCO_3$ and dried ($Na_2SO_4$). The product was isolated by flash chromatography (cyclohexane:EtOAc 70:30 to 0:100, then to EtOAc:MeOH 95:5), obtaining 74 mg of the title compound.

HPLC: Peak @ 5.30 min, 98% purity (UV).

1H NMR (500 MHz, DMSO-d$_6$) δ ppm 8.03 (s, 1H) 8.01 (s, 1H) 7.74 (br. s., 2H) 7.15 (d, 1H) 7.10 (br. s., 2H) 6.77 (s, 1H) 3.72 (br. s., 1H) 3.65 (d, 1H) 3.55-3.62 (m, 1H) 3.53 (t, 1H) 3.37-3.48 (m, 1H) 3.20 (t, 1H) 2.94-3.01 (m, 1H) 2.77-2.91 (m, 1H) 2.64 (d, 1H) 2.59 (br. s., 3H) 2.40-2.46 (m, 1H) 2.30-2.38 (m, 1H) 2.09 (s, 3H) 2.03-2.13 (m, 1H) 1.33 (s, 3H) 1.13 (br. s., 6H).

Example 91

2-[3,5-bis(trifluoromethyl)phenyl]-N-{4-(4-fluoro-2-methylphenyl)-6-[(7R,9aS or 9aR)-7-methylhexahydropyrazino[2,1-c][1,4]oxazin-8(1H)-yl]-3-pyridinyl}-N,2-dimethylpropanamide (E91—Diastereoisomer 2)

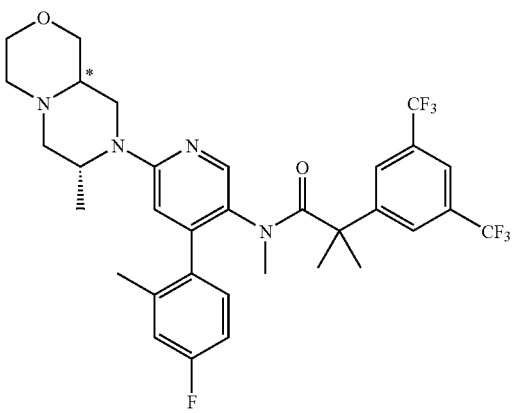

To a solution of (7R,9aS or 9aR)-7-methyloctahydropyrazino[2,1-c][1,4]oxazine (D95, 28 mg, 0.18 mmol) in 1.2 mL of toluene was added 2-[3,5-bis(trifluoromethyl)phenyl]-N-[6-chloro-4-(4-fluoro-2-methylphenyl)-3-pyridinyl]-N,2-dimethylpropanamide [WO 2005/002577] (73.5 mg, 0.138 mmol), bis-tri-tert-butylphosphine palladium (14 mg, 0.028 mmol), hexadecyltrimethylammonium chloride (9 µL of a 25% aqueous solution) and, at last, sodium hydroxide solution (16.5 µL of a 50% aqueous solution). The solution was degassed by three freeze-pump-thaw cycles, then stirred at 90° C. for 2 h. It was checked by UPLC/MS, which showed peaks for the expected product at 0.78 min. (m/z=653 (M+1), 327 (M+2)/2). The solution was diluted with EtOAc, extracted with sat. NaHCO$_3$ and dried (Na$_2$SO$_4$). The product was isolated by flash chromatography (cyclohexane:EtOAc 100:30 to 0:100), obtaining 49.6 mg of the title compound.

HPLC: Peak @ 5.35 min, 98% purity (UV).

1H NMR (500 MHz, DMSO-d$_6$) δ ppm 8.02 (s, 1H) 7.87 (s, 1H) 7.74 (br. s., 2H) 7.14 (d, 1H) 7.10 (br. s., 2H) 6.60 (br. s., 1H) 4.49 (br. s., 1H) 3.89-4.01 (m, 1H) 3.70-3.80 (m, 2H) 3.55 (t, 1H) 3.17 (t, 1H) 2.59-2.69 (m, 2H) 2.54 (br. s., 3H) 2.25-2.38 (m, 1H) 2.23 (br. s., 3H) 2.00-2.19 (m, 3H) 1.34 (br. s., 3H) 1.16 (br. s., 3H) 1.14 (d, 3H).

Example 92

N-[6-[(7R)-8-acetyl-7-(hydroxymethyl)octahydro-2H-pyrazino[1,2-a]pyrazin-2-yl]-4-(4-fluoro-2-methylphenyl)-3-pyridinyl]-2-[3,5-bis(trifluoromethyl)phenyl]-N,2-dimethylpropanamide (E92)

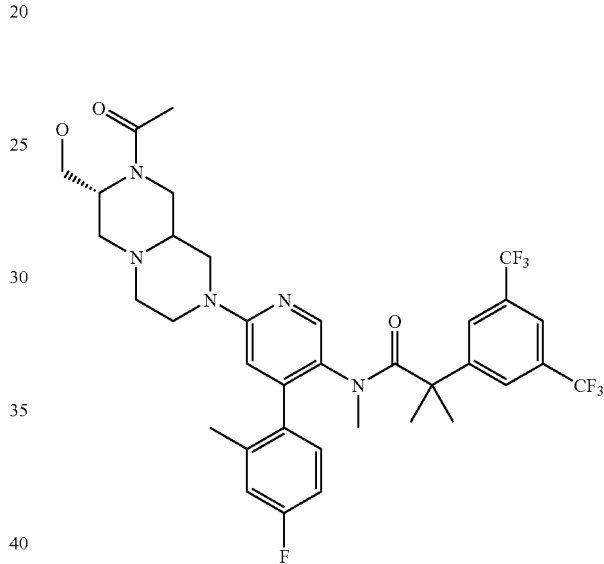

To a solution of {(3R)-2-acetyl-8-[5-[{2-[3,5-bis(trifluoromethyl)phenyl]-2-methylpropanoyl}methyl)amino]-4-(4-fluoro-2-methylphenyl)-2-pyridinyl]octahydro-2H-pyrazino[1,2-a]pyrazin-3-yl}methyl acetate (D97, 27 mg, 0.0472 mmol) in 2 mL of THF and 0.5 mL of water was added 1M NaOH (1 mL) and the resulting solution was stirred at room temperature for 30 min. It was checked by UPLC/MS, which showed a peak for the expected product at 0.76 min. (m/z=710 (M+1), 355 (M+2)/2). The target compound was isolated by SCX, obtaining 21 mg of the title compound.

1H NMR (500 MHz, DMSO-d$_6$) δ ppm 8.01 (s, 1H) 7.88 (s, 1H) 7.63-7.79 (m, 2H) 6.99-7.18 (m, 3H) 6.76 (s, 1H) 4.84 (t, 1H) 4.13-4.42 (m, 3H) 3.78-3.91 (m, 1H) 3.63-3.77 (m, 1H) 3.51-3.65 (m, 1H) 2.72-2.95 (m, 2H) 2.49 (s, 3H) 2.08 (s, 3H) 2.03 (s, 3H) 1.90-2.67 (m, 6H) 1.33 (s, 6H)

Ratio of Diastereoisomers 1 and 2 not determined.

Example 93

N-[6-[(3R,9aR or 9aS)-8-acetyl-3-methyloctahydro-2H-pyrazino[1,2-a]pyrazin-2-yl]-4-(4-fluoro-2-methylphenyl)-3-pyridinyl]-2-[3,5-bis(trifluoromethyl)phenyl]-N,2-dimethylpropanamide (E93—Diatereoisomer 1)

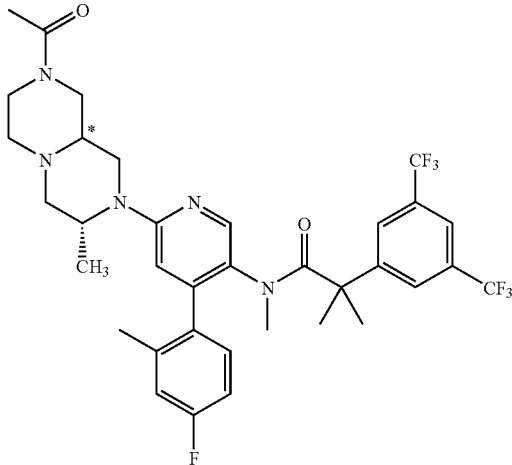

To a solution of (7R,9aR or 9aS)-2-acetyl-7-methyloctahydro-2H-pyrazino[1,2-a]pyrazine (D100, 50 mg, 0.253 mmol) in 1.1 mL of toluene was added 2-[3,5-bis(trifluoromethyl)phenyl]-N-[6-chloro-4-(4-fluoro-2-methylphenyl)-3-pyridinyl]-N,2-dimethylpropanamide [WO 2005/002577] (112.6 mg, 0.211 mmol), bis-tri-tert-butylphosphine palladium (27 mg, 0.053 mmol), hexadecyltrimethylammonium chloride (14 μL of a 25% aqueous solution) and, at last, sodium hydroxide solution (25 μL of a 50% aqueous solution). The solution was degassed by three freeze-pump-thaw cycles, then stirred at 90° C. for 2.5 h. It was checked by HPLC/MS, which showed a peak for the expected product at 2.07 min. (m/z=694 (M+1)). The solution was diluted with EtOAc, extracted with sat. NaHCO$_3$ and dried (Na$_2$SO$_4$). The product was isolated by flash chromatography (EtOAc to EtOAc:MeOH 90:10), obtaining 138 mg of the title compound.

O.A. HPLC: peak @ 5.20 min, 97% purity (UV).

1H NMR (500 MHz, DMSO-d$_6$) d ppm 8.03 (s, 1H) 7.98 (s, 1H) 7.75 (br. s., 2H) 7.16 (d, 1H) 7.10 (br. s., 2H) 6.76 (s, 1H) 4.16 (d, 1H) 3.82-3.95 (m, 1H) 3.61 (t, 1H) 3.48 (br. s., 1H) 3.14-3.26 (m, 1H) 2.95-3.10 (m, 2H) 2.64-2.82 (m, 1H) 2.50 (br. s., 3H) 2.43-2.61 (m, 1H) 2.16-2.40 (m, 2H) 2.05-2.18 (m, 4H) 1.97 (s, 3H) 1.48 (br. s., 3H) 1.34 (br. s., 3H) 1.15 (d, 3H).

Example 94

N-[6-[(3R,9aS or 9aR)-8-acetyl-3-methyloctahydro-2H-pyrazino[1,2-a]pyrazin-2-yl]-4-(4-fluoro-2-methylphenyl)-3-pyridinyl]-2-[3,5-bis(trifluoromethyl)phenyl]-N,2-dimethylpropanamide (E94—Diastereoisomer 2)

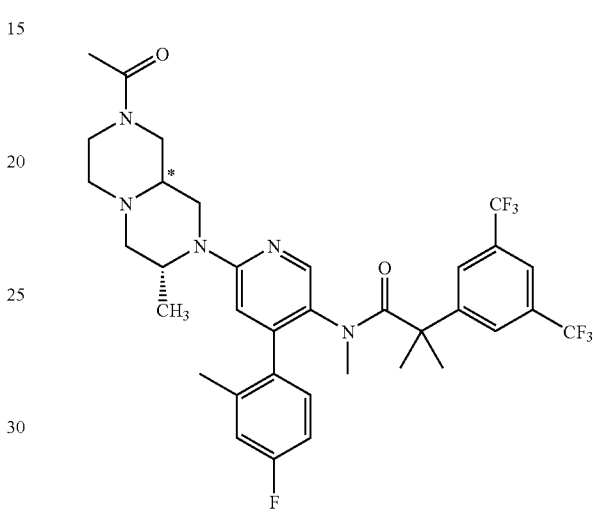

To a solution of (7R,9aR or 9aS)-2-acetyl-7-methyloctahydro-2H-pyrazino[1,2-a]pyrazine and (7R,9aS or 9aR)-2-acetyl-7-methyloctahydro-2H-pyrazino[1,2-a]pyrazine (D100 plus D101, 75 mg, 0.38 mmol) in 1.1 mL of toluene was added 2-[3,5-bis(trifluoromethyl)phenyl]-N-[6-chloro-4-(4-fluoro-2-methylphenyl)-3-pyridinyl]-N,2-dimethylpropanamide [WO 2005/002577] (169 mg, 0.317 mmol), bis-tri-tert-butylphosphine palladium (40.5 mg, 0.079 mmol), hexadecyltrimethylammonium chloride (20 μL of a 25% aqueous solution) and, at last, sodium hydroxide solution (38 μL of a 50% aqueous solution). The solution was degassed by three freeze-pump-thaw cycles, stirred at 90° C. for 6.5 h. It was checked by HPLC/MS, which showed a peaks for the expected products at 1.98 and 2.28 min. (m/z=694 (M+1)). The solution was diluted with EtOAc, extracted with sat. NaHCO$_3$ and dried (Na$_2$SO$_4$). The product was isolated by flash chromatography (dichloromethane to dichloromethane:MeOH 90:10). Obtained 32.4 mg of the title compound.

O.A. HPLC: peak @ 5.25 min, 95% purity (UV).

1H NMR (500 MHz, DMSO-d$_6$) δ ppm 8.02 (s, 1H) 7.88 (s, 1H) 7.74 (br. s., 2H) 7.15 (d, 1H) 7.10 (br. s., 2H) 6.61 (br. s., 1H) 4.52 (br. s., 1H) 4.34 (t, 1H) 4.08 (br. s., 1H) 3.81 (dd, 1H) 3.28-3.35 (m, 1H) 2.85 (t, 1H) 2.59-2.78 (m, 3H) 2.50 (br. s., 3H) 2.10-2.38 (m, 2H) 2.10 (br. s., 3H) 1.99 (s, 3H) 1.77-1.96 (m, 1H) 1.48 (br. s., 3H) 1.33 (br. s., 3H) 1.16 (d, 3H).

Example 95 and 96

2-[3,5-bis(trifluoromethyl)phenyl]-N-{4-(4-fluoro-2-methylphenyl)-6-[(4S or 4R,8aR)-4-(hydroxymethyl)hexahydropyrrolo[1,2-a]pyrazin-2(1H)-yl]-3-pyridinyl}-N,2-dimethylpropanamide (E95—Diastereoisomer 1) 2-[3,5-bis(trifluoromethyl)phenyl]-N-{4-(4-fluoro-2-methylphenyl)-6-[(4R or 4S,8aR)-4-(hydroxymethyl)hexahydropyrrolo[1,2-a]pyrazin-2(1H)-yl]-3-pyridinyl}-N,2-dimethylpropanamide (E96—Diastereoisomer 2)

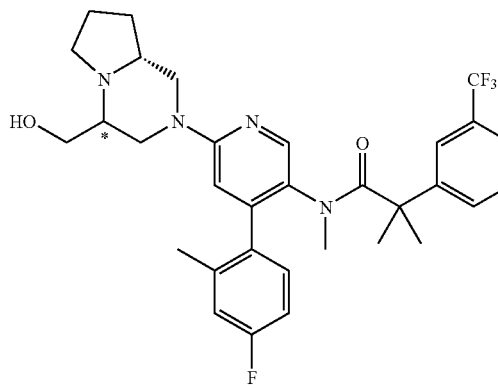

To a solution of (8aR)-octahydropyrrolo[1,2-a]pyrazin-4-ylmethanol (D112, 73 mg, 0.468 mmol) and 2-[3,5-bis(trifluoromethyl)phenyl]-N-[6-chloro-4-(4-fluoro-2-methylphenyl)-3-pyridinyl]-N,2-dimethylpropanamide [WO 2005/002577] (124 mg, 0.234 mmol) in DMSO (0.75 ml) was added K$_2$CO$_3$ (96 mg, 0.702 mmol) and the reaction mixture was stirred for 36 hrs at 120/150° C. The two diastereoisomers were isolated after purification by SCX and the by chromatography (silica, CH$_2$Cl$_2$:MeOH 98:2).

E95—Diastereoisomer 1 (40 mg)

MS: m/z=653 (M+1) and 327 (M/2+1)

HPLC: peak @ t=5.22 min

1H NMR (500 MHz, DMSO-d$_6$) δ ppm 8.02 (s, 1H) 7.88 (s, 1H) 7.73 (br. s., 2H) 7.14 (d, 1H) 7.10 (br. s., 2H) 6.63 (br. s., 1H) 4.62 (s, 1H) 4.32-4.44 (m, 2H) 3.57-3.66 (m, 1H) 3.30-3.36 (m, 2H) 3.11-3.20 (m, 1H) 2.48 (s, 3H) 2.41-2.58 (m, 2H) 2.24 (br. s., 1H) 2.15 (s, 3H) 2.10 (br. s., 1H) 1.73-1.83 (m, 1H) 1.60-1.70 (m, 4H) 1.33 (s, 3H) 1.10-1.54 (m, 2H)

E96—Diastereoisomer 2 (33 mg)

MS: m/z=653 (M+1) and 327 (M/2+1)

HPLC: peak @ t=5.152 min

1H NMR (500 MHz, DMSO-d$_6$) δ ppm 8.02 (s, 1H) 7.84 (s, 1H) 7.73 (br. s., 2H) 7.14 (d, 1H) 7.10 (br. s., 2H) 6.51 (s, 1H) 4.48-4.57 (m, 1H) 3.88-3.98 (m, 1H) 3.48-3.61 (m, 3H) 3.33-3.37 (m, 1H) 3.06-3.18 (m, 1H) 2.81-2.94 (m, 3H) 2.68-2.76 (m, 1H) 2.49 (s, 3H) 2.11 (s, 3H) 1.79-1.90 (m, 1H) 1.70-1.79 (m, 1H) 1.56-1.69 (m, 1H) 1.33 (s, 6H) 1.23-1.41 (m, 1H).

Example 97 and 98

2-[3,5-bis(trifluoromethyl)phenyl]-N-{4-(4-fluoro-2-methylphenyl)-6-[(4S or 4R,8aS)-4-(hydroxymethyl)hexahydropyrrolo[1,2-a]pyrazin-2(1H)-yl]-3-pyridinyl}-N,2-dimethylpropanamide (E97—Diastereoisomer 1) 2-[3,5-bis(trifluoromethyl)phenyl]-N-{4-(4-fluoro-2-methylphenyl)-6-[(4R or 4S,8aS)-4-(hydroxymethyl)hexahydropyrrolo[1,2-a]pyrazin-2(1H)-yl]-3-pyridinyl}-N,2-dimethylpropanamide (E98—Diastereoisomer 2)

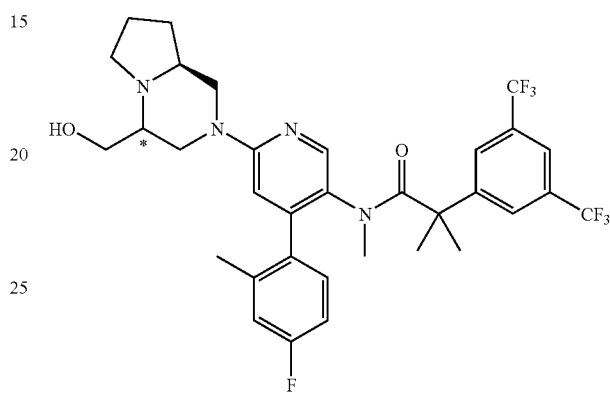

To 2-[3,5-bis(trifluoromethyl)phenyl]-N-[6-chloro-4-(4-fluoro-2-methylphenyl)-3-pyridinyl]-N,2-dimethylpropanamide [WO 2005/002577] (375 mg, 0.705 mmol) and K$_2$CO$_3$ (389 mg) was added a solution of (8aS)-octahydropyrrolo[1,2-a]pyrazin-4-ylmethanol (D117, 220 mg, 1.41 mmol) in DMSO (2.3 ml) and the reaction mixture was stirred for 30 hrs at 150° C.

The two diastereoisomers were isolated after purification by SCX and then by chromatography (silica cartridge, CH$_2$Cl$_2$:MeOH 98:2).

E97—Diastereoisomer 1 (150 mg):

MS: m/z=653 (M+1) and 327 (M/2+1)

HPLC: peak @ t=5.18 min

UPLC/MS: m/z=653 (M+1) and 327 (M/2+1) @ t=0.70 min

1H NMR (500 MHz, DMSO-d$_6$) δ ppm 8.02 (s, 1H) 7.88 (s, 1H) 7.73 (br. s., 2H) 7.14 (d, 1H) 7.10 (br. s., 2H) 6.63 (br. s., 1H) 4.62 (s, 1H) 4.32-4.44 (m, 2H) 3.57-3.66 (m, 1H) 3.30-3.36 (m, 2H) 3.11-3.20 (m, 1H) 2.48 (s, 3H) 2.41-2.58 (m, 2H) 2.24 (br. s., 1H) 2.15 (s, 3H) 2.10 (br. s., 1H) 1.73-1.83 (m, 1H) 1.60-1.70 (m, 4H) 1.33 (s, 3H) 1.10-1.54 (m, 2H)

E98—Diastereoisomer 2 (75 mg):

MS: m/z=653 (M+1) and 327 (M/2+1)

HPLC: peak @ t=5.15 min

UPLC/MS: m/z=653 (M+1) and 327 (M/2+1) @ t=0.72 min

1H NMR (500 MHz, DMSO-d$_6$) δ ppm 8.02 (s, 1H) 7.84 (s, 1H) 7.73 (br. s., 2H) 7.14 (d, 1H) 7.10 (br. s., 2H) 6.51 (s, 1H) 4.48-4.57 (m, 1H) 3.88-3.98 (m, 1H) 3.48-3.61 (m, 3H) 3.33-3.37 (m, 1H) 3.06-3.18 (m, 1H) 2.81-2.94 (m, 3H) 2.68-2.76 (m, 1H) 2.49 (s, 3H) 2.11 (s, 3H) 1.79-1.90 (m, 1H) 1.70-1.79 (m, 1H) 1.56-1.69 (m, 1H) 1.33 (s, 6H) 1.23-1.41 (m, 1H).

Example 99

2-[3,5-bis(trifluoromethyl)phenyl]-N-{4-(4-fluoro-2-methylphenyl)-6-[(7R,9aR or 9aS)-7-(hydroxymethyl)-2,2-dioxidohexahydropyrazino[2,1-c][1,4]thiazin-8(1H)-yl]-3-pyridinyl}-N,2-dimethylpropanamide (E99—Diastereoisomer 1)

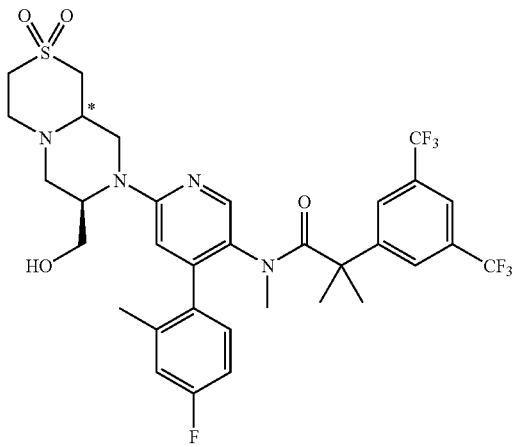

To a solution of 2-[3,5-bis(trifluoromethyl)phenyl]-N-[6-[(7R,9aR or 9aS)-7-({[(1,1-dimethylethyl)(dimethyl)silyl]oxy}methyl)-2,2-dioxidohexahydropyrazino[2,1-c][1,4]thiazin-8(1H)-yl]-4-(4-fluoro-2-methylphenyl)-3-pyridinyl]-N,2-dimethylpropanamide (D124, 201 mg, 0.24 mmol) in methanol (8 ml), cooled to 0° C., was added HCl 12 N dropwise (0.47 ml). The reaction mixture was stirred at room temperature for 1 hr, then it was purified by SCX cartridge. The fractions eluted with 2M methanolic ammonia were combined and evaporated to dryness to give the title compound as a white solid (155 mg, y=90%).

HPLC: peak @ t=5.65 min
HPLC/MS: m/z=717 (M+1) @ t=2.88 min
1H NMR (500 MHz, DMSO-$d_6$) δ ppm 7.95-8.10 (m, 1H) 7.80-7.93 (m, 1H) 7.59-7.81 (m, 2H) 6.86-7.24 (m, 3H) 6.49-6.76 (m, 1H) 4.63-4.79 (m, 1H) 3.94-4.42 (m, 2H) 3.55-3.84 (m, 1H) 2.86-3.52 (m, 7H) 1.00-2.83 (m, 16H).

Example 100

2-[3,5-bis(trifluoromethyl)phenyl]-N-{4-(4-fluoro-2-methylphenyl)-6-[(7R,9aS or 9aR)-7-(hydroxymethyl)-2,2-dioxidohexahydropyrazino[2,1-c][1,4]thiazin-8(1H)-yl]-3-pyridinyl}-N,2-dimethylpropanamide (E100—Diastereoisomer 2)

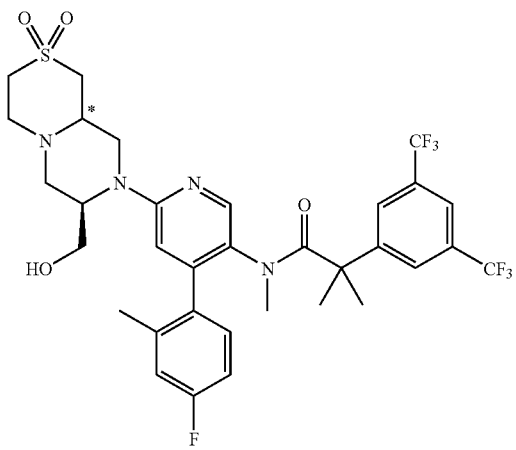

To a solution of 2-[3,5-bis(trifluoromethyl)phenyl]-N-[6-[(7R,9aS or 9aR)-7-({[(1,1-dimethylethyl)(dimethyl)silyl]oxy}methyl)-2,2-dioxidohexahydropyrazino[2,1-c][1,4]thiazin-8(1H)-yl]-4-(4-fluoro-2-methylphenyl)-3-pyridinyl]-N,2-dimethylpropanamide (D125, 127.4 mg, 0.153 mmol) in methanol (5 ml), cooled to at 0° C., was added dropwise HCl 12 N (0.3 ml). The reaction mixture was stirred at room temperature for 2 hrs, then it was purified by SCX cartridge. The fractions eluted with 2M methanolic ammonia were combined and evaporated to dryness to give the title compound as a white solid (104 mg, y=95%).

HPLC: peak @ t=5.54 min
HPLC/MS: m/z=717 (M+1) @ t=2.91 min
1H NMR (500 MHz, DMSO-$d_6$) δ ppm 8.01 (s, 1H) 7.85 (s, 1H) 7.63-7.81 (m, 2H) 7.16 (d, 1H) 7.03-7.17 (m, 2H) 6.67 (s, 1H) 4.71 (t, 1H) 4.19-4.36 (m, 1H) 4.02-4.19 (m, 1H) 3.65-3.80 (m, 1H) 3.36-3.53 (m, 1H) 3.15-3.36 (m, 4H) 3.10 (d, 1H) 2.86-3.01 (m, 1H) 2.72-2.84 (m, 1H) 2.65 (d, 1H) 1.10-2.56 (m, 14H).

Example 101

2-[3,5-bis(trifluoromethyl)phenyl]-N-{4-(4-fluoro-2-methylphenyl)-6-[(7R,9aR or 9aS)-7-[(methyloxy)methyl]-2,2-dioxidohexahydropyrazino[2,1-c][1,4]thiazin-8(1H)-yl]-3-pyridinyl}-N,2-dimethylpropanamide (E101—Diastereoisomer 1)

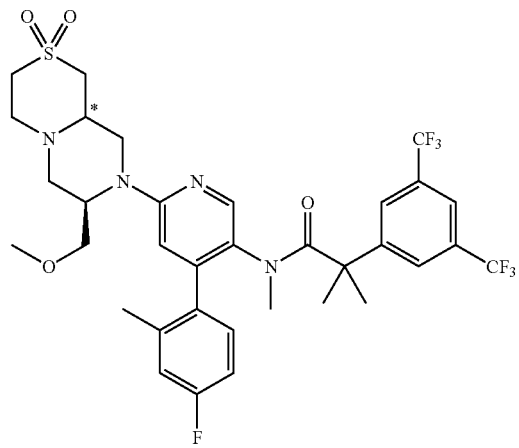

To a solution of 2-[3,5-bis(trifluoromethyl)phenyl]-N-{4-(4-fluoro-2-methylphenyl)-6-[(7R,9aR or 9aS)-7-(hydroxymethyl)-2,2-dioxidohexahydropyrazino[2,1-c][1,4]thiazin-8(1H)-yl]-3-pyridinyl}-N,2-dimethylpropanamide (E99, 15 mg, 0.021 mmol) in THF (1 ml) was added under $N_2$, at r.t., 60% NaH (1 mg, 0.023 mmol) and the reaction mixture was stirred for 30 mins. Then MeI (2 μl, 0.021 mmol) was added and the reaction mixture was stirred for 6 hrs. During this reaction time further amounts of NaH (2 mg, 0.046 mmol) and MeI (4 μl, 0.042 mmol) were added portionwise.

Water was added to the reaction mixture and the aqueous phase was extracted with EtOAc (3×). The combined organic phases were dried and evaporated to dryness. The crude was purified twice by chromatography (silica, $CH_2Cl_2$:MeOH 1:0 to 8:2 the 1$^{st}$ time and $CH_2Cl_2$:MeOH 1:0 to 9:1 the 2$^{nd}$ time) to give the title compound (12.4 mg, y=81%)

MS: m/z=731 (M+1); 753 (M+Na); 366 (M/2+1)

1H NMR (500 MHz, DMSO-d$_6$) δ ppm 8.01 (s, 1H) 7.87 (s, 1H) 7.63-7.81 (m, 2H) 7.15 (d, 1H) 7.02-7.19 (m, 2H) 6.66 (s, 1H) 4.44-4.77 (m, 1H) 3.99-4.27 (m, 1H) 3.67 (t, 1H) 3.37-3.50 (m, 1H) 3.23 (s, 3H) 2.91-3.39 (m, 7H) 2.68-2.85 (m, 1H) 2.51 (s, 3H) 2.40-2.66 (m, 1H) 2.11-2.29 (m, 1H) 2.11 (s, 3H) 1.49 (s, 3H) 1.34 (s, 3H).

Example 102

2-[3,5-bis(trifluoromethyl)phenyl]-N-[6-[(7S,9aS)-7-(fluoromethyl)hexahydropyrazino[2,1-c][1,4]oxazin-8(1H)-yl]-4-(4-fluoro-2-methylphenyl)-3-pyridinyl]-N,2-dimethylpropanamide (E102)

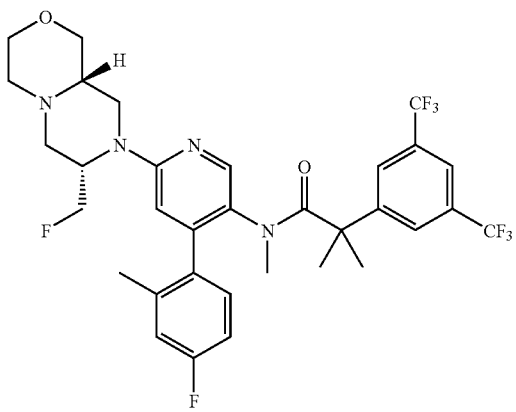

To a solution of (7S,9aS)-7-(fluoromethyl)octahydropyrazino[2,1-c][1,4]oxazine (D129, 14.9 mg, 0.086 mmol) in toluene (1 ml) was added under N$_2$, at r.t., 2-chloropyridine (35 mg, 0.066 mmol) and then hexadecyltrimethylammonium chloride (4 μL of a 25% aqueous solution), bis-tri-tert-butylphosphine palladium (7 mg), and sodium hydroxide solution (8 L of a 50% aqueous solution). The reaction mixture was degassed by freeze-pump-thaw cycles and then it was stirred at 90° C. for 1 hr. EtOAc and NaHCO$_3$ were added to the reaction mixture, the two phases were separated and the aqueous phase was extracted with EtOAc (3×). The combined organic phases were dried (Na$_2$SO$_4$) and evaporated to dryness. The crude was purified by chromatography (silica, cyclohexane:EtOAc 7:3 to 0:1) to give the title compound as a brownish foam (30 mg, y=68%).

UPLC/MS: m/z=671 (M+1) @ t=0.93 min

1H NMR (500 MHz, DMSO-d$_6$) δ ppm 8.01 (s, 1H) 7.88 (s, 1H) 7.60-7.80 (m, 2H) 6.99-7.23 (m, 3H) 6.69 (s, 1H) 4.66-4.89 (m, 1H) 4.56-4.73 (m, 1H) 3.96-4.09 (m, 1H) 3.67-3.79 (m, 2H) 3.54 (t, 1H) 3.14 (t, 1H) 2.89 (d, 1H) 2.49-2.69 (m, 1H) 2.50 (s, 3H) 2.04-2.38 (m, 2H) 2.09 (s, 3H) 1.53-1.74 (m, 1H) 1.34 (s, 6H) 1.11-1.46 (m, 1H) 1.03-1.43 (m, 1H).

Example 103 HCl

N-[6-[(9aR or 9aS)-8-acetyloctahydro-2H-pyrazino[1,2-a]pyrazin-2-yl]-4-(4-fluoro-2-methylphenyl)-3-pyridinyl]-2-[3,5-bis(trifluoromethyl)phenyl]-N,2-dimethylpropanamide hydrochloride (E103-Enantiomer 2)

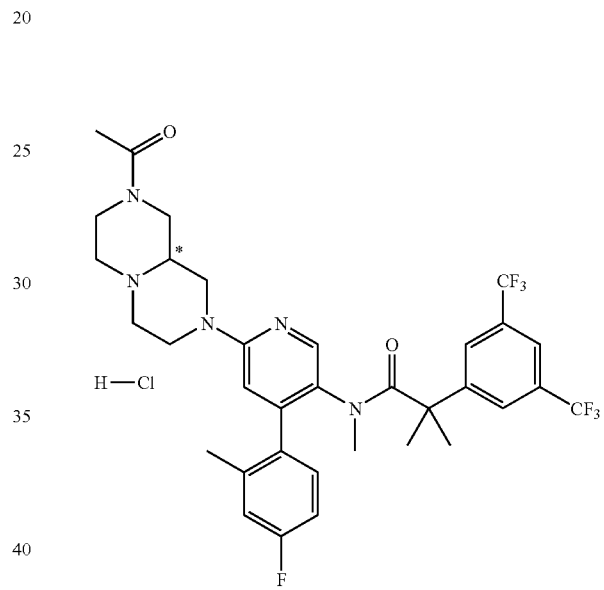

To a solution of N-[6-(8-acetyloctahydro-2H-pyrazino[1,2-a]pyrazin-2-yl]-4-(4-fluoro-2-methylphenyl)-3-pyridinyl]-2-[3,5-bis(trifluoromethyl)phenyl]-N,2-dimethylpropanamide, enantiomer 2 (E72, 19 mg, sample from a different preparation having comparable analytical characteristics to the reported one) in diethyl ether at 0° C. were added 33.5 μL of a 1M HCl solution in diethyl ether. The solution was stirred for 10 minutes and the solvent was removed under a nitrogen stream. The residue was triturated with diethyl ether and pentane and collected by filtration. Obtained 20 mg of the target compound.

1H NMR (500 MHz, DMSO-d$_6$) δ ppm 10.27-10.61 (m, 1H) 8.04 (s, 1H) 7.94 (s, 1H) 7.62-7.81 (m, 2H) 7.17 (d, 1H) 7.04-7.16 (m, 2H) 6.86 (s, 1H) 4.44-4.76 (m, 3H) 3.97-4.26 (m, 1H) 2.73-3.91 (m, 7H) 2.48 (s, 3H) 2.09-2.54 (m, 2H) 2.11 (s, 3H) 2.05 (s, 3H) 1.49 (s, 3H) 1.38 (s, 3H).

Example 104

2-[3,5-bis(trifluoromethyl)phenyl]-N-{4-(4-fluoro-2-methylphenyl)-6-[(7R,9aR)-7-(hydroxymethyl)hexahydropyrazino[2,1-c][1,4]oxazin-8(1H)-yl]-3-pyridinyl}-N,2-dimethylpropanamide (E104)

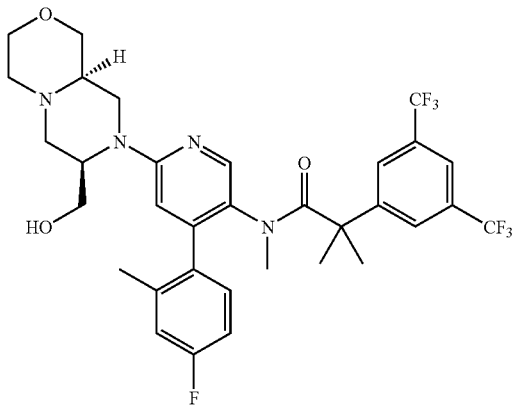

(7R,9aR)-7-({[(1,1-dimethylethyl)(dimethyl)silyl]oxy}methyl)octahydropyrazino[2,1-c][1,4]oxazine (D132, 85 mg, 0.297 mmol) was dissolved in 1 mL of toluene by stirring at room temperature. Additional 1 mL of toluene was added to obtain complete dissolution. A sample of 2-[3,5-bis(trifluoromethyl)phenyl]-N-[6-chloro-4-(4-fluoro-2-methylphenyl)-3-pyridinyl]-N,2-dimethylpropanamide [WO 2005/002577] (143 mg, 0.268 mmol) was added, followed by a solution of 2-dicyclohexylphosphino-2'-(N,N-dimethylamino)biphenyl (ligand) (13 mg, 0.033 mmol) and Pd(dba)$_2$ (8 mg, 0.014 mmol) in 1 mL of toluene. Potassium tert-butoxide (39 mg, 0.406 mmol) was added and the reaction vessel closed, evacuated and back-filled with argon. The mixture was reacted under microwave irradiation at 140° C. for 15 min. and then for additional 30 min. The mixture was diluted with 30 mL of EtOAc and extracted sat. NaHCO$_3$, dried (Na$_2$SO$_4$) and the solvent removed. Product purified by flash chromatography: silica, cyclohexane: EtOAc 100:0 to 80:20. Obtained a partially purified sample: analyzed by UPLC/MS (purity: 24% by UV trace, 58% by MS trace), used directly in the deprotection step.

UPLC/MS: peak @ 1.21 min, m/z=783 (M+1), 392 (M+2/2).

The intermediate (55 mg) was dissolved in 2 mL of methanol and added 0.1 mL of conc. HCl. The solution was stirred at room temperature for 1 h. It was loaded on a SCX cartridge, washed with MeOH, and the product was eluted with 1 M ammonia in MeOH. UPLC/MS analysis showed the expected product peak at 0.75 min (m/z=669, M+1; 335, (M+2)/2). It was purified further by flash chromatography (silica, cyclohexane:EtOAc 50:50 to 0:100). Obtained 12 mg.

1H NMR (500 MHz, DMSO-d$_6$) δ ppm 8.02 (s, 1H) 7.84 (s, 1H) 7.74 (br. s., 2H) 7.15 (d, 1H) 7.10 (br. s., 2H) 6.60 (s, 1H) 4.65-4.75 (m, 1H) 4.22 (br. s., 1H) 4.08 (br. s., 1H) 3.68-3.80 (m, 3H) 3.53 (t, 1H) 3.34-3.43 (m, 1H) 3.14 (t, 1H) 3.01 (d, 1H) 2.63 (d, 1H) 2.48 (s, 3H) 2.17 (s, 3H) 2.00-2.29 (m, 4H) 1.46 (s, 3H) 1.34 (s, 3H)

Biological Data

Compounds of the invention may be tested for in vitro biological activity in accordance with the following assays:

Measurement of NK Binding Affinity

The NK binding affinity of the compounds in the invention was determined using the following scintillation proximity assay (SPA) (see H. M. Sarau et al, J. Pharmacol. Experimental Therapeutics 1997, 281(3), 1303-1311; H. M. Sarau et al, J. Pharmacol. Experimental Therapeutics 2000, 295(1), 373-381; G. A. M. Giardina et al J. Med. Chem. 1999, 42, 1053-1065). $^{125}$I-Substance P, $^{125}$I-NKA and $^{125}$I-[MePhe7]-NKB were used in the binding SPA of NK1, NK2 and NK3 receptor, respectively. Polystyrene Leadseeker WGA-SPA beads (Amersham Biosciences) were mixed with plasma membrane prepared from CHO cell lines expressing NK1, NK2 or NK3 in a bead/membrane ratio of 20:1 (w/w) in assay buffer (75 mM Tris pH 7.8, 75 mM NaCl, 4 mM MnCl$_2$, 1 mM EDTA, 0.05% Chaps, 1 mM PMSF). The mixture was placed on ice for 20 minutes to allow the formation of membrane/bead complex before BSA was added to a final concentration of 1%. After another 20 minutes of incubation on ice, the bead/membrane complex was washed twice and suspended in assay buffer. $^{125}$I-labelled ligands were then added to the bead/membrane complex. 10 μl of the resulting mixture was then dispensed into each well of a low volume Greiner 384-well plate with 100 mL compound pre-dispensed in 100% DMSO. The plates were then sealed and pulse spun at 1100 rpm. After 2-3 hours incubation at room temperature with shaking, the plates were spun for 2 min at 1100 rpm and measured in Viewlux imager (PerkinElmer) for 5 minutes with a 618-nm filter. Inhibition of radioactive ligand binding to its respective receptor was measured by the reduction of signal. p$K_i$ was calculated using $K_d$ of each radioactive ligand determined in a separate experiment.

Measurement of NK Functional Affinity:

Calcium Mobilization Assay in (FLIPR): Bacman Expressed NK Receptors

Compounds of the invention were further characterised in a functional assay using FLIPR technology for the determination of their effect to inhibit the intracellular calcium release induced by interaction of NK receptors with its perspective ligands. Human U2OS cells transiently transduced with recombinant BacMan virus expressing NK1, NK2 and NK3 receptors were used in the studies (see J. P. Condreay et al, Proc. Natl. Acad. Sci. USA 1999, 96(1): 127-132). Briefly, U2OS cells were harvested from tissue culture flasks, re-suspended to a cell density of 200-300K/ml and mixed with recombinant BacMan virus carrying NKR gene in a virus/cell ratio of 1% (v/v). 10K-15K cells/well were then seeded in 384-well Greiner bio-one plate in culture medium (DMEM with 10% FBS), incubated overnight in CO$_2$ at 37° C. After aspirating the medium, cells were loaded 18-24 hr later with cytoplasmic calcium indicator Calcium 3 dye (Molecular Devices Co.) in 30 uL/well buffer (Hank's balanced salts with 20 mM Hepes) and incubated in CO$_2$ at 37° C. for 60 minutes. 10 uL/well assay buffer (Hank's balanced salts with 20 mM Hepes) containing different concentrations of compounds were then added to the cells for 30 minutes incubation at 37° C. Finally, 10 uL/well of NKR ligands in assay buffer containing 0.1% BSA was added to the cells and fluorescence signal read on a FLIPR system. Substance P, NKA and NKB peptides were used as the ligands for NK1, NK2 and NK3 receptor, respectively. IC50 values of each compound were determined by an 11-point 3x-dilution inhibition curve. The potency each antagonist (fp$K_i$) was calculated from pIC50 by the Cheng-Prusoff equation using EC50 of ligand determined in a separate experiment.

Measurement of NK3 Functional Affinity

Calcium Mobilization Assay in (FLIPR): Stably Expressed NK Receptors

Human cloned neurokinin 3 (NK$_3$) receptors stably expressed in human embryonic kidney (HEK 293) cells were maintained in Minimum Essential Medium (MEM, 31095-029 Invitrogen Life Technologies, Paisley, UK) supplemented with 5% foetal bovine serum, 1% L-glutamine and 400-500 μg geneticin and were sub-cultured using Accutase (PAA Labs, Austria). Cells were maintained at 37° C. 5% $CO_2/O_2$ in a humidified incubator. Changes in intracellular $Ca^{2+}$ were determined using a Fluorescence Imaging Plate Reader (FLIPR) (Molecular Devices, Sunnyvale Calif., USA) by a method similar to that described by Jerman et al, (2001). HEK 293 cells stably expressing the human $NK_3$ receptor were seeded into black walled, clear-base poly-d-lysine coated 96 well plates (Costar, UK) at a density of 25,000 cells per well incubated overnight. Cells were incubated (37° C. for 60 min) with Calcium Plus Reagent (Molecular Devices) in Tyrodes buffer (NaCl, 145 mM; KCl, 2.5 mM; HEPES, 10 mM; Glucose, 10 mM; $MgCl_2$, 1.2 mM; $CaCl_2$, 1.5 mM) containing probenecid (2.5 mM), before incubation (30 min at 37° C.) with either buffer or antagonist (50 µl). The plates were then placed on the FLIPR and 50 µl NKB was added (10 pM-1 µM final concentration) changes in fluorescence were monitored. Peak changes in fluorescence occurred within the first 5 sec and were reported following baseline subtraction. Concentration-response curves were analysed using a 4-parameter logistic equation (GraphPad Prism, GraphPad Software Inc.) to obtain $pEC_{50}$ values ($-\log EC_{50}$), $pA_2$ values were obtained by Schild analysis. Data are the mean±s.e.mean of three separate experiments.

[$^3$H] Inositol Phosphates Accumulation Assay

[$^3$H] Inositol phosphates accumulation was measured using the methodology of Brandish et al., (2003). Briefly, human osteosarcoma cells (U-205 cells) were cultured in Dulbecco's Modified Eagle's Medium (DMEM) with 10% foetal calf serum. Cells were maintained at 5% $CO_2/O_2$ in a humidified incubator at 37° C. All cell culture reagents were obtained from Invitrogen, Paisley, UK. U-205 cells were grown to confluence, harvested and suspended in growth media at a density of 250000 cells per mL. Human $NK_3$ Bacmam virus was then added at a concentration of 50 plaque forming units per cell. 25000 cells per well were seeded into black walled clear-base 96 well plates (Corning Costar, UK) incubated overnight. Following aspiration of growth media, cells were washed with 2×200 µL inositol free (IF) assay medium, 3% bovine serum albumin, 2 pM L-Glutamine. The cells were incubated for 16 h with inositol-free DMEM in the presence of [$^3$H]-myo-inositol 1 µCi per well (Amersham U.K).

Growth media was then aspirated and the cells washed with 2×200 µL IF DMEM. The cells were pre-incubated (30 min, 37° C.) in the absence or presence of test compounds before the addition of various concentrations of NKB (0.1 nM-10 mM) in the presence of LiCl (5 mM). After 30 min incubation with the agonist, the assay was terminated by aspiration of the assay media and the addition of 200 uL 0.1 M formic acid to the cells. Following an hour incubation, 20 uL aliquots were mixed with 80 uL of yttrium silicate beads into solid white pico-plates (PerkinElmer). Plates were agitated gently for 1 h before allowing the bead mixture to settle for 2 h. Plates were counted on TopCount (PerkinElmer). Data is presented as a percentage of the maximal NKB response. Concentration-response curves were analysed using a 4-parameter logistic equation (GraphPad Prism, GraphPad Software Inc.) $pA_2$ values were obtained by Schild analysis. Data are the mean±s.e.mean of three separate experiments.

Results

The compounds of Examples E1 to E33 were tested in the NK1 binding affinity assay and exhibited binding affinity>8.0 $pK_i$.

The compounds of Examples E34-E40 and E72 exhibited binding affinity in the NK1 binding affinity assay>8.5 $pK_i$ The compounds of Examples E41-E71 and E73-E104 exhibited binding affinity in the NK1 binding affinity assay>8.0 $pK_i$ The compounds of Examples E1 to E33 were also tested in the NK3 binding affinity assay and exhibited binding affinity>5.5 $pK_i$.

The compounds of Examples E34-E40 and E72 exhibited binding affinity in the NK3 binding affinity assay ≧8.0 $pK_i$.

The compounds of Examples E41-E71 and E73-E104 exhibited binding affinity in the NK3 binding affinity assay>5.0 $pK_i$.

The invention claimed is:

1. A method of treatment of alcohol dependence which comprises administering to a human in need thereof an effective amount of a compound of formula

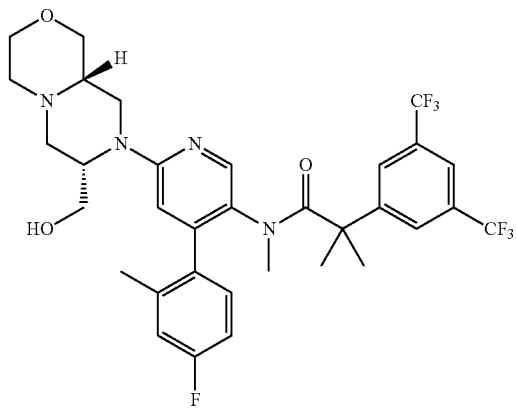

or a pharmaceutically acceptable salt thereof.

2. The method of claim 1, wherein the compound is 2-[3,5-Bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide.

3. The method of claim 1, wherein the compound is 2-[3,5-Bis(trifluoromethyl)phenyl]-N-{4-(4-fluoro-2-methylphenyl)-6-[(7S,9aS)-7-(hydroxymethyl)hexahydropyrazino[2,1-c][1,4]oxazin-8(1H)-yl]-3-pyridinyl}-N,2-dimethylpropanamide hydrochloride.

4. The method of claim 1, wherein the compound is administered together with a pharmaceutically acceptable carrier or excipient.

5. The method of claim 2, wherein the compound is administered together with a pharmaceutically acceptable carrier or excipient.

6. The method of claim 3, wherein the compound is administered together with a pharmaceutically acceptable carrier or excipient.

* * * * *